US012753240B2

(12) United States Patent
Amit et al.

(10) Patent No.: US 12,753,240 B2
(45) Date of Patent: Oct. 6, 2026

(54) ANTI-TUMOR NECROSIS FACTOR RECEPTOR (TNFR2) ANTIBODIES AND USES THEREOF

(71) Applicant: Biolojic Design Ltd., Ness Ziona (IL)

(72) Inventors: Inbar Amit, Modi'in (IL); Itay Levin, Herzeliya (IL); Ayelet Chen, Jerusalem (IL); Tal Vana, Holon (IL); Nino Oren, Rishon-Lezion (IL); Dor Samet, Kfar Saba (IL); Efrat Choen Zada, Rechelim (IL); Natalia Levitin, Ashdod (IL); Guy Nimrod, Tel Aviv (IL); Yehezkel Sasson, Tzur Yigal (IL); Alik Demishtein, Rosh Haayin (IL); Timothy Wyant, Bellingham, MA (US); Reut Barak Fuchs, Rehovot (IL); Yair Fastman, Jerusalem (IL); Sharon Fischman, Modi'in (IL); Marek Strajbl, Jerulsalem (IL); Michael Zhenin, Jerusalem (IL); Olga Bluvshtein Yermolaev, Rishon-Lezion (IL); Noam Grossman, Mazkeret Batyia (IL); Oshrat Shir Twito, Rishon-Lezion (IL); Nevet Zur Biton, Bat Yam (IL); Liron Danielpur, Hadera (IL); May Sofia Ben Mayor, Tel Aviv (IL); Yanay Ofran, Tel Aviv (IL)

(73) Assignee: Biolojic Design Ltd., Rehovot (IL)

( * ) Notice: Subject to any disclaimer, the term of this patent is extended or adjusted under 35 U.S.C. 154(b) by 790 days.

(21) Appl. No.: 18/011,251

(22) PCT Filed: Jul. 1, 2021

(86) PCT No.: PCT/IL2021/050807

§ 371 (c)(1),
(2) Date: Dec. 19, 2022

(87) PCT Pub. No.: WO2022/003690

PCT Pub. Date: Jan. 6, 2022

(65) Prior Publication Data

US 2023/0167188 A1 Jun. 1, 2023

Related U.S. Application Data

(60) Provisional application No. 63/047,490, filed on Jul. 2, 2020.

(51) Int. Cl.
*A61K 39/395* (2006.01)
*A61K 35/17* (2015.01)
(Continued)

(52) U.S. Cl.
CPC .......... *C07K 16/2878* (2013.01); *A61K 35/17* (2013.01); *A61P 37/02* (2018.01);
(Continued)

(58) Field of Classification Search
None
See application file for complete search history.

(56) References Cited

U.S. PATENT DOCUMENTS 11,859,002 B2 * 1/2024 Faustman ............... A61P 31/18
2017/0362338 A1 12/2017 Davidson et al.
(Continued)

FOREIGN PATENT DOCUMENTS

WO WO 2013/188855 A1 12/2013
WO WO 2018/213064 A1 11/2018
(Continued)

OTHER PUBLICATIONS

Chen et al., Editorial: The Role of TNF-TNFR2 Signal in Immunosuppressive Cells and Its Therapeutic Implications, Front Immunol. 0:2126, 4 pages, Sep. 6, 2019.*
(Continued)

*Primary Examiner* — Claire Kaufman

(57) ABSTRACT

The present disclosure describes a number of anti-TNFR2 (tumor necrosis factor receptor 2) antibodies. These antibodies are TNFR2 agonists. In certain cases, these antibod-
(Continued)

ies agonize TNFR2 in an Fc independent manner. These antibodies can modulate the proliferation and/or functions of regulatory T cells and myeloid-derived suppressor cells. In certain instances, these antibodies can be used to treat diseases such as GvHD or autoimmune diseases.

16 Claims, 37 Drawing Sheets

Specification includes a Sequence Listing.

(51) Int. Cl.
*A61P 37/02* (2006.01)
*C07K 16/28* (2006.01)
*C12N 15/63* (2006.01)

(52) U.S. Cl.
CPC ........ *C12N 15/63* (2013.01); *C07K 2317/565* (2013.01); *C07K 2317/92* (2013.01)

(56) References Cited

U.S. PATENT DOCUMENTS

2018/0068055 A1 3/2018 Ofran et al.
2019/0135929 A1 5/2019 Faustman

FOREIGN PATENT DOCUMENTS

WO WO 2020/061210 A1 3/2020
WO WO 2020/089473 A2 5/2020

OTHER PUBLICATIONS

ENBREL® (etanercept) Highlights of Prescribing Information, Retrieved online from <URL:https://www.accessdata.fda.gov/drugsatfda_docs/label/2020/103795s5574s5577lbl.pdf> [retireved on Sep. 22, 2025], 99 pages, Mar. 2020.*
Chen et al., Therapeutic potential of TNFR2 agonists_ a mechanistic perspective, Front. Immunol. 14:1209188, 11 pages, 2022.*
Liang et al., Distinct Role of TNFR1 and TNFR2 in Protective Immunity Against Orientia tsutsugamushi Infection in Mice, Front. Immunol.13:867924, Apr. 11, 2022.*
Pandey et al., Targeting tumour necrosis factor to ameliorate viral pneumonia, FEBS J. I 289:883-900, 2021.*
Benatuil et al. "An improved yeast transformation method for the generation of very large human antibody libraries" Protein Engineering, Design and Selection. Apr. 1, 2010;23(4):155-9.
Chao et al. "Isolating and engineering human antibodies using yeast surface display" Nature protocols. Aug. 2006:1(2):755-68.
Chothia et al. "Canonical structures for the hypervariable regions of immunoglobulins" Journal of molecular biology. Aug. 20, 1987;196(4):901-17.
International Search Report for PCT Application No. PCT/IL2021/050807 dated Dec. 23, 2021.
Kunik et al. "Structural consensus among antibodies defines the antigen binding site" PLoS computational biology. Feb. 23, 2012;8(2):e1002388.
Lefranc et al. "IMGTO, the international ImMunoGeneTics information system® 25 years on" Nucleic acids research. Jan. 28, 2015;43(D1):D413-22.
Lefranc et al. "IMGT unique numbering for immunoglobulin and T cell receptor variable domains and Ig superfamily V-like domains" Developmental & Comparative Immunology. Jan. 1, 2003;27(1):55-77.
Nimrod et al. "Computational design of epitope-specific functional antibodies" Cell reports. Nov. 20, 2018;25(8):2121-31.
Ofran et al. "Automated identification of complementarity determining regions (CDRs) reveals peculiar characteristics of CDRs and B cell epitopes" The Journal of Immunology. Nov. 1, 2008;181(9):6230-5.
Wu et al. "An analysis of the sequences of the variable regions of Bence Jones proteins and myeloma light chains and their implications for antibody complementarity" The Journal of experimental medicine. Aug. 1, 1970;132(2):211-50.
European Partial Search Report corresponding to European Patent Application No. 21833858.0 dated Jun. 17, 2024.
European Extended Search Report corresponding to European Patent Application No. 21833858.0 dated Sep. 9, 2024.
European Office Communication corresponding to European Patent Application No. 21833858.0 dated Jan. 21, 2026.
English Translation of Notice of Reasons for Rejection corresponding to Japanese Patent Application No. 2022-581712 mailing date Jul. 28, 2025.

* cited by examiner 30.024

30.116

30.202

30.202

30.203

30.115

30.200

30.201

30.114

30.117

30.122

30.118

EC50= 0.43nM

SEQUENCE LISTING

<160> NUMBER OF SEQ ID NOS: 439

<210> SEQ ID NO 1
<211> LENGTH: 756
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: CID251 DNA sequence

<400> SEQUENCE: 1
gaagtgcagt tagtgcaatc tggtgccgaa gttaagaaac caggcagctc cgttaaagtg 60
tcttgtaagg catctggcga cactttcacc tcttatagtt ttaactgggt tcgtcaggct 120
ccaggccagg gtttggagtg gatgggtcgt atcattacca tcctggatga tactgagtac 180
gctcctcatt tacagggtcg tgtaaccatc acagcagaca agtccacatc taccgtatac 240
ttggaactgc gtaacttacg tagcgatgat accgccgttt acttctgcgc aggtgtgtac 300
gaaggtccga actctgaagg ctcgtacgat gactatggtt tcctgaaaca ctggggtcag 360
ggcactctgg tgactgttag ttctggcggt ggtggtagcg gaggcggagg atcaggtgga 420
ggcggcagtg atatcgttat gactcagtcc ccagcaaccc tgtctgtatc tcctggtgag 480
cgtgccaccc tgagctgccg tgcttcagaa tctgtagcta acgatctggc ctggtatcag 540
cagaaaccag gtcaggttcc acgtctgctg atttatggcg cttccacccg tgctaccggt 600
gtaccagctc gtttctctgg gtccggctcc ggcgccgagt tcaccctgac tatctcctct 660
ctgcagtccg aagactttgc cgtgtactac tgccagcagt acgcgaactg gccaccacgt 720
gagacctttg gtcaagggac acgtttagag attaaa 756

<210> SEQ ID NO 2
<211> LENGTH: 237
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID251 Protein sequence, VH+VL

<400> SEQUENCE: 2

Glu Val Gln Leu Val Gln Ser Gly Ala Glu Val Lys Lys Pro Gly Ser
1 5 10 15

Ser Val Lys Val Ser Cys Lys Ala Ser Gly Asp Thr Phe Thr Ser Tyr

```
            20                  25                  30

Ser Phe Asn Trp Val Arg Gln Ala Pro Gly Gln Gly Leu Glu Trp Met
        35                  40                  45

Gly Arg Ile Ile Thr Ile Leu Asp Asp Thr Glu Tyr Ala Pro His Leu
    50                  55                  60

Gln Gly Arg Val Thr Ile Thr Ala Asp Lys Ser Thr Ser Thr Val Tyr
65                  70                  75                  80

Leu Glu Leu Arg Asn Leu Arg Ser Asp Asp Thr Ala Val Tyr Phe Cys
                85                  90                  95

Ala Gly Val Tyr Glu Gly Pro Asn Ser Glu Gly Ser Tyr Asp Asp Tyr
            100                 105                 110

Gly Phe Leu Lys His Trp Gly Gln Gly Thr Leu Val Thr Val Ser Ser
        115                 120                 125

Asp Ile Val Met Thr Gln Ser Pro Ala Thr Leu Ser Val Ser Pro Gly
    130                 135                 140

Glu Arg Ala Thr Leu Ser Cys Arg Ala Ser Glu Ser Val Ala Asn Asp
145                 150                 155                 160

Leu Ala Trp Tyr Gln Gln Lys Pro Gly Gln Val Pro Arg Leu Leu Ile
                165                 170                 175

Tyr Gly Ala Ser Thr Arg Ala Thr Gly Val Pro Ala Arg Phe Ser Gly
            180                 185                 190

Ser Gly Ser Gly Ala Glu Phe Thr Leu Thr Ile Ser Ser Leu Gln Ser
        195                 200                 205

Glu Asp Phe Ala Val Tyr Tyr Cys Gln Gln Tyr Ala Asn Trp Pro Pro
    210                 215                 220

Arg Glu Thr Phe Gly Gln Gly Thr Arg Leu Glu Ile Lys
225                 230                 235


<210> SEQ ID NO 3
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID251 protein sequence - VH

<400> SEQUENCE: 3

Glu Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Thr Ser Tyr
            20                  25                  30

Ser Phe Asn Trp Val Arg Gln Ala Pro Gly Gln Gly Leu Glu Trp Met
        35                  40                  45

Gly Arg Ile Ile Thr Ile Leu Asp Asp Thr Glu Tyr Ala Pro His Leu
    50                  55                  60

Gln Gly Arg Val Thr Ile Thr Ala Asp Lys Ser Thr Ser Thr Val Tyr
65                  70                  75                  80

Leu Glu Leu Arg Asn Leu Arg Ser Asp Asp Thr Ala Val Tyr Phe Cys
                85                  90                  95

Ala Gly Val Tyr Glu Gly Pro Asn Ser Glu Gly Ser Tyr Asp Asp Tyr
            100                 105                 110

Gly Phe Leu Lys His Trp Gly Gln Gly Thr Leu Val Thr Val Ser Ser
        115                 120                 125
```

<210> SEQ ID NO 4
<211> LENGTH: 109
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: CID251 protein sequence - VL

<400> SEQUENCE: 4

```
Asp Ile Val Met Thr Gln Ser Pro Ala Thr Leu Ser Val Ser Pro Gly
1               5                   10                  15

Glu Arg Ala Thr Leu Ser Cys Arg Ala Ser Glu Ser Val Ala Asn Asp
            20                  25                  30

Leu Ala Trp Tyr Gln Gln Lys Pro Gly Gln Val Pro Arg Leu Leu Ile
        35                  40                  45

Tyr Gly Ala Ser Thr Arg Ala Thr Gly Val Pro Ala Arg Phe Ser Gly
    50                  55                  60

Ser Gly Ser Gly Ala Glu Phe Thr Leu Thr Ile Ser Ser Leu Gln Ser
65                  70                  75                  80

Glu Asp Phe Ala Val Tyr Tyr Cys Gln Gln Tyr Ala Asn Trp Pro Pro
                85                  90                  95

Arg Glu Thr Phe Gly Gln Gly Thr Arg Leu Glu Ile Lys
            100                 105
```

<210> SEQ ID NO 5
<211> LENGTH: 756
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: CID_252 DNA sequence

<400> SEQUENCE: 5

```
gaagtgcagt tagtgcaatc tggtgccgaa gttaagaaac caggcagctc cgttaaagtg     60

tcttgtaagg catctggcga cactttcacc tcttatagtt ttaactgggt tcgtcaggct    120

ccaggccagg gtttggagtg gatgggtcgt atcattacca tcctggatga tactgagtac    180

gctcctcatt tacagggtcg tgtaaccatc acagcagaca agtccacatc taccgtatac    240

ttggaactgc gtaacttacg tagcgatgat accgccgttt acttctgcgc aggtgtgtac    300

gaaggtccga actctgaagg ctcgtacgat gactatggtt tcctgaaaca ctggggtcag    360

ggcactctgg tgactgttag ttctggcggt ggtggtagcg gaggcggagg atcaggtgga    420

ggcggcagtg atatcgttat gactcagtcc ccagcaaccc tgtctgtatc tcctggtgag    480

cgtgccaccc tgagctgccg tgcttcagaa tctgtagcta acgatctggc ctggtatcag    540

cagaaaccag gtcaggttcc acgtctgctg atttatggcg cttccacccg tgctaccggt    600

gtaccagctc gtttctctgg gtccggctcc ggcgccgagt tcaccctgac tatctcctct    660

ctgcagtccg aagactttgc cgtgtactac tgccagcagt acgcgaactg gccaccacgt    720

gagacctttg gtcaagggac acgtttagag attaaa                              756
```

<210> SEQ ID NO 6
<211> LENGTH: 237
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_252 Protein sequence, VH+VL

<400> SEQUENCE: 6

Glu Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Thr Ser Tyr
            20                  25                  30

Ser Phe Asn Trp Val Arg Gln Ala Pro Gly Gln Gly Leu Glu Trp Met
        35                  40                  45

Gly Arg Ile Ile Thr Ile Leu Asp Asp Thr Glu Tyr Ala Pro His Leu
    50                  55                  60

Gln Gly Arg Val Thr Ile Thr Ala Asp Lys Ser Thr Ser Thr Val Tyr
65                  70                  75                  80

Leu Glu Leu Arg Asn Leu Arg Ser Asp Asp Thr Ala Val Tyr Phe Cys
                85                  90                  95

Ala Gly Val Tyr Glu Gly Pro Asn Ser Glu Gly Ser Tyr Asp Asp Tyr
            100                 105                 110

Gly Phe Leu Lys His Trp Gly Gln Gly Thr Leu Val Thr Val Ser Ser
        115                 120                 125

Asp Ile Val Met Thr Gln Ser Pro Ala Thr Leu Ser Val Ser Pro Gly
    130                 135                 140

Glu Arg Ala Thr Leu Ser Cys Arg Ala Ser Glu Ser Val Ala Asn Asp
145                 150                 155                 160

Leu Ala Trp Tyr Gln Gln Lys Pro Gly Gln Val Pro Arg Leu Leu Ile
                165                 170                 175

Tyr Gly Ala Ser Thr Arg Ala Thr Gly Val Pro Ala Arg Phe Ser Gly
            180                 185                 190

Ser Gly Ser Gly Ala Glu Phe Thr Leu Thr Ile Ser Ser Leu Gln Ser
        195                 200                 205

Glu Asp Phe Ala Val Tyr Tyr Cys Gln Gln Tyr Ala Asn Trp Pro Pro
    210                 215                 220

Arg Glu Thr Phe Gly Gln Gly Thr Arg Leu Glu Ile Lys
225                 230                 235

<210> SEQ ID NO 7
<211> LENGTH: 128
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: CID_252 protein sequence - VH

<400> SEQUENCE: 7

Glu Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Thr Ser Tyr
            20                  25                  30

Ser Phe Asn Trp Val Arg Gln Ala Pro Gly Gln Gly Leu Glu Trp Met
        35                  40                  45

Gly Arg Ile Ile Thr Ile Leu Asp Asp Thr Glu Tyr Ala Pro His Leu
    50                  55                  60

Gln Gly Arg Val Thr Ile Thr Ala Asp Lys Ser Thr Ser Thr Val Tyr
65                  70                  75                  80

```
Leu Glu Leu Arg Asn Leu Arg Ser Asp Asp Thr Ala Val Tyr Phe Cys
                85                  90                  95

Ala Gly Val Tyr Glu Gly Pro Asn Ser Glu Gly Ser Tyr Asp Asp Tyr
            100                 105                 110

Gly Phe Leu Lys His Trp Gly Gln Gly Thr Leu Val Thr Val Ser Ser
        115                 120                 125
```

<210> SEQ ID NO 8
<211> LENGTH: 109
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_252 protein sequence - VL

<400> SEQUENCE: 8

```
Asp Ile Val Met Thr Gln Ser Pro Ala Thr Leu Ser Val Ser Pro Gly
1               5                   10                  15

Glu Arg Ala Thr Leu Ser Cys Arg Ala Ser Glu Ser Val Ala Asn Asp
            20                  25                  30

Leu Ala Trp Tyr Gln Gln Lys Pro Gly Gln Val Pro Arg Leu Leu Ile
        35                  40                  45

Tyr Gly Ala Ser Thr Arg Ala Thr Gly Val Pro Ala Arg Phe Ser Gly
    50                  55                  60

Ser Gly Ser Gly Ala Glu Phe Thr Leu Thr Ile Ser Ser Leu Gln Ser
65                  70                  75                  80

Glu Asp Phe Ala Val Tyr Tyr Cys Gln Gln Tyr Ala Asn Trp Pro Pro
                85                  90                  95

Arg Glu Thr Phe Gly Gln Gly Thr Arg Leu Glu Ile Lys
            100                 105
```

<210> SEQ ID NO 9
<211> LENGTH: 756
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: CID_253 DNA sequence

<400> SEQUENCE: 9

```
gaagtgcagt tagtgcaatc tggtgccgaa gttaagaaac caggcagctc cgttaaagtg     60

tcttgtaagg catctggcga cactttcacc tcttatagtt ggaactgggt tcgtcaggct    120

ccaggccagg gtttggagtg gatgggtcgt atcattaccg acctggatga tactgagtac    180

gctcctcatt tacagggtcg tgtaaccatc acagcagaca agtccacatc taccgtatac    240

ttggaactgc gtaacttacg tagcgatgat accgccgttt acttctgcgc aggtgtgtac    300

gaaggtccga actctgaagg ctcgtacgat gactatggtt tcctgaaaca ctggggtcag    360

ggcactctgg tgactgttag ttctggcggt ggtggtagcg gaggcggagg atcaggtgga    420

ggcggcagtg atatcgttat gactcagtcc ccagcaaccc tgtctgtatc tcctggtgag    480

cgtgccaccc tgagctgccg tgcttcagaa tctggggcta acgatctggc ctggtatcag    540

cagaaaccag gtcaggttcc acgtctgctg tgctatggcg cttccacccg tgctaccggt    600

gtaccagctc gtttctctgg gtccggctcc ggcgccgagt tcaccctgac tatctcctct    660

ctgcagtccg aagactttgc cgtgtactac tgccagcagt acgcgaactg gccaccacgt    720
```

```
ggcacctttg gtcaagggac acgtttagag attaaa                             756


<210> SEQ ID NO 10
<211> LENGTH: 237
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_253 Protein sequence, VH+VL

<400> SEQUENCE: 10

Glu Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Thr Ser Tyr
            20                  25                  30

Ser Trp Asn Trp Val Arg Gln Ala Pro Gly Gln Gly Leu Glu Trp Met
        35                  40                  45

Gly Arg Ile Ile Thr Asp Leu Asp Asp Thr Glu Tyr Ala Pro His Leu
    50                  55                  60

Gln Gly Arg Val Thr Ile Thr Ala Asp Lys Ser Thr Ser Thr Val Tyr
65                  70                  75                  80

Leu Glu Leu Arg Asn Leu Arg Ser Asp Asp Thr Ala Val Tyr Phe Cys
                85                  90                  95

Ala Gly Val Tyr Glu Gly Pro Asn Ser Glu Gly Ser Tyr Asp Asp Tyr
            100                 105                 110

Gly Phe Leu Lys His Trp Gly Gln Gly Thr Leu Val Thr Val Ser Ser
        115                 120                 125

Asp Ile Val Met Thr Gln Ser Pro Ala Thr Leu Ser Val Ser Pro Gly
    130                 135                 140

Glu Arg Ala Thr Leu Ser Cys Arg Ala Ser Glu Ser Gly Ala Asn Asp
145                 150                 155                 160

Leu Ala Trp Tyr Gln Gln Lys Pro Gly Gln Val Pro Arg Leu Leu Cys
                165                 170                 175

Tyr Gly Ala Ser Thr Arg Ala Thr Gly Val Pro Ala Arg Phe Ser Gly
            180                 185                 190

Ser Gly Ser Gly Ala Glu Phe Thr Leu Thr Ile Ser Ser Leu Gln Ser
        195                 200                 205

Glu Asp Phe Ala Val Tyr Tyr Cys Gln Gln Tyr Ala Asn Trp Pro Pro
    210                 215                 220

Arg Gly Thr Phe Gly Gln Gly Thr Arg Leu Glu Ile Lys
225                 230                 235


<210> SEQ ID NO 11
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_253 protein sequence - VH

<400> SEQUENCE: 11

Glu Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Thr Ser Tyr
            20                  25                  30
```

Ser Trp Asn Trp Val Arg Gln Ala Pro Gly Gln Gly Leu Glu Trp Met
35 40 45

Gly Arg Ile Ile Thr Asp Leu Asp Asp Thr Glu Tyr Ala Pro His Leu
50 55 60

Gln Gly Arg Val Thr Ile Thr Ala Asp Lys Ser Thr Ser Thr Val Tyr
65 70 75 80

Leu Glu Leu Arg Asn Leu Arg Ser Asp Asp Thr Ala Val Tyr Phe Cys
85 90 95

Ala Gly Val Tyr Glu Gly Pro Asn Ser Glu Gly Ser Tyr Asp Asp Tyr
100 105 110

Gly Phe Leu Lys His Trp Gly Gln Gly Thr Leu Val Thr Val Ser Ser
115 120 125

<210> SEQ ID NO 12
<211> LENGTH: 109
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_253 protein sequence - VL

<400> SEQUENCE: 12

Asp Ile Val Met Thr Gln Ser Pro Ala Thr Leu Ser Val Ser Pro Gly
1 5 10 15

Glu Arg Ala Thr Leu Ser Cys Arg Ala Ser Glu Ser Gly Ala Asn Asp
20 25 30

Leu Ala Trp Tyr Gln Gln Lys Pro Gly Gln Val Pro Arg Leu Leu Cys
35 40 45

Tyr Gly Ala Ser Thr Arg Ala Thr Gly Val Pro Ala Arg Phe Ser Gly
50 55 60

Ser Gly Ser Gly Ala Glu Phe Thr Leu Thr Ile Ser Ser Leu Gln Ser
65 70 75 80

Glu Asp Phe Ala Val Tyr Tyr Cys Gln Gln Tyr Ala Asn Trp Pro Pro
85 90 95

Arg Gly Thr Phe Gly Gln Gly Thr Arg Leu Glu Ile Lys
100 105

<210> SEQ ID NO 13
<211> LENGTH: 756
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: CID_254 DNA sequence

<400> SEQUENCE: 13
gaagtgcagt tagtgcaatc tggtgccgaa gttaagaaac caggcagctc cgttaaagtg 60
tcttgtaagg catctggcga cactttcacc tcttatagtt ttaactgggt tcgtcaggct 120
ccaggccagg gtttggagtg gatgggtcgt atcattacca tcctggatga tactgagtac 180
gctcctcatt tacagggtcg tgtaaccatc acagcagaca agtccacatc taccgtatac 240
ttggaactgc gtaacttacg tagcgatgat accgccgttt acttctgcgc aggtgtgtac 300
gaaggtccga actctgaagg ctcgtacgat gactatggtt tcctgaaaca ctggggtcag 360
ggcactctgg tgactgttag ttctggcggt ggtggtagcg gaggcggagg atcaggtgga 420

```
ggcggcagtg atatcgttat gactcagtcc ccagcaaccc tgtctgtatc tcctggtgag    480

cgtgccaccc tgagctgccg tgcttcagaa tctgtagcta acgatctggc ctggtatcag    540

cagaaaccag gtcaggttcc acgtctgctg atttatggcg cttccacccg tgctaggggt    600

gtaccagctc gtttctctgg gtccggctcc ggcgccgagt tcaccctgac tatctcctct    660

ctgcagtccg aagactttgc cgtgtactac tgccagcagt acaccaactg gccaccacgt    720

gagacctttg gtcaagggac acgtttagag attaaa                              756
```

```
<210> SEQ ID NO 14
<211> LENGTH: 237
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_254 Protein sequence, VH+VL

<400> SEQUENCE: 14

Glu Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Thr Ser Tyr
            20                  25                  30

Ser Phe Asn Trp Val Arg Gln Ala Pro Gly Gln Gly Leu Glu Trp Met
        35                  40                  45

Gly Arg Ile Ile Thr Ile Leu Asp Asp Thr Glu Tyr Ala Pro His Leu
    50                  55                  60

Gln Gly Arg Val Thr Ile Thr Ala Asp Lys Ser Thr Ser Thr Val Tyr
65                  70                  75                  80

Leu Glu Leu Arg Asn Leu Arg Ser Asp Asp Thr Ala Val Tyr Phe Cys
                85                  90                  95

Ala Gly Val Tyr Glu Gly Pro Asn Ser Glu Gly Ser Tyr Asp Asp Tyr
            100                 105                 110

Gly Phe Leu Lys His Trp Gly Gln Gly Thr Leu Val Thr Val Ser Ser
        115                 120                 125

Asp Ile Val Met Thr Gln Ser Pro Ala Thr Leu Ser Val Ser Pro Gly
    130                 135                 140

Glu Arg Ala Thr Leu Ser Cys Arg Ala Ser Glu Ser Val Ala Asn Asp
145                 150                 155                 160

Leu Ala Trp Tyr Gln Gln Lys Pro Gly Gln Val Pro Arg Leu Leu Ile
                165                 170                 175

Tyr Gly Ala Ser Thr Arg Ala Arg Gly Val Pro Ala Arg Phe Ser Gly
            180                 185                 190

Ser Gly Ser Gly Ala Glu Phe Thr Leu Thr Ile Ser Ser Leu Gln Ser
        195                 200                 205

Glu Asp Phe Ala Val Tyr Tyr Cys Gln Gln Tyr Thr Asn Trp Pro Pro
    210                 215                 220

Arg Glu Thr Phe Gly Gln Gly Thr Arg Leu Glu Ile Lys
225                 230                 235


<210> SEQ ID NO 15
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide
```

<220> FEATURE:
<223> OTHER INFORMATION: CID_254 protein sequence - VH

<400> SEQUENCE: 15

```
Glu Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Thr Ser Tyr
            20                  25                  30

Ser Phe Asn Trp Val Arg Gln Ala Pro Gly Gln Gly Leu Glu Trp Met
        35                  40                  45

Gly Arg Ile Ile Thr Ile Leu Asp Asp Thr Glu Tyr Ala Pro His Leu
    50                  55                  60

Gln Gly Arg Val Thr Ile Thr Ala Asp Lys Ser Thr Ser Thr Val Tyr
65                  70                  75                  80

Leu Glu Leu Arg Asn Leu Arg Ser Asp Asp Thr Ala Val Tyr Phe Cys
                85                  90                  95

Ala Gly Val Tyr Glu Gly Pro Asn Ser Glu Gly Ser Tyr Asp Asp Tyr
            100                 105                 110

Gly Phe Leu Lys His Trp Gly Gln Gly Thr Leu Val Thr Val Ser Ser
        115                 120                 125
```

<210> SEQ ID NO 16
<211> LENGTH: 109
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_254 protein sequence - VL

<400> SEQUENCE: 16

```
Asp Ile Val Met Thr Gln Ser Pro Ala Thr Leu Ser Val Ser Pro Gly
1               5                   10                  15

Glu Arg Ala Thr Leu Ser Cys Arg Ala Ser Glu Ser Val Ala Asn Asp
            20                  25                  30

Leu Ala Trp Tyr Gln Gln Lys Pro Gly Gln Val Pro Arg Leu Leu Ile
        35                  40                  45

Tyr Gly Ala Ser Thr Arg Ala Arg Gly Val Pro Ala Arg Phe Ser Gly
    50                  55                  60

Ser Gly Ser Gly Ala Glu Phe Thr Leu Thr Ile Ser Ser Leu Gln Ser
65                  70                  75                  80

Glu Asp Phe Ala Val Tyr Tyr Cys Gln Gln Tyr Thr Asn Trp Pro Pro
                85                  90                  95

Arg Glu Thr Phe Gly Gln Gly Thr Arg Leu Glu Ile Lys
            100                 105
```

<210> SEQ ID NO 17
<211> LENGTH: 756
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: CID_255 DNA sequence

<400> SEQUENCE: 17

```
gaagtgcagt tagtgcaatc tggtgccgaa gttaagaaac caggcagctc cgttaaagtg     60

tcttgtaagg catctggcga cactttcacc tcttatagtt ttaactgggt tcgtcaggct    120
```

ccaggccagg gtttggagtg gatgggtcgt atcattacca tcctggatga tactgagtac 180
gctcctcatt tacagggtcg tgtaaccatc acagcagaca agtccacatc taccgtatac 240
ttggaactgc gtaacttacg tagcgatgat accgccgttt acttctgcgc aggtgtgtac 300
gaaggtccga actctgaagg ctcgtacgat gactatggtt tcctgaaaca ctggggtcag 360
ggcactctgg tgactgttag ttctggcggt ggtggtagcg gaggcggagg atcaggtgga 420
ggcggcagtg atatcgttat gactcagtcc ccagcaaccc tgtctgtatc tcctggtgag 480
cgtgccaccc tgagctgccg tgcttcagaa tctgtagcta acgatctggc ctggtatcag 540
cagaaaccag gtcaggttcc acgtctgctg cgctatggcg cttccacccg tgctaccggt 600
gtaccagctc gtttctctgg gtccggctcc ggcgccgagt tcaccctgac tatctcctct 660
ctgcagtccg aagactttgc cgtgtactac tgccagcagt acgcgatctg gccaccacgt 720
gagacctttg gtcaagggac acgtttagag attaaa 756

<210> SEQ ID NO 18
<211> LENGTH: 237
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_255 Protein sequence, VH+VL

<400> SEQUENCE: 18

Glu Val Gln Leu Val Gln Ser Gly Ala Glu Val Lys Lys Pro Gly Ser
1 5 10 15

Ser Val Lys Val Ser Cys Lys Ala Ser Gly Asp Thr Phe Thr Ser Tyr
20 25 30

Ser Phe Asn Trp Val Arg Gln Ala Pro Gly Gln Gly Leu Glu Trp Met
35 40 45

Gly Arg Ile Ile Thr Ile Leu Asp Asp Thr Glu Tyr Ala Pro His Leu
50 55 60

Gln Gly Arg Val Thr Ile Thr Ala Asp Lys Ser Thr Ser Thr Val Tyr
65 70 75 80

Leu Glu Leu Arg Asn Leu Arg Ser Asp Asp Thr Ala Val Tyr Phe Cys
85 90 95

Ala Gly Val Tyr Glu Gly Pro Asn Ser Glu Gly Ser Tyr Asp Asp Tyr
100 105 110

Gly Phe Leu Lys His Trp Gly Gln Gly Thr Leu Val Thr Val Ser Ser
115 120 125

Asp Ile Val Met Thr Gln Ser Pro Ala Thr Leu Ser Val Ser Pro Gly
130 135 140

Glu Arg Ala Thr Leu Ser Cys Arg Ala Ser Glu Ser Val Ala Asn Asp
145 150 155 160

Leu Ala Trp Tyr Gln Gln Lys Pro Gly Gln Val Pro Arg Leu Leu Arg
165 170 175

Tyr Gly Ala Ser Thr Arg Ala Thr Gly Val Pro Ala Arg Phe Ser Gly
180 185 190

Ser Gly Ser Gly Ala Glu Phe Thr Leu Thr Ile Ser Ser Leu Gln Ser
195 200 205

Glu Asp Phe Ala Val Tyr Tyr Cys Gln Gln Tyr Ala Ile Trp Pro Pro
210 215 220

Arg Glu Thr Phe Gly Gln Gly Thr Arg Leu Glu Ile Lys

```
225                 230                 235


<210> SEQ ID NO 19
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_255 protein sequence - VH

<400> SEQUENCE: 19

Glu Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Thr Ser Tyr
            20                  25                  30

Ser Phe Asn Trp Val Arg Gln Ala Pro Gly Gln Gly Leu Glu Trp Met
        35                  40                  45

Gly Arg Ile Ile Thr Ile Leu Asp Asp Thr Glu Tyr Ala Pro His Leu
    50                  55                  60

Gln Gly Arg Val Thr Ile Thr Ala Asp Lys Ser Thr Ser Thr Val Tyr
65                  70                  75                  80

Leu Glu Leu Arg Asn Leu Arg Ser Asp Asp Thr Ala Val Tyr Phe Cys
                85                  90                  95

Ala Gly Val Tyr Glu Gly Pro Asn Ser Glu Gly Ser Tyr Asp Asp Tyr
            100                 105                 110

Gly Phe Leu Lys His Trp Gly Gln Gly Thr Leu Val Thr Val Ser Ser
        115                 120                 125


<210> SEQ ID NO 20
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_255 protein sequence - VL

<400> SEQUENCE: 20

Asp Ile Val Met Thr Gln Ser Pro Ala Thr Leu Ser Val Ser Pro Gly
1               5                   10                  15

Glu Arg Ala Thr Leu Ser Cys Arg Ala Ser Glu Ser Val Ala Asn Asp
            20                  25                  30

Leu Ala Trp Tyr Gln Gln Lys Pro Gly Gln Val Pro Arg Leu Leu Arg
        35                  40                  45

Tyr Gly Ala Ser Thr Arg Ala Thr Gly Val Pro Ala Arg Phe Ser Gly
    50                  55                  60

Ser Gly Ser Gly Ala Glu Phe Thr Leu Thr Ile Ser Ser Leu Gln Ser
65                  70                  75                  80

Glu Asp Phe Ala Val Tyr Tyr Cys Gln Gln Tyr Ala Ile Trp Pro Pro
                85                  90                  95

Arg Glu Thr Phe Gly Gln Gly Thr Arg Leu Glu Ile Lys
            100                 105


<210> SEQ ID NO 21
<211> LENGTH: 756
<212> TYPE: DNA
<213> ORGANISM: Artificial Sequence
<220> FEATURE:
```

<223> OTHER INFORMATION: Description of Artificial Sequence: Synthetic
      polynucleotide
<220> FEATURE:
<223> OTHER INFORMATION: CID_256 DNA sequence

<400> SEQUENCE: 21

```
gaagtgcagt tagtgcaatc tggtgccgaa gttaagaaac caggcagctc cgttaaagtg      60

tcttgtaagg catctggcga cactttcacc tcttatagtt acaactgggt tcgtcaggct     120

ccaggccagg gtttggagtg gatgggtcgt atcattacca tcctggatga tactgagtac     180

gctcctcatt tacagggtcg tgtaaccatc acagcagaca agtccacatc taccgtatac     240

ttggaactgc gtaacttacg tagcgatgat accgccgttt acttctgcgc aggtgtgtac     300

gaaggtccga actctgaagg ctcgtacgat gactatggtt tcctgaaaca ctggggtcag     360

ggcactctgg tgactgttag ttctggcggt ggtggtagcg gaggcggagg atcaggtgga     420

ggcggcagtg atatcgttat gactcagtcc ccagcaaccc tgtctgtatc tcctggtgag     480

cgtgccaccc tgagctgccg tgcttcaagg tctgtagcta acgatctggc ctggtatcag     540

cagaaaccag gtcaggttcc acgtctgctg atttatggcg cttccacccg tgctaccggt     600

gtaccagctc gtttctctgg gtccggctcc ggcgccgagt tcaccctgac tatctcctct     660

ctgcagtccg aagactttgc cgtgtactac tgccagcagt acgcgatctg gccaccacgt     720

gagacctttg gtcaagggac acgtttagag attaaa                                756
```

<210> SEQ ID NO 22
<211> LENGTH: 237
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_256 Protein sequence, VH+VL

<400> SEQUENCE: 22

```
Glu Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Thr Ser Tyr
            20                  25                  30

Ser Tyr Asn Trp Val Arg Gln Ala Pro Gly Gln Gly Leu Glu Trp Met
        35                  40                  45

Gly Arg Ile Ile Thr Ile Leu Asp Asp Thr Glu Tyr Ala Pro His Leu
    50                  55                  60

Gln Gly Arg Val Thr Ile Thr Ala Asp Lys Ser Thr Ser Thr Val Tyr
65                  70                  75                  80

Leu Glu Leu Arg Asn Leu Arg Ser Asp Asp Thr Ala Val Tyr Phe Cys
                85                  90                  95

Ala Gly Val Tyr Glu Gly Pro Asn Ser Glu Gly Ser Tyr Asp Asp Tyr
            100                 105                 110

Gly Phe Leu Lys His Trp Gly Gln Gly Thr Leu Val Thr Val Ser Ser
        115                 120                 125

Asp Ile Val Met Thr Gln Ser Pro Ala Thr Leu Ser Val Ser Pro Gly
    130                 135                 140

Glu Arg Ala Thr Leu Ser Cys Arg Ala Ser Arg Ser Val Ala Asn Asp
145                 150                 155                 160

Leu Ala Trp Tyr Gln Gln Lys Pro Gly Gln Val Pro Arg Leu Leu Ile
                165                 170                 175
```

```
Tyr Gly Ala Ser Thr Arg Ala Thr Gly Val Pro Ala Arg Phe Ser Gly
            180                 185                 190

Ser Gly Ser Gly Ala Glu Phe Thr Leu Thr Ile Ser Ser Leu Gln Ser
        195                 200                 205

Glu Asp Phe Ala Val Tyr Tyr Cys Gln Gln Tyr Ala Ile Trp Pro Pro
    210                 215                 220

Arg Glu Thr Phe Gly Gln Gly Thr Arg Leu Glu Ile Lys
225                 230                 235


<210> SEQ ID NO 23
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_256 protein sequence - VH

<400> SEQUENCE: 23

Glu Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Thr Ser Tyr
            20                  25                  30

Ser Tyr Asn Trp Val Arg Gln Ala Pro Gly Gln Gly Leu Glu Trp Met
        35                  40                  45

Gly Arg Ile Ile Thr Ile Leu Asp Asp Thr Glu Tyr Ala Pro His Leu
    50                  55                  60

Gln Gly Arg Val Thr Ile Thr Ala Asp Lys Ser Thr Ser Thr Val Tyr
65                  70                  75                  80

Leu Glu Leu Arg Asn Leu Arg Ser Asp Asp Thr Ala Val Tyr Phe Cys
                85                  90                  95

Ala Gly Val Tyr Glu Gly Pro Asn Ser Glu Gly Ser Tyr Asp Asp Tyr
            100                 105                 110

Gly Phe Leu Lys His Trp Gly Gln Gly Thr Leu Val Thr Val Ser Ser
        115                 120                 125


<210> SEQ ID NO 24
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_256 protein sequence - VL

<400> SEQUENCE: 24

Asp Ile Val Met Thr Gln Ser Pro Ala Thr Leu Ser Val Ser Pro Gly
1               5                   10                  15

Glu Arg Ala Thr Leu Ser Cys Arg Ala Ser Arg Ser Val Ala Asn Asp
            20                  25                  30

Leu Ala Trp Tyr Gln Gln Lys Pro Gly Gln Val Pro Arg Leu Leu Ile
        35                  40                  45

Tyr Gly Ala Ser Thr Arg Ala Thr Gly Val Pro Ala Arg Phe Ser Gly
    50                  55                  60

Ser Gly Ser Gly Ala Glu Phe Thr Leu Thr Ile Ser Ser Leu Gln Ser
65                  70                  75                  80

Glu Asp Phe Ala Val Tyr Tyr Cys Gln Gln Tyr Ala Ile Trp Pro Pro
                85                  90                  95
```

```
Arg Glu Thr Phe Gly Gln Gly Thr Arg Leu Glu Ile Lys
            100                 105


<210> SEQ ID NO 25
<211> LENGTH: 756
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CID_257 DNA sequence

<400> SEQUENCE: 25

gaagtgcagt tagtgcaatc tggtgccgaa gttaagaaac caggcagctc cgttaaagtg     60

tcttgtaagg catctggcga cactttcacc tcttatagtt ttaactgggt tcgtcaggct    120

ccaggccagg gtttggagtg gatgggtcgt atcattacca tcctggatga tactgagtac    180

gctcctcatt tacagggtcg tgtaaccatc acagcagaca agtccacatc taccgtatac    240

ttggaactgc gtaacttacg tagcgatgat accgccgttt acttctgcgc aggtgtgtac    300

gaaggtccga actctgaagg ctcgtacgat gactatggtt tcctgaaaca ctggggtcag    360

ggcactctgg tgactgttag ttctggcggt ggtggtagcg gaggcggagg atcaggtgga    420

ggcggcagtg atatcgttat gactcagtcc ccagcaaccc tgtctgtatc tcctggtgag    480

cgtgccaccc tgagctgccg tgcttcagaa tctgtagcta acaacctggc ctggtatcag    540

cagaaaccag gtcaggttcc acgtctgctg atttatggcg cttccacccg tgctaccggt    600

gtaccagctc gtttctctgg gtccggctcc ggcgccgagt tcaccctgac tatctcctct    660

ctgcagtccg aagactttgc cgtgtactac tgccagcagt acgcgcgctg gccaccaacc    720

gagacctttg gtcaagggac acgtttagag attaaa                              756


<210> SEQ ID NO 26
<211> LENGTH: 237
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_257 Protein sequence, VH+VL

<400> SEQUENCE: 26

Glu Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Thr Ser Tyr
            20                  25                  30

Ser Phe Asn Trp Val Arg Gln Ala Pro Gly Gln Gly Leu Glu Trp Met
        35                  40                  45

Gly Arg Ile Ile Thr Ile Leu Asp Asp Thr Glu Tyr Ala Pro His Leu
    50                  55                  60

Gln Gly Arg Val Thr Ile Thr Ala Asp Lys Ser Thr Ser Thr Val Tyr
65                  70                  75                  80

Leu Glu Leu Arg Asn Leu Arg Ser Asp Asp Thr Ala Val Tyr Phe Cys
                85                  90                  95

Ala Gly Val Tyr Glu Gly Pro Asn Ser Glu Gly Ser Tyr Asp Asp Tyr
            100                 105                 110

Gly Phe Leu Lys His Trp Gly Gln Gly Thr Leu Val Thr Val Ser Ser
        115                 120                 125
```

```
Asp Ile Val Met Thr Gln Ser Pro Ala Thr Leu Ser Val Ser Pro Gly
    130                 135                 140

Glu Arg Ala Thr Leu Ser Cys Arg Ala Ser Glu Ser Val Ala Asn Asn
145                 150                 155                 160

Leu Ala Trp Tyr Gln Gln Lys Pro Gly Gln Val Pro Arg Leu Leu Ile
                165                 170                 175

Tyr Gly Ala Ser Thr Arg Ala Thr Gly Val Pro Ala Arg Phe Ser Gly
            180                 185                 190

Ser Gly Ser Gly Ala Glu Phe Thr Leu Thr Ile Ser Ser Leu Gln Ser
        195                 200                 205

Glu Asp Phe Ala Val Tyr Tyr Cys Gln Gln Tyr Ala Arg Trp Pro Pro
    210                 215                 220

Thr Glu Thr Phe Gly Gln Gly Thr Arg Leu Glu Ile Lys
225                 230                 235


<210> SEQ ID NO 27
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_257 protein sequence - VH

<400> SEQUENCE: 27

Glu Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Thr Ser Tyr
            20                  25                  30

Ser Phe Asn Trp Val Arg Gln Ala Pro Gly Gln Gly Leu Glu Trp Met
        35                  40                  45

Gly Arg Ile Ile Thr Ile Leu Asp Asp Thr Glu Tyr Ala Pro His Leu
    50                  55                  60

Gln Gly Arg Val Thr Ile Thr Ala Asp Lys Ser Thr Ser Thr Val Tyr
65                  70                  75                  80

Leu Glu Leu Arg Asn Leu Arg Ser Asp Asp Thr Ala Val Tyr Phe Cys
                85                  90                  95

Ala Gly Val Tyr Glu Gly Pro Asn Ser Glu Gly Ser Tyr Asp Asp Tyr
            100                 105                 110

Gly Phe Leu Lys His Trp Gly Gln Gly Thr Leu Val Thr Val Ser Ser
        115                 120                 125


<210> SEQ ID NO 28
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_257 protein sequence - VL

<400> SEQUENCE: 28

Asp Ile Val Met Thr Gln Ser Pro Ala Thr Leu Ser Val Ser Pro Gly
1               5                   10                  15

Glu Arg Ala Thr Leu Ser Cys Arg Ala Ser Glu Ser Val Ala Asn Asn
            20                  25                  30

Leu Ala Trp Tyr Gln Gln Lys Pro Gly Gln Val Pro Arg Leu Leu Ile
```

```
        35                  40                  45

Tyr Gly Ala Ser Thr Arg Ala Thr Gly Val Pro Ala Arg Phe Ser Gly
    50                  55                  60

Ser Gly Ser Gly Ala Glu Phe Thr Leu Thr Ile Ser Ser Leu Gln Ser
65                  70                  75                  80

Glu Asp Phe Ala Val Tyr Tyr Cys Gln Gln Tyr Ala Arg Trp Pro Pro
                85                  90                  95

Thr Glu Thr Phe Gly Gln Gly Thr Arg Leu Glu Ile Lys
            100                 105


<210> SEQ ID NO 29
<211> LENGTH: 756
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CID_258 DNA sequence

<400> SEQUENCE: 29

gaagtgcagt tagtgcaatc tggtgccgaa gttaagaaac caggcagctc cgttaaagtg      60

tcttgtaagg catctggcga cactttcacc tcttatagtt ttaactgggt tcgtcaggct     120

ccaggccagg gtttggagtg gatgggtcgt atcattacca tcccggatga tactgagtac     180

gctcctcatt tacagggtcg tgtaaccatc acagcagaca agtccacatc taccgtatac     240

ttggaactgc gtaacttacg tagcgatgat accgccgttt acttctgcgc aggtgtgtac     300

gaaggtccga actctgaagg ctcgtacgat gactatggtt tcctgaaaca ctggggtcag     360

ggcactctgg tgactgttag ttctggcggt ggtggtagcg gaggcggagg atcaggtgga     420

ggcggcagtg atatcgttat gactcagtcc ccagcaaccc tgtctgtatc tcctggtgag     480

cgtgccaccc tgagctgccg tgcttcagaa tctgtagcta ccgatctggc ctggtatcag     540

cagaaaccag gtcaggttcc acgtctgctg atttatggcg cttccacccg tgctaccggt     600

gtaccagctc gtttctctgg gtccggctcc ggcgccgagt tcaccctgac tatctcctct     660

ctgcagtccg aagactttgc cgtgtactac tgccagcagt acgacaactg gccaccacgt     720

gagacctttg gtcaagggac acgtttagag attaaa                               756


<210> SEQ ID NO 30
<211> LENGTH: 237
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_258 Protein sequence, VH+VL

<400> SEQUENCE: 30

Glu Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Thr Ser Tyr
            20                  25                  30

Ser Phe Asn Trp Val Arg Gln Ala Pro Gly Gln Gly Leu Glu Trp Met
        35                  40                  45

Gly Arg Ile Ile Thr Ile Pro Asp Asp Thr Glu Tyr Ala Pro His Leu
    50                  55                  60

Gln Gly Arg Val Thr Ile Thr Ala Asp Lys Ser Thr Ser Thr Val Tyr
```

```
65                  70                  75                  80

Leu Glu Leu Arg Asn Leu Arg Ser Asp Asp Thr Ala Val Tyr Phe Cys
                85                  90                  95

Ala Gly Val Tyr Glu Gly Pro Asn Ser Glu Gly Ser Tyr Asp Asp Tyr
            100                 105                 110

Gly Phe Leu Lys His Trp Gly Gln Gly Thr Leu Val Thr Val Ser Ser
        115                 120                 125

Asp Ile Val Met Thr Gln Ser Pro Ala Thr Leu Ser Val Ser Pro Gly
    130                 135                 140

Glu Arg Ala Thr Leu Ser Cys Arg Ala Ser Glu Ser Val Ala Thr Asp
145                 150                 155                 160

Leu Ala Trp Tyr Gln Gln Lys Pro Gly Gln Val Pro Arg Leu Leu Ile
                165                 170                 175

Tyr Gly Ala Ser Thr Arg Ala Thr Gly Val Pro Ala Arg Phe Ser Gly
            180                 185                 190

Ser Gly Ser Gly Ala Glu Phe Thr Leu Thr Ile Ser Ser Leu Gln Ser
        195                 200                 205

Glu Asp Phe Ala Val Tyr Tyr Cys Gln Gln Tyr Asp Asn Trp Pro Pro
    210                 215                 220

Arg Glu Thr Phe Gly Gln Gly Thr Arg Leu Glu Ile Lys
225                 230                 235


<210> SEQ ID NO 31
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_258 protein sequence - VH

<400> SEQUENCE: 31

Glu Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Thr Ser Tyr
            20                  25                  30

Ser Phe Asn Trp Val Arg Gln Ala Pro Gly Gln Gly Leu Glu Trp Met
        35                  40                  45

Gly Arg Ile Ile Thr Ile Pro Asp Asp Thr Glu Tyr Ala Pro His Leu
    50                  55                  60

Gln Gly Arg Val Thr Ile Thr Ala Asp Lys Ser Thr Ser Thr Val Tyr
65                  70                  75                  80

Leu Glu Leu Arg Asn Leu Arg Ser Asp Asp Thr Ala Val Tyr Phe Cys
                85                  90                  95

Ala Gly Val Tyr Glu Gly Pro Asn Ser Glu Gly Ser Tyr Asp Asp Tyr
            100                 105                 110

Gly Phe Leu Lys His Trp Gly Gln Gly Thr Leu Val Thr Val Ser Ser
        115                 120                 125


<210> SEQ ID NO 32
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_258 protein sequence - VL
```

<400> SEQUENCE: 32

```
Asp Ile Val Met Thr Gln Ser Pro Ala Thr Leu Ser Val Ser Pro Gly
1               5                   10                  15

Glu Arg Ala Thr Leu Ser Cys Arg Ala Ser Glu Ser Val Ala Thr Asp
            20                  25                  30

Leu Ala Trp Tyr Gln Gln Lys Pro Gly Gln Val Pro Arg Leu Leu Ile
        35                  40                  45

Tyr Gly Ala Ser Thr Arg Ala Thr Gly Val Pro Ala Arg Phe Ser Gly
    50                  55                  60

Ser Gly Ser Gly Ala Glu Phe Thr Leu Thr Ile Ser Ser Leu Gln Ser
65                  70                  75                  80

Glu Asp Phe Ala Val Tyr Tyr Cys Gln Gln Tyr Asp Asn Trp Pro Pro
                85                  90                  95

Arg Glu Thr Phe Gly Gln Gly Thr Arg Leu Glu Ile Lys
            100                 105
```

<210> SEQ ID NO 33
<211> LENGTH: 756
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: CID_259 DNA sequence

<400> SEQUENCE: 33

```
gaagtgcagt tagtgcaatc tggtgccgaa gttaagaaac caggcagctc cgttaaagtg     60

tcttgtaagg catctggcga cactttcacc tcttatagtt ttaactgggt tcgtcaggct    120

ccaggccagg gtttggagtg gatgggtcgt atcattacca tcctggatga tactgagtac    180

gctcctcatt tacagggtcg tgtaaccatc acagcagaca agtccacatc taccgtatac    240

ttggaactgc gtaacttacg tagcgatgat accgccgttt acttctgcgc aggtgtgtac    300

gaaggtccga actctgaagg ctcgtacgat gactatggtt tcctgaaaca ctggggtcag    360

ggcactctgg tgactgttag ttctggcggt ggtggtagcg gaggcggagg atcaggtgga    420

ggcggcagtg atatcgttat gactcagtcc ccagcaaccc tgtctgtatc tcctggtgag    480

cgtgccaccc tgagctgccg tgcttcagaa tctgtaagga acgatctggc ctggtatcag    540

cagaaaccag gtcaggttcc acgtctgctg atttatggcg cttccacccg tgctaccggt    600

gtaccagctc gtttctctgg gtccggctcc ggcgccgagt tcaccctgac tatctcctct    660

ctgcagtccg aagactttgc cgtgtactac tgccagcagt acgcgaactg gccaccacac    720

gagacctttg gtcaagggac acgtttagag attaaa                              756
```

<210> SEQ ID NO 34
<211> LENGTH: 237
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_259 Protein sequence, VH+VL

<400> SEQUENCE: 34

```
Glu Val Gln Leu Val Gln Ser Gly Ala Glu Val Lys Lys Pro Gly Ser
1               5                   10                  15
```

```
Ser Val Lys Val Ser Cys Lys Ala Ser Gly Asp Thr Phe Thr Ser Tyr
            20                  25                  30

Ser Phe Asn Trp Val Arg Gln Ala Pro Gly Gln Gly Leu Glu Trp Met
        35                  40                  45

Gly Arg Ile Ile Thr Ile Leu Asp Asp Thr Glu Tyr Ala Pro His Leu
    50                  55                  60

Gln Gly Arg Val Thr Ile Thr Ala Asp Lys Ser Thr Ser Thr Val Tyr
65                  70                  75                  80

Leu Glu Leu Arg Asn Leu Arg Ser Asp Asp Thr Ala Val Tyr Phe Cys
                85                  90                  95

Ala Gly Val Tyr Glu Gly Pro Asn Ser Glu Gly Ser Tyr Asp Asp Tyr
            100                 105                 110

Gly Phe Leu Lys His Trp Gly Gln Gly Thr Leu Val Thr Val Ser Ser
        115                 120                 125

Asp Ile Val Met Thr Gln Ser Pro Ala Thr Leu Ser Val Ser Pro Gly
    130                 135                 140

Glu Arg Ala Thr Leu Ser Cys Arg Ala Ser Glu Ser Val Arg Asn Asp
145                 150                 155                 160

Leu Ala Trp Tyr Gln Gln Lys Pro Gly Gln Val Pro Arg Leu Leu Ile
                165                 170                 175

Tyr Gly Ala Ser Thr Arg Ala Thr Gly Val Pro Ala Arg Phe Ser Gly
            180                 185                 190

Ser Gly Ser Gly Ala Glu Phe Thr Leu Thr Ile Ser Ser Leu Gln Ser
        195                 200                 205

Glu Asp Phe Ala Val Tyr Tyr Cys Gln Gln Tyr Ala Asn Trp Pro Pro
    210                 215                 220

His Glu Thr Phe Gly Gln Gly Thr Arg Leu Glu Ile Lys
225                 230                 235


<210> SEQ ID NO 35
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_259 protein sequence - VH

<400> SEQUENCE: 35

Glu Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Thr Ser Tyr
            20                  25                  30

Ser Phe Asn Trp Val Arg Gln Ala Pro Gly Gln Gly Leu Glu Trp Met
        35                  40                  45

Gly Arg Ile Ile Thr Ile Leu Asp Asp Thr Glu Tyr Ala Pro His Leu
    50                  55                  60

Gln Gly Arg Val Thr Ile Thr Ala Asp Lys Ser Thr Ser Thr Val Tyr
65                  70                  75                  80

Leu Glu Leu Arg Asn Leu Arg Ser Asp Asp Thr Ala Val Tyr Phe Cys
                85                  90                  95

Ala Gly Val Tyr Glu Gly Pro Asn Ser Glu Gly Ser Tyr Asp Asp Tyr
            100                 105                 110

Gly Phe Leu Lys His Trp Gly Gln Gly Thr Leu Val Thr Val Ser Ser
        115                 120                 125
```

<210> SEQ ID NO 36
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_259 protein sequence - VL

<400> SEQUENCE: 36

```
Asp Ile Val Met Thr Gln Ser Pro Ala Thr Leu Ser Val Ser Pro Gly
1               5                   10                  15

Glu Arg Ala Thr Leu Ser Cys Arg Ala Ser Glu Ser Val Arg Asn Asp
            20                  25                  30

Leu Ala Trp Tyr Gln Gln Lys Pro Gly Gln Val Pro Arg Leu Leu Ile
        35                  40                  45

Tyr Gly Ala Ser Thr Arg Ala Thr Gly Val Pro Ala Arg Phe Ser Gly
    50                  55                  60

Ser Gly Ser Gly Ala Glu Phe Thr Leu Thr Ile Ser Ser Leu Gln Ser
65                  70                  75                  80

Glu Asp Phe Ala Val Tyr Tyr Cys Gln Gln Tyr Ala Asn Trp Pro Pro
                85                  90                  95

His Glu Thr Phe Gly Gln Gly Thr Arg Leu Glu Ile Lys
            100                 105
```

<210> SEQ ID NO 37
<211> LENGTH: 756
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CID_272 DNA sequence

<400> SEQUENCE: 37

```
gaagtgcagt tagtgcaatc tggtgccgaa gttaagaaac caggcagctc cgttaaagtg     60

tcttgtaagg catctggcga cactttcacc tcttatagtt ttaactgggt tcgtcaggct    120

ccaggccagg gtttggagtg gatgggtcgt atcattacca tcgacgatga tactgagtac    180

gctcctcatt tacagggtcg tgtaaccatc acagcagaca agtccacatc taccgtatac    240

ttggaactgc gtaacttacg tagcgatgat accgccgttt acttctgcgc aggtgtgtac    300

gaaggtccga actctgaagg ctcgtacgat gactatggtt tctacaaaca ctggggtcag    360

ggcactctgg tgactgttag ttctggcggt ggtggtagcg gaggcggagg atcaggtgga    420

ggcggcagtg atatcgttat gactcagtcc ccagcaaccc tgtctgtatc tcctggtgag    480

cgtgccaccc tgagctgccg tgcttcagaa tctgtaggga acgatctggc ctggtatcag    540

cagaaaccag gtcaggttcc acgtctgctg atttatggcg cttccacccg tgctccgggt    600

gtaccagctc gtttctctgg gtccggctcc ggcgccgagt tcaccctgac tatctcctct    660

ctgcagtccg aagactttgc cgtgtactac tgccagcagt acgcgaactg gccgccacgt    720

gagacctttg gtcaagggac acgtttagag attaaa                              756
```

<210> SEQ ID NO 38
<211> LENGTH: 237
<212> TYPE: PRT
<213> ORGANISM: Artificial Sequence
<220> FEATURE:

<223> OTHER INFORMATION: Description of Artificial Sequence: Synthetic
      polypeptide
<220> FEATURE:
<223> OTHER INFORMATION: CID_272 Protein sequence, VH+VL

<400> SEQUENCE: 38

Glu Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Thr Ser Tyr
            20                  25                  30

Ser Phe Asn Trp Val Arg Gln Ala Pro Gly Gln Gly Leu Glu Trp Met
        35                  40                  45

Gly Arg Ile Ile Thr Ile Asp Asp Asp Thr Glu Tyr Ala Pro His Leu
    50                  55                  60

Gln Gly Arg Val Thr Ile Thr Ala Asp Lys Ser Thr Ser Thr Val Tyr
65                  70                  75                  80

Leu Glu Leu Arg Asn Leu Arg Ser Asp Asp Thr Ala Val Tyr Phe Cys
                85                  90                  95

Ala Gly Val Tyr Glu Gly Pro Asn Ser Glu Gly Ser Tyr Asp Asp Tyr
            100                 105                 110

Gly Phe Tyr Lys His Trp Gly Gln Gly Thr Leu Val Thr Val Ser Ser
        115                 120                 125

Asp Ile Val Met Thr Gln Ser Pro Ala Thr Leu Ser Val Ser Pro Gly
    130                 135                 140

Glu Arg Ala Thr Leu Ser Cys Arg Ala Ser Glu Ser Val Gly Asn Asp
145                 150                 155                 160

Leu Ala Trp Tyr Gln Gln Lys Pro Gly Gln Val Pro Arg Leu Leu Ile
                165                 170                 175

Tyr Gly Ala Ser Thr Arg Ala Pro Gly Val Pro Ala Arg Phe Ser Gly
            180                 185                 190

Ser Gly Ser Gly Ala Glu Phe Thr Leu Thr Ile Ser Ser Leu Gln Ser
        195                 200                 205

Glu Asp Phe Ala Val Tyr Tyr Cys Gln Gln Tyr Ala Asn Trp Pro Pro
    210                 215                 220

Arg Glu Thr Phe Gly Gln Gly Thr Arg Leu Glu Ile Lys
225                 230                 235

<210> SEQ ID NO 39
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_272 protein sequence - VH

<400> SEQUENCE: 39

Glu Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Thr Ser Tyr
            20                  25                  30

Ser Phe Asn Trp Val Arg Gln Ala Pro Gly Gln Gly Leu Glu Trp Met
        35                  40                  45

Gly Arg Ile Ile Thr Ile Asp Asp Asp Thr Glu Tyr Ala Pro His Leu
    50                  55                  60

Gln Gly Arg Val Thr Ile Thr Ala Asp Lys Ser Thr Ser Thr Val Tyr
65                  70                  75                  80

```
Leu Glu Leu Arg Asn Leu Arg Ser Asp Asp Thr Ala Val Tyr Phe Cys
                85                  90                  95

Ala Gly Val Tyr Glu Gly Pro Asn Ser Glu Gly Ser Tyr Asp Asp Tyr
            100                 105                 110

Gly Phe Tyr Lys His Trp Gly Gln Gly Thr Leu Val Thr Val Ser Ser
        115                 120                 125
```

<210> SEQ ID NO 40
<211> LENGTH: 109
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_272 protein sequence - VL

<400> SEQUENCE: 40

```
Asp Ile Val Met Thr Gln Ser Pro Ala Thr Leu Ser Val Ser Pro Gly
1               5                   10                  15

Glu Arg Ala Thr Leu Ser Cys Arg Ala Ser Glu Ser Val Gly Asn Asp
            20                  25                  30

Leu Ala Trp Tyr Gln Gln Lys Pro Gly Gln Val Pro Arg Leu Leu Ile
        35                  40                  45

Tyr Gly Ala Ser Thr Arg Ala Pro Gly Val Pro Ala Arg Phe Ser Gly
    50                  55                  60

Ser Gly Ser Gly Ala Glu Phe Thr Leu Thr Ile Ser Ser Leu Gln Ser
65                  70                  75                  80

Glu Asp Phe Ala Val Tyr Tyr Cys Gln Gln Tyr Ala Asn Trp Pro Pro
                85                  90                  95

Arg Glu Thr Phe Gly Gln Gly Thr Arg Leu Glu Ile Lys
            100                 105
```

<210> SEQ ID NO 41
<211> LENGTH: 756
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: CID_274 DNA sequence

<400> SEQUENCE: 41

```
gaagtgcagt tagtgcaatc tggtgccgaa gttaagaaac caggcagctc cgttaaagtg     60

tcttgtaagg catctggcga cactttcacc tcttatagtt ttaactgggt tcgtcaggct    120

ccaggccagg gtttggagtg gatgggtcgt atcattacca tcctggatga ttcggagtac    180

gctcctcatt tacagggtcg tgtaaccatc acagcagaca agtccacatc taccgtatac    240

ttggaactgc gtaacttacg tagcgatgat accgccgttt acttctgcgc aggtgtgtac    300

gaaggtccga actctgaagg ctcgtacgat gactatggtt tcctgaaaca ctggggtcag    360

ggcactctgg tgactgttag ttctggcggt ggtggtagcg gaggcggagg atcaggtgga    420

ggcggcagtg atatcgttat gactcagtcc ccagcaaccc tgtctgtatc tcctggtgag    480

cgtgccaccc tgagctgccg tgcttcagaa tctgtagcta acgatctggc ctggtatcag    540

cagaaaccag gtcaggttcc acgtctgctg atttatgacg cttccacccg tgctaccggt    600

gtaccagctc gtttctctgg gtccggctcc ggcgccgagt tcaccctgac tatctcctct    660
```

ctgcagtccg aagactttgc cgtgtactac tgccagcagt acgcgaactg gccatggcgt 720
gagacctttg gtcaagggac acgtttagag attaaa 756

<210> SEQ ID NO 42
<211> LENGTH: 237
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: CID_274 Protein sequence, VH+VL

<400> SEQUENCE: 42

```
Glu Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Thr Ser Tyr
            20                  25                  30

Ser Phe Asn Trp Val Arg Gln Ala Pro Gly Gln Gly Leu Glu Trp Met
        35                  40                  45

Gly Arg Ile Ile Thr Ile Leu Asp Asp Ser Glu Tyr Ala Pro His Leu
    50                  55                  60

Gln Gly Arg Val Thr Ile Thr Ala Asp Lys Ser Thr Ser Thr Val Tyr
65                  70                  75                  80

Leu Glu Leu Arg Asn Leu Arg Ser Asp Asp Thr Ala Val Tyr Phe Cys
                85                  90                  95

Ala Gly Val Tyr Glu Gly Pro Asn Ser Glu Gly Ser Tyr Asp Asp Tyr
            100                 105                 110

Gly Phe Leu Lys His Trp Gly Gln Gly Thr Leu Val Thr Val Ser Ser
        115                 120                 125

Asp Ile Val Met Thr Gln Ser Pro Ala Thr Leu Ser Val Ser Pro Gly
    130                 135                 140

Glu Arg Ala Thr Leu Ser Cys Arg Ala Ser Glu Ser Val Ala Asn Asp
145                 150                 155                 160

Leu Ala Trp Tyr Gln Gln Lys Pro Gly Gln Val Pro Arg Leu Leu Ile
                165                 170                 175

Tyr Asp Ala Ser Thr Arg Ala Thr Gly Val Pro Ala Arg Phe Ser Gly
            180                 185                 190

Ser Gly Ser Gly Ala Glu Phe Thr Leu Thr Ile Ser Ser Leu Gln Ser
        195                 200                 205

Glu Asp Phe Ala Val Tyr Tyr Cys Gln Gln Tyr Ala Asn Trp Pro Trp
    210                 215                 220

Arg Glu Thr Phe Gly Gln Gly Thr Arg Leu Glu Ile Lys
225                 230                 235
```

<210> SEQ ID NO 43
<211> LENGTH: 128
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: CID_274 protein sequence - VH

<400> SEQUENCE: 43

```
Glu Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Thr Ser Tyr
```

```
            20                  25                  30

Ser Phe Asn Trp Val Arg Gln Ala Pro Gly Gln Gly Leu Glu Trp Met
        35                  40                  45

Gly Arg Ile Ile Thr Ile Leu Asp Asp Ser Glu Tyr Ala Pro His Leu
    50                  55                  60

Gln Gly Arg Val Thr Ile Thr Ala Asp Lys Ser Thr Ser Thr Val Tyr
65                  70                  75                  80

Leu Glu Leu Arg Asn Leu Arg Ser Asp Asp Thr Ala Val Tyr Phe Cys
                85                  90                  95

Ala Gly Val Tyr Glu Gly Pro Asn Ser Glu Gly Ser Tyr Asp Asp Tyr
            100                 105                 110

Gly Phe Leu Lys His Trp Gly Gln Gly Thr Leu Val Thr Val Ser Ser
        115                 120                 125
```

<210> SEQ ID NO 44
<211> LENGTH: 109
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_274 protein sequence - VL

<400> SEQUENCE: 44

```
Asp Ile Val Met Thr Gln Ser Pro Ala Thr Leu Ser Val Ser Pro Gly
1               5                   10                  15

Glu Arg Ala Thr Leu Ser Cys Arg Ala Ser Glu Ser Val Ala Asn Asp
            20                  25                  30

Leu Ala Trp Tyr Gln Gln Lys Pro Gly Gln Val Pro Arg Leu Leu Ile
        35                  40                  45

Tyr Asp Ala Ser Thr Arg Ala Thr Gly Val Pro Ala Arg Phe Ser Gly
    50                  55                  60

Ser Gly Ser Gly Ala Glu Phe Thr Leu Thr Ile Ser Ser Leu Gln Ser
65                  70                  75                  80

Glu Asp Phe Ala Val Tyr Tyr Cys Gln Gln Tyr Ala Asn Trp Pro Trp
                85                  90                  95

Arg Glu Thr Phe Gly Gln Gly Thr Arg Leu Glu Ile Lys
            100                 105
```

<210> SEQ ID NO 45
<211> LENGTH: 756
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: CID_275 DNA sequence

<400> SEQUENCE: 45

```
gaagtgcagt tagtgcaatc tggtgccgaa gttaagaaac caggcagctc cgttaaagtg     60

tcttgtaagg catctggcga cactttcacc tcttatagtt acaactgggt tcgtcaggct    120

ccaggccagg gtttggagtg gatgggtcgt atcattacca tcgacgatga tactgagtac    180

gctcctcatt tacagggtcg tgtaaccatc acagcagaca agtccacatc taccgtatac    240

ttggaactgc gtaacttacg tagcgatgat accgccgttt acttctgcgc aggtgtgtac    300

gaaggtccga actctgaagg ctcgtacgat gactatggtt tctacaaaca ctggggtcag    360
```

```
ggcactctgg tgactgttag ttctggcggt ggtggtagcg gaggcggagg atcaggtgga    420

ggcggcagtg atatcgttat gactcagtcc ccagcaaccc tgtctgtatc tcctggtgag    480

cgtgccaccc tgagctgccg tgcttcagaa tctgtagcta acgatctggc ctggtatcag    540

cagaaaccag gtcaggttcc acgtctgctg atttatggcg cttccacccg tgctaccggt    600

gtaccagctc gtttctctgg gtccggctcc ggcgccgagt tcaccctgac tatctcctct    660

ctgcagtccg aagactttgc cgtgtactac tgccagcagg gggcgaactg gccaccacgt    720

gagacctttg gtcaagggac acgtttagag attaaa                              756
```

<210> SEQ ID NO 46
<211> LENGTH: 237
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: CID_275 Protein sequence, VH+VL

<400> SEQUENCE: 46

```
Glu Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Thr Ser Tyr
            20                  25                  30

Ser Tyr Asn Trp Val Arg Gln Ala Pro Gly Gln Gly Leu Glu Trp Met
        35                  40                  45

Gly Arg Ile Ile Thr Ile Asp Asp Asp Thr Glu Tyr Ala Pro His Leu
    50                  55                  60

Gln Gly Arg Val Thr Ile Thr Ala Asp Lys Ser Thr Ser Thr Val Tyr
65                  70                  75                  80

Leu Glu Leu Arg Asn Leu Arg Ser Asp Asp Thr Ala Val Tyr Phe Cys
                85                  90                  95

Ala Gly Val Tyr Glu Gly Pro Asn Ser Glu Gly Ser Tyr Asp Asp Tyr
            100                 105                 110

Gly Phe Tyr Lys His Trp Gly Gln Gly Thr Leu Val Thr Val Ser Ser
        115                 120                 125

Asp Ile Val Met Thr Gln Ser Pro Ala Thr Leu Ser Val Ser Pro Gly
    130                 135                 140

Glu Arg Ala Thr Leu Ser Cys Arg Ala Ser Glu Ser Val Ala Asn Asp
145                 150                 155                 160

Leu Ala Trp Tyr Gln Gln Lys Pro Gly Gln Val Pro Arg Leu Leu Ile
                165                 170                 175

Tyr Gly Ala Ser Thr Arg Ala Thr Gly Val Pro Ala Arg Phe Ser Gly
            180                 185                 190

Ser Gly Ser Gly Ala Glu Phe Thr Leu Thr Ile Ser Ser Leu Gln Ser
        195                 200                 205

Glu Asp Phe Ala Val Tyr Tyr Cys Gln Gln Gly Ala Asn Trp Pro Pro
    210                 215                 220

Arg Glu Thr Phe Gly Gln Gly Thr Arg Leu Glu Ile Lys
225                 230                 235
```

<210> SEQ ID NO 47
<211> LENGTH: 128
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_275 protein sequence - VH

<400> SEQUENCE: 47

Glu Val Gln Leu Val Gln Ser Gly Ala Glu Val Lys Lys Pro Gly Ser
1 5 10 15

Ser Val Lys Val Ser Cys Lys Ala Ser Gly Asp Thr Phe Thr Ser Tyr
20 25 30

Ser Tyr Asn Trp Val Arg Gln Ala Pro Gly Gln Gly Leu Glu Trp Met
35 40 45

Gly Arg Ile Ile Thr Ile Asp Asp Asp Thr Glu Tyr Ala Pro His Leu
50 55 60

Gln Gly Arg Val Thr Ile Thr Ala Asp Lys Ser Thr Ser Thr Val Tyr
65 70 75 80

Leu Glu Leu Arg Asn Leu Arg Ser Asp Asp Thr Ala Val Tyr Phe Cys
85 90 95

Ala Gly Val Tyr Glu Gly Pro Asn Ser Glu Gly Ser Tyr Asp Asp Tyr
100 105 110

Gly Phe Tyr Lys His Trp Gly Gln Gly Thr Leu Val Thr Val Ser Ser
115 120 125

<210> SEQ ID NO 48
<211> LENGTH: 109
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: CID_275 protein sequence - VL

<400> SEQUENCE: 48

Asp Ile Val Met Thr Gln Ser Pro Ala Thr Leu Ser Val Ser Pro Gly
1 5 10 15

Glu Arg Ala Thr Leu Ser Cys Arg Ala Ser Glu Ser Val Ala Asn Asp
20 25 30

Leu Ala Trp Tyr Gln Gln Lys Pro Gly Gln Val Pro Arg Leu Leu Ile
35 40 45

Tyr Gly Ala Ser Thr Arg Ala Thr Gly Val Pro Ala Arg Phe Ser Gly
50 55 60

Ser Gly Ser Gly Ala Glu Phe Thr Leu Thr Ile Ser Ser Leu Gln Ser
65 70 75 80

Glu Asp Phe Ala Val Tyr Tyr Cys Gln Gln Gly Ala Asn Trp Pro Pro
85 90 95

Arg Glu Thr Phe Gly Gln Gly Thr Arg Leu Glu Ile Lys
100 105

<210> SEQ ID NO 49
<211> LENGTH: 756
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: CID_276 DNA sequence

<400> SEQUENCE: 49
gaagtgcagt tagtgcaatc tggtgccgaa gttaagaaac caggcagctc cgttaaagtg 60

```
tcttgtaagg catctggcga cactttcacc tcttatagtt ttaactgggt tcgtcaggct    120

ccaggccagg gtttggagtg gatgggtcgt atcattacca tctacgatga tactgagtac    180

gctcctcatt tacagggtcg tgtaaccatc acagcagaca agtccacatc taccgtatac    240

ttggaactgc gtaacttacg tagcgatgat accgccgttt acttctgcgc aggtgtgtac    300

gaaggtccga actctgaagg ctcgtacgat gactatggtt tcttcaaaca ctggggtcag    360

ggcactctgg tgactgttag ttctggcggt ggtggtagcg gaggcggagg atcaggtgga    420

ggcggcagtg atatcgttat gactcagtcc ccagcaaccc tgtctgtatc tcctggtgag    480

cgtgccaccc tgagctgccg tgcttcagaa tctgtagcta acgatctggc ctggtatcag    540

cagaaaccag gtcaggttcc acgtctgctg atttatggcg cttccacccg tgctaccggt    600

gtaccagctc gtttctctgg gtccggctcc ggcgccgagt tcaccctgac tatctcctct    660

ctgcagtccg aagactttgc cgtgtactac tgccagcagt acgcgaactg gccaccacgt    720

gagacctttg gtcaagggac acgtttagag attaaa                              756


<210> SEQ ID NO 50
<211> LENGTH: 237
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_276 Protein sequence, VH+VL

<400> SEQUENCE: 50

Glu Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Thr Ser Tyr
            20                  25                  30

Ser Phe Asn Trp Val Arg Gln Ala Pro Gly Gln Gly Leu Glu Trp Met
        35                  40                  45

Gly Arg Ile Ile Thr Ile Tyr Asp Asp Thr Glu Tyr Ala Pro His Leu
    50                  55                  60

Gln Gly Arg Val Thr Ile Thr Ala Asp Lys Ser Thr Ser Thr Val Tyr
65                  70                  75                  80

Leu Glu Leu Arg Asn Leu Arg Ser Asp Asp Thr Ala Val Tyr Phe Cys
                85                  90                  95

Ala Gly Val Tyr Glu Gly Pro Asn Ser Glu Gly Ser Tyr Asp Asp Tyr
            100                 105                 110

Gly Phe Phe Lys His Trp Gly Gln Gly Thr Leu Val Thr Val Ser Ser
        115                 120                 125

Asp Ile Val Met Thr Gln Ser Pro Ala Thr Leu Ser Val Ser Pro Gly
    130                 135                 140

Glu Arg Ala Thr Leu Ser Cys Arg Ala Ser Glu Ser Val Ala Asn Asp
145                 150                 155                 160

Leu Ala Trp Tyr Gln Gln Lys Pro Gly Gln Val Pro Arg Leu Leu Ile
                165                 170                 175

Tyr Gly Ala Ser Thr Arg Ala Thr Gly Val Pro Ala Arg Phe Ser Gly
            180                 185                 190

Ser Gly Ser Gly Ala Glu Phe Thr Leu Thr Ile Ser Ser Leu Gln Ser
        195                 200                 205

Glu Asp Phe Ala Val Tyr Tyr Cys Gln Gln Tyr Ala Asn Trp Pro Pro
    210                 215                 220
```

```
Arg Glu Thr Phe Gly Gln Gly Thr Arg Leu Glu Ile Lys
225                 230                 235


<210> SEQ ID NO 51
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_276 protein sequence - VH

<400> SEQUENCE: 51

Glu Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Thr Ser Tyr
            20                  25                  30

Ser Phe Asn Trp Val Arg Gln Ala Pro Gly Gln Gly Leu Glu Trp Met
        35                  40                  45

Gly Arg Ile Ile Thr Ile Tyr Asp Asp Thr Glu Tyr Ala Pro His Leu
    50                  55                  60

Gln Gly Arg Val Thr Ile Thr Ala Asp Lys Ser Thr Ser Thr Val Tyr
65                  70                  75                  80

Leu Glu Leu Arg Asn Leu Arg Ser Asp Asp Thr Ala Val Tyr Phe Cys
                85                  90                  95

Ala Gly Val Tyr Glu Gly Pro Asn Ser Glu Gly Ser Tyr Asp Asp Tyr
            100                 105                 110

Gly Phe Phe Lys His Trp Gly Gln Gly Thr Leu Val Thr Val Ser Ser
        115                 120                 125


<210> SEQ ID NO 52
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_276 protein sequence - VL

<400> SEQUENCE: 52

Asp Ile Val Met Thr Gln Ser Pro Ala Thr Leu Ser Val Ser Pro Gly
1               5                   10                  15

Glu Arg Ala Thr Leu Ser Cys Arg Ala Ser Glu Ser Val Ala Asn Asp
            20                  25                  30

Leu Ala Trp Tyr Gln Gln Lys Pro Gly Gln Val Pro Arg Leu Leu Ile
        35                  40                  45

Tyr Gly Ala Ser Thr Arg Ala Thr Gly Val Pro Ala Arg Phe Ser Gly
    50                  55                  60

Ser Gly Ser Gly Ala Glu Phe Thr Leu Thr Ile Ser Ser Leu Gln Ser
65                  70                  75                  80

Glu Asp Phe Ala Val Tyr Tyr Cys Gln Gln Tyr Ala Asn Trp Pro Pro
                85                  90                  95

Arg Glu Thr Phe Gly Gln Gly Thr Arg Leu Glu Ile Lys
            100                 105


<210> SEQ ID NO 53
<211> LENGTH: 756
<212> TYPE: DNA
<213> ORGANISM: Artificial Sequence
```

<220> FEATURE:
<223> OTHER INFORMATION: Description of Artificial Sequence: Synthetic
polynucleotide
<220> FEATURE:
<223> OTHER INFORMATION: CID_277 DNA sequence

<400> SEQUENCE: 53
gaagtgcagt tagtgcaatc tggtgccgaa gttaagaaac caggcagctc cgttaaagtg 60
tcttgtaagg catctggcga cactttcacc tcttatagtt ttaactgggt tcgtcaggct 120
ccaggccagg gtttggagtg gatgggtcgt atcattacca tcctggatga tactgagtac 180
gctcctcatt tacagggtcg tgtaaccatc acagcagaca agtccacatc taccgtatac 240
ttggaactgc gtaacttacg tagcgatgat accgccgttt acttctgcgc aggtgtgtac 300
gaaggtccga actctgaagg ctcgtacgat gactatggtt tcctgaaata ctggggtcag 360
ggcactctgg tgactgttag ttctggcggt ggtggtagcg gaggcggagg atcaggtgga 420
ggcggcagtg atatcgttat gactcagtcc ccagcaaccc tgtctgtatc tcctggtgag 480
cgtgccaccc tgagctgccg tgcttcagaa tctgtagctg tggatctggc ctggtatcag 540
cagaaaccag gtcaggttcc acgtctgctg atttatggcg cttccacccg tgctaccggt 600
gtaccagctc gtttctctgg gtccggctcc ggcgccgagt tcaccctgac tatctcctct 660
ctgcagtccg aagactttgc cgtgtactac tgccagcagt acgcgaacaa gccaccacgt 720
gagacctttg gtcaagggac acgtttagag attaaa 756

<210> SEQ ID NO 54
<211> LENGTH: 237
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: CID_277 Protein sequence, VH+VL

<400> SEQUENCE: 54

Glu Val Gln Leu Val Gln Ser Gly Ala Glu Val Lys Lys Pro Gly Ser
1 5 10 15

Ser Val Lys Val Ser Cys Lys Ala Ser Gly Asp Thr Phe Thr Ser Tyr
20 25 30

Ser Phe Asn Trp Val Arg Gln Ala Pro Gly Gln Gly Leu Glu Trp Met
35 40 45

Gly Arg Ile Ile Thr Ile Leu Asp Asp Thr Glu Tyr Ala Pro His Leu
50 55 60

Gln Gly Arg Val Thr Ile Thr Ala Asp Lys Ser Thr Ser Thr Val Tyr
65 70 75 80

Leu Glu Leu Arg Asn Leu Arg Ser Asp Asp Thr Ala Val Tyr Phe Cys
85 90 95

Ala Gly Val Tyr Glu Gly Pro Asn Ser Glu Gly Ser Tyr Asp Asp Tyr
100 105 110

Gly Phe Leu Lys Tyr Trp Gly Gln Gly Thr Leu Val Thr Val Ser Ser
115 120 125

Asp Ile Val Met Thr Gln Ser Pro Ala Thr Leu Ser Val Ser Pro Gly
130 135 140

Glu Arg Ala Thr Leu Ser Cys Arg Ala Ser Glu Ser Val Ala Val Asp
145 150 155 160

Leu Ala Trp Tyr Gln Gln Lys Pro Gly Gln Val Pro Arg Leu Leu Ile
165 170 175

```
Tyr Gly Ala Ser Thr Arg Ala Thr Gly Val Pro Ala Arg Phe Ser Gly
            180                 185                 190

Ser Gly Ser Gly Ala Glu Phe Thr Leu Thr Ile Ser Ser Leu Gln Ser
        195                 200                 205

Glu Asp Phe Ala Val Tyr Tyr Cys Gln Gln Tyr Ala Asn Lys Pro Pro
    210                 215                 220

Arg Glu Thr Phe Gly Gln Gly Thr Arg Leu Glu Ile Lys
225                 230                 235


<210> SEQ ID NO 55
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_277 protein sequence - VH

<400> SEQUENCE: 55

Glu Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Thr Ser Tyr
            20                  25                  30

Ser Phe Asn Trp Val Arg Gln Ala Pro Gly Gln Gly Leu Glu Trp Met
        35                  40                  45

Gly Arg Ile Ile Thr Ile Leu Asp Asp Thr Glu Tyr Ala Pro His Leu
    50                  55                  60

Gln Gly Arg Val Thr Ile Thr Ala Asp Lys Ser Thr Ser Thr Val Tyr
65                  70                  75                  80

Leu Glu Leu Arg Asn Leu Arg Ser Asp Asp Thr Ala Val Tyr Phe Cys
                85                  90                  95

Ala Gly Val Tyr Glu Gly Pro Asn Ser Glu Gly Ser Tyr Asp Asp Tyr
            100                 105                 110

Gly Phe Leu Lys Tyr Trp Gly Gln Gly Thr Leu Val Thr Val Ser Ser
        115                 120                 125


<210> SEQ ID NO 56
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_277 protein sequence - VL

<400> SEQUENCE: 56

Asp Ile Val Met Thr Gln Ser Pro Ala Thr Leu Ser Val Ser Pro Gly
1               5                   10                  15

Glu Arg Ala Thr Leu Ser Cys Arg Ala Ser Glu Ser Val Ala Val Asp
            20                  25                  30

Leu Ala Trp Tyr Gln Gln Lys Pro Gly Gln Val Pro Arg Leu Leu Ile
        35                  40                  45

Tyr Gly Ala Ser Thr Arg Ala Thr Gly Val Pro Ala Arg Phe Ser Gly
    50                  55                  60

Ser Gly Ser Gly Ala Glu Phe Thr Leu Thr Ile Ser Ser Leu Gln Ser
65                  70                  75                  80

Glu Asp Phe Ala Val Tyr Tyr Cys Gln Gln Tyr Ala Asn Lys Pro Pro
```

85 90 95

Arg Glu Thr Phe Gly Gln Gly Thr Arg Leu Glu Ile Lys
100 105

<210> SEQ ID NO 57
<211> LENGTH: 756
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: CID_278 DNA sequence

<400> SEQUENCE: 57
gaagtgcagt tagtgcaatc tggtgccgaa gttaagaaac caggcagctc cgttaaagtg 60
tcttgtaagg catctggcga cactttcacc tcttatagtt ttaactgggt tcgtcaggct 120
ccaggccagg gtttggagtg gatgggtcgt atcattacca tcctggatga tactgagtac 180
gctcctcatt tacagggtcg tgtaaccatc acagcagaca agtccacatc taccgtatac 240
ttggaactgc gtaacttacg tagcgatgat accgccgttt acttctgcgc aggtgtgtac 300
gaaggtccga actctgaagg ctcgtacgat gactatggtg ccctgaaaca ctggggtcag 360
ggcactctgg tgactgttag ttctggcggt ggtggtagcg gaggcggagg atcaggtgga 420
ggcggcagtg atatcgttat gactcagtcc ccagcaaccc tgtctgtatc tcctggtgag 480
cgtgccaccc tgagctgccg tgcttcagaa tctgtagcta acgatctggc ctggtatcag 540
cagaaaccag gtcaggttcc acgtctgctg atttatggcg cttccacccg tgctaccggt 600
gtaccagctc gtttctctgg gtccggctcc ggcgccgagt tcaccctgac tatctcctct 660
ctgcagtccg aagactttgc cgtgtactac tgccagcagt acgcgaactg gccaccacgt 720
gagacctttg gtcaagggac acgtttagag attaaa 756

<210> SEQ ID NO 58
<211> LENGTH: 237
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_278 Protein sequence, VH+VL

<400> SEQUENCE: 58

Glu Val Gln Leu Val Gln Ser Gly Ala Glu Val Lys Lys Pro Gly Ser
1 5 10 15

Ser Val Lys Val Ser Cys Lys Ala Ser Gly Asp Thr Phe Thr Ser Tyr
20 25 30

Ser Phe Asn Trp Val Arg Gln Ala Pro Gly Gln Gly Leu Glu Trp Met
35 40 45

Gly Arg Ile Ile Thr Ile Leu Asp Asp Thr Glu Tyr Ala Pro His Leu
50 55 60

Gln Gly Arg Val Thr Ile Thr Ala Asp Lys Ser Thr Ser Thr Val Tyr
65 70 75 80

Leu Glu Leu Arg Asn Leu Arg Ser Asp Asp Thr Ala Val Tyr Phe Cys
85 90 95

Ala Gly Val Tyr Glu Gly Pro Asn Ser Glu Gly Ser Tyr Asp Asp Tyr
100 105 110

Gly Ala Leu Lys His Trp Gly Gln Gly Thr Leu Val Thr Val Ser Ser

```
        115                 120                 125

Asp Ile Val Met Thr Gln Ser Pro Ala Thr Leu Ser Val Ser Pro Gly
    130                 135                 140

Glu Arg Ala Thr Leu Ser Cys Arg Ala Ser Glu Ser Val Ala Asn Asp
145                 150                 155                 160

Leu Ala Trp Tyr Gln Gln Lys Pro Gly Gln Val Pro Arg Leu Leu Ile
                165                 170                 175

Tyr Gly Ala Ser Thr Arg Ala Thr Gly Val Pro Ala Arg Phe Ser Gly
            180                 185                 190

Ser Gly Ser Gly Ala Glu Phe Thr Leu Thr Ile Ser Ser Leu Gln Ser
        195                 200                 205

Glu Asp Phe Ala Val Tyr Tyr Cys Gln Gln Tyr Ala Asn Trp Pro Pro
    210                 215                 220

Arg Glu Thr Phe Gly Gln Gly Thr Arg Leu Glu Ile Lys
225                 230                 235
```

<210> SEQ ID NO 59
<211> LENGTH: 128
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_278 protein sequence - VH

<400> SEQUENCE: 59

```
Glu Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Thr Ser Tyr
            20                  25                  30

Ser Phe Asn Trp Val Arg Gln Ala Pro Gly Gln Gly Leu Glu Trp Met
        35                  40                  45

Gly Arg Ile Ile Thr Ile Leu Asp Asp Thr Glu Tyr Ala Pro His Leu
    50                  55                  60

Gln Gly Arg Val Thr Ile Thr Ala Asp Lys Ser Thr Ser Thr Val Tyr
65                  70                  75                  80

Leu Glu Leu Arg Asn Leu Arg Ser Asp Asp Thr Ala Val Tyr Phe Cys
                85                  90                  95

Ala Gly Val Tyr Glu Gly Pro Asn Ser Glu Gly Ser Tyr Asp Asp Tyr
            100                 105                 110

Gly Ala Leu Lys His Trp Gly Gln Gly Thr Leu Val Thr Val Ser Ser
        115                 120                 125
```

<210> SEQ ID NO 60
<211> LENGTH: 109
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_278 protein sequence - VL

<400> SEQUENCE: 60

```
Asp Ile Val Met Thr Gln Ser Pro Ala Thr Leu Ser Val Ser Pro Gly
1               5                   10                  15

Glu Arg Ala Thr Leu Ser Cys Arg Ala Ser Glu Ser Val Ala Asn Asp
            20                  25                  30
```

```
Leu Ala Trp Tyr Gln Gln Lys Pro Gly Gln Val Pro Arg Leu Leu Ile
        35                  40                  45

Tyr Gly Ala Ser Thr Arg Ala Thr Gly Val Pro Ala Arg Phe Ser Gly
    50                  55                  60

Ser Gly Ser Gly Ala Glu Phe Thr Leu Thr Ile Ser Ser Leu Gln Ser
65                  70                  75                  80

Glu Asp Phe Ala Val Tyr Tyr Cys Gln Gln Tyr Ala Asn Trp Pro Pro
                85                  90                  95

Arg Glu Thr Phe Gly Gln Gly Thr Arg Leu Glu Ile Lys
            100                 105


<210> SEQ ID NO 61
<211> LENGTH: 756
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CID_280 DNA sequence

<400> SEQUENCE: 61

gaagtgcagt tagtgcaatc tggtgccgaa gttaagaaac caggcagctc cgttaaagtg      60

tcttgtaagg catctggcga cactttcacc tcttatagtt ttaactgggt tcgtcaggct     120

ccaggccagg gtttggagtg gatgggtcgt atcattaccg acctggatga tactgagtac     180

gctcctcatt tacagggtcg tgtaaccatc acagcagaca agtccacatc taccgtatac     240

ttggaactgc gtaacttacg tagcgatgat accgccgttt acttctgcgc aggtgtgtac     300

gaaggtccga actctgaagg ctcgtacgat gactatggtc agctgaaaca ctggggtcag     360

ggcactctgg tgactgttag ttctggcggt ggtggtagcg gaggcggagg atcaggtgga     420

ggcggcagtg atatcgttat gactcagtcc ccagcaaccc tgtctgtatc tcctggtgag     480

cgtgccaccc tgagctgccg tgcttcagaa tctgtagcta acgatctggc ctggtatcag     540

cagaaaccag gtcaggttcc acgtctgctg atttatggcg cttccacccg tgctaccggt     600

gtaccagctc gtttctctgg gtccggctcc ggcgccgagt tcaccctgac tatctcctct     660

ctgcagtccg aagactttgc cgtgtactac tgccagcagt acgcgaactg gccaccacgt     720

gagacctttg gtcaagggac acgtttagag attaaa                               756


<210> SEQ ID NO 62
<211> LENGTH: 237
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_280 Protein sequence, VH+VL

<400> SEQUENCE: 62

Glu Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Thr Ser Tyr
            20                  25                  30

Ser Phe Asn Trp Val Arg Gln Ala Pro Gly Gln Gly Leu Glu Trp Met
        35                  40                  45

Gly Arg Ile Ile Thr Asp Leu Asp Asp Thr Glu Tyr Ala Pro His Leu
    50                  55                  60
```

```
Gln Gly Arg Val Thr Ile Thr Ala Asp Lys Ser Thr Ser Thr Val Tyr
65                  70                  75                  80

Leu Glu Leu Arg Asn Leu Arg Ser Asp Asp Thr Ala Val Tyr Phe Cys
                85                  90                  95

Ala Gly Val Tyr Glu Gly Pro Asn Ser Glu Gly Ser Tyr Asp Asp Tyr
            100                 105                 110

Gly Gln Leu Lys His Trp Gly Gln Gly Thr Leu Val Thr Val Ser Ser
        115                 120                 125

Asp Ile Val Met Thr Gln Ser Pro Ala Thr Leu Ser Val Ser Pro Gly
    130                 135                 140

Glu Arg Ala Thr Leu Ser Cys Arg Ala Ser Glu Ser Val Ala Asn Asp
145                 150                 155                 160

Leu Ala Trp Tyr Gln Gln Lys Pro Gly Gln Val Pro Arg Leu Leu Ile
                165                 170                 175

Tyr Gly Ala Ser Thr Arg Ala Thr Gly Val Pro Ala Arg Phe Ser Gly
            180                 185                 190

Ser Gly Ser Gly Ala Glu Phe Thr Leu Thr Ile Ser Ser Leu Gln Ser
        195                 200                 205

Glu Asp Phe Ala Val Tyr Tyr Cys Gln Gln Tyr Ala Asn Trp Pro Pro
    210                 215                 220

Arg Glu Thr Phe Gly Gln Gly Thr Arg Leu Glu Ile Lys
225                 230                 235
```

<210> SEQ ID NO 63
<211> LENGTH: 128
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_280 protein sequence - VH

<400> SEQUENCE: 63

```
Glu Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Thr Ser Tyr
            20                  25                  30

Ser Phe Asn Trp Val Arg Gln Ala Pro Gly Gln Gly Leu Glu Trp Met
        35                  40                  45

Gly Arg Ile Ile Thr Asp Leu Asp Asp Thr Glu Tyr Ala Pro His Leu
    50                  55                  60

Gln Gly Arg Val Thr Ile Thr Ala Asp Lys Ser Thr Ser Thr Val Tyr
65                  70                  75                  80

Leu Glu Leu Arg Asn Leu Arg Ser Asp Asp Thr Ala Val Tyr Phe Cys
                85                  90                  95

Ala Gly Val Tyr Glu Gly Pro Asn Ser Glu Gly Ser Tyr Asp Asp Tyr
            100                 105                 110

Gly Gln Leu Lys His Trp Gly Gln Gly Thr Leu Val Thr Val Ser Ser
        115                 120                 125
```

<210> SEQ ID NO 64
<211> LENGTH: 109
<212> TYPE: PRT
<213> ORGANISM: Artificial Sequence
<220> FEATURE:
<223> OTHER INFORMATION: Description of Artificial Sequence: Synthetic polypeptide
<220> FEATURE:

<223> OTHER INFORMATION: CID_280 protein sequence - VL

<400> SEQUENCE: 64

Asp Ile Val Met Thr Gln Ser Pro Ala Thr Leu Ser Val Ser Pro Gly
1               5                   10                  15

Glu Arg Ala Thr Leu Ser Cys Arg Ala Ser Glu Ser Val Ala Asn Asp
            20                  25                  30

Leu Ala Trp Tyr Gln Gln Lys Pro Gly Gln Val Pro Arg Leu Leu Ile
        35                  40                  45

Tyr Gly Ala Ser Thr Arg Ala Thr Gly Val Pro Ala Arg Phe Ser Gly
    50                  55                  60

Ser Gly Ser Gly Ala Glu Phe Thr Leu Thr Ile Ser Ser Leu Gln Ser
65                  70                  75                  80

Glu Asp Phe Ala Val Tyr Tyr Cys Gln Gln Tyr Ala Asn Trp Pro Pro
                85                  90                  95

Arg Glu Thr Phe Gly Gln Gly Thr Arg Leu Glu Ile Lys
            100                 105

<210> SEQ ID NO 65
<211> LENGTH: 756
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CID_281 DNA sequence

<400> SEQUENCE: 65
gaagtgcagt tagtgcaatc tggtgccgaa gttaagaaac caggcagctc cgttaaagtg     60
tcttgtaagg catctggcga cactttcacc tcttatagtt ttaactgggt tcgtcaggct    120
ccaggccagg gtttggagtg gatgggtcgt atcattacca tcctggatga tactgagtac    180
gctcctcatt tacagggtcg tgtaaccatc acagcagaca agtccacatc taccgtatac    240
ttggaactgc gtaacttacg tagcgatgat accgccgttt acttctgcgc aggtgtgtac    300
gaaggtccga actctgaagg ctcgtacgat gactatggtc agctgaaaca ctggggtcag    360
ggcactctgg tgactgttag ttctggcggt ggtggtagcg gaggcggagg atcaggtgga    420
ggcggcagtg atatcgttat gactcagtcc ccagcaaccc tgtctgtatc tcctggtgag    480
cgtgccaccc tgagctgccg tgcttcagaa tctgtagcta acgatctggc ctggtatcag    540
cagaaaccag gtcaggttcc acgtctgctg atttatggcg cttccacccg tgctccgggt    600
gtaccagctc gtttctctgg gtccggctcc ggcgccgagt tcaccctgac tatctcctct    660
ctgcagtccg aagactttgc cgtgtactac tgccagcagt acgcgaacac cccaccacgt    720
gagacctttg gtcaagggac acgtttagag attaaa                              756

<210> SEQ ID NO 66
<211> LENGTH: 237
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_281 Protein sequence, VH+VL

<400> SEQUENCE: 66

Glu Val Gln Leu Val Gln Ser Gly Ala Glu Val Lys Lys Pro Gly Ser
1               5                   10                  15

```
Ser Val Lys Val Ser Cys Lys Ala Ser Gly Asp Thr Phe Thr Ser Tyr
            20                  25                  30

Ser Phe Asn Trp Val Arg Gln Ala Pro Gly Gln Gly Leu Glu Trp Met
        35                  40                  45

Gly Arg Ile Ile Thr Ile Leu Asp Asp Thr Glu Tyr Ala Pro His Leu
    50                  55                  60

Gln Gly Arg Val Thr Ile Thr Ala Asp Lys Ser Thr Ser Thr Val Tyr
65                  70                  75                  80

Leu Glu Leu Arg Asn Leu Arg Ser Asp Asp Thr Ala Val Tyr Phe Cys
                85                  90                  95

Ala Gly Val Tyr Glu Gly Pro Asn Ser Glu Gly Ser Tyr Asp Asp Tyr
            100                 105                 110

Gly Gln Leu Lys His Trp Gly Gln Gly Thr Leu Val Thr Val Ser Ser
        115                 120                 125

Asp Ile Val Met Thr Gln Ser Pro Ala Thr Leu Ser Val Ser Pro Gly
    130                 135                 140

Glu Arg Ala Thr Leu Ser Cys Arg Ala Ser Glu Ser Val Ala Asn Asp
145                 150                 155                 160

Leu Ala Trp Tyr Gln Gln Lys Pro Gly Gln Val Pro Arg Leu Leu Ile
                165                 170                 175

Tyr Gly Ala Ser Thr Arg Ala Pro Gly Val Pro Ala Arg Phe Ser Gly
            180                 185                 190

Ser Gly Ser Gly Ala Glu Phe Thr Leu Thr Ile Ser Ser Leu Gln Ser
        195                 200                 205

Glu Asp Phe Ala Val Tyr Tyr Cys Gln Gln Tyr Ala Asn Thr Pro Pro
    210                 215                 220

Arg Glu Thr Phe Gly Gln Gly Thr Arg Leu Glu Ile Lys
225                 230                 235
```

```
<210> SEQ ID NO 67
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_281 protein sequence - VH

<400> SEQUENCE: 67

Glu Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Thr Ser Tyr
            20                  25                  30

Ser Phe Asn Trp Val Arg Gln Ala Pro Gly Gln Gly Leu Glu Trp Met
        35                  40                  45

Gly Arg Ile Ile Thr Ile Leu Asp Asp Thr Glu Tyr Ala Pro His Leu
    50                  55                  60

Gln Gly Arg Val Thr Ile Thr Ala Asp Lys Ser Thr Ser Thr Val Tyr
65                  70                  75                  80

Leu Glu Leu Arg Asn Leu Arg Ser Asp Asp Thr Ala Val Tyr Phe Cys
                85                  90                  95

Ala Gly Val Tyr Glu Gly Pro Asn Ser Glu Gly Ser Tyr Asp Asp Tyr
            100                 105                 110

Gly Gln Leu Lys His Trp Gly Gln Gly Thr Leu Val Thr Val Ser Ser
        115                 120                 125
```

<210> SEQ ID NO 68
<211> LENGTH: 109
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_281 protein sequence - VL

<400> SEQUENCE: 68

Asp Ile Val Met Thr Gln Ser Pro Ala Thr Leu Ser Val Ser Pro Gly
1               5                   10                  15

Glu Arg Ala Thr Leu Ser Cys Arg Ala Ser Glu Ser Val Ala Asn Asp
            20                  25                  30

Leu Ala Trp Tyr Gln Gln Lys Pro Gly Gln Val Pro Arg Leu Leu Ile
        35                  40                  45

Tyr Gly Ala Ser Thr Arg Ala Pro Gly Val Pro Ala Arg Phe Ser Gly
    50                  55                  60

Ser Gly Ser Gly Ala Glu Phe Thr Leu Thr Ile Ser Ser Leu Gln Ser
65                  70                  75                  80

Glu Asp Phe Ala Val Tyr Tyr Cys Gln Gln Tyr Ala Asn Thr Pro Pro
                85                  90                  95

Arg Glu Thr Phe Gly Gln Gly Thr Arg Leu Glu Ile Lys
            100                 105

<210> SEQ ID NO 69
<211> LENGTH: 756
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: CID_282 DNA sequence

<400> SEQUENCE: 69
gaagtgcagt tagtgcaatc tggtgccgaa gttaagaaac caggcagctc cgttaaagtg 60
tcttgtaagg catctggcga cactttcacc tcttatagtt ttaactgggt tcgtcaggct 120
ccaggccagg gtttggagtg gatgggtcgt atcattaccg acctggatga tactgagtac 180
gctcctcatt tacagggtcg tgtaaccatc acagcagaca agtccacatc taccgtatac 240
ttggaactgc gtaacttacg tagcgatgat accgccgttt acttctgcgc aggtgtgtac 300
gaaggtccga actctgaagg ctcgtacgat gactatggtt tcctgaaaca ctggggtcag 360
ggcactctgg tgactgttag ttctggcggt ggtggtagcg gaggcggagg atcaggtgga 420
ggcggcagtg atatcgttat gactcagtcc ccagcaaccc tgtctgtatc tcctggtgag 480
cgtgccaccc tgagctgccg tgcttcagaa tctgtagcta acgatctgac gtggtatcag 540
cagaaaccag gtcaggttcc acgtctgctg atttatggcg cttccacccg tgctaccggt 600
gtaccagctc gtttctctgg gtccggctcc ggcgccgagt tcaccctgac tatctcctct 660
ctgcagtccg aagactttgc cgtgtactac tgccagcagt acgcgaactg gccaccacgt 720
gagacctttg gtcaagggac acgtttagag attaaa 756

<210> SEQ ID NO 70
<211> LENGTH: 237
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: CID_282 Protein sequence, VH+VL

<400> SEQUENCE: 70

```
Glu Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Thr Ser Tyr
            20                  25                  30

Ser Phe Asn Trp Val Arg Gln Ala Pro Gly Gln Gly Leu Glu Trp Met
        35                  40                  45

Gly Arg Ile Ile Thr Asp Leu Asp Asp Thr Glu Tyr Ala Pro His Leu
    50                  55                  60

Gln Gly Arg Val Thr Ile Thr Ala Asp Lys Ser Thr Ser Thr Val Tyr
65                  70                  75                  80

Leu Glu Leu Arg Asn Leu Arg Ser Asp Asp Thr Ala Val Tyr Phe Cys
                85                  90                  95

Ala Gly Val Tyr Glu Gly Pro Asn Ser Glu Gly Ser Tyr Asp Asp Tyr
            100                 105                 110

Gly Phe Leu Lys His Trp Gly Gln Gly Thr Leu Val Thr Val Ser Ser
        115                 120                 125

Asp Ile Val Met Thr Gln Ser Pro Ala Thr Leu Ser Val Ser Pro Gly
    130                 135                 140

Glu Arg Ala Thr Leu Ser Cys Arg Ala Ser Glu Ser Val Ala Asn Asp
145                 150                 155                 160

Leu Thr Trp Tyr Gln Gln Lys Pro Gly Gln Val Pro Arg Leu Leu Ile
                165                 170                 175

Tyr Gly Ala Ser Thr Arg Ala Thr Gly Val Pro Ala Arg Phe Ser Gly
            180                 185                 190

Ser Gly Ser Gly Ala Glu Phe Thr Leu Thr Ile Ser Ser Leu Gln Ser
        195                 200                 205

Glu Asp Phe Ala Val Tyr Tyr Cys Gln Gln Tyr Ala Asn Trp Pro Pro
    210                 215                 220

Arg Glu Thr Phe Gly Gln Gly Thr Arg Leu Glu Ile Lys
225                 230                 235
```

<210> SEQ ID NO 71
<211> LENGTH: 128
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: CID_282 protein sequence - VH

<400> SEQUENCE: 71

```
Glu Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Thr Ser Tyr
            20                  25                  30

Ser Phe Asn Trp Val Arg Gln Ala Pro Gly Gln Gly Leu Glu Trp Met
        35                  40                  45

Gly Arg Ile Ile Thr Asp Leu Asp Asp Thr Glu Tyr Ala Pro His Leu
    50                  55                  60

Gln Gly Arg Val Thr Ile Thr Ala Asp Lys Ser Thr Ser Thr Val Tyr
```

```
65                  70                  75                  80

Leu Glu Leu Arg Asn Leu Arg Ser Asp Asp Thr Ala Val Tyr Phe Cys
                85                  90                  95

Ala Gly Val Tyr Glu Gly Pro Asn Ser Glu Gly Ser Tyr Asp Asp Tyr
            100                 105                 110

Gly Phe Leu Lys His Trp Gly Gln Gly Thr Leu Val Thr Val Ser Ser
        115                 120                 125


<210> SEQ ID NO 72
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_282 protein sequence - VL

<400> SEQUENCE: 72

Asp Ile Val Met Thr Gln Ser Pro Ala Thr Leu Ser Val Ser Pro Gly
1               5                   10                  15

Glu Arg Ala Thr Leu Ser Cys Arg Ala Ser Glu Ser Val Ala Asn Asp
            20                  25                  30

Leu Thr Trp Tyr Gln Gln Lys Pro Gly Gln Val Pro Arg Leu Leu Ile
        35                  40                  45

Tyr Gly Ala Ser Thr Arg Ala Thr Gly Val Pro Ala Arg Phe Ser Gly
    50                  55                  60

Ser Gly Ser Gly Ala Glu Phe Thr Leu Thr Ile Ser Ser Leu Gln Ser
65                  70                  75                  80

Glu Asp Phe Ala Val Tyr Tyr Cys Gln Gln Tyr Ala Asn Trp Pro Pro
                85                  90                  95

Arg Glu Thr Phe Gly Gln Gly Thr Arg Leu Glu Ile Lys
            100                 105


<210> SEQ ID NO 73
<211> LENGTH: 756
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CID_283 DNA sequence

<400> SEQUENCE: 73

gaagtgcagt tagtgcaatc tggtgccgaa gttaagaaac caggcagctc cgttaaagtg     60

tcttgtaagg catctggcga cactttcacc tcttatagtt ttaactgggt tcgtcaggct    120

ccaggccagg gtttggagtg gatgggtcgt atcattacca tcctggatga tactgagtac    180

gctcctcatt tacagggtcg tgtaaccatc acagcagaca agtccacatc taccgtatac    240

ttggaactgc gtaacttacg tagcgatgat accgccgttt acttctgcgc aggtgtgtac    300

gaaggtccga actctgaagg ctcgtacgat gactatggtt tcctgaaaca ctggggtcag    360

ggcactctgg tgactgttag ttctggcggt ggtggtagcg gaggcggagg atcaggtgga    420

ggcggcagtg atatcgttat gactcagtcc ccagcaaccc tgtctgtatc tcctggtgag    480

cgtgccaccc tgagctgccg tgcttcagaa tctgtaggga acgatctggc ctggtatcag    540

cagaaaccag gtcaggttcc acgtctgctg atttatggcg cttccacccg tgctaccggt    600

gtaccagctc gtttctctgg gtccggctcc ggcgccgagt tcaccctgac tatctcctct    660
```

ctgcagtccg aagactttgc cgtgtactac tgccagcagt acgcgaactg gccaccacgg 720
gagacctttg gtcaagggac acgtttagag attaaa 756

<210> SEQ ID NO 74
<211> LENGTH: 237
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_283 Protein sequence, VH+VL

<400> SEQUENCE: 74

Glu Val Gln Leu Val Gln Ser Gly Ala Glu Val Lys Lys Pro Gly Ser
1 5 10 15

Ser Val Lys Val Ser Cys Lys Ala Ser Gly Asp Thr Phe Thr Ser Tyr
20 25 30

Ser Phe Asn Trp Val Arg Gln Ala Pro Gly Gln Gly Leu Glu Trp Met
35 40 45

Gly Arg Ile Ile Thr Ile Leu Asp Asp Thr Glu Tyr Ala Pro His Leu
50 55 60

Gln Gly Arg Val Thr Ile Thr Ala Asp Lys Ser Thr Ser Thr Val Tyr
65 70 75 80

Leu Glu Leu Arg Asn Leu Arg Ser Asp Asp Thr Ala Val Tyr Phe Cys
85 90 95

Ala Gly Val Tyr Glu Gly Pro Asn Ser Glu Gly Ser Tyr Asp Asp Tyr
100 105 110

Gly Phe Leu Lys His Trp Gly Gln Gly Thr Leu Val Thr Val Ser Ser
115 120 125

Asp Ile Val Met Thr Gln Ser Pro Ala Thr Leu Ser Val Ser Pro Gly
130 135 140

Glu Arg Ala Thr Leu Ser Cys Arg Ala Ser Glu Ser Val Gly Asn Asp
145 150 155 160

Leu Ala Trp Tyr Gln Gln Lys Pro Gly Gln Val Pro Arg Leu Leu Ile
165 170 175

Tyr Gly Ala Ser Thr Arg Ala Thr Gly Val Pro Ala Arg Phe Ser Gly
180 185 190

Ser Gly Ser Gly Ala Glu Phe Thr Leu Thr Ile Ser Ser Leu Gln Ser
195 200 205

Glu Asp Phe Ala Val Tyr Tyr Cys Gln Gln Tyr Ala Asn Trp Pro Pro
210 215 220

Arg Glu Thr Phe Gly Gln Gly Thr Arg Leu Glu Ile Lys
225 230 235

<210> SEQ ID NO 75
<211> LENGTH: 128
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_283 protein sequence - VH

<400> SEQUENCE: 75

Glu Val Gln Leu Val Gln Ser Gly Ala Glu Val Lys Lys Pro Gly Ser
1 5 10 15

```
Ser Val Lys Val Ser Cys Lys Ala Ser Gly Asp Thr Phe Thr Ser Tyr
            20                  25                  30

Ser Phe Asn Trp Val Arg Gln Ala Pro Gly Gln Gly Leu Glu Trp Met
        35                  40                  45

Gly Arg Ile Ile Thr Ile Leu Asp Asp Thr Glu Tyr Ala Pro His Leu
    50                  55                  60

Gln Gly Arg Val Thr Ile Thr Ala Asp Lys Ser Thr Ser Thr Val Tyr
65                  70                  75                  80

Leu Glu Leu Arg Asn Leu Arg Ser Asp Asp Thr Ala Val Tyr Phe Cys
                85                  90                  95

Ala Gly Val Tyr Glu Gly Pro Asn Ser Glu Gly Ser Tyr Asp Asp Tyr
            100                 105                 110

Gly Phe Leu Lys His Trp Gly Gln Gly Thr Leu Val Thr Val Ser Ser
        115                 120                 125


<210> SEQ ID NO 76
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_283 protein sequence - VL

<400> SEQUENCE: 76

Asp Ile Val Met Thr Gln Ser Pro Ala Thr Leu Ser Val Ser Pro Gly
1               5                   10                  15

Glu Arg Ala Thr Leu Ser Cys Arg Ala Ser Glu Ser Val Gly Asn Asp
            20                  25                  30

Leu Ala Trp Tyr Gln Gln Lys Pro Gly Gln Val Pro Arg Leu Leu Ile
        35                  40                  45

Tyr Gly Ala Ser Thr Arg Ala Thr Gly Val Pro Ala Arg Phe Ser Gly
    50                  55                  60

Ser Gly Ser Gly Ala Glu Phe Thr Leu Thr Ile Ser Ser Leu Gln Ser
65                  70                  75                  80

Glu Asp Phe Ala Val Tyr Tyr Cys Gln Gln Tyr Ala Asn Trp Pro Pro
                85                  90                  95

Arg Glu Thr Phe Gly Gln Gly Thr Arg Leu Glu Ile Lys
            100                 105


<210> SEQ ID NO 77
<211> LENGTH: 756
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CID_284 DNA sequence

<400> SEQUENCE: 77

gaagtgcagt tagtgcaatc tggtgccgaa gttaagaaac caggcagctc cgttaaagtg      60

tcttgtaagg catctggcga cactttcacc tcttatagtt ttaactgggt tcgtcaggct     120

ccaggccagg gtttggagtg gatgggtcgt atcattacca tcgacgatga tactgagtac     180

gctcctcatt tacagggtcg tgtaaccatc acagcagaca agtccacatc taccgtatac     240

ttggaactgc gtaacttacg tagcgatgat accgccgttt acttctgcgc aggtgtgtac     300

gaaggtccga actctgaagg ctcgtacgat gactatggtc agctgaaaca ctggggtcag     360
```

```
ggcactctgg tgactgttag ttctggcggt ggtggtagcg gaggcggagg atcaggtgga    420

ggcggcagtg atatcgttat gactcagtcc ccagcaaccc tgtctgtatc tcctggtgag    480

cgtgccaccc tgagctgccg tgcttcagaa tctgtaggca acgatctggc ctggtatcag    540

cagaaaccag gtcaggttcc acgtctgctg atttatggcg cttccacccg tgctaccggt    600

gtaccagctc gtttctctgg gtccggctcc ggcgccgagt tcaccctgac tatctcctct    660

ctgcagtccg aagactttgc cgtgtactac tgccagcagt acgcgaacgt gccaccacgt    720

gagacctttg gtcaagggac acgtttagag attaaa                               756
```

```
<210> SEQ ID NO 78
<211> LENGTH: 237
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_284 Protein sequence, VH+VL

<400> SEQUENCE: 78

Glu Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Thr Ser Tyr
            20                  25                  30

Ser Phe Asn Trp Val Arg Gln Ala Pro Gly Gln Gly Leu Glu Trp Met
        35                  40                  45

Gly Arg Ile Ile Thr Ile Asp Asp Asp Thr Glu Tyr Ala Pro His Leu
    50                  55                  60

Gln Gly Arg Val Thr Ile Thr Ala Asp Lys Ser Thr Ser Thr Val Tyr
65                  70                  75                  80

Leu Glu Leu Arg Asn Leu Arg Ser Asp Asp Thr Ala Val Tyr Phe Cys
                85                  90                  95

Ala Gly Val Tyr Glu Gly Pro Asn Ser Glu Gly Ser Tyr Asp Asp Tyr
            100                 105                 110

Gly Gln Leu Lys His Trp Gly Gln Gly Thr Leu Val Thr Val Ser Ser
        115                 120                 125

Asp Ile Val Met Thr Gln Ser Pro Ala Thr Leu Ser Val Ser Pro Gly
    130                 135                 140

Glu Arg Ala Thr Leu Ser Cys Arg Ala Ser Glu Ser Val Gly Asn Asp
145                 150                 155                 160

Leu Ala Trp Tyr Gln Gln Lys Pro Gly Gln Val Pro Arg Leu Leu Ile
                165                 170                 175

Tyr Gly Ala Ser Thr Arg Ala Thr Gly Val Pro Ala Arg Phe Ser Gly
            180                 185                 190

Ser Gly Ser Gly Ala Glu Phe Thr Leu Thr Ile Ser Ser Leu Gln Ser
        195                 200                 205

Glu Asp Phe Ala Val Tyr Tyr Cys Gln Gln Tyr Ala Asn Val Pro Pro
    210                 215                 220

Arg Glu Thr Phe Gly Gln Gly Thr Arg Leu Glu Ile Lys
225                 230                 235


<210> SEQ ID NO 79
<211> LENGTH: 128
<212> TYPE: PRT
<213> ORGANISM: Artificial Sequence
<220> FEATURE:
```

<223> OTHER INFORMATION: Description of Artificial Sequence: Synthetic
polypeptide
<220> FEATURE:
<223> OTHER INFORMATION: CID_284 protein sequence - VH

<400> SEQUENCE: 79

Glu Val Gln Leu Val Gln Ser Gly Ala Glu Val Lys Lys Pro Gly Ser
1 5 10 15

Ser Val Lys Val Ser Cys Lys Ala Ser Gly Asp Thr Phe Thr Ser Tyr
20 25 30

Ser Phe Asn Trp Val Arg Gln Ala Pro Gly Gln Gly Leu Glu Trp Met
35 40 45

Gly Arg Ile Ile Thr Ile Asp Asp Asp Thr Glu Tyr Ala Pro His Leu
50 55 60

Gln Gly Arg Val Thr Ile Thr Ala Asp Lys Ser Thr Ser Thr Val Tyr
65 70 75 80

Leu Glu Leu Arg Asn Leu Arg Ser Asp Asp Thr Ala Val Tyr Phe Cys
85 90 95

Ala Gly Val Tyr Glu Gly Pro Asn Ser Glu Gly Ser Tyr Asp Asp Tyr
100 105 110

Gly Gln Leu Lys His Trp Gly Gln Gly Thr Leu Val Thr Val Ser Ser
115 120 125

<210> SEQ ID NO 80
<211> LENGTH: 109
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: CID_284 protein sequence - VL

<400> SEQUENCE: 80

Asp Ile Val Met Thr Gln Ser Pro Ala Thr Leu Ser Val Ser Pro Gly
1 5 10 15

Glu Arg Ala Thr Leu Ser Cys Arg Ala Ser Glu Ser Val Gly Asn Asp
20 25 30

Leu Ala Trp Tyr Gln Gln Lys Pro Gly Gln Val Pro Arg Leu Leu Ile
35 40 45

Tyr Gly Ala Ser Thr Arg Ala Thr Gly Val Pro Ala Arg Phe Ser Gly
50 55 60

Ser Gly Ser Gly Ala Glu Phe Thr Leu Thr Ile Ser Ser Leu Gln Ser
65 70 75 80

Glu Asp Phe Ala Val Tyr Tyr Cys Gln Gln Tyr Ala Asn Val Pro Pro
85 90 95

Arg Glu Thr Phe Gly Gln Gly Thr Arg Leu Glu Ile Lys
100 105

<210> SEQ ID NO 81
<211> LENGTH: 756
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: CID_285 DNA sequence

<400> SEQUENCE: 81
gaagtgcagt tagtgcaatc tggtgccgaa gttaagaaac caggcagctc cgttaaagtg 60

```
tcttgtaagg catctggcga cactttcacc tcttatagtt ttaactgggt tcgtcaggct    120

ccaggccagg gtttggagtg gatgggtcgt atcattacca tcgacgatga tactgagtac    180

gctcctcatt tacagggtcg tgtaaccatc acagcagaca agtccacatc taccgtatac    240

ttggaactgc gtaacttacg tagcgatgat accgccgttt acttctgcgc aggtgtgtac    300

gaaggtccga actctgaagg ctcgtacgat gactatggtc agctgaaaca ctggggtcag    360

ggcactctgg tgactgttag ttctggcggt ggtggtagcg gaggcggagg atcaggtgga    420

ggcggcagtg atatcgttat gactcagtcc ccagcaaccc tgtctgtatc tcctggtgag    480

cgtgccaccc tgagctgccg tgcttcagaa tctgtaggca acgatctggc ctggtatcag    540

cagaaaccag gtcaggttcc acgtctgctg atttatggca tctccacccg tgctaccggt    600

gtaccagctc gtttctctgg gtccggctcc ggcgccgagt tcaccctgac tatctcctct    660

ctgcagtccg aagactttgc cgtgtactac tgccagcagt acgcgaacga cccaccacgt    720

gagacctttg gtcaagggac acgtttagag attaaa                              756
```

```
<210> SEQ ID NO 82
<211> LENGTH: 237
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_285 Protein sequence, VH+VL

<400> SEQUENCE: 82

Glu Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Thr Ser Tyr
            20                  25                  30

Ser Phe Asn Trp Val Arg Gln Ala Pro Gly Gln Gly Leu Glu Trp Met
        35                  40                  45

Gly Arg Ile Ile Thr Ile Asp Asp Asp Thr Glu Tyr Ala Pro His Leu
    50                  55                  60

Gln Gly Arg Val Thr Ile Thr Ala Asp Lys Ser Thr Ser Thr Val Tyr
65                  70                  75                  80

Leu Glu Leu Arg Asn Leu Arg Ser Asp Asp Thr Ala Val Tyr Phe Cys
                85                  90                  95

Ala Gly Val Tyr Glu Gly Pro Asn Ser Glu Gly Ser Tyr Asp Asp Tyr
            100                 105                 110

Gly Gln Leu Lys His Trp Gly Gln Gly Thr Leu Val Thr Val Ser Ser
        115                 120                 125

Asp Ile Val Met Thr Gln Ser Pro Ala Thr Leu Ser Val Ser Pro Gly
    130                 135                 140

Glu Arg Ala Thr Leu Ser Cys Arg Ala Ser Glu Ser Val Gly Asn Asp
145                 150                 155                 160

Leu Ala Trp Tyr Gln Gln Lys Pro Gly Gln Val Pro Arg Leu Leu Ile
                165                 170                 175

Tyr Gly Ile Ser Thr Arg Ala Thr Gly Val Pro Ala Arg Phe Ser Gly
            180                 185                 190

Ser Gly Ser Gly Ala Glu Phe Thr Leu Thr Ile Ser Ser Leu Gln Ser
        195                 200                 205

Glu Asp Phe Ala Val Tyr Tyr Cys Gln Gln Tyr Ala Asn Asp Pro Pro
    210                 215                 220
```

```
Arg Glu Thr Phe Gly Gln Gly Thr Arg Leu Glu Ile Lys
225                 230                 235


<210> SEQ ID NO 83
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_285 protein sequence - VH

<400> SEQUENCE: 83

Glu Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Thr Ser Tyr
            20                  25                  30

Ser Phe Asn Trp Val Arg Gln Ala Pro Gly Gln Gly Leu Glu Trp Met
        35                  40                  45

Gly Arg Ile Ile Thr Ile Asp Asp Asp Thr Glu Tyr Ala Pro His Leu
    50                  55                  60

Gln Gly Arg Val Thr Ile Thr Ala Asp Lys Ser Thr Ser Thr Val Tyr
65                  70                  75                  80

Leu Glu Leu Arg Asn Leu Arg Ser Asp Asp Thr Ala Val Tyr Phe Cys
                85                  90                  95

Ala Gly Val Tyr Glu Gly Pro Asn Ser Glu Gly Ser Tyr Asp Asp Tyr
            100                 105                 110

Gly Gln Leu Lys His Trp Gly Gln Gly Thr Leu Val Thr Val Ser Ser
        115                 120                 125


<210> SEQ ID NO 84
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_285 protein sequence - VL

<400> SEQUENCE: 84

Asp Ile Val Met Thr Gln Ser Pro Ala Thr Leu Ser Val Ser Pro Gly
1               5                   10                  15

Glu Arg Ala Thr Leu Ser Cys Arg Ala Ser Glu Ser Val Gly Asn Asp
            20                  25                  30

Leu Ala Trp Tyr Gln Gln Lys Pro Gly Gln Val Pro Arg Leu Leu Ile
        35                  40                  45

Tyr Gly Ile Ser Thr Arg Ala Thr Gly Val Pro Ala Arg Phe Ser Gly
    50                  55                  60

Ser Gly Ser Gly Ala Glu Phe Thr Leu Thr Ile Ser Ser Leu Gln Ser
65                  70                  75                  80

Glu Asp Phe Ala Val Tyr Tyr Cys Gln Gln Tyr Ala Asn Asp Pro Pro
                85                  90                  95

Arg Glu Thr Phe Gly Gln Gly Thr Arg Leu Glu Ile Lys
            100                 105


<210> SEQ ID NO 85
<211> LENGTH: 741
<212> TYPE: DNA
```

<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: CID_436 DNA sequence

<400> SEQUENCE: 85
gatatccaga tgacccagtc cccaatcctg ctgtctgcct ccgttggtga tcgtgtgacc 60
attacctgcc gtgcttcaca ggacgtaagc actgccgtag cttggtctca acagcgtacc 120
aacggcagcc cacgtctgct gatttactcc gcaagttctc tgtatagtgg cgtcccaagc 180
cgttttagcg gctcacgttc cggtactgat ttcaccctga ccatttccag cctgcagcca 240
gaggatatcg cagactacta ctgccagcag cctacttaca ccccaccaac cttcggtgcc 300
ggtaccaagg tagaaatcaa aggcggtggt ggtagcggag gcggaggatc aggtggaggc 360
ggcagtggcg gtggtggttc tgaagtacag ctggttgaat ctggtggtgg tctggtacag 420
ccaggcggtt ctcttcgtct gtcttgcgct gcctctggtt tcaacattcg tgatacctac 480
atccactggg tccgtcagtc tccaggtaaa ggcctggaat gggtcgctga tatcgatcca 540
gacaacggtg atacccgtta cgccgattct gtcaaaggcc gtttcactat cagcgccgac 600
acttccaaaa acaccgccta cctgcagatg aacagcctgc gtgccgaaga caccgccatc 660
tactactgtt ctcgtgacct ggcggatggc tacaacgcat tcgataggtg gggtcagggc 720
accctggtaa ctgtctccag c 741

<210> SEQ ID NO 86
<211> LENGTH: 227
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: CID_436 Protein sequence, VH+VL

<400> SEQUENCE: 86

Asp Ile Gln Met Thr Gln Ser Pro Ile Leu Leu Ser Ala Ser Val Gly
1 5 10 15

Asp Arg Val Thr Ile Thr Cys Arg Ala Ser Gln Asp Val Ser Thr Ala
20 25 30

Val Ala Trp Ser Gln Gln Arg Thr Asn Gly Ser Pro Arg Leu Leu Ile
35 40 45

Tyr Ser Ala Ser Ser Leu Tyr Ser Gly Val Pro Ser Arg Phe Ser Gly
50 55 60

Ser Arg Ser Gly Thr Asp Phe Thr Leu Thr Ile Ser Ser Leu Gln Pro
65 70 75 80

Glu Asp Ile Ala Asp Tyr Tyr Cys Gln Gln Pro Thr Tyr Thr Pro Pro
85 90 95

Thr Phe Gly Ala Gly Thr Lys Val Glu Ile Lys Glu Val Gln Leu Val
100 105 110

Glu Ser Gly Gly Gly Leu Val Gln Pro Gly Gly Ser Leu Arg Leu Ser
115 120 125

Cys Ala Ala Ser Gly Phe Asn Ile Arg Asp Thr Tyr Ile His Trp Val
130 135 140

Arg Gln Ser Pro Gly Lys Gly Leu Glu Trp Val Ala Asp Ile Asp Pro
145 150 155 160

Asp Asn Gly Asp Thr Arg Tyr Ala Asp Ser Val Lys Gly Arg Phe Thr

```
                165                 170                 175

Ile Ser Ala Asp Thr Ser Lys Asn Thr Ala Tyr Leu Gln Met Asn Ser
            180                 185                 190

Leu Arg Ala Glu Asp Thr Ala Ile Tyr Tyr Cys Ser Arg Asp Leu Ala
        195                 200                 205

Asp Gly Tyr Asn Ala Phe Asp Arg Trp Gly Gln Gly Thr Leu Val Thr
    210                 215                 220

Val Ser Ser
225
```

<210> SEQ ID NO 87
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_436 protein sequence - VH

<400> SEQUENCE: 87

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Arg Asp Thr
            20                  25                  30

Tyr Ile His Trp Val Arg Gln Ser Pro Gly Lys Gly Leu Glu Trp Val
        35                  40                  45

Ala Asp Ile Asp Pro Asp Asn Gly Asp Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Ile Tyr Tyr Cys
                85                  90                  95

Ser Arg Asp Leu Ala Asp Gly Tyr Asn Ala Phe Asp Arg Trp Gly Gln
            100                 105                 110

Gly Thr Leu Val Thr Val Ser Ser
        115                 120
```

<210> SEQ ID NO 88
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_436 protein sequence - VL

<400> SEQUENCE: 88

```
Asp Ile Gln Met Thr Gln Ser Pro Ile Leu Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Ser Gln Gln Arg Thr Asn Gly Ser Pro Arg Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80
```

```
Glu Asp Ile Ala Asp Tyr Tyr Cys Gln Gln Pro Thr Tyr Thr Pro Pro
                85                  90                  95

Thr Phe Gly Ala Gly Thr Lys Val Glu Ile Lys
            100                 105


<210> SEQ ID NO 89
<211> LENGTH: 741
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CID_437 DNA sequence

<400> SEQUENCE: 89

gatatccaga tgacccagtc cccaatcctg ctgtctgcct ccgttggtga tcgtgtgacc     60

attacctgcc gtgcttcaca ggacgtaagc actgccgtag cttggtctca acagcgtacc    120

aacggcagcc cacgtctgct gatttactct gcaagttctc tgtatagtgg cgtcccaagc    180

cgttttagcg gctcacgttc cggtactgat ttcaccctga ccatttccag cctgcagcca    240

gaggatatcg cagactacta ctgccagcag ccccccttaca ccccaccaac cttcggtgcc    300

ggtaccaagg tagaaatcaa aggcggtggt ggtagcggag gcggaggatc aggtggaggc    360

ggcagtggcg gtggtggttc tgaagtacag ctggttgaat ctggtggtgg tctggtacag    420

ccaggcggtt ctcttcgtct gtcttgcgct gcctctggtt tcaacattcg tgataccttc    480

atccactggg tccgtcagtc tccaggtaaa ggcctggaat gggtcgctga tatcgatcca    540

gacaacggtg atacccgtta cgccgattct gtcaaaggcc gtttcactat cagcgccgac    600

acttccaaaa acaccgccta cctgcagatg aacagcctgc gtgccgaaga caccgccatc    660

tactactgtt cccgtgaagg tgaggatggc tacaacgcat gggatctgtg gggtcagggc    720

accctggtaa ctgtctccag c                                              741


<210> SEQ ID NO 90
<211> LENGTH: 227
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_437 Protein sequence, VH+VL

<400> SEQUENCE: 90

Asp Ile Gln Met Thr Gln Ser Pro Ile Leu Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Ser Gln Gln Arg Thr Asn Gly Ser Pro Arg Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Ile Ala Asp Tyr Tyr Cys Gln Gln Pro Pro Tyr Thr Pro Pro
                85                  90                  95

Thr Phe Gly Ala Gly Thr Lys Val Glu Ile Lys Glu Val Gln Leu Val
            100                 105                 110
```

```
Glu Ser Gly Gly Gly Leu Val Gln Pro Gly Gly Ser Leu Arg Leu Ser
        115                 120                 125

Cys Ala Ala Ser Gly Phe Asn Ile Arg Asp Thr Phe Ile His Trp Val
    130                 135                 140

Arg Gln Ser Pro Gly Lys Gly Leu Glu Trp Val Ala Asp Ile Asp Pro
145                 150                 155                 160

Asp Asn Gly Asp Thr Arg Tyr Ala Asp Ser Val Lys Gly Arg Phe Thr
                165                 170                 175

Ile Ser Ala Asp Thr Ser Lys Asn Thr Ala Tyr Leu Gln Met Asn Ser
            180                 185                 190

Leu Arg Ala Glu Asp Thr Ala Ile Tyr Tyr Cys Ser Arg Glu Gly Glu
        195                 200                 205

Asp Gly Tyr Asn Ala Trp Asp Leu Trp Gly Gln Gly Thr Leu Val Thr
    210                 215                 220

Val Ser Ser
225


<210> SEQ ID NO 91
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_437 protein sequence - VH

<400> SEQUENCE: 91

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Arg Asp Thr
            20                  25                  30

Phe Ile His Trp Val Arg Gln Ser Pro Gly Lys Gly Leu Glu Trp Val
        35                  40                  45

Ala Asp Ile Asp Pro Asp Asn Gly Asp Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Ile Tyr Tyr Cys
                85                  90                  95

Ser Arg Glu Gly Glu Asp Gly Tyr Asn Ala Trp Asp Leu Trp Gly Gln
            100                 105                 110

Gly Thr Leu Val Thr Val Ser Ser
        115                 120


<210> SEQ ID NO 92
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_437 protein sequence - VL

<400> SEQUENCE: 92

Asp Ile Gln Met Thr Gln Ser Pro Ile Leu Leu Ser Ala Ser Val Gly
1               5                   10                  15

Asp Arg Val Thr Ile Thr Cys Arg Ala Ser Gln Asp Val Ser Thr Ala
            20                  25                  30
```

Val Ala Trp Ser Gln Gln Arg Thr Asn Gly Ser Pro Arg Leu Leu Ile
35 40 45

Tyr Ser Ala Ser Ser Leu Tyr Ser Gly Val Pro Ser Arg Phe Ser Gly
50 55 60

Ser Arg Ser Gly Thr Asp Phe Thr Leu Thr Ile Ser Ser Leu Gln Pro
65 70 75 80

Glu Asp Ile Ala Asp Tyr Tyr Cys Gln Gln Pro Pro Tyr Thr Pro Pro
85 90 95

Thr Phe Gly Ala Gly Thr Lys Val Glu Ile Lys
100 105

<210> SEQ ID NO 93
<211> LENGTH: 729
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: CID_331 DNA sequence

<400> SEQUENCE: 93
caggtacagc tggttcagtc cggcgccgaa gtcaaaaagc caggttcttc cgtgaaagtt 60
tcctgtaaag cttctggtta caccttcact gacctgggca ttggctgggt tcgtcaggct 120
ccaggtcagg gtctggaatg gatgggctgg attaacacta tcactggtga gccattctat 180
aacccaaaat tcaaaggccg tgttaccatc acagccgata aaagcactag cactgcctac 240
atggaactga gtagtctgcg ttccgaggac accgctgttt actactgcac tcgtgatcat 300
ccactcggtc tggattattg gggtcagggc acaaccgtga ccgtttcctc cggcggtggt 360
ggtagcggag gcggaggatc aggtggaggc ggcagtgaca tcgttatgac ccaatctcca 420
gacagcctgg ccgtgtctct tggcgaacgt gcaaccatta actgccgtgc ttctcagtct 480
ctcgatgtta acggcgtttc ctacctgaac tggtaccaac agaaaccagg ccagccacca 540
aaatttctga tctacaaagc cagcaacctt gaatctggcg ttccagatcg tttctctggc 600
tctgggagcg gcactgactt cactcttacc atcagcagcc tgcaagctga agatgtcgct 660
gtttattatt gccagcagtc ccgtgaagac ccatacacct ttgggggcgg caccaaagtg 720
gaaatcaaa 729

<210> SEQ ID NO 94
<211> LENGTH: 228
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_331 Protein sequence, VH+VL

<400> SEQUENCE: 94

Gln Val Gln Leu Val Gln Ser Gly Ala Glu Val Lys Lys Pro Gly Ser
1 5 10 15

Ser Val Lys Val Ser Cys Lys Ala Ser Gly Tyr Thr Phe Thr Asp Leu
20 25 30

Gly Ile Gly Trp Val Arg Gln Ala Pro Gly Gln Gly Leu Glu Trp Met
35 40 45

Gly Trp Ile Asn Thr Ile Thr Gly Glu Pro Phe Tyr Asn Pro Lys Phe
50 55 60

Lys Gly Arg Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Thr Arg Asp His Pro Leu Gly Leu Asp Tyr Trp Gly Gln Gly Thr Thr
100 105 110

Val Thr Val Ser Ser Asp Ile Val Met Thr Gln Ser Pro Asp Ser Leu
115 120 125

Ala Val Ser Leu Gly Glu Arg Ala Thr Ile Asn Cys Arg Ala Ser Gln
130 135 140

Ser Leu Asp Val Asn Gly Val Ser Tyr Leu Asn Trp Tyr Gln Gln Lys
145 150 155 160

Pro Gly Gln Pro Pro Lys Phe Leu Ile Tyr Lys Ala Ser Asn Leu Glu
165 170 175

Ser Gly Val Pro Asp Arg Phe Ser Gly Ser Gly Ser Gly Thr Asp Phe
180 185 190

Thr Leu Thr Ile Ser Ser Leu Gln Ala Glu Asp Val Ala Val Tyr Tyr
195 200 205

Cys Gln Gln Ser Arg Glu Asp Pro Tyr Thr Phe Gly Gly Gly Thr Lys
210 215 220

Val Glu Ile Lys
225

<210> SEQ ID NO 95
<211> LENGTH: 117
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: CID_331 protein sequence - VH

<400> SEQUENCE: 95

Gln Val Gln Leu Val Gln Ser Gly Ala Glu Val Lys Lys Pro Gly Ser
1 5 10 15

Ser Val Lys Val Ser Cys Lys Ala Ser Gly Tyr Thr Phe Thr Asp Leu
20 25 30

Gly Ile Gly Trp Val Arg Gln Ala Pro Gly Gln Gly Leu Glu Trp Met
35 40 45

Gly Trp Ile Asn Thr Ile Thr Gly Glu Pro Phe Tyr Asn Pro Lys Phe
50 55 60

Lys Gly Arg Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Thr Arg Asp His Pro Leu Gly Leu Asp Tyr Trp Gly Gln Gly Thr Thr
100 105 110

Val Thr Val Ser Ser
115

<210> SEQ ID NO 96
<211> LENGTH: 111
<212> TYPE: PRT
<213> ORGANISM: Artificial Sequence
<220> FEATURE:
<223> OTHER INFORMATION: Description of Artificial Sequence: Synthetic
polypeptide <220> FEATURE:
<223> OTHER INFORMATION: CID_331 protein sequence - VL

<400> SEQUENCE: 96

Asp Ile Val Met Thr Gln Ser Pro Asp Ser Leu Ala Val Ser Leu Gly
1               5                   10                  15

Glu Arg Ala Thr Ile Asn Cys Arg Ala Ser Gln Ser Leu Asp Val Asn
            20                  25                  30

Gly Val Ser Tyr Leu Asn Trp Tyr Gln Gln Lys Pro Gly Gln Pro Pro
        35                  40                  45

Lys Phe Leu Ile Tyr Lys Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Arg
                85                  90                  95

Glu Asp Pro Tyr Thr Phe Gly Gly Gly Thr Lys Val Glu Ile Lys
            100                 105                 110

<210> SEQ ID NO 97
<211> LENGTH: 729
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: CID_332 DNA sequence

<400> SEQUENCE: 97
caggtacagc tggttcagtc cggcgccgaa gtcaaaaagc caggttcttc cgtgaaagtt 60
tcctgtaaag cttctggtta caccttcact gacctgggca ttggctgggt tcgtcaggct 120
ccaggtcagg gtctggaatg gatgggctgg attaacactc atactggtga gccatacgac 180
aacccaaaat tcaaaggccg tgttaccatc acagccgata aaagcactag cactgcctac 240
atggaactga gtagtctgcg ttccgaggac accgctgttt actactgcac tcgtgatcat 300
ccactcggtc tggattattg gggtcagggc acaaccgtga ccgtttcctc cggcggtggt 360
ggtagcggag gcggaggatc aggtggaggc ggcagtgaca tcgttatgac ccaatctcca 420
gacagcctgg ccgtgtctct tggcgaacgt gcaaccatta actgccgttc ttctcagtct 480
gttgatgtta acggcgtttc ctacctggac tggtaccaac agaaaccagg ccagccacca 540
aaacttctga tcacgaaagc cagcaaccgg gaatctggcg ttccagatcg tttctctggc 600
tctgggagcg gcactgactt cactcttacc atcagcagcc tgcaagctga agatgtcgct 660
gtttattatt gccagcagaa ccgtgaagac ccatacacct ttgggggcgg caccaaagtg 720
gaaatcaaa 729

<210> SEQ ID NO 98
<211> LENGTH: 228
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_332 Protein sequence, VH+VL

<400> SEQUENCE: 98

Gln Val Gln Leu Val Gln Ser Gly Ala Glu Val Lys Lys Pro Gly Ser

```
1               5                   10                  15

Ser Val Lys Val Ser Cys Lys Ala Ser Gly Tyr Thr Phe Thr Asp Leu
            20                  25                  30

Gly Ile Gly Trp Val Arg Gln Ala Pro Gly Gln Gly Leu Glu Trp Met
        35                  40                  45

Gly Trp Ile Asn Thr His Thr Gly Glu Pro Tyr Asp Asn Pro Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Asp His Pro Leu Gly Leu Asp Tyr Trp Gly Gln Gly Thr Thr
            100                 105                 110

Val Thr Val Ser Ser Asp Ile Val Met Thr Gln Ser Pro Asp Ser Leu
        115                 120                 125

Ala Val Ser Leu Gly Glu Arg Ala Thr Ile Asn Cys Arg Ser Ser Gln
    130                 135                 140

Ser Val Asp Val Asn Gly Val Ser Tyr Leu Asp Trp Tyr Gln Gln Lys
145                 150                 155                 160

Pro Gly Gln Pro Pro Lys Leu Leu Ile Thr Lys Ala Ser Asn Arg Glu
                165                 170                 175

Ser Gly Val Pro Asp Arg Phe Ser Gly Ser Gly Ser Gly Thr Asp Phe
            180                 185                 190

Thr Leu Thr Ile Ser Ser Leu Gln Ala Glu Asp Val Ala Val Tyr Tyr
        195                 200                 205

Cys Gln Gln Asn Arg Glu Asp Pro Tyr Thr Phe Gly Gly Gly Thr Lys
    210                 215                 220

Val Glu Ile Lys
225


<210> SEQ ID NO 99
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_332 protein sequence - VH

<400> SEQUENCE: 99

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Leu
            20                  25                  30

Gly Ile Gly Trp Val Arg Gln Ala Pro Gly Gln Gly Leu Glu Trp Met
        35                  40                  45

Gly Trp Ile Asn Thr His Thr Gly Glu Pro Tyr Asp Asn Pro Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Asp His Pro Leu Gly Leu Asp Tyr Trp Gly Gln Gly Thr Thr
            100                 105                 110

Val Thr Val Ser Ser
```

115

<210> SEQ ID NO 100
<211> LENGTH: 111
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: CID_332 protein sequence - VL

<400> SEQUENCE: 100

Asp Ile Val Met Thr Gln Ser Pro Asp Ser Leu Ala Val Ser Leu Gly
1 5 10 15

Glu Arg Ala Thr Ile Asn Cys Arg Ser Ser Gln Ser Val Asp Val Asn
20 25 30

Gly Val Ser Tyr Leu Asp Trp Tyr Gln Gln Lys Pro Gly Gln Pro Pro
35 40 45

Lys Leu Leu Ile Thr Lys Ala Ser Asn Arg Glu Ser Gly Val Pro Asp
50 55 60

Arg Phe Ser Gly Ser Gly Ser Gly Thr Asp Phe Thr Leu Thr Ile Ser
65 70 75 80

Ser Leu Gln Ala Glu Asp Val Ala Val Tyr Tyr Cys Gln Gln Asn Arg
85 90 95

Glu Asp Pro Tyr Thr Phe Gly Gly Gly Thr Lys Val Glu Ile Lys
100 105 110

<210> SEQ ID NO 101
<211> LENGTH: 729
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: CID_333 DNA sequence

<400> SEQUENCE: 101
caggtacagc tggttcagtc cggcgccgaa gtcaaaaagc caggttcttc cgtgaaagtt 60
tcctgtaaag cttctggtta caccttcact gacctgggca ttggttgggt tcgtcaggct 120
ccaggtcagg gtctggaatg gatgggctgg attaacacta tcactggtga gccattctat 180
aacccaaaat tcaaaggccg tgttaccatc acagccgata aaagcactag cactgcctac 240
atggaactga gtagtctgcg ttccgaggac accgctgttt actactgcac tcgtgatcat 300
ccactcggtc tggattattg gggtcagggc acaaccgtga ccgtttcctc cggcggtggt 360
ggtagcggag gcggaggatc aggtggaggc ggcagtgaca tcgttatgac ccaatctcca 420
gacagcctgg ccgtgtctct tggcgaacgt gcaaccatta actgccgtgc ttctcagtct 480
gttgatgtta acggcgtttc ctacctgaac tggtaccaac agaaaccagg ccagccacca 540
aaatttctga tctacaaagc cagcaacctt gaatctggcg ttccagatcg tttctctggc 600
tctgggagcg gcactgactt cactcttacc atcagcagcc tgcaagctga agatgtcgct 660
gtttattatt gccagcagtc ccgtgaagac ccatacacct ttgggggcgg caccaaagtg 720
gaaatcaaa 729

<210> SEQ ID NO 102
<211> LENGTH: 228
<212> TYPE: PRT

<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: CID_333 Protein sequence, VH+VL

<400> SEQUENCE: 102

Gln Val Gln Leu Val Gln Ser Gly Ala Glu Val Lys Lys Pro Gly Ser
1 5 10 15

Ser Val Lys Val Ser Cys Lys Ala Ser Gly Tyr Thr Phe Thr Asp Leu
20 25 30

Gly Ile Gly Trp Val Arg Gln Ala Pro Gly Gln Gly Leu Glu Trp Met
35 40 45

Gly Trp Ile Asn Thr Ile Thr Gly Glu Pro Phe Tyr Asn Pro Lys Phe
50 55 60

Lys Gly Arg Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Thr Arg Asp His Pro Leu Gly Leu Asp Tyr Trp Gly Gln Gly Thr Thr
100 105 110

Val Thr Val Ser Ser Asp Ile Val Met Thr Gln Ser Pro Asp Ser Leu
115 120 125

Ala Val Ser Leu Gly Glu Arg Ala Thr Ile Asn Cys Arg Ala Ser Gln
130 135 140

Ser Val Asp Val Asn Gly Val Ser Tyr Leu Asn Trp Tyr Gln Gln Lys
145 150 155 160

Pro Gly Gln Pro Pro Lys Phe Leu Ile Tyr Lys Ala Ser Asn Leu Glu
165 170 175

Ser Gly Val Pro Asp Arg Phe Ser Gly Ser Gly Ser Gly Thr Asp Phe
180 185 190

Thr Leu Thr Ile Ser Ser Leu Gln Ala Glu Asp Val Ala Val Tyr Tyr
195 200 205

Cys Gln Gln Ser Arg Glu Asp Pro Tyr Thr Phe Gly Gly Gly Thr Lys
210 215 220

Val Glu Ile Lys
225

<210> SEQ ID NO 103
<211> LENGTH: 117
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: CID_333 protein sequence - VH

<400> SEQUENCE: 103

Gln Val Gln Leu Val Gln Ser Gly Ala Glu Val Lys Lys Pro Gly Ser
1 5 10 15

Ser Val Lys Val Ser Cys Lys Ala Ser Gly Tyr Thr Phe Thr Asp Leu
20 25 30

Gly Ile Gly Trp Val Arg Gln Ala Pro Gly Gln Gly Leu Glu Trp Met
35 40 45

Gly Trp Ile Asn Thr Ile Thr Gly Glu Pro Phe Tyr Asn Pro Lys Phe
50 55 60

Lys Gly Arg Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Thr Arg Asp His Pro Leu Gly Leu Asp Tyr Trp Gly Gln Gly Thr Thr
100 105 110

Val Thr Val Ser Ser
115

<210> SEQ ID NO 104
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_333 protein sequence - VL

<400> SEQUENCE: 104

Asp Ile Val Met Thr Gln Ser Pro Asp Ser Leu Ala Val Ser Leu Gly
1 5 10 15

Glu Arg Ala Thr Ile Asn Cys Arg Ala Ser Gln Ser Val Asp Val Asn
20 25 30

Gly Val Ser Tyr Leu Asn Trp Tyr Gln Gln Lys Pro Gly Gln Pro Pro
35 40 45

Lys Phe Leu Ile Tyr Lys Ala Ser Asn Leu Glu Ser Gly Val Pro Asp
50 55 60

Arg Phe Ser Gly Ser Gly Ser Gly Thr Asp Phe Thr Leu Thr Ile Ser
65 70 75 80

Ser Leu Gln Ala Glu Asp Val Ala Val Tyr Tyr Cys Gln Gln Ser Arg
85 90 95

Glu Asp Pro Tyr Thr Phe Gly Gly Gly Thr Lys Val Glu Ile Lys
100 105 110

<210> SEQ ID NO 105
<211> LENGTH: 729
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: CID_323 DNA sequence

<400> SEQUENCE: 105
gaagtccaac tggtgcaatc tggcccagaa ctgaagaaac caggcgcaag cgtgaaagtt 60
tcttgcaaag cttccggcta taccttcacc gaccttggta tgaattgggt gcgtcaggct 120
ccaggccagg gtctggaatg gatgggctgg attaacaccc acaccggcat gccattctat 180
gccgatgact tcaaaggtcg tttcgtcttc agcctggata cttccgtgtc tactgcatac 240
ctgcaaattt caagcttaaa agcagaagat actgctgttt actactgtgc ccgtgatcac 300
ccactgggcc tggactattg gggccagggc accctggtaa ccgtttcctc tggcggtggt 360
ggtagcggag gcggaggatc aggtggaggc ggcagtgaca ttcaggtaac tcagagccct 420
tcttctcttt ccgcatctgt tggtgaccgt gttaccatca cctgtatcac ctctcaatcc 480
gtcgatgtta acggtgtttc ctacctgaac tggtaccagc agaaaccagg caaggtccca 540
aaatttctga tctacaaggc ctccaacctg cggcctggtg tcccttcccg tttctctggt 600

```
tccggctcag gtacagactt cactctgacc atctccagcc tgcaaccaga agatgttgct    660

acctactatt gtcagcagag ccgtgaagac ccatacacct tcggccaggg caccaaagtg    720

gaaatcaaa                                                            729


<210> SEQ ID NO 106
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_323 Protein sequence, VH+VL

<400> SEQUENCE: 106

Glu Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asp Leu
            20                  25                  30

Gly Met Asn Trp Val Arg Gln Ala Pro Gly Gln Gly Leu Glu Trp Met
        35                  40                  45

Gly Trp Ile Asn Thr His Thr Gly Met Pro Phe Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Asp His Pro Leu Gly Leu Asp Tyr Trp Gly Gln Gly Thr Leu
            100                 105                 110

Val Thr Val Ser Ser Asp Ile Gln Val Thr Gln Ser Pro Ser Ser Leu
        115                 120                 125

Ser Ala Ser Val Gly Asp Arg Val Thr Ile Thr Cys Ile Thr Ser Gln
    130                 135                 140

Ser Val Asp Val Asn Gly Val Ser Tyr Leu Asn Trp Tyr Gln Gln Lys
145                 150                 155                 160

Pro Gly Lys Val Pro Lys Phe Leu Ile Tyr Lys Ala Ser Asn Leu Arg
                165                 170                 175

Pro Gly Val Pro Ser Arg Phe Ser Gly Ser Gly Ser Gly Thr Asp Phe
            180                 185                 190

Thr Leu Thr Ile Ser Ser Leu Gln Pro Glu Asp Val Ala Thr Tyr Tyr
        195                 200                 205

Cys Gln Gln Ser Arg Glu Asp Pro Tyr Thr Phe Gly Gln Gly Thr Lys
    210                 215                 220

Val Glu Ile Lys
225


<210> SEQ ID NO 107
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_323 protein sequence - VH

<400> SEQUENCE: 107

Glu Val Gln Leu Val Gln Ser Gly Pro Glu Leu Lys Lys Pro Gly Ala
1               5                   10                  15
```

```
Ser Val Lys Val Ser Cys Lys Ala Ser Gly Tyr Thr Phe Thr Asp Leu
            20                  25                  30

Gly Met Asn Trp Val Arg Gln Ala Pro Gly Gln Gly Leu Glu Trp Met
        35                  40                  45

Gly Trp Ile Asn Thr His Thr Gly Met Pro Phe Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Asp His Pro Leu Gly Leu Asp Tyr Trp Gly Gln Gly Thr Leu
            100                 105                 110

Val Thr Val Ser Ser
        115


<210> SEQ ID NO 108
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_323 protein sequence - VL

<400> SEQUENCE: 108

Asp Ile Gln Val Thr Gln Ser Pro Ser Ser Leu Ser Ala Ser Val Gly
1               5                   10                  15

Asp Arg Val Thr Ile Thr Cys Ile Thr Ser Gln Ser Val Asp Val Asn
            20                  25                  30

Gly Val Ser Tyr Leu Asn Trp Tyr Gln Gln Lys Pro Gly Lys Val Pro
        35                  40                  45

Lys Phe Leu Ile Tyr Lys Ala Ser Asn Leu Arg Pro Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Val Ala Thr Tyr Tyr Cys Gln Gln Ser Arg
                85                  90                  95

Glu Asp Pro Tyr Thr Phe Gly Gln Gly Thr Lys Val Glu Ile Lys
            100                 105                 110


<210> SEQ ID NO 109
<211> LENGTH: 729
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CID_324 DNA sequence

<400> SEQUENCE: 109

gaagtccaac tggtgcaatc tggcccagaa ctgaagaaac caggcgcaag cgtgaaagtt     60

tcttgcaaag gttccggcta taccttcacc gaccttggta tcaattgggt gcgtcaggct    120

ccaggccagg gtctggaatg gatgggctgg attaacaccc acaccggcga accattctat    180

gccgatgact tcaaaggtcg tttcgtcttc agcctggata cttccgtgtc tactgcatac    240

ctgcaaattt caagcttaaa agcagaagat actgctgttt actactgtac tcgtgatcac    300
```

```
ccactgggcc tggactattg gggccagggc accctggtaa ccgtttcctc tggcggtggt    360

ggtagcggag gcggaggatc aggtggaggc ggcagtgaca ttcaggtaac tcagagccct    420

tcttctcttt ccgcatctgt tggtgaccgt gttaccatca cctgtatcac ctctcaatcc    480

gtcgatgtta acggtgtttc ctacctgaac tggtaccagc agaaaccagg caaggtccca    540

aaatttctga tctacaaggc ctcccgcctg cggtctggtg tcccttcccg tttctctggt    600

tccggctcag gtacagactt cactctgacc atctccagcc tgcaaccaga agatgttgct    660

acctactatt gtcagcagag ccgtgaagac ccatacacct tcggccaggg caccaaagtg    720

gaaatcaaa                                                            729


<210> SEQ ID NO 110
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_324 Protein sequence, VH+VL

<400> SEQUENCE: 110

Glu Val Gln Leu Val Gln Ser Gly Pro Glu Leu Lys Lys Pro Gly Ala
1               5                   10                  15

Ser Val Lys Val Ser Cys Lys Gly Ser Gly Tyr Thr Phe Thr Asp Leu
            20                  25                  30

Gly Ile Asn Trp Val Arg Gln Ala Pro Gly Gln Gly Leu Glu Trp Met
        35                  40                  45

Gly Trp Ile Asn Thr His Thr Gly Glu Pro Phe Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Thr Arg Asp His Pro Leu Gly Leu Asp Tyr Trp Gly Gln Gly Thr Leu
            100                 105                 110

Val Thr Val Ser Ser Asp Ile Gln Val Thr Gln Ser Pro Ser Ser Leu
        115                 120                 125

Ser Ala Ser Val Gly Asp Arg Val Thr Ile Thr Cys Ile Thr Ser Gln
    130                 135                 140

Ser Val Asp Val Asn Gly Val Ser Tyr Leu Asn Trp Tyr Gln Gln Lys
145                 150                 155                 160

Pro Gly Lys Val Pro Lys Phe Leu Ile Tyr Lys Ala Ser Arg Leu Arg
                165                 170                 175

Ser Gly Val Pro Ser Arg Phe Ser Gly Ser Gly Ser Gly Thr Asp Phe
            180                 185                 190

Thr Leu Thr Ile Ser Ser Leu Gln Pro Glu Asp Val Ala Thr Tyr Tyr
        195                 200                 205

Cys Gln Gln Ser Arg Glu Asp Pro Tyr Thr Phe Gly Gln Gly Thr Lys
    210                 215                 220

Val Glu Ile Lys
225


<210> SEQ ID NO 111
<211> LENGTH: 117
<212> TYPE: PRT
<213> ORGANISM: Artificial Sequence
```

<220> FEATURE:
<223> OTHER INFORMATION: Description of Artificial Sequence: Synthetic
polypeptide
<220> FEATURE:
<223> OTHER INFORMATION: CID_324 protein sequence - VH

<400> SEQUENCE: 111

Glu Val Gln Leu Val Gln Ser Gly Pro Glu Leu Lys Lys Pro Gly Ala
1 5 10 15

Ser Val Lys Val Ser Cys Lys Gly Ser Gly Tyr Thr Phe Thr Asp Leu
20 25 30

Gly Ile Asn Trp Val Arg Gln Ala Pro Gly Gln Gly Leu Glu Trp Met
35 40 45

Gly Trp Ile Asn Thr His Thr Gly Glu Pro Phe Tyr Ala Asp Asp Phe
50 55 60

Lys Gly Arg Phe Val Phe Ser Leu Asp Thr Ser Val Ser Thr Ala Tyr
65 70 75 80

Leu Gln Ile Ser Ser Leu Lys Ala Glu Asp Thr Ala Val Tyr Tyr Cys
85 90 95

Thr Arg Asp His Pro Leu Gly Leu Asp Tyr Trp Gly Gln Gly Thr Leu
100 105 110

Val Thr Val Ser Ser
115

<210> SEQ ID NO 112
<211> LENGTH: 111
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: CID_324 protein sequence - VL

<400> SEQUENCE: 112

Asp Ile Gln Val Thr Gln Ser Pro Ser Ser Leu Ser Ala Ser Val Gly
1 5 10 15

Asp Arg Val Thr Ile Thr Cys Ile Thr Ser Gln Ser Val Asp Val Asn
20 25 30

Gly Val Ser Tyr Leu Asn Trp Tyr Gln Gln Lys Pro Gly Lys Val Pro
35 40 45

Lys Phe Leu Ile Tyr Lys Ala Ser Arg Leu Arg Ser Gly Val Pro Ser
50 55 60

Arg Phe Ser Gly Ser Gly Ser Gly Thr Asp Phe Thr Leu Thr Ile Ser
65 70 75 80

Ser Leu Gln Pro Glu Asp Val Ala Thr Tyr Tyr Cys Gln Gln Ser Arg
85 90 95

Glu Asp Pro Tyr Thr Phe Gly Gln Gly Thr Lys Val Glu Ile Lys
100 105 110

<210> SEQ ID NO 113
<211> LENGTH: 729
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: CID_325 DNA sequence

<400> SEQUENCE: 113

```
gaagtccaac tggtgcaatc tggcccagaa ctgaagaaac caggcgcaag cgtgaaagtt     60

tcttgcaaag cttccggcta taccttcacc gaccttggta tcggttgggt gcgtcaggct    120

ccaggccagg gtctggaatg gatgggctgg attaacaccc acaccggcga accattctat    180

gccgatgact tcaaaggtcg tttcgtcttc agcctggata cttccgtgtc tactgcatac    240

ctgcaaattt caagcttaaa agcagaagat actgctgttt actactgtac tcgtgatcac    300

ccattgggcc tggactattg gggccagggc accctggtaa ccgtttcctc tggcggtggt    360

ggtagcggag gcggaggatc aggtggaggc ggcagtgaca ttcaggtaac tcagagccct    420

tcttctcttt ccgcatctgt tggtgaccgt gttaccatca cctgtatcac ctctcaatcc    480

gtcgatgtta acggtctttc ctacctgaac tggtaccagc agaaaccagg caaggtcaca    540

aaatttctga tctacaaggc ctccaacctg ggtctggtg tcccttcccg tttctctggt     600

tccggctcag gtacagactt cactctgacc atctccagcc tgcaaccaga agatgttgct    660

acctactatt gtcagcagag ccgtgaagac ccatacacct tcggccaggg caccaaagtg    720

gaaatcaaa                                                            729
```

```
<210> SEQ ID NO 114
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_325 Protein sequence, VH+VL

<400> SEQUENCE: 114

Glu Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asp Leu
            20                  25                  30

Gly Ile Gly Trp Val Arg Gln Ala Pro Gly Gln Gly Leu Glu Trp Met
        35                  40                  45

Gly Trp Ile Asn Thr His Thr Gly Glu Pro Phe Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Thr Arg Asp His Pro Leu Gly Leu Asp Tyr Trp Gly Gln Gly Thr Leu
            100                 105                 110

Val Thr Val Ser Ser Asp Ile Gln Val Thr Gln Ser Pro Ser Ser Leu
        115                 120                 125

Ser Ala Ser Val Gly Asp Arg Val Thr Ile Thr Cys Ile Thr Ser Gln
    130                 135                 140

Ser Val Asp Val Asn Gly Leu Ser Tyr Leu Asn Trp Tyr Gln Gln Lys
145                 150                 155                 160

Pro Gly Lys Val Thr Lys Phe Leu Ile Tyr Lys Ala Ser Asn Leu Gly
                165                 170                 175

Ser Gly Val Pro Ser Arg Phe Ser Gly Ser Gly Ser Gly Thr Asp Phe
            180                 185                 190

Thr Leu Thr Ile Ser Ser Leu Gln Pro Glu Asp Val Ala Thr Tyr Tyr
        195                 200                 205

Cys Gln Gln Ser Arg Glu Asp Pro Tyr Thr Phe Gly Gln Gly Thr Lys
```

```
    210                 215                 220

Val Glu Ile Lys
225


<210> SEQ ID NO 115
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_325 protein sequence - VH

<400> SEQUENCE: 115

Glu Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asp Leu
            20                  25                  30

Gly Ile Gly Trp Val Arg Gln Ala Pro Gly Gln Gly Leu Glu Trp Met
        35                  40                  45

Gly Trp Ile Asn Thr His Thr Gly Glu Pro Phe Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Thr Arg Asp His Pro Leu Gly Leu Asp Tyr Trp Gly Gln Gly Thr Leu
            100                 105                 110

Val Thr Val Ser Ser
        115


<210> SEQ ID NO 116
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_325 protein sequence - VL

<400> SEQUENCE: 116

Asp Ile Gln Val Thr Gln Ser Pro Ser Ser Leu Ser Ala Ser Val Gly
1               5                   10                  15

Asp Arg Val Thr Ile Thr Cys Ile Thr Ser Gln Ser Val Asp Val Asn
            20                  25                  30

Gly Leu Ser Tyr Leu Asn Trp Tyr Gln Gln Lys Pro Gly Lys Val Thr
        35                  40                  45

Lys Phe Leu Ile Tyr Lys Ala Ser Asn Leu Gly Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Val Ala Thr Tyr Tyr Cys Gln Gln Ser Arg
                85                  90                  95

Glu Asp Pro Tyr Thr Phe Gly Gln Gly Thr Lys Val Glu Ile Lys
            100                 105                 110


<210> SEQ ID NO 117
<211> LENGTH: 729
```

<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: CID_326 DNA sequence

<400> SEQUENCE: 117

```
gaagtccaac tggtgcaatc tggcccagaa ctgaagaaac caggcgcaag cgtgaaagtt     60

tcttgcaaag cttccggcta taccttcacc gaccttggta tgaattgggt gcgtcaggct    120

ccaggccagg gtctggaatg gatgggctgg attaacaccc acaccggcaa gccattctat    180

gccgatgact tcaaaggtcg tttcgtcttc agcctggata cttccgtgtc tactgcatac    240

ctgcaaattt caagcttaaa agcagaagat actgctgttt actactgtac tcgtgatcac    300

ccattgggcc tggactattg gggccagggc accctggtaa ccgtttcctc tggcggtggt    360

ggtagcggag gcggaggatc aggtggaggc ggcagtgaca ttcaggtaac tcagagccct    420

tcttctcttt ccgcatctgt tggtgaccgt gttaccatca cctgtatcac ctctcaatcc    480

gtcgatgtta acggtgtttc ctacctgaac tggtaccagc agaaaccagg caaggtccca    540

aaatttctga tctacaaggc ctccaacctg cggtctggtg tcccttcccg tttctctggt    600

tccggctcag gtacagactt cactctgacc atctccagcc tgcaaccaga agatgttgct    660

acctactatt gtcagcagag ccgtgaagac ccatacacct tcggccaggg caccaaagtg    720

gaaatcaaa                                                            729
```

<210> SEQ ID NO 118
<211> LENGTH: 228
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_326 Protein sequence, VH+VL

<400> SEQUENCE: 118

```
Glu Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asp Leu
            20                  25                  30

Gly Met Asn Trp Val Arg Gln Ala Pro Gly Gln Gly Leu Glu Trp Met
        35                  40                  45

Gly Trp Ile Asn Thr His Thr Gly Lys Pro Phe Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Thr Arg Asp His Pro Leu Gly Leu Asp Tyr Trp Gly Gln Gly Thr Leu
            100                 105                 110

Val Thr Val Ser Ser Asp Ile Gln Val Thr Gln Ser Pro Ser Ser Leu
        115                 120                 125

Ser Ala Ser Val Gly Asp Arg Val Thr Ile Thr Cys Ile Thr Ser Gln
    130                 135                 140

Ser Val Asp Val Asn Gly Val Ser Tyr Leu Asn Trp Tyr Gln Gln Lys
145                 150                 155                 160
```

```
Pro Gly Lys Val Pro Lys Phe Leu Ile Tyr Lys Ala Ser Asn Leu Arg
                165                 170                 175

Ser Gly Val Pro Ser Arg Phe Ser Gly Ser Gly Ser Gly Thr Asp Phe
            180                 185                 190

Thr Leu Thr Ile Ser Ser Leu Gln Pro Glu Asp Val Ala Thr Tyr Tyr
        195                 200                 205

Cys Gln Gln Ser Arg Glu Asp Pro Tyr Thr Phe Gly Gln Gly Thr Lys
    210                 215                 220

Val Glu Ile Lys
225
```

<210> SEQ ID NO 119
<211> LENGTH: 117
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_326 protein sequence - VH

<400> SEQUENCE: 119

```
Glu Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asp Leu
            20                  25                  30

Gly Met Asn Trp Val Arg Gln Ala Pro Gly Gln Gly Leu Glu Trp Met
        35                  40                  45

Gly Trp Ile Asn Thr His Thr Gly Lys Pro Phe Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Thr Arg Asp His Pro Leu Gly Leu Asp Tyr Trp Gly Gln Gly Thr Leu
            100                 105                 110

Val Thr Val Ser Ser
        115
```

<210> SEQ ID NO 120
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_326 protein sequence - VL

<400> SEQUENCE: 120

```
Asp Ile Gln Val Thr Gln Ser Pro Ser Ser Leu Ser Ala Ser Val Gly
1               5                   10                  15

Asp Arg Val Thr Ile Thr Cys Ile Thr Ser Gln Ser Val Asp Val Asn
            20                  25                  30

Gly Val Ser Tyr Leu Asn Trp Tyr Gln Gln Lys Pro Gly Lys Val Pro
        35                  40                  45

Lys Phe Leu Ile Tyr Lys Ala Ser Asn Leu Arg Ser Gly Val Pro Ser
    50                  55                  60

Arg Phe Ser Gly Ser Gly Ser Gly Thr Asp Phe Thr Leu Thr Ile Ser
65                  70                  75                  80
```

```
Ser Leu Gln Pro Glu Asp Val Ala Thr Tyr Tyr Cys Gln Gln Ser Arg
                85                  90                  95

Glu Asp Pro Tyr Thr Phe Gly Gln Gly Thr Lys Val Glu Ile Lys
            100                 105                 110


<210> SEQ ID NO 121
<211> LENGTH: 729
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CID_327 DNA sequence

<400> SEQUENCE: 121

gaagtccaac tggtgcaatc tggcccagaa ctgaagaaac caggcgcaag cgtgaaagtt      60

tcttgcaaag gttccggcta taccttcacc gaccttggta tgggctgggt gcgtcaggct     120

ccaggccagg gtctggaatg gatgggctgg attaacaccc agaccggcga accattctat     180

gccgatgact tcaaaggtcg tttcgtcttc agcctggata cttccgtgtc tactgcatac     240

ctgcaaattt caagcttaaa agcagaagat actgctgttt actactgtac tcgtgatcac     300

ccattgggcc tggactattg gggccagggc accctggtaa ccgtttcctc tggcggtggt     360

ggtagcggag gcggaggatc aggtggaggc ggcagtgaca ttcaggtaac tcagagccct     420

tcttctcttt ccgcatctgt tggtgaccgt gttaccatca cctgtatcac ctctcaatcc     480

gtcgatgttg cgggtgtttc ctacctgaac tggtaccagc agaaaccagg caaggtccca     540

aaatttctga tccacaaggc ctccaacctg cggtctggtg tcccttcccg tttctctggt     600

tccggctcag gtacagactt cactctgacc atctccagcc tgcaaccaga agatgttgct     660

acctactatt gtcagcaggc gcgtgaagac ccatacacct tcggccaggg caccaaagtg     720

gaaatcaaa                                                             729


<210> SEQ ID NO 122
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_327 Protein sequence, VH+VL

<400> SEQUENCE: 122

Glu Val Gln Leu Val Gln Ser Gly Pro Glu Leu Lys Lys Pro Gly Ala
1               5                   10                  15

Ser Val Lys Val Ser Cys Lys Gly Ser Gly Tyr Thr Phe Thr Asp Leu
            20                  25                  30

Gly Met Gly Trp Val Arg Gln Ala Pro Gly Gln Gly Leu Glu Trp Met
        35                  40                  45

Gly Trp Ile Asn Thr Gln Thr Gly Glu Pro Phe Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Thr Arg Asp His Pro Leu Gly Leu Asp Tyr Trp Gly Gln Gly Thr Leu
            100                 105                 110
```

```
Val Thr Val Ser Ser Asp Ile Gln Val Thr Gln Ser Pro Ser Ser Leu
        115                 120                 125

Ser Ala Ser Val Gly Asp Arg Val Thr Ile Thr Cys Ile Thr Ser Gln
    130                 135                 140

Ser Val Asp Val Ala Gly Val Ser Tyr Leu Asn Trp Tyr Gln Gln Lys
145                 150                 155                 160

Pro Gly Lys Val Pro Lys Phe Leu Ile His Lys Ala Ser Asn Leu Arg
                165                 170                 175

Ser Gly Val Pro Ser Arg Phe Ser Gly Ser Gly Ser Gly Thr Asp Phe
            180                 185                 190

Thr Leu Thr Ile Ser Ser Leu Gln Pro Glu Asp Val Ala Thr Tyr Tyr
        195                 200                 205

Cys Gln Gln Ala Arg Glu Asp Pro Tyr Thr Phe Gly Gln Gly Thr Lys
    210                 215                 220

Val Glu Ile Lys
225
```

<210> SEQ ID NO 123
<211> LENGTH: 117
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_327 protein sequence - VH

<400> SEQUENCE: 123

```
Glu Val Gln Leu Val Gln Ser Gly Pro Glu Leu Lys Lys Pro Gly Ala
1               5                   10                  15

Ser Val Lys Val Ser Cys Lys Gly Ser Gly Tyr Thr Phe Thr Asp Leu
            20                  25                  30

Gly Met Gly Trp Val Arg Gln Ala Pro Gly Gln Gly Leu Glu Trp Met
        35                  40                  45

Gly Trp Ile Asn Thr Gln Thr Gly Glu Pro Phe Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Thr Arg Asp His Pro Leu Gly Leu Asp Tyr Trp Gly Gln Gly Thr Leu
            100                 105                 110

Val Thr Val Ser Ser
        115
```

<210> SEQ ID NO 124
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_327 protein sequence - VL

<400> SEQUENCE: 124

```
Asp Ile Gln Val Thr Gln Ser Pro Ser Ser Leu Ser Ala Ser Val Gly
1               5                   10                  15

Asp Arg Val Thr Ile Thr Cys Ile Thr Ser Gln Ser Val Asp Val Ala
```

```
            20                  25                  30

Gly Val Ser Tyr Leu Asn Trp Tyr Gln Gln Lys Pro Gly Lys Val Pro
        35                  40                  45

Lys Phe Leu Ile His Lys Ala Ser Asn Leu Arg Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Val Ala Thr Tyr Tyr Cys Gln Gln Ala Arg
                85                  90                  95

Glu Asp Pro Tyr Thr Phe Gly Gln Gly Thr Lys Val Glu Ile Lys
            100                 105                 110


<210> SEQ ID NO 125
<211> LENGTH: 729
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CID_328 DNA sequence

<400> SEQUENCE: 125

gaagtccaac tggtgcaatc tggcccagaa ctgaagaaac caggcgcaag cgtgaaagtt     60

tcttgcaaag gttccggcta taccttcacc gaccttggta tgaattgggt gcgtcaggct    120

ccaggccagg gtctggaatg gatgggctgg attaacaccc agaccggcga accattctat    180

gccgatgact tcaaaggtcg tttcgtcttc agcctggata cttccgtgtc tactgcatac    240

ctgcaaattt caagcttaaa agcagaagat actgctgttt acttctgtgc gcgtgatcac    300

ccattgggcc tggactattg gggccagggc accctggtaa ccgtttcctc tggcggtggt    360

ggtagcggag gcggaggatc aggtggaggc ggcagtgaca ttcaggtaac tcagagccct    420

tcttctcttt ccgcatctgt tggtgaccgt gttaccatca cctgtatcac ctctcaatcc    480

gtcgatgtta acggtgtttc ctacctgaac tggtaccagc agaaaccagg caaggtccca    540

aaatttctga tctacaaggc ctccatcctg cggtctggtg tcccttcccg tttctctggt    600

tccggctcag gtacagactt cactctgacc atctccagcc tgcaaccaga agatgttgct    660

acctactatt gtcagcagag ccgtgaagac ccatacacct tcggccaggg caccaaagtg    720

gaaatcaaa                                                            729


<210> SEQ ID NO 126
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_328 Protein sequence, VH+VL

<400> SEQUENCE: 126

Glu Val Gln Leu Val Gln Ser Gly Pro Glu Leu Lys Lys Pro Gly Ala
1               5                   10                  15

Ser Val Lys Val Ser Cys Lys Gly Ser Gly Tyr Thr Phe Thr Asp Leu
            20                  25                  30

Gly Met Asn Trp Val Arg Gln Ala Pro Gly Gln Gly Leu Glu Trp Met
        35                  40                  45

Gly Trp Ile Asn Thr Gln Thr Gly Glu Pro Phe Tyr Ala Asp Asp Phe
```

50 55 60

Lys Gly Arg Phe Val Phe Ser Leu Asp Thr Ser Val Ser Thr Ala Tyr
65 70 75 80

Leu Gln Ile Ser Ser Leu Lys Ala Glu Asp Thr Ala Val Tyr Phe Cys
85 90 95

Ala Arg Asp His Pro Leu Gly Leu Asp Tyr Trp Gly Gln Gly Thr Leu
100 105 110

Val Thr Val Ser Ser Asp Ile Gln Val Thr Gln Ser Pro Ser Ser Leu
115 120 125

Ser Ala Ser Val Gly Asp Arg Val Thr Ile Thr Cys Ile Thr Ser Gln
130 135 140

Ser Val Asp Val Asn Gly Val Ser Tyr Leu Asn Trp Tyr Gln Gln Lys
145 150 155 160

Pro Gly Lys Val Pro Lys Phe Leu Ile Tyr Lys Ala Ser Ile Leu Arg
165 170 175

Ser Gly Val Pro Ser Arg Phe Ser Gly Ser Gly Ser Gly Thr Asp Phe
180 185 190

Thr Leu Thr Ile Ser Ser Leu Gln Pro Glu Asp Val Ala Thr Tyr Tyr
195 200 205

Cys Gln Gln Ser Arg Glu Asp Pro Tyr Thr Phe Gly Gln Gly Thr Lys
210 215 220

Val Glu Ile Lys
225

<210> SEQ ID NO 127
<211> LENGTH: 117
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: CID_328 protein sequence - VH

<400> SEQUENCE: 127

Glu Val Gln Leu Val Gln Ser Gly Pro Glu Leu Lys Lys Pro Gly Ala
1 5 10 15

Ser Val Lys Val Ser Cys Lys Gly Ser Gly Tyr Thr Phe Thr Asp Leu
20 25 30

Gly Met Asn Trp Val Arg Gln Ala Pro Gly Gln Gly Leu Glu Trp Met
35 40 45

Gly Trp Ile Asn Thr Gln Thr Gly Glu Pro Phe Tyr Ala Asp Asp Phe
50 55 60

Lys Gly Arg Phe Val Phe Ser Leu Asp Thr Ser Val Ser Thr Ala Tyr
65 70 75 80

Leu Gln Ile Ser Ser Leu Lys Ala Glu Asp Thr Ala Val Tyr Phe Cys
85 90 95

Ala Arg Asp His Pro Leu Gly Leu Asp Tyr Trp Gly Gln Gly Thr Leu
100 105 110

Val Thr Val Ser Ser
115

<210> SEQ ID NO 128
<211> LENGTH: 111
<212> TYPE: PRT
<213> ORGANISM: Artificial Sequence
<220> FEATURE:
<223> OTHER INFORMATION: Description of Artificial Sequence: Synthetic

```
      polypeptide
<220> FEATURE:
<223> OTHER INFORMATION: CID_328 protein sequence - VL

<400> SEQUENCE: 128

Asp Ile Gln Val Thr Gln Ser Pro Ser Ser Leu Ser Ala Ser Val Gly
1               5                   10                  15

Asp Arg Val Thr Ile Thr Cys Ile Thr Ser Gln Ser Val Asp Val Asn
            20                  25                  30

Gly Val Ser Tyr Leu Asn Trp Tyr Gln Gln Lys Pro Gly Lys Val Pro
        35                  40                  45

Lys Phe Leu Ile Tyr Lys Ala Ser Ile Leu Arg Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Val Ala Thr Tyr Tyr Cys Gln Gln Ser Arg
                85                  90                  95

Glu Asp Pro Tyr Thr Phe Gly Gln Gly Thr Lys Val Glu Ile Lys
            100                 105                 110


<210> SEQ ID NO 129
<211> LENGTH: 729
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CID_329 DNA sequence

<400> SEQUENCE: 129

gaagtccaac tggtgcaatc tggcccagaa ctgaagaaac caggcgcaag cgtgaaagtt     60

tcttgcaaag gttccggcta taccttcacc gaccttggta tcaattgggt gcgtcaggct    120

ccaggccagg gtctggaatg gatgggctgg attaacaccc acaccggcga accattctat    180

gccgatgact tcaaaggtcg tttcgtcttc agcctggata cttccgtgtc tactgcatac    240

ctgcaaattt caagcttaaa agcagaagat actgctgttt acttctgtac tcgtgatcac    300

ccattgggcc tggactattg gggccagggc accctggtaa ccgtttcctc tggcggtggt    360

ggtagcggag gcggaggatc aggtggaggc ggcagtgaca ttcaggtaac tcagagccct    420

tcttctcttt ccgcatctgt tggtgaccgt gttaccatca cctgtatcac ctctcaatcc    480

gtcgatgtta acggtgtttc ctacctgaac tggtaccagc agaaaccagg caaggtccca    540

aaatttctga tctacaaggc ctccaacctg cggcctggtg tcccttcccg tttctctggt    600

tccggctcag gtacagactt cactctgacc atctccagcc tgcaaccaga agatgttgct    660

acctactatt gtcagcagag ccgtgaagac ccatacacct tcggccaggg caccaaagtg    720

gaaatcaaa                                                            729


<210> SEQ ID NO 130
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_329 Protein sequence, VH+VL

<400> SEQUENCE: 130
```

```
Glu Val Gln Leu Val Gln Ser Gly Pro Glu Leu Lys Lys Pro Gly Ala
1               5                   10                  15

Ser Val Lys Val Ser Cys Lys Gly Ser Gly Tyr Thr Phe Thr Asp Leu
            20                  25                  30

Gly Ile Asn Trp Val Arg Gln Ala Pro Gly Gln Gly Leu Glu Trp Met
        35                  40                  45

Gly Trp Ile Asn Thr His Thr Gly Glu Pro Phe Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Phe Cys
                85                  90                  95

Thr Arg Asp His Pro Leu Gly Leu Asp Tyr Trp Gly Gln Gly Thr Leu
            100                 105                 110

Val Thr Val Ser Ser Asp Ile Gln Val Thr Gln Ser Pro Ser Ser Leu
        115                 120                 125

Ser Ala Ser Val Gly Asp Arg Val Thr Ile Thr Cys Ile Thr Ser Gln
    130                 135                 140

Ser Val Asp Val Asn Gly Val Ser Tyr Leu Asn Trp Tyr Gln Gln Lys
145                 150                 155                 160

Pro Gly Lys Val Pro Lys Phe Leu Ile Tyr Lys Ala Ser Asn Leu Arg
                165                 170                 175

Pro Gly Val Pro Ser Arg Phe Ser Gly Ser Gly Ser Gly Thr Asp Phe
            180                 185                 190

Thr Leu Thr Ile Ser Ser Leu Gln Pro Glu Asp Val Ala Thr Tyr Tyr
        195                 200                 205

Cys Gln Gln Ser Arg Glu Asp Pro Tyr Thr Phe Gly Gln Gly Thr Lys
    210                 215                 220

Val Glu Ile Lys
225
```

<210> SEQ ID NO 131
<211> LENGTH: 117
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_329 protein sequence - VH

<400> SEQUENCE: 131

```
Glu Val Gln Leu Val Gln Ser Gly Pro Glu Leu Lys Lys Pro Gly Ala
1               5                   10                  15

Ser Val Lys Val Ser Cys Lys Gly Ser Gly Tyr Thr Phe Thr Asp Leu
            20                  25                  30

Gly Ile Asn Trp Val Arg Gln Ala Pro Gly Gln Gly Leu Glu Trp Met
        35                  40                  45

Gly Trp Ile Asn Thr His Thr Gly Glu Pro Phe Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Phe Cys
                85                  90                  95

Thr Arg Asp His Pro Leu Gly Leu Asp Tyr Trp Gly Gln Gly Thr Leu
            100                 105                 110
```

Val Thr Val Ser Ser
        115

<210> SEQ ID NO 132
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_329 protein sequence - VL

<400> SEQUENCE: 132

Asp Ile Gln Val Thr Gln Ser Pro Ser Ser Leu Ser Ala Ser Val Gly
1               5                   10                  15

Asp Arg Val Thr Ile Thr Cys Ile Thr Ser Gln Ser Val Asp Val Asn
            20                  25                  30

Gly Val Ser Tyr Leu Asn Trp Tyr Gln Gln Lys Pro Gly Lys Val Pro
        35                  40                  45

Lys Phe Leu Ile Tyr Lys Ala Ser Asn Leu Arg Pro Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Val Ala Thr Tyr Tyr Cys Gln Gln Ser Arg
                85                  90                  95

Glu Asp Pro Tyr Thr Phe Gly Gln Gly Thr Lys Val Glu Ile Lys
            100                 105                 110

<210> SEQ ID NO 133
<211> LENGTH: 729
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CID_330 DNA sequence

<400> SEQUENCE: 133
gaagtccaac tggtgcaatc tggcccagaa ctgaagaaac caggcgcaag cgtgaaagtt      60
tcttgcaaag gttccggcta taccttcacc gaccttggta tcaattgggt gcgtcaggct     120
ccaggccagg gtctggaatg gatgggctgg attaacaccc acaccggcga accatactat     180
gccgatgact tcaaaggtcg tttcgtcttc agcctggata cttccgtgtc tactgcatac     240
ctgcaaattt caagcttaaa agcagaagat actgctgttt actactgtgc ccgtgatcac     300
ccactcggcc tggactattg gggccagggc accctggtaa ccgtttcctc tggcggtggt     360
ggtagcggag gcggaggatc aggtggaggc ggcagtgaca ttcaggtaac tcagagccct     420
tcttctcttt ccgcatctgt tggtgaccgt gttaccatca cctgtatcac ctctcaatcc     480
gtcgatgtta acggtgtttc ctacatgaac tggtaccagc agaaaccagg caaggtccca     540
aaatttctga tctacaaggc cgtcaacctg cggcctggtg tcccttcccg tttctctggt     600
tccggctcag gtacagactt cactctgacc atctccagcc tgcaaccaga agatgttgct     660
acctactatt gtcagcagag ccgtgaagac ccatacacct tcggccaggg caccaaagtg     720
gaaatcaaa                                                             729

<210> SEQ ID NO 134
<211> LENGTH: 228

<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_330 Protein sequence, VH+VL

<400> SEQUENCE: 134

```
Glu Val Gln Leu Val Gln Ser Gly Pro Glu Leu Lys Lys Pro Gly Ala
1               5                   10                  15

Ser Val Lys Val Ser Cys Lys Gly Ser Gly Tyr Thr Phe Thr Asp Leu
            20                  25                  30

Gly Ile Asn Trp Val Arg Gln Ala Pro Gly Gln Gly Leu Glu Trp Met
        35                  40                  45

Gly Trp Ile Asn Thr His Thr Gly Glu Pro Tyr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Asp His Pro Leu Gly Leu Asp Tyr Trp Gly Gln Gly Thr Leu
            100                 105                 110

Val Thr Val Ser Ser Asp Ile Gln Val Thr Gln Ser Pro Ser Ser Leu
        115                 120                 125

Ser Ala Ser Val Gly Asp Arg Val Thr Ile Thr Cys Ile Thr Ser Gln
    130                 135                 140

Ser Val Asp Val Asn Gly Val Ser Tyr Met Asn Trp Tyr Gln Gln Lys
145                 150                 155                 160

Pro Gly Lys Val Pro Lys Phe Leu Ile Tyr Lys Ala Val Asn Leu Arg
                165                 170                 175

Pro Gly Val Pro Ser Arg Phe Ser Gly Ser Gly Ser Gly Thr Asp Phe
            180                 185                 190

Thr Leu Thr Ile Ser Ser Leu Gln Pro Glu Asp Val Ala Thr Tyr Tyr
        195                 200                 205

Cys Gln Gln Ser Arg Glu Asp Pro Tyr Thr Phe Gly Gln Gly Thr Lys
    210                 215                 220

Val Glu Ile Lys
225
```

<210> SEQ ID NO 135
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_330 protein sequence - VH

<400> SEQUENCE: 135

```
Glu Val Gln Leu Val Gln Ser Gly Pro Glu Leu Lys Lys Pro Gly Ala
1               5                   10                  15

Ser Val Lys Val Ser Cys Lys Gly Ser Gly Tyr Thr Phe Thr Asp Leu
            20                  25                  30

Gly Ile Asn Trp Val Arg Gln Ala Pro Gly Gln Gly Leu Glu Trp Met
        35                  40                  45

Gly Trp Ile Asn Thr His Thr Gly Glu Pro Tyr Tyr Ala Asp Asp Phe
    50                  55                  60
```

```
Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Asp His Pro Leu Gly Leu Asp Tyr Trp Gly Gln Gly Thr Leu
            100                 105                 110

Val Thr Val Ser Ser
        115


<210> SEQ ID NO 136
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_330 protein sequence - VL

<400> SEQUENCE: 136

Asp Ile Gln Val Thr Gln Ser Pro Ser Ser Leu Ser Ala Ser Val Gly
1               5                   10                  15

Asp Arg Val Thr Ile Thr Cys Ile Thr Ser Gln Ser Val Asp Val Asn
            20                  25                  30

Gly Val Ser Tyr Met Asn Trp Tyr Gln Gln Lys Pro Gly Lys Val Pro
        35                  40                  45

Lys Phe Leu Ile Tyr Lys Ala Val Asn Leu Arg Pro Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Val Ala Thr Tyr Tyr Cys Gln Gln Ser Arg
                85                  90                  95

Glu Asp Pro Tyr Thr Phe Gly Gln Gly Thr Lys Val Glu Ile Lys
            100                 105                 110


<210> SEQ ID NO 137
<211> LENGTH: 729
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CID_350 DNA sequence

<400> SEQUENCE: 137

caggtacagc tggttcagtc cggcgccgaa gtcaaaaagc caggttcttc cgtgaaagtt      60

tcctgtaaag gttctggtta caccttcact gacctgggca ttggttgggt tcgtcaggct     120

ccaggtcagg gtctggaatg gatgggctgg attaacactc atactggtga gccattctat     180

aacccaaaat tcaaaggccg tgttaccatc acagccgata aaagcactag cactgcctac     240

atggaactga gtagtctgcg ttccgaggac accgctgttt actactgcac tcgtgatcat     300

ccactcggtc tggattattg gggtcagggc acaaccgtga ccgtttcctc cggcggtggt     360

ggtagcggag gcggaggatc aggtggaggc ggcagtgaca tcgttatgac ccaatctcca     420

gacagcctgg ccgtgtctct tggcgaacgt gcaaccatta actgccgttc ttctcagtct     480

gttgatgtta acggcgtttc ctacctgaac tggtaccaac agaaaccagg ccagccacca     540

aaatttctga tctacaaagc cagcaaccgg gaatctggcg ttccagatcg tttctctggc     600
```

tctgggagcg gcactgactt cactcttacc atcagcagcc tgcaagctga agatgtcgct 660
gtttattatt gccagcaggc ccgtgaagac ccatacacct ttgggggcgg caccaaagtg 720
gaaatcaaa 729

<210> SEQ ID NO 138
<211> LENGTH: 228
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: CID_350 Protein sequence, VH+VL

<400> SEQUENCE: 138

Gln Val Gln Leu Val Gln Ser Gly Ala Glu Val Lys Lys Pro Gly Ser
1 5 10 15

Ser Val Lys Val Ser Cys Lys Gly Ser Gly Tyr Thr Phe Thr Asp Leu
20 25 30

Gly Ile Gly Trp Val Arg Gln Ala Pro Gly Gln Gly Leu Glu Trp Met
35 40 45

Gly Trp Ile Asn Thr His Thr Gly Glu Pro Phe Tyr Asn Pro Lys Phe
50 55 60

Lys Gly Arg Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Thr Arg Asp His Pro Leu Gly Leu Asp Tyr Trp Gly Gln Gly Thr Thr
100 105 110

Val Thr Val Ser Ser Asp Ile Val Met Thr Gln Ser Pro Asp Ser Leu
115 120 125

Ala Val Ser Leu Gly Glu Arg Ala Thr Ile Asn Cys Arg Ser Ser Gln
130 135 140

Ser Val Asp Val Asn Gly Val Ser Tyr Leu Asn Trp Tyr Gln Gln Lys
145 150 155 160

Pro Gly Gln Pro Pro Lys Phe Leu Ile Tyr Lys Ala Ser Asn Arg Glu
165 170 175

Ser Gly Val Pro Asp Arg Phe Ser Gly Ser Gly Ser Gly Thr Asp Phe
180 185 190

Thr Leu Thr Ile Ser Ser Leu Gln Ala Glu Asp Val Ala Val Tyr Tyr
195 200 205

Cys Gln Gln Ala Arg Glu Asp Pro Tyr Thr Phe Gly Gly Gly Thr Lys
210 215 220

Val Glu Ile Lys
225

<210> SEQ ID NO 139
<211> LENGTH: 117
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: CID_350 protein sequence - VH

<400> SEQUENCE: 139

Gln Val Gln Leu Val Gln Ser Gly Ala Glu Val Lys Lys Pro Gly Ser

```
1               5                   10                  15

Ser Val Lys Val Ser Cys Lys Gly Ser Gly Tyr Thr Phe Thr Asp Leu
            20                  25                  30

Gly Ile Gly Trp Val Arg Gln Ala Pro Gly Gln Gly Leu Glu Trp Met
        35                  40                  45

Gly Trp Ile Asn Thr His Thr Gly Glu Pro Phe Tyr Asn Pro Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Asp His Pro Leu Gly Leu Asp Tyr Trp Gly Gln Gly Thr Thr
            100                 105                 110

Val Thr Val Ser Ser
        115
```

<210> SEQ ID NO 140
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_350 protein sequence - VL

<400> SEQUENCE: 140

```
Asp Ile Val Met Thr Gln Ser Pro Asp Ser Leu Ala Val Ser Leu Gly
1               5                   10                  15

Glu Arg Ala Thr Ile Asn Cys Arg Ser Ser Gln Ser Val Asp Val Asn
            20                  25                  30

Gly Val Ser Tyr Leu Asn Trp Tyr Gln Gln Lys Pro Gly Gln Pro Pro
        35                  40                  45

Lys Phe Leu Ile Tyr Lys Ala Ser Asn Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ala Arg
                85                  90                  95

Glu Asp Pro Tyr Thr Phe Gly Gly Gly Thr Lys Val Glu Ile Lys
            100                 105                 110
```

<210> SEQ ID NO 141
<211> LENGTH: 756
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: CID_279 DNA sequence

<400> SEQUENCE: 141

```
gaagtgcagt tagtgcaatc tggtgccgaa gttaagaaac caggcagctc cgttaaagtg     60

tcttgtaagg catctggcga cactttcacc tcttatagtt ggaactgggt tcgtcaggct    120

ccaggccagg gtttggagtg gatgggtcgt atcattaccg acctggatga tactgagtac    180

gctcctcatt tacagggtcg tgtaaccatc acagcagaca agtccacatc taccgtatac    240

ttggaactgc gtaacttacg tagcgatgat accgccgttt acttctgcgc aggtgtgtac    300
```

```
gaaggtccga actctgaagg ctcgtacgat gactatggtt tcctgaaaca ctggggtcag    360

ggcactctgg tgactgttag ttctggcggt ggtggtagcg gaggcggagg atcaggtgga    420

ggcggcagtg atatcgttat gactcagtcc ccagcaaccc tgtctgtatc tcctggtgag    480

cgtgccaccc tgagctgccg tgcttcagaa tctggggcta acgatctggc ctggtatcag    540

cagaaaccag gtcaggttcc acgtctgctg tgctatggcg cttccacccg tgctaccggt    600

gtaccagctc gtttctctgg gtccggctcc ggcgccgagt tcaccctgac tatctcctct    660

ctgcagtccg aagactttgc cgtgtactac tgccagcagt acgcgaactg gccaccacgt    720

ggcacctttg gtcaagggac acgtttagag attaaa                              756
```

```
<210> SEQ ID NO 142
<211> LENGTH: 237
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_279 Protein sequence, VH+VL

<400> SEQUENCE: 142

Glu Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Thr Ser Tyr
            20                  25                  30

Ser Trp Asn Trp Val Arg Gln Ala Pro Gly Gln Gly Leu Glu Trp Met
        35                  40                  45

Gly Arg Ile Ile Thr Asp Leu Asp Asp Thr Glu Tyr Ala Pro His Leu
    50                  55                  60

Gln Gly Arg Val Thr Ile Thr Ala Asp Lys Ser Thr Ser Thr Val Tyr
65                  70                  75                  80

Leu Glu Leu Arg Asn Leu Arg Ser Asp Asp Thr Ala Val Tyr Phe Cys
                85                  90                  95

Ala Gly Val Tyr Glu Gly Pro Asn Ser Glu Gly Ser Tyr Asp Asp Tyr
            100                 105                 110

Gly Phe Leu Lys His Trp Gly Gln Gly Thr Leu Val Thr Val Ser Ser
        115                 120                 125

Asp Ile Val Met Thr Gln Ser Pro Ala Thr Leu Ser Val Ser Pro Gly
    130                 135                 140

Glu Arg Ala Thr Leu Ser Cys Arg Ala Ser Glu Ser Gly Ala Asn Asp
145                 150                 155                 160

Leu Ala Trp Tyr Gln Gln Lys Pro Gly Gln Val Pro Arg Leu Leu Cys
                165                 170                 175

Tyr Gly Ala Ser Thr Arg Ala Thr Gly Val Pro Ala Arg Phe Ser Gly
            180                 185                 190

Ser Gly Ser Gly Ala Glu Phe Thr Leu Thr Ile Ser Ser Leu Gln Ser
        195                 200                 205

Glu Asp Phe Ala Val Tyr Tyr Cys Gln Gln Tyr Ala Asn Trp Pro Pro
    210                 215                 220

Arg Gly Thr Phe Gly Gln Gly Thr Arg Leu Glu Ile Lys
225                 230                 235


<210> SEQ ID NO 143
<211> LENGTH: 128
<212> TYPE: PRT
```

<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: CID_279 protein sequence - VH

<400> SEQUENCE: 143

```
Glu Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Thr Ser Tyr
            20                  25                  30

Ser Trp Asn Trp Val Arg Gln Ala Pro Gly Gln Gly Leu Glu Trp Met
        35                  40                  45

Gly Arg Ile Ile Thr Asp Leu Asp Asp Thr Glu Tyr Ala Pro His Leu
    50                  55                  60

Gln Gly Arg Val Thr Ile Thr Ala Asp Lys Ser Thr Ser Thr Val Tyr
65                  70                  75                  80

Leu Glu Leu Arg Asn Leu Arg Ser Asp Asp Thr Ala Val Tyr Phe Cys
                85                  90                  95

Ala Gly Val Tyr Glu Gly Pro Asn Ser Glu Gly Ser Tyr Asp Asp Tyr
            100                 105                 110

Gly Phe Leu Lys His Trp Gly Gln Gly Thr Leu Val Thr Val Ser Ser
        115                 120                 125
```

<210> SEQ ID NO 144
<211> LENGTH: 109
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: CID_279 protein sequence - VL

<400> SEQUENCE: 144

```
Asp Ile Val Met Thr Gln Ser Pro Ala Thr Leu Ser Val Ser Pro Gly
1               5                   10                  15

Glu Arg Ala Thr Leu Ser Cys Arg Ala Ser Glu Ser Gly Ala Asn Asp
            20                  25                  30

Leu Ala Trp Tyr Gln Gln Lys Pro Gly Gln Val Pro Arg Leu Leu Cys
        35                  40                  45

Tyr Gly Ala Ser Thr Arg Ala Thr Gly Val Pro Ala Arg Phe Ser Gly
    50                  55                  60

Ser Gly Ser Gly Ala Glu Phe Thr Leu Thr Ile Ser Ser Leu Gln Ser
65                  70                  75                  80

Glu Asp Phe Ala Val Tyr Tyr Cys Gln Gln Tyr Ala Asn Trp Pro Pro
                85                  90                  95

Arg Gly Thr Phe Gly Gln Gly Thr Arg Leu Glu Ile Lys
            100                 105
```

<210> SEQ ID NO 145
<211> LENGTH: 741
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: CID_438 DNA sequence

<400> SEQUENCE: 145

```
gatatccaga tgacccagtc cccaatcctg ctgtctgcct ccgttggtga tcgtgtgacc     60
attacctgcc gtgcttcaca ggacgtaagc actgccgtag cttggtctca acagcgtacc    120
aacggcagcc cacgtctgct gatttactcc gcaagttctc tgtatagtgg cgtcccaagc    180
cgttttagcg gctcacgttc cggtactgat ttcaccctga ccatttccag cctgcagcca    240
gaggatatcg cagactacta cagccagcag ccttcgtaca ccccaccaac cttcggtgcc    300
ggtaccaagg tagaaatcaa aggcggtggt ggtagcggag gcggaggatc aggtggaggc    360
ggcagtggcg gtggtggttc tgaagtacag ctggttgaat ctggtggtgg tctggtacag    420
ccaggcggtt ctcttcgtct gtcttgcgct gcctctggtt tcaacattcg tgctacctac    480
atccactggg tccgtcagtc tccaggtaaa ggcctggaat gggtcgctga tatcgatcca    540
accaacggtg atacccgtta cgccgattct gtcaaaggcc gtttcactat cagcgccgac    600
acttccaaaa acaccgccta cctgcagatg aacagcctgc gtgccgaaga caccgccatc    660
tactactgta ctcgtgaagg tgatgatggc tacaacgcat gggataaatg gggtcagggc    720
accctggtaa ctgtctccag c                                               741
```

<210> SEQ ID NO 146
<211> LENGTH: 227
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_438 Protein sequence, VH+VL

<400> SEQUENCE: 146

```
Asp Ile Gln Met Thr Gln Ser Pro Ile Leu Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Ser Gln Gln Arg Thr Asn Gly Ser Pro Arg Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Ile Ala Asp Tyr Tyr Ser Gln Gln Pro Ser Tyr Thr Pro Pro
                85                  90                  95

Thr Phe Gly Ala Gly Thr Lys Val Glu Ile Lys Glu Val Gln Leu Val
            100                 105                 110

Glu Ser Gly Gly Gly Leu Val Gln Pro Gly Gly Ser Leu Arg Leu Ser
        115                 120                 125

Cys Ala Ala Ser Gly Phe Asn Ile Arg Ala Thr Tyr Ile His Trp Val
    130                 135                 140

Arg Gln Ser Pro Gly Lys Gly Leu Glu Trp Val Ala Asp Ile Asp Pro
145                 150                 155                 160

Thr Asn Gly Asp Thr Arg Tyr Ala Asp Ser Val Lys Gly Arg Phe Thr
                165                 170                 175

Ile Ser Ala Asp Thr Ser Lys Asn Thr Ala Tyr Leu Gln Met Asn Ser
            180                 185                 190

Leu Arg Ala Glu Asp Thr Ala Ile Tyr Tyr Cys Thr Arg Glu Gly Asp
        195                 200                 205
```

```
Asp Gly Tyr Asn Ala Trp Asp Lys Trp Gly Gln Gly Thr Leu Val Thr
    210                 215                 220

Val Ser Ser
225


<210> SEQ ID NO 147
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_438 protein sequence - VH

<400> SEQUENCE: 147

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Arg Ala Thr
            20                  25                  30

Tyr Ile His Trp Val Arg Gln Ser Pro Gly Lys Gly Leu Glu Trp Val
        35                  40                  45

Ala Asp Ile Asp Pro Thr Asn Gly Asp Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Ile Tyr Tyr Cys
                85                  90                  95

Thr Arg Glu Gly Asp Asp Gly Tyr Asn Ala Trp Asp Lys Trp Gly Gln
            100                 105                 110

Gly Thr Leu Val Thr Val Ser Ser
        115                 120


<210> SEQ ID NO 148
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_438 protein sequence - VL

<400> SEQUENCE: 148

Asp Ile Gln Met Thr Gln Ser Pro Ile Leu Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Ser Gln Gln Arg Thr Asn Gly Ser Pro Arg Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Ile Ala Asp Tyr Tyr Ser Gln Gln Pro Ser Tyr Thr Pro Pro
                85                  90                  95

Thr Phe Gly Ala Gly Thr Lys Val Glu Ile Lys
            100                 105


<210> SEQ ID NO 149
```

<211> LENGTH: 654
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: CID_229 DNA - VH+CH1

<400> SEQUENCE: 149

```
gaagtacagc tggttgaatc tggtggtggt ctggtacagc caggcggttc tcttcgtctg     60

tcttgcgctg cctctggttt caacattcgt gctatgtaca tccactgggt ccgtcagtct    120

ccaggtaaag gcctggaatg ggtcgctgat atcgatccaa ccaacggtga tacccgttac    180

gccgattctg tcaaaggccg tttcactatc agcgccgaca cttccaaaaa caccgcctac    240

ctgcagatga acagcctgcg tgccgaagac accgccatct actactgtac ccgtgaaggt    300

caggatggct acaacgcatt cgataaatgg ggtcagggca ccctggtaac tgtctccagc    360

gccagcacca agggacctag cgtgttccct ctggcccctt cctccaagag caccagcggc    420

ggaacagctg ccctgggatg cctggtgaaa gactacttcc ccgagcccgt gaccgtgagc    480

tggaacagcg gagccctgac atccggcgtg cacacattcc ccgccgtgct gcaatcctcc    540

ggcctgtaca gcctgtcctc cgtggtgaca gtgcctagca gcagcctggg cacccagacc    600

tacatctgca atgtgaacca caagcccagc aacaccaagg tggacaagaa ggtg          654
```

<210> SEQ ID NO 150
<211> LENGTH: 642
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: CID_229 DNA - VL+CL

<400> SEQUENCE: 150

```
gatatccaga tgacccagtc cccaatcctg ctgtctgcct ccgttggtga tcgtgtgacc     60

attacctgcc gtgcttcaca ggacgtaagc actgccgtag cttggtctca acagcgtacc    120

aacggcagcc cacgtctgct gatttactcc gcaagttctc tgtatagtgg cgtcccaagc    180

cgttttagcg gctcacgttc cggtactgat ttcaccctga ccatttccag cctgcagcca    240

gaggatatcg cagactacta ctgccagcag catcgttaca ccccaccaac cttcggtgcc    300

ggtaccaagg tagaaatcaa aagaaccgtg gccgcccccca gcgtgttcat cttccctccc    360

agcgacgagc agctgaagag cggcaccgcc agcgtggtgt gtctgctgaa caacttctac    420

cccagggagg ccaaggtcca gtggaaggtg gacaacgccc tgcagagcgg caacagccag    480

gagagcgtga ccgagcagga cagcaaggac agcacctaca gcctgagcag caccctcacc    540

ctgagcaagg ccgactacga gaagcacaag gtgtacgcct gtgaggtgac ccaccagggc    600

ctgagcagcc ctgtgaccaa gagcttcaac aggggcgagt gc                       642
```

<210> SEQ ID NO 151
<211> LENGTH: 120
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: CID_229 Amino acid sequence - VH

<400> SEQUENCE: 151

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Arg Ala Met
            20                  25                  30

Tyr Ile His Trp Val Arg Gln Ser Pro Gly Lys Gly Leu Glu Trp Val
        35                  40                  45

Ala Asp Ile Asp Pro Thr Asn Gly Asp Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Ile Tyr Tyr Cys
                85                  90                  95

Thr Arg Glu Gly Gln Asp Gly Tyr Asn Ala Phe Asp Lys Trp Gly Gln
            100                 105                 110

Gly Thr Leu Val Thr Val Ser Ser
        115                 120

<210> SEQ ID NO 152
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_229 Amino acid sequence - VL

<400> SEQUENCE: 152

Asp Ile Gln Met Thr Gln Ser Pro Ile Leu Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Ser Gln Gln Arg Thr Asn Gly Ser Pro Arg Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Ile Ala Asp Tyr Tyr Cys Gln Gln His Arg Tyr Thr Pro Pro
                85                  90                  95

Thr Phe Gly Ala Gly Thr Lys Val Glu Ile Lys
            100                 105

<210> SEQ ID NO 153
<211> LENGTH: 98
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_229 Amino acid sequence - CH1

<400> SEQUENCE: 153

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

```
Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val
```

```
<210> SEQ ID NO 154
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_229 Amino acid sequence - CL

<400> SEQUENCE: 154

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

```
<210> SEQ ID NO 155
<211> LENGTH: 654
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CID_231 DNA - VH+CH1

<400> SEQUENCE: 155

gaagtacagc tggttgaatc tggtggtggt ctggtacagc caggcggttc tcttcgtctg     60

tcttgcgctg cctctggttt caacattcgt gctacctaca tccactgggt ccgtcagtct    120

ccaggtaaag gcctggaatg ggtcgctgat atctctccag acaacggtga tacccgttac    180

gccgattctg tcaaaggccg tttcactatc agcgccgaca cttccaaaaa caccgcctac    240

ctgcagatga acagcctgcg tgccgaagac accgccatct actactgttc tcgtgacctg    300

gcggatggct acaacgcatt cgatctgtgg ggtcagggca ccctggtaac tgtctccagc    360

gccagcacca agggacctag cgtgttccct ctggcccctt cctccaagag caccagcggc    420

ggaacagctg ccctgggatg cctggtgaaa gactacttcc ccgagcccgt gaccgtgagc    480

tggaacagcg gagccctgac atccggcgtg cacacattcc ccgccgtgct gcaatcctcc    540
```

ggcctgtaca gcctgtcctc cgtggtgaca gtgcctagca gcagcctggg cacccagacc 600
tacatctgca atgtgaacca caagcccagc aacaccaagg tggacaagaa ggtg 654

<210> SEQ ID NO 156
<211> LENGTH: 642
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: CID_231 DNA - VL+CL

<400> SEQUENCE: 156
gatatccaga tgacccagtc cccaatcctg ctgtctgcct ccgttggtga tcgtgtgacc 60
attacctgcc gtgcttcaca ggacgtaagc actgccgtag cttggtctca acagcgtacc 120
aacggcagcc cacgtctgct gatttactcc gcaagttctc tgtatagtgg cgtcccaagc 180
cgttttagcg gctcacgttc cggtactgat ttcaccctga ccatttccag cctgcagcca 240
gaggatatcg cagactacta ctgccagcag cacggttaca ccccaccaac cttcggtgcc 300
ggtaccaagg tagaaatcaa aagaaccgtg gccgccccca gcgtgttcat cttccctccc 360
agcgacgagc agctgaagag cggcaccgcc agcgtggtgt gtctgctgaa caacttctac 420
cccagggagg ccaaggtcca gtggaaggtg gacaacgccc tgcagagcgg caacagccag 480
gagagcgtga ccgagcagga cagcaaggac agcacctaca gcctgagcag caccctcacc 540
ctgagcaagg ccgactacga gaagcacaag gtgtacgcct gtgaggtgac ccaccagggc 600
ctgagcagcc ctgtgaccaa gagcttcaac aggggcgagt gc 642

<210> SEQ ID NO 157
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_231 Amino acid sequence - VH

<400> SEQUENCE: 157

Glu Val Gln Leu Val Glu Ser Gly Gly Gly Leu Val Gln Pro Gly Gly
1 5 10 15

Ser Leu Arg Leu Ser Cys Ala Ala Ser Gly Phe Asn Ile Arg Ala Thr
20 25 30

Tyr Ile His Trp Val Arg Gln Ser Pro Gly Lys Gly Leu Glu Trp Val
35 40 45

Ala Asp Ile Ser Pro Asp Asn Gly Asp Thr Arg Tyr Ala Asp Ser Val
50 55 60

Lys Gly Arg Phe Thr Ile Ser Ala Asp Thr Ser Lys Asn Thr Ala Tyr
65 70 75 80

Leu Gln Met Asn Ser Leu Arg Ala Glu Asp Thr Ala Ile Tyr Tyr Cys
85 90 95

Ser Arg Asp Leu Ala Asp Gly Tyr Asn Ala Phe Asp Leu Trp Gly Gln
100 105 110

Gly Thr Leu Val Thr Val Ser Ser
115 120

<210> SEQ ID NO 158
<211> LENGTH: 107

<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_231 Amino acid sequence - VL

<400> SEQUENCE: 158

```
Asp Ile Gln Met Thr Gln Ser Pro Ile Leu Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Ser Gln Gln Arg Thr Asn Gly Ser Pro Arg Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Ile Ala Asp Tyr Tyr Cys Gln Gln His Gly Tyr Thr Pro Pro
                85                  90                  95

Thr Phe Gly Ala Gly Thr Lys Val Glu Ile Lys
            100                 105
```

<210> SEQ ID NO 159
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_231 Amino acid sequence - CH1

<400> SEQUENCE: 159

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val
```

<210> SEQ ID NO 160
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_231 Amino acid sequence - CL

<400> SEQUENCE: 160

```
Arg Thr Val Ala Ala Pro Ser Val Phe Ile Phe Pro Pro Ser Asp Glu
1               5                   10                  15
```

Gln Leu Lys Ser Gly Thr Ala Ser Val Val Cys Leu Leu Asn Asn Phe
20 25 30

Tyr Pro Arg Glu Ala Lys Val Gln Trp Lys Val Asp Asn Ala Leu Gln
35 40 45

Ser Gly Asn Ser Gln Glu Ser Val Thr Glu Gln Asp Ser Lys Asp Ser
50 55 60

Thr Tyr Ser Leu Ser Ser Thr Leu Thr Leu Ser Lys Ala Asp Tyr Glu
65 70 75 80

Lys His Lys Val Tyr Ala Cys Glu Val Thr His Gln Gly Leu Ser Ser
85 90 95

Pro Val Thr Lys Ser Phe Asn Arg Gly Glu Cys
100 105

<210> SEQ ID NO 161
<211> LENGTH: 654
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: CID_232 DNA - VH+CH1

<400> SEQUENCE: 161
gaagtacagc tggttgaatc tggtggtggt ctggtacagc caggcggttc tcttcgtctg 60
tcttgcgctg cctctggttt caacattcgt gatacctaca tccactgggt ccgtcagtct 120
ccaggtaaag gcctggaatg ggtcgctgat atcgatccag acaacggtga tacccgttac 180
gccgattctg tcaaaggccg tttcactatc agcgccgaca cttccaaaaa caccgcctac 240
ctgcagatga acagcctgcg tgccgaagac accgccatct actactgtac tcgtgaaggt 300
gcagatggct acaacgcatt cgatctgtgg ggtcagggca ccctggtaac tgtctccagc 360
gccagcacca agggacctag cgtgttccct ctggcccctt cctccaagag caccagcggc 420
ggaacagctg ccctgggatg cctggtgaaa gactacttcc ccgagcccgt gaccgtgagc 480
tggaacagcg gagccctgac atccggcgtg cacacattcc ccgccgtgct gcaatcctcc 540
ggcctgtaca gcctgtcctc cgtggtgaca gtgcctagca gcagcctggg cacccagacc 600
tacatctgca atgtgaacca caagcccagc aacaccaagg tggacaagaa ggtg 654

<210> SEQ ID NO 162
<211> LENGTH: 642
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: CID_232 DNA - VL+CL

<400> SEQUENCE: 162
gatatccaga tgacccagtc cccaatcctg ctgtctgcct ccgttggtga tcgtgtgacc 60
attacctgcc gtgcttcaca ggacgtaagc actgccgtag cttggtctca acagcgtacc 120
aacggcagcc cacgtctgct gatttacccc gcaagttctc tgtatagtgg cgtcccaagc 180
cgttttagcg gctcacgttc cggtactgat ttcaccctga ccatttccag cctgcagcca 240
gaggatatcg cagactacta ctgccagcag cccgactaca ccccaccaac cttcggtgcc 300
ggtaccaagg tagaaatcaa aagaaccgtg gccgccccca gcgtgttcat cttccctccc 360
agcgacgagc agctgaagag cggcaccgcc agcgtggtgt gtctgctgaa caacttctac 420
cccagggagg ccaaggtcca gtggaaggtg gacaacgccc tgcagagcgg caacagccag 480
gagagcgtga ccgagcagga cagcaaggac agcacctaca gcctgagcag caccctcacc 540
ctgagcaagg ccgactacga gaagcacaag gtgtacgcct gtgaggtgac ccaccagggc 600
ctgagcagcc ctgtgaccaa gagcttcaac aggggcgagt gc 642

<210> SEQ ID NO 163
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_232 Amino acid sequence - VH

<400> SEQUENCE: 163

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Arg Asp Thr
            20                  25                  30

Tyr Ile His Trp Val Arg Gln Ser Pro Gly Lys Gly Leu Glu Trp Val
        35                  40                  45

Ala Asp Ile Asp Pro Asp Asn Gly Asp Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Ile Tyr Tyr Cys
                85                  90                  95

Thr Arg Glu Gly Ala Asp Gly Tyr Asn Ala Phe Asp Leu Trp Gly Gln
            100                 105                 110

Gly Thr Leu Val Thr Val Ser Ser
        115                 120
```

<210> SEQ ID NO 164
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_232 Amino acid sequence - VL

<400> SEQUENCE: 164

```
Asp Ile Gln Met Thr Gln Ser Pro Ile Leu Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Ser Gln Gln Arg Thr Asn Gly Ser Pro Arg Leu Leu Ile
        35                  40                  45

Tyr Pro Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Ile Ala Asp Tyr Tyr Cys Gln Gln Pro Asp Tyr Thr Pro Pro
                85                  90                  95

Thr Phe Gly Ala Gly Thr Lys Val Glu Ile Lys
```

100 105

<210> SEQ ID NO 165
<211> LENGTH: 98
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_232 Amino acid sequence - CH1

<400> SEQUENCE: 165

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val

<210> SEQ ID NO 166
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_232 Amino acid sequence - CL

<400> SEQUENCE: 166

Arg Thr Val Ala Ala Pro Ser Val Phe Ile Phe Pro Pro Ser Asp Glu
1 5 10 15

Gln Leu Lys Ser Gly Thr Ala Ser Val Val Cys Leu Leu Asn Asn Phe
20 25 30

Tyr Pro Arg Glu Ala Lys Val Gln Trp Lys Val Asp Asn Ala Leu Gln
35 40 45

Ser Gly Asn Ser Gln Glu Ser Val Thr Glu Gln Asp Ser Lys Asp Ser
50 55 60

Thr Tyr Ser Leu Ser Ser Thr Leu Thr Leu Ser Lys Ala Asp Tyr Glu
65 70 75 80

Lys His Lys Val Tyr Ala Cys Glu Val Thr His Gln Gly Leu Ser Ser
85 90 95

Pro Val Thr Lys Ser Phe Asn Arg Gly Glu Cys
100 105

<210> SEQ ID NO 167
<211> LENGTH: 654
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: CID_234 DNA - VH+CH1

<400> SEQUENCE: 167
gaagtacagc tggttgaatc tggtggtggt ctggtacagc caggcggttc tcttcgtctg 60
tcttgcgctg cctctggttt caacattcgt gctttctaca tccactgggt ccgtcagtct 120
ccaggtaaag gcctggaatg ggtcgctgat atcgatccaa ccaacggtga tacccgttac 180
gccgattctg tcaaaggccg tttcactatc agcgccgaca cttccaaaaa caccgcctac 240
ctgcagatga acagcctgcg tgccgaagac accgccatct actactgtac ccgtgaaggt 300
gaggatggct acaacgcatt cgatcaatgg ggtcagggca ccctggtaac tgtctccagc 360
gccagcacca agggacctag cgtgttccct ctggcccctt cctccaagag caccagcggc 420
ggaacagctg ccctgggatg cctggtgaaa gactacttcc ccgagcccgt gaccgtgagc 480
tggaacagcg gagccctgac atccggcgtg cacacattcc ccgccgtgct gcaatcctcc 540
ggcctgtaca gcctgtcctc cgtggtgaca gtgcctagca gcagcctggg cacccagacc 600
tacatctgca atgtgaacca caagcccagc aacaccaagg tggacaagaa ggtg 654

<210> SEQ ID NO 168
<211> LENGTH: 642
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: CID_234 DNA - VL+CL

<400> SEQUENCE: 168
gatatccaga tgacccagtc cccaatcctg ctgtctgcct ccgttggtga tcgtgtgacc 60
attacctgcc gtgcttcaca ggacgtaagc actgccgtag cttggtatca acagcgtacc 120
aacggcagcc cacgtctgct gatttaccct gcaagttctc tgtatagtgg cgtcccaagc 180
cgttttagcg gctcacgttc cggtactgat ttcaccctga ccatttccag cctgcagcca 240
gaggatatcg cagactacta ctgccagcag ccccgttaca ccccaccaac cttcggtgcc 300
ggtaccaagg tagaaatcaa aagaaccgtg gccgccccca gcgtgttcat cttccctccc 360
agcgacgagc agctgaagag cggcaccgcc agcgtggtgt gtctgctgaa caacttctac 420
cccagggagg ccaaggtcca gtggaaggtg gacaacgccc tgcagagcgg caacagccag 480
gagagcgtga ccgagcagga cagcaaggac agcacctaca gcctgagcag caccctcacc 540
ctgagcaagg ccgactacga gaagcacaag gtgtacgcct gtgaggtgac ccaccagggc 600
ctgagcagcc ctgtgaccaa gagcttcaac aggggcgagt gc 642

<210> SEQ ID NO 169
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_234 Amino acid sequence - VH

<400> SEQUENCE: 169

Glu Val Gln Leu Val Glu Ser Gly Gly Gly Leu Val Gln Pro Gly Gly
1 5 10 15

Ser Leu Arg Leu Ser Cys Ala Ala Ser Gly Phe Asn Ile Arg Ala Phe
20 25 30

```
Tyr Ile His Trp Val Arg Gln Ser Pro Gly Lys Gly Leu Glu Trp Val
        35                  40                  45

Ala Asp Ile Asp Pro Thr Asn Gly Asp Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Ile Tyr Tyr Cys
                85                  90                  95

Thr Arg Glu Gly Glu Asp Gly Tyr Asn Ala Phe Asp Gln Trp Gly Gln
            100                 105                 110

Gly Thr Leu Val Thr Val Ser Ser
        115                 120


<210> SEQ ID NO 170
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_234 Amino acid sequence - VL

<400> SEQUENCE: 170

Asp Ile Gln Met Thr Gln Ser Pro Ile Leu Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Arg Thr Asn Gly Ser Pro Arg Leu Leu Ile
        35                  40                  45

Tyr Pro Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Ile Ala Asp Tyr Tyr Cys Gln Gln Pro Arg Tyr Thr Pro Pro
                85                  90                  95

Thr Phe Gly Ala Gly Thr Lys Val Glu Ile Lys
            100                 105


<210> SEQ ID NO 171
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_234 Amino acid sequence - CH1

<400> SEQUENCE: 171

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80
```

```
Tyr Ile Cys Asn Val Asn His Lys Pro Ser Asn Thr Lys Val Asp Lys
                85                  90                  95

Lys Val


<210> SEQ ID NO 172
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_234 Amino acid sequence - CL

<400> SEQUENCE: 172

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 173
<211> LENGTH: 654
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CID_261 DNA - VH+CH1

<400> SEQUENCE: 173

gaggttcagc ttgttgagtc tggcggcggt ctggttcagc caggtggttc tctgcgtctg     60

tcctgtgctg cctctggttt caacatcaaa gatttcttca tccactgggt gcgtcaggca    120

ccaggcaaag gcctggaatg ggttgccgat atcgatccaa ccaacgggga tacccgttac    180

gccgattctg tgaagggtcg tttcactatt tctgcagaca cctccaagaa caccgcttac    240

ctgcaaatga actcactgcg tgctgaagac accgcagttt attattgttc tcgtgaaggt    300

caagatggtt acaacgcctg ggacctgtgg ggtcagggca ccctggtaac cgtttcttcc    360

gccagcacca agggacctag cgtgttccct ctggcccctt cctccaagag caccagcggc    420

ggaacagctg ccctgggatg cctggtgaaa gactacttcc ccgagcccgt gaccgtgagc    480

tggaacagcg gagccctgac atccggcgtg cacacattcc ccgccgtgct gcaatcctcc    540

ggcctgtaca gcctgtcctc cgtggtgaca gtgcctagca gcagcctggg cacccagacc    600

tacatctgca atgtgaacca caagcccagc aacaccaagg tggacaagaa ggtg          654


<210> SEQ ID NO 174
<211> LENGTH: 642
<212> TYPE: DNA
```

<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: CID_261 DNA - VL+CL

<400> SEQUENCE: 174

```
gacattcaga tgacccagag cccaagctct ctgtccgcct ccgttggcga ccgtgtcacc     60

atcacctgtc gtgcaagcca agatatctct accgccgttg cttggtctca gcagaaacca    120

ggtaaagcac ctaaactgct gatctactct gcctcttcac tgtacagcgg tgttccatca    180

cgttttagcg gttcacgtag cggcaccgat ttcacactga ccatttcttc cttacagcca    240

gaagattttg caacctacta ttgccagcag ccttcgctga cccctccaac ttttggtcag    300

ggcaccaaag tagaaattaa aagaaccgtg gccgccccca gcgtgttcat cttccctccc    360

agcgacgagc agctgaagag cggcaccgcc agcgtggtgt gtctgctgaa caacttctac    420

cccagggagg ccaaggtcca gtggaaggtg gacaacgccc tgcagagcgg caacagccag    480

gagagcgtga ccgagcagga cagcaaggac agcacctaca gcctgagcag caccctcacc    540

ctgagcaagg ccgactacga gaagcacaag gtgtacgcct gtgaggtgac ccaccagggc    600

ctgagcagcc ctgtgaccaa gagcttcaac aggggcgagt gc                       642
```

<210> SEQ ID NO 175
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_261 Amino acid sequence - VH

<400> SEQUENCE: 175

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Phe
            20                  25                  30

Phe Ile His Trp Val Arg Gln Ala Pro Gly Lys Gly Leu Glu Trp Val
        35                  40                  45

Ala Asp Ile Asp Pro Thr Asn Gly Asp Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Glu Gly Gln Asp Gly Tyr Asn Ala Trp Asp Leu Trp Gly Gln
            100                 105                 110

Gly Thr Leu Val Thr Val Ser Ser
        115                 120
```

<210> SEQ ID NO 176
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_261 Amino acid sequence - VL

<400> SEQUENCE: 176

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asp Ile Ser Thr Ala
20 25 30

Val Ala Trp Ser Gln Gln Lys Pro Gly Lys Ala Pro Lys Leu Leu Ile
35 40 45

Tyr Ser Ala Ser Ser Leu Tyr Ser Gly Val Pro Ser Arg Phe Ser Gly
50 55 60

Ser Arg Ser Gly Thr Asp Phe Thr Leu Thr Ile Ser Ser Leu Gln Pro
65 70 75 80

Glu Asp Phe Ala Thr Tyr Tyr Cys Gln Gln Pro Ser Leu Thr Pro Pro
85 90 95

Thr Phe Gly Gln Gly Thr Lys Val Glu Ile Lys
100 105

<210> SEQ ID NO 177
<211> LENGTH: 98
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_261 Amino acid sequence - CH1

<400> SEQUENCE: 177

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val

<210> SEQ ID NO 178
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_261 Amino acid sequence - CL

<400> SEQUENCE: 178

Arg Thr Val Ala Ala Pro Ser Val Phe Ile Phe Pro Pro Ser Asp Glu
1 5 10 15

Gln Leu Lys Ser Gly Thr Ala Ser Val Val Cys Leu Leu Asn Asn Phe
20 25 30

Tyr Pro Arg Glu Ala Lys Val Gln Trp Lys Val Asp Asn Ala Leu Gln
35 40 45

Ser Gly Asn Ser Gln Glu Ser Val Thr Glu Gln Asp Ser Lys Asp Ser

```
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 179
<211> LENGTH: 654
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CID_262 DNA - VH+CH1

<400> SEQUENCE: 179

gaggttcagc ttgttgagtc tggcggcggt ctggttcagc caggtggttc tctgcgtctg      60

tcctgtgctg cctctggttt caacatcaaa gattacttca tccactgggt gcgtcaggca     120

ccaggcaaag gcctggaatg ggttgccgat atcgatccaa ccaacgggga tacccgttac     180

gccgattctg tgaagggtcg tttcactatt tctgcagaca cctccaagaa caccgcttac     240

ctgcaaatga actcactgcg tgctgaagac accgcagttt attattgttc ccgtgaaggt     300

caggatggtt acaacgcctg ggaccaatgg ggtcagggca ccctggtaac cgtttcttcc     360

gccagcacca agggacctag cgtgttccct ctggcccctt cctccaagag caccagcggc     420

ggaacagctg ccctgggatg cctggtgaaa gactacttcc ccgagcccgt gaccgtgagc     480

tggaacagcg gagccctgac atccggcgtg cacacattcc ccgccgtgct gcaatcctcc     540

ggcctgtaca gcctgtcctc cgtggtgaca gtgcctagca gcagcctggg cacccagacc     600

tacatctgca atgtgaacca caagcccagc aacaccaagg tggacaagaa ggtg           654


<210> SEQ ID NO 180
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CID_262 DNA - VL+CL

<400> SEQUENCE: 180

gacattcaga tgacccagag cccaagctct ctgtccgcct ccgttggcga ccgtgtcacc      60

atcacctgtc gtgcaagcca agatatttct accgccgttg cttggtctca gcagaaacca     120

ggtaaagcac ctaaactgct gatctacccc gcctcttcac tgtacagcgg tgttccatca     180

cgttttagcg gttcacgtag cggcaccgat ttcacactga ccatttcttc cttacagcca     240

gaagattttg caacctacta ttgccagcag catccttaca cccctccaac ttttggtcag     300

ggcaccaaag tagaaattaa aagaaccgtg gccgccccca gcgtgttcat cttccctccc     360

agcgacgagc agctgaagag cggcaccgcc agcgtggtgt gtctgctgaa caacttctac     420

cccagggagg ccaaggtcca gtggaaggtg gacaacgccc tgcagagcgg caacagccag     480

gagagcgtga ccgagcagga cagcaaggac agcacctaca gcctgagcag caccctcacc     540

ctgagcaagg ccgactacga gaagcacaag gtgtacgcct gtgaggtgac ccaccagggc     600
```

ctgagcagcc ctgtgaccaa gagcttcaac aggggcgagt gc 642

<210> SEQ ID NO 181
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_262 Amino acid sequence - VH

<400> SEQUENCE: 181

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Tyr
            20                  25                  30

Phe Ile His Trp Val Arg Gln Ala Pro Gly Lys Gly Leu Glu Trp Val
        35                  40                  45

Ala Asp Ile Asp Pro Thr Asn Gly Asp Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Glu Gly Gln Asp Gly Tyr Asn Ala Trp Asp Gln Trp Gly Gln
            100                 105                 110

Gly Thr Leu Val Thr Val Ser Ser
        115                 120

<210> SEQ ID NO 182
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_262 Amino acid sequence - VL

<400> SEQUENCE: 182

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Thr Ala
            20                  25                  30

Val Ala Trp Ser Gln Gln Lys Pro Gly Lys Ala Pro Lys Leu Leu Ile
        35                  40                  45

Tyr Pro Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Pro Tyr Thr Pro Pro
                85                  90                  95

Thr Phe Gly Gln Gly Thr Lys Val Glu Ile Lys
            100                 105

<210> SEQ ID NO 183
<211> LENGTH: 98
<212> TYPE: PRT
<213> ORGANISM: Artificial Sequence
<220> FEATURE:

<223> OTHER INFORMATION: Description of Artificial Sequence: Synthetic polypeptide
<220> FEATURE:
<223> OTHER INFORMATION: CID_262 Amino acid sequence - CH1

<400> SEQUENCE: 183

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val

<210> SEQ ID NO 184
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_262 Amino acid sequence - CL

<400> SEQUENCE: 184

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 185
<211> LENGTH: 8
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: CDRH1

<400> SEQUENCE: 185

Gly Asp Thr Phe Thr Ser Tyr Ser
1               5

<210> SEQ ID NO 186

<211> LENGTH: 8
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: CDRH1

<400> SEQUENCE: 186

Gly Tyr Thr Phe Thr Asp Leu Gly
1 5

<210> SEQ ID NO 187
<211> LENGTH: 8
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: CDRH1

<400> SEQUENCE: 187

Gly Phe Asn Ile Arg Asp Thr Tyr
1 5

<210> SEQ ID NO 188
<211> LENGTH: 8
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: CDRH1

<400> SEQUENCE: 188

Gly Phe Asn Ile Arg Asp Thr Phe
1 5

<210> SEQ ID NO 189
<211> LENGTH: 8
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: CDRH1

<400> SEQUENCE: 189

Gly Phe Asn Ile Arg Ala Thr Tyr
1 5

<210> SEQ ID NO 190
<211> LENGTH: 8
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: CDRH2

<400> SEQUENCE: 190

Ile Ile Thr Ile Leu Asp Asp Thr
1 5

<210> SEQ ID NO 191
<211> LENGTH: 654
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: CID_264 DNA - VH+CH1

<400> SEQUENCE: 191
gaggttcagc ttgttgagtc tggcggcggt ctggttcagc caggtggttc tctgcgtctg 60
tcctgtgctg cctctggttt caacatcaaa gcttactaca tccactgggt gcgtcaggca 120
ccaggcaaag gcctggaatg ggttgccgat atcgatccag acaacgggga tacccgttac 180
gccgattctg tgaagggtcg tttcactatt tctgcagaca cctccaagaa caccgcttac 240
ctgcaaatga actcactgcg tgctgaagac accgcagttt attattgttc tcgtgaaggt 300
caggatggtt acaacgcctg ggaccaatgg ggtcagggca ccctggtaac cgtttcttcc 360
gccagcacca agggacctag cgtgttccct ctggcccctt cctccaagag caccagcggc 420
ggaacagctg ccctgggatg cctggtgaaa gactacttcc ccgagcccgt gaccgtgagc 480
tggaacagcg gagccctgac atccggcgtg cacacattcc ccgccgtgct gcaatcctcc 540
ggcctgtaca gcctgtcctc cgtggtgaca gtgcctagca gcagcctggg cacccagacc 600
tacatctgca atgtgaacca caagcccagc aacaccaagg tggacaagaa ggtg 654

<210> SEQ ID NO 192
<211> LENGTH: 642
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: CID_264 DNA - VL+CL

<400> SEQUENCE: 192
gacattcaga tgacccagag cccaagctct ctgtccgcct ccgttggcga ccgtgtcacc 60
atcacctgtc gtgcaagcca agatgtctct accgccgttg cttggtctca gcagaaacca 120
ggtaaagcac ctaaactgct gatctaccct gcctcttcac tgtacagcgg tgttccatca 180
cgttttagcg gttcacgtag cggcaccgat ttcacactga ccatttcttc cttacagcca 240
gaagattttg caacctacta ttgccagcag cctaccctga cccctccaac ttttggtcag 300
ggcaccaaag tagaaattaa aagaaccgtg gccgccccca gcgtgttcat cttccctccc 360
agcgacgagc agctgaagag cggcaccgcc agcgtggtgt gtctgctgaa caacttctac 420
cccagggagg ccaaggtcca gtggaaggtg gacaacgccc tgcagagcgg caacagccag 480
gagagcgtga ccgagcagga cagcaaggac agcacctaca gcctgagcag caccctcacc 540
ctgagcaagg ccgactacga gaagcacaag gtgtacgcct gtgaggtgac ccaccagggc 600
ctgagcagcc ctgtgaccaa gagcttcaac aggggcgagt gc 642

<210> SEQ ID NO 193
<211> LENGTH: 120
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: CID_264 Amino acid sequence - VH

<400> SEQUENCE: 193

Glu Val Gln Leu Val Glu Ser Gly Gly Gly Leu Val Gln Pro Gly Gly
1 5 10 15

Ser Leu Arg Leu Ser Cys Ala Ala Ser Gly Phe Asn Ile Lys Ala Tyr
20 25 30

Tyr Ile His Trp Val Arg Gln Ala Pro Gly Lys Gly Leu Glu Trp Val
35 40 45

Ala Asp Ile Asp Pro Asp Asn Gly Asp Thr Arg Tyr Ala Asp Ser Val
50 55 60

Lys Gly Arg Phe Thr Ile Ser Ala Asp Thr Ser Lys Asn Thr Ala Tyr
65 70 75 80

Leu Gln Met Asn Ser Leu Arg Ala Glu Asp Thr Ala Val Tyr Tyr Cys
85 90 95

Ser Arg Glu Gly Gln Asp Gly Tyr Asn Ala Trp Asp Gln Trp Gly Gln
100 105 110

Gly Thr Leu Val Thr Val Ser Ser
115 120

<210> SEQ ID NO 194
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_264 Amino acid sequence - VL

<400> SEQUENCE: 194

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asp Val Ser Thr Ala
20 25 30

Val Ala Trp Ser Gln Gln Lys Pro Gly Lys Ala Pro Lys Leu Leu Ile
35 40 45

Tyr Pro Ala Ser Ser Leu Tyr Ser Gly Val Pro Ser Arg Phe Ser Gly
50 55 60

Ser Arg Ser Gly Thr Asp Phe Thr Leu Thr Ile Ser Ser Leu Gln Pro
65 70 75 80

Glu Asp Phe Ala Thr Tyr Tyr Cys Gln Gln Pro Thr Leu Thr Pro Pro
85 90 95

Thr Phe Gly Gln Gly Thr Lys Val Glu Ile Lys
100 105

<210> SEQ ID NO 195
<211> LENGTH: 98
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_264 Amino acid sequence - CH1

<400> SEQUENCE: 195

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

```
Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val
```

<210> SEQ ID NO 196
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_264 Amino acid sequence - CL

<400> SEQUENCE: 196

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 197
<211> LENGTH: 654
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: CID_266 DNA - VH+CH1

<400> SEQUENCE: 197

```
gaggttcagc ttgttgagtc tggcggcggt ctggttcagc caggtggttc tctgcgtctg     60

tcctgtgctg cctctggttt caacatccgt gcttactaca tccactgggt gcgtcaggca    120

ccaggcaaag gcctggaatg ggttgccgat atcgatccaa ccaacgggga tacccgttac    180

gccgattctg tgaagggtcg tttcactatt tctgcagaca cctccaagaa caccgcttac    240

ctgcaaatga actcactgcg tgctgaagac accgcagttt attattgttc tcgtgaaggt    300

caggatggtt acaacgcctg ggacctgtgg ggtcagggca ccctggtaac cgtttcttcc    360

gccagcacca agggacctag cgtgttccct ctggcccctt cctccaagag caccagcggc    420

ggaacagctg ccctgggatg cctggtgaaa gactacttcc ccgagcccgt gaccgtgagc    480

tggaacagcg gagccctgac atccggcgtg cacacattcc ccgccgtgct gcaatcctcc    540
```

ggcctgtaca gcctgtcctc cgtggtgaca gtgcctagca gcagcctggg cacccagacc 600
tacatctgca atgtgaacca caagcccagc aacaccaagg tggacaagaa ggtg 654

<210> SEQ ID NO 198
<211> LENGTH: 642
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: CID_266 DNA - VL+CL

<400> SEQUENCE: 198
gacattcaga tgacccagag cccaagctct ctgtccgcct ccgttggcga ccgtgtcacc 60
atcacctgtc gtgcaagcca agatgtttct accgccgttg cttggtatca gcagaaacca 120
ggtaaagcac ctaaactgct gatctaccct gcctcttcac tgtacagcgg tgttccatca 180
cgttttagcg gttcacgtag cggcaccgat ttcacactga ccatttcttc cttacagcca 240
gaagattttg caacctacta ttgccagcag cctggttaca cccctccaac ttttggtcag 300
ggcaccaaag tagaaattaa aagaaccgtg gccgccccca gcgtgttcat cttccctccc 360
agcgacgagc agctgaagag cggcaccgcc agcgtggtgt gtctgctgaa caacttctac 420
cccagggagg ccaaggtcca gtggaaggtg gacaacgccc tgcagagcgg caacagccag 480
gagagcgtga ccgagcagga cagcaaggac agcacctaca gcctgagcag caccctcacc 540
ctgagcaagg ccgactacga gaagcacaag gtgtacgcct gtgaggtgac ccaccagggc 600
ctgagcagcc ctgtgaccaa gagcttcaac aggggcgagt gc 642

<210> SEQ ID NO 199
<211> LENGTH: 120
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: CID_266 Amino acid sequence - VH

<400> SEQUENCE: 199

Glu Val Gln Leu Val Glu Ser Gly Gly Gly Leu Val Gln Pro Gly Gly
1 5 10 15

Ser Leu Arg Leu Ser Cys Ala Ala Ser Gly Phe Asn Ile Arg Ala Tyr
20 25 30

Tyr Ile His Trp Val Arg Gln Ala Pro Gly Lys Gly Leu Glu Trp Val
35 40 45

Ala Asp Ile Asp Pro Thr Asn Gly Asp Thr Arg Tyr Ala Asp Ser Val
50 55 60

Lys Gly Arg Phe Thr Ile Ser Ala Asp Thr Ser Lys Asn Thr Ala Tyr
65 70 75 80

Leu Gln Met Asn Ser Leu Arg Ala Glu Asp Thr Ala Val Tyr Tyr Cys
85 90 95

Ser Arg Glu Gly Gln Asp Gly Tyr Asn Ala Trp Asp Leu Trp Gly Gln
100 105 110

Gly Thr Leu Val Thr Val Ser Ser
115 120

<210> SEQ ID NO 200

```
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_266 Amino acid sequence - VL

<400> SEQUENCE: 200

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Pro Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Pro Gly Tyr Thr Pro Pro
                85                  90                  95

Thr Phe Gly Gln Gly Thr Lys Val Glu Ile Lys
            100                 105


<210> SEQ ID NO 201
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_266 Amino acid sequence - CH1

<400> SEQUENCE: 201

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val


<210> SEQ ID NO 202
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_266 Amino acid sequence - CL

<400> SEQUENCE: 202

Arg Thr Val Ala Ala Pro Ser Val Phe Ile Phe Pro Pro Ser Asp Glu
```

```
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 203
<211> LENGTH: 654
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: CID_267 DNA - VH+CH1

<400> SEQUENCE: 203

```
gaggttcagc ttgttgagtc tggcggcggt ctggttcagc caggtggttc tctgcgtctg     60

tcctgtgctg cctctggttt caacatccgt gattactaca tccactgggt gcgtcaggca    120

ccaggcaaag gcctggaatg ggttgccgat atcgatccaa ccaacgggga tacccgttac    180

gccgattctg tgaagggtcg tttcactatt tctgcagaca cctccaagaa caccgcttac    240

ctgcaaatga actcactgcg tgctgaagac accgcagttt attattgttc ccgtgaaggt    300

caagatggtt acaacgcctg ggacctgtgg ggtcagggca ccctggtaac cgtttcttcc    360

gccagcacca agggacctag cgtgttccct ctggcccctt cctccaagag caccagcggc    420

ggaacagctg ccctgggatg cctggtgaaa gactacttcc ccgagcccgt gaccgtgagc    480

tggaacagcg gagccctgac atccggcgtg cacacattcc ccgccgtgct gcaatcctcc    540

ggcctgtaca gcctgtcctc cgtggtgaca gtgcctagca gcagcctggg cacccagacc    600

tacatctgca atgtgaacca caagcccagc aacaccaagg tggacaagaa ggtg          654
```

<210> SEQ ID NO 204
<211> LENGTH: 642
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: CID_267 DNA - VL+CL

<400> SEQUENCE: 204

```
gacattcaga tgacccagag cccaagctct ctgtccgcct ccgttggcga ccgtgtcacc     60

atcacctgtc gtgcaagcca agatgtttct accgccgttg cttggtatca gcagaaacca    120

ggtaaagcac ctaaactgct gatctacccc gcctcttcac tgtacagcgg tgttccatca    180

cgttttagcg gttcacgtag cggcaccgat ttcacactga ccatttcttc cttacagcca    240

gaagattttg caacctacta ttgccagcag caccccttaca cccctccaac ttttggtcag    300

ggcaccaaag tagaaattaa aagaaccgtg gccgccccca gcgtgttcat cttccctccc    360
```

agcgacgagc agctgaagag cggcaccgcc agcgtggtgt gtctgctgaa caacttctac 420
cccagggagg ccaaggtcca gtggaaggtg gacaacgccc tgcagagcgg caacagccag 480
gagagcgtga ccgagcagga cagcaaggac agcacctaca gcctgagcag caccctcacc 540
ctgagcaagg ccgactacga gaagcacaag gtgtacgcct gtgaggtgac ccaccagggc 600
ctgagcagcc ctgtgaccaa gagcttcaac aggggcgagt gc 642

<210> SEQ ID NO 205
<211> LENGTH: 120
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: CID_267 Amino acid sequence - VH

<400> SEQUENCE: 205

Glu Val Gln Leu Val Glu Ser Gly Gly Gly Leu Val Gln Pro Gly Gly
1 5 10 15

Ser Leu Arg Leu Ser Cys Ala Ala Ser Gly Phe Asn Ile Arg Asp Tyr
20 25 30

Tyr Ile His Trp Val Arg Gln Ala Pro Gly Lys Gly Leu Glu Trp Val
35 40 45

Ala Asp Ile Asp Pro Thr Asn Gly Asp Thr Arg Tyr Ala Asp Ser Val
50 55 60

Lys Gly Arg Phe Thr Ile Ser Ala Asp Thr Ser Lys Asn Thr Ala Tyr
65 70 75 80

Leu Gln Met Asn Ser Leu Arg Ala Glu Asp Thr Ala Val Tyr Tyr Cys
85 90 95

Ser Arg Glu Gly Gln Asp Gly Tyr Asn Ala Trp Asp Leu Trp Gly Gln
100 105 110

Gly Thr Leu Val Thr Val Ser Ser
115 120

<210> SEQ ID NO 206
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: CID_267 Amino acid sequence - VL

<400> SEQUENCE: 206

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asp Val Ser Thr Ala
20 25 30

Val Ala Trp Tyr Gln Gln Lys Pro Gly Lys Ala Pro Lys Leu Leu Ile
35 40 45

Tyr Pro Ala Ser Ser Leu Tyr Ser Gly Val Pro Ser Arg Phe Ser Gly
50 55 60

Ser Arg Ser Gly Thr Asp Phe Thr Leu Thr Ile Ser Ser Leu Gln Pro
65 70 75 80

Glu Asp Phe Ala Thr Tyr Tyr Cys Gln Gln His Pro Tyr Thr Pro Pro
85 90 95

```
Thr Phe Gly Gln Gly Thr Lys Val Glu Ile Lys
            100                 105


<210> SEQ ID NO 207
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_267 Amino acid sequence - CH1

<400> SEQUENCE: 207

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val


<210> SEQ ID NO 208
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_267 Amino acid sequence - CL

<400> SEQUENCE: 208

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 209
<211> LENGTH: 654
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
```

<223> OTHER INFORMATION: CID_268 DNA - VH+CH1

<400> SEQUENCE: 209
gaggttcagc ttgttgagtc tggcggcggt ctggttcagc caggtggttc tctgcgtctg 60
tcctgtgctg cctctggttt caacatcaaa gattacttca tccactgggt gcgtcaggca 120
ccaggcaaag gcctggaatg ggttgccgat atcgatccaa ccaacgggga tacccgttac 180
gccgattctg tgaagggtcg tttcactatt tctgcagaca cctccaagaa caccgcttac 240
ctgcaaatga actcactgcg tgctgaagac accgcagttt attattgttc tcgtgaaggt 300
caggatggtt acaacgcctg ggacatgtgg ggtcagggca ccctggtaac cgtttcttcc 360
gccagcacca agggacctag cgtgttccct ctggcccctt cctccaagag caccagcggc 420
ggaacagctg ccctgggatg cctggtgaaa gactacttcc ccgagcccgt gaccgtgagc 480
tggaacagcg gagccctgac atccggcgtg cacacattcc ccgccgtgct gcaatcctcc 540
ggcctgtaca gcctgtcctc cgtggtgaca gtgcctagca gcagcctggg cacccagacc 600
tacatctgca atgtgaacca caagcccagc aacaccaagg tggacaagaa ggtg 654

<210> SEQ ID NO 210
<211> LENGTH: 642
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: CID_268 DNA - VL+CL

<400> SEQUENCE: 210
gacattcaga tgacccagag cccaagctct ctgtccgcct ccgttggcga ccgtgtcacc 60
atcacctgtc gtgcaagcca agatatttct accgccgttg cttggtctca gcagaaacca 120
ggtaaagcac ctaaactgct gatctacccc gcctcttcac tgtacagcgg tgttccatca 180
cgttttagcg gttcacgtag cggcaccgat ttcacactga ccatttcttc cttacagcca 240
gaagattttg caacctacta ttgccagcag cctttgtaca cccctccaac ttttggtcag 300
ggcaccaaag tagaaattaa aagaaccgtg gccgccccca gcgtgttcat cttccctccc 360
agcgacgagc agctgaagag cggcaccgcc agcgtggtgt gtctgctgaa caacttctac 420
cccagggagg ccaaggtcca gtggaaggtg gacaacgccc tgcagagcgg caacagccag 480
gagagcgtga ccgagcagga cagcaaggac agcacctaca gcctgagcag caccctcacc 540
ctgagcaagg ccgactacga gaagcacaag gtgtacgcct gtgaggtgac ccaccagggc 600
ctgagcagcc ctgtgaccaa gagcttcaac aggggcgagt gc 642

<210> SEQ ID NO 211
<211> LENGTH: 120
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: CID_268 Amino acid sequence - VH

<400> SEQUENCE: 211

Glu Val Gln Leu Val Glu Ser Gly Gly Gly Leu Val Gln Pro Gly Gly
1 5 10 15

Ser Leu Arg Leu Ser Cys Ala Ala Ser Gly Phe Asn Ile Lys Asp Tyr
20 25 30

```
Phe Ile His Trp Val Arg Gln Ala Pro Gly Lys Gly Leu Glu Trp Val
        35                  40                  45

Ala Asp Ile Asp Pro Thr Asn Gly Asp Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Glu Gly Gln Asp Gly Tyr Asn Ala Trp Asp Met Trp Gly Gln
            100                 105                 110

Gly Thr Leu Val Thr Val Ser Ser
        115                 120


<210> SEQ ID NO 212
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_268 Amino acid sequence - VL

<400> SEQUENCE: 212

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Thr Ala
            20                  25                  30

Val Ala Trp Ser Gln Gln Lys Pro Gly Lys Ala Pro Lys Leu Leu Ile
        35                  40                  45

Tyr Pro Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Pro Leu Tyr Thr Pro Pro
                85                  90                  95

Thr Phe Gly Gln Gly Thr Lys Val Glu Ile Lys
            100                 105


<210> SEQ ID NO 213
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_268 Amino acid sequence - CH1

<400> SEQUENCE: 213

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
```

```
65                  70                  75                  80

Tyr Ile Cys Asn Val Asn His Lys Pro Ser Asn Thr Lys Val Asp Lys
                85                  90                  95

Lys Val
```

<210> SEQ ID NO 214
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_268 Amino acid sequence - CL

<400> SEQUENCE: 214

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 215
<211> LENGTH: 654
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: CID_271 DNA - VH+CH1

<400> SEQUENCE: 215

```
gaagtacagc tggttgaatc tggtggtggt ctggtacagc caggcggttc tcttcgtctg     60

tcttgcgctg cctctggttt caacattcgt gatatgttca tccactgggt ccgtcagtct    120

ccaggtaaag gcctggaatg ggtcgctgat atctctccag acaacggtga tacccgttac    180

gccgattctg tcaaaggccg tttcactatc agcgccgaca cttccaaaaa caccgcctac    240

ctgcagatga acagcctgcg tgccgaagac accgccatct actactgtac ccgtgaaggt    300

gaagatggct acaacgcatt cgatatgtgg ggtcagggca ccctggtaac tgtctccagc    360

gccagcacca agggacctag cgtgttccct ctggcccctt cctccaagag caccagcggc    420

ggaacagctg ccctgggatg cctggtgaaa gactacttcc ccgagcccgt gaccgtgagc    480

tggaacagcg gagccctgac atccggcgtg cacacattcc ccgccgtgct gcaatcctcc    540

ggcctgtaca gcctgtcctc cgtggtgaca gtgcctagca gcagcctggg cacccagacc    600

tacatctgca atgtgaacca caagcccagc aacaccaagg tggacaagaa ggtg          654
```

<210> SEQ ID NO 216
<211> LENGTH: 642

<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: CID_271 DNA - VL+CL

<400> SEQUENCE: 216
gatatccaga tgacccagtc cccaatcctg ctgtctgcct ccgttggtga tcgtgtgacc 60
attacctgcc gtgcttcaca ggacgtaagc actgccgtag cttggtctca acagcgtacc 120
aacggcagcc cacgtctgct gatttactcc gcaagttctc tgtatagtgg cgtcccaagc 180
cgttttagcg gctcacgttc cggtactgat ttcaccctga ccatttccag cctgcagcca 240
gaggatatcg cagactacta ctgccagcag catgcctaca ccccaccaac cttcggtgcc 300
ggtaccaagg tagaaatcaa aagaaccgtg gccgccccca gcgtgttcat cttccctccc 360
agcgacgagc agctgaagag cggcaccgcc agcgtggtgt gtctgctgaa caacttctac 420
cccagggagg ccaaggtcca gtggaaggtg gacaacgccc tgcagagcgg caacagccag 480
gagagcgtga ccgagcagga cagcaaggac agcacctaca gcctgagcag caccctcacc 540
ctgagcaagg ccgactacga gaagcacaag gtgtacgcct gtgaggtgac ccaccagggc 600
ctgagcagcc ctgtgaccaa gagcttcaac aggggcgagt gc 642

<210> SEQ ID NO 217
<211> LENGTH: 120
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: CID_271 Amino acid sequence - VH

<400> SEQUENCE: 217

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Arg Asp Met
            20                  25                  30

Phe Ile His Trp Val Arg Gln Ser Pro Gly Lys Gly Leu Glu Trp Val
        35                  40                  45

Ala Asp Ile Ser Pro Asp Asn Gly Asp Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Ile Tyr Tyr Cys
                85                  90                  95

Thr Arg Glu Gly Glu Asp Gly Tyr Asn Ala Phe Asp Met Trp Gly Gln
            100                 105                 110

Gly Thr Leu Val Thr Val Ser Ser
        115                 120

<210> SEQ ID NO 218
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: CID_271 Amino acid sequence - VL

<400> SEQUENCE: 218

Asp Ile Gln Met Thr Gln Ser Pro Ile Leu Leu Ser Ala Ser Val Gly
1 5 10 15

Asp Arg Val Thr Ile Thr Cys Arg Ala Ser Gln Asp Val Ser Thr Ala
20 25 30

Val Ala Trp Ser Gln Gln Arg Thr Asn Gly Ser Pro Arg Leu Leu Ile
35 40 45

Tyr Ser Ala Ser Ser Leu Tyr Ser Gly Val Pro Ser Arg Phe Ser Gly
50 55 60

Ser Arg Ser Gly Thr Asp Phe Thr Leu Thr Ile Ser Ser Leu Gln Pro
65 70 75 80

Glu Asp Ile Ala Asp Tyr Tyr Cys Gln Gln His Ala Tyr Thr Pro Pro
85 90 95

Thr Phe Gly Ala Gly Thr Lys Val Glu Ile Lys
100 105

<210> SEQ ID NO 219
<211> LENGTH: 98
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_271 Amino acid sequence - CH1

<400> SEQUENCE: 219

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val

<210> SEQ ID NO 220
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_271 Amino acid sequence - CL

<400> SEQUENCE: 220

Arg Thr Val Ala Ala Pro Ser Val Phe Ile Phe Pro Pro Ser Asp Glu
1 5 10 15

Gln Leu Lys Ser Gly Thr Ala Ser Val Val Cys Leu Leu Asn Asn Phe
20 25 30

Tyr Pro Arg Glu Ala Lys Val Gln Trp Lys Val Asp Asn Ala Leu Gln
35 40 45

```
Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 221
<211> LENGTH: 654
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CID_230 DNA - VH+CH1

<400> SEQUENCE: 221

gaagtacagc tggttgaatc tggtggtggt ctggtacagc caggcggttc tcttcgtctg     60

tcttgcgctg cctctggttt caacattcgt gatacctaca tccactgggt ccgtcagtct    120

ccaggtaaag gcctggaatg ggtcgctgat atcgatccaa ccaacggtga tacccgttac    180

gccgattctg tcaaaggccg tttcactatc agcgccgaca cttccaaaaa caccgcctac    240

ctgcagatga acagcctgcg tgccgaagac accgccatct actactgttc ccgtgaaatg    300

gcagatggct acaacgcatt cgatctgtgg ggtcagggca ccctggtaac tgtctccagc    360

gccagcacca agggacctag cgtgttccct ctggcccctt cctccaagag caccagcggc    420

ggaacagctg ccctgggatg cctggtgaaa gactacttcc ccgagcccgt gaccgtgagc    480

tggaacagcg gagccctgac atccggcgtg cacacattcc ccgccgtgct gcaatcctcc    540

ggcctgtaca gcctgtcctc cgtggtgaca gtgcctagca gcagcctggg cacccagacc    600

tacatctgca atgtgaacca caagcccagc aacaccaagg tggacaagaa ggtg          654


<210> SEQ ID NO 222
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CID_230 DNA - VL+CL

<400> SEQUENCE: 222

gatatccaga tgacccagtc cccaatcctg ctgtctgcct ccgttggtga tcgtgtgacc     60

attacctgcc gtgcttcaca ggacgtaagc actgccgtag cttggtctca acagcgtacc    120

aacggcagcc cacgtctgct gatttactct gcaagttctc tgtatagtgg cgtcccaagc    180

cgttttagcg gctcacgttc cggtactgat ttcaccctga ccatttccag cctgcagcca    240

gaggatatcg cagactacta ctgccagcag cctaattaca ccccaccaac cttcggtgcc    300

ggtaccaagg tagaaatcaa aagaaccgtg gccgccccca gcgtgttcat cttccctccc    360

agcgacgagc agctgaagag cggcaccgcc agcgtggtgt gtctgctgaa caacttctac    420

cccagggagg ccaaggtcca gtggaaggtg gacaacgccc tgcagagcgg caacagccag    480

gagagcgtga ccgagcagga cagcaaggac agcacctaca gcctgagcag caccctcacc    540

ctgagcaagg ccgactacga gaagcacaag gtgtacgcct gtgaggtgac ccaccagggc    600
```

ctgagcagcc ctgtgaccaa gagcttcaac aggggcgagt gc 642

<210> SEQ ID NO 223
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_230 Amino acid sequence - VH

<400> SEQUENCE: 223

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Arg Asp Thr
            20                  25                  30

Tyr Ile His Trp Val Arg Gln Ser Pro Gly Lys Gly Leu Glu Trp Val
        35                  40                  45

Ala Asp Ile Asp Pro Thr Asn Gly Asp Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Ile Tyr Tyr Cys
                85                  90                  95

Ser Arg Glu Met Ala Asp Gly Tyr Asn Ala Phe Asp Leu Trp Gly Gln
            100                 105                 110

Gly Thr Leu Val Thr Val Ser Ser
        115                 120
```

<210> SEQ ID NO 224
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_230 Amino acid sequence - VL

<400> SEQUENCE: 224

```
Asp Ile Gln Met Thr Gln Ser Pro Ile Leu Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Ser Gln Gln Arg Thr Asn Gly Ser Pro Arg Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Ile Ala Asp Tyr Tyr Cys Gln Gln Pro Asn Tyr Thr Pro Pro
                85                  90                  95

Thr Phe Gly Ala Gly Thr Lys Val Glu Ile Lys
            100                 105
```

<210> SEQ ID NO 225
<211> LENGTH: 98
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: CID_230 Amino acid sequence - CH1

<400> SEQUENCE: 225

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val

<210> SEQ ID NO 226
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: CID_230 Amino acid sequence - CL

<400> SEQUENCE: 226

Arg Thr Val Ala Ala Pro Ser Val Phe Ile Phe Pro Pro Ser Asp Glu
1 5 10 15

Gln Leu Lys Ser Gly Thr Ala Ser Val Val Cys Leu Leu Asn Asn Phe
20 25 30

Tyr Pro Arg Glu Ala Lys Val Gln Trp Lys Val Asp Asn Ala Leu Gln
35 40 45

Ser Gly Asn Ser Gln Glu Ser Val Thr Glu Gln Asp Ser Lys Asp Ser
50 55 60

Thr Tyr Ser Leu Ser Ser Thr Leu Thr Leu Ser Lys Ala Asp Tyr Glu
65 70 75 80

Lys His Lys Val Tyr Ala Cys Glu Val Thr His Gln Gly Leu Ser Ser
85 90 95

Pro Val Thr Lys Ser Phe Asn Arg Gly Glu Cys
100 105

<210> SEQ ID NO 227
<211> LENGTH: 654
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: CID_265 DNA - VH+CH1

<400> SEQUENCE: 227
gaggttcagc ttgttgagtc tggcggcggt ctggttcagc caggtggttc tctgcgtctg 60
tcctgtgctg cctctggttt caacatccgt gctatgtaca tccactgggt gcgtcaggca 120

```
ccaggcaaag gcctggaatg ggttgccgat atcgatccaa ccaacgggga tacccgttac    180

gccgattctg tgaagggtcg tttcactatt tctgcagaca cctccaagaa caccgcttac    240

ctgcaaatga actcactgcg tgctgaagac accgcagttt attattgtac tcgtgaaggt    300

caagatggtt acaacgcctt cgacatgtgg ggtcagggca ccctggtaac cgtttcttcc    360

gccagcacca agggacctag cgtgttccct ctggcccctt cctccaagag caccagcggc    420

ggaacagctg ccctgggatg cctggtgaaa gactacttcc ccgagcccgt gaccgtgagc    480

tggaacagcg gagccctgac atccggcgtg cacacattcc ccgccgtgct gcaatcctcc    540

ggcctgtaca gcctgtcctc cgtggtgaca gtgcctagca gcagcctggg cacccagacc    600

tacatctgca atgtgaacca caagcccagc aacaccaagg tggacaagaa ggtg          654
```

<210> SEQ ID NO 228
<211> LENGTH: 642
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: CID_265 DNA - VL+CL

<400> SEQUENCE: 228

```
gacattcaga tgacccagag cccaagctct ctgtccgcct ccgttggcga ccgtgtcacc     60

atcacctgtc gtgcaagcca agatatctct accgccgttg cttggtctca gcagaaacca    120

ggtaaagcac ctaaactgct gatctactcc gcctcttcac tgtacagcgg tgttccatca    180

cgttttagcg gttcacgtag cggcaccgat ttcacactga ccatttcttc cttacagcca    240

gaagattttg caacctacta ttgccagcag cccaacctga cccctccaac ttttggtcag    300

ggcaccaaag tagaaattaa aagaaccgtg gccgccccca gcgtgttcat cttccctccc    360

agcgacgagc agctgaagag cggcaccgcc agcgtggtgt gtctgctgaa caacttctac    420

cccagggagg ccaaggtcca gtggaaggtg gacaacgccc tgcagagcgg caacagccag    480

gagagcgtga ccgagcagga cagcaaggac agcacctaca gcctgagcag caccctcacc    540

ctgagcaagg ccgactacga gaagcacaag gtgtacgcct gtgaggtgac ccaccagggc    600

ctgagcagcc ctgtgaccaa gagcttcaac aggggcgagt gc                       642
```

<210> SEQ ID NO 229
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_265 Amino acid sequence - VH

<400> SEQUENCE: 229

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Arg Ala Met
            20                  25                  30

Tyr Ile His Trp Val Arg Gln Ala Pro Gly Lys Gly Leu Glu Trp Val
        35                  40                  45

Ala Asp Ile Asp Pro Thr Asn Gly Asp Thr Arg Tyr Ala Asp Ser Val
    50                  55                  60

Lys Gly Arg Phe Thr Ile Ser Ala Asp Thr Ser Lys Asn Thr Ala Tyr
```

```
65                  70                  75                  80

Leu Gln Met Asn Ser Leu Arg Ala Glu Asp Thr Ala Val Tyr Tyr Cys
                85                  90                  95

Thr Arg Glu Gly Gln Asp Gly Tyr Asn Ala Phe Asp Met Trp Gly Gln
            100                 105                 110

Gly Thr Leu Val Thr Val Ser Ser
        115                 120


<210> SEQ ID NO 230
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_265 Amino acid sequence - VL

<400> SEQUENCE: 230

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Thr Ala
            20                  25                  30

Val Ala Trp Ser Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Pro Asn Leu Thr Pro Pro
                85                  90                  95

Thr Phe Gly Gln Gly Thr Lys Val Glu Ile Lys
            100                 105


<210> SEQ ID NO 231
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_265 Amino acid sequence - CH1

<400> SEQUENCE: 231

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val
```

<210> SEQ ID NO 232
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_265 Amino acid sequence - CL

<400> SEQUENCE: 232

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 233
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID251; BDG30.046; Human IgG1; protein
      sequence - VH

<400> SEQUENCE: 233

```
Glu Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Thr Ser Tyr
            20                  25                  30

Ser Phe Asn Trp Val Arg Gln Ala Pro Gly Gln Gly Leu Glu Trp Met
        35                  40                  45

Gly Arg Ile Ile Thr Ile Leu Asp Asp Thr Glu Tyr Ala Pro His Leu
    50                  55                  60

Gln Gly Arg Val Thr Ile Thr Ala Asp Lys Ser Thr Ser Thr Val Tyr
65                  70                  75                  80

Leu Glu Leu Arg Asn Leu Arg Ser Asp Asp Thr Ala Val Tyr Phe Cys
                85                  90                  95

Ala Gly Val Tyr Glu Gly Pro Asn Ser Glu Gly Ser Tyr Asp Asp Tyr
            100                 105                 110

Gly Phe Leu Lys His Trp Gly Gln Gly Thr Leu Val Thr Val Ser Ser
        115                 120                 125
```

<210> SEQ ID NO 234
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide <220> FEATURE:
<223> OTHER INFORMATION: CID251; BDG30.046; Human IgG1; protein
sequence - VL

<400> SEQUENCE: 234

Asp Ile Val Met Thr Gln Ser Pro Ala Thr Leu Ser Val Ser Pro Gly
1 5 10 15

Glu Arg Ala Thr Leu Ser Cys Arg Ala Ser Glu Ser Val Ala Asn Asp
20 25 30

Leu Ala Trp Tyr Gln Gln Lys Pro Gly Gln Val Pro Arg Leu Leu Ile
35 40 45

Tyr Gly Ala Ser Thr Arg Ala Thr Gly Val Pro Ala Arg Phe Ser Gly
50 55 60

Ser Gly Ser Gly Ala Glu Phe Thr Leu Thr Ile Ser Ser Leu Gln Ser
65 70 75 80

Glu Asp Phe Ala Val Tyr Tyr Cys Gln Gln Tyr Ala Asn Trp Pro Pro
85 90 95

Arg Glu Thr Phe Gly Gln Gly Thr Arg Leu Glu Ile Lys
100 105

<210> SEQ ID NO 235
<211> LENGTH: 458
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: CID251; BDG30.046; Human IgG1; H chain
(VH+CH1+hinge+CH2+CH3)

<400> SEQUENCE: 235

Glu Val Gln Leu Val Gln Ser Gly Ala Glu Val Lys Lys Pro Gly Ser
1 5 10 15

Ser Val Lys Val Ser Cys Lys Ala Ser Gly Asp Thr Phe Thr Ser Tyr
20 25 30

Ser Phe Asn Trp Val Arg Gln Ala Pro Gly Gln Gly Leu Glu Trp Met
35 40 45

Gly Arg Ile Ile Thr Ile Leu Asp Asp Thr Glu Tyr Ala Pro His Leu
50 55 60

Gln Gly Arg Val Thr Ile Thr Ala Asp Lys Ser Thr Ser Thr Val Tyr
65 70 75 80

Leu Glu Leu Arg Asn Leu Arg Ser Asp Asp Thr Ala Val Tyr Phe Cys
85 90 95

Ala Gly Val Tyr Glu Gly Pro Asn Ser Glu Gly Ser Tyr Asp Asp Tyr
100 105 110

Gly Phe Leu Lys His Trp Gly Gln Gly Thr Leu Val Thr Val Ser Ser
115 120 125

Ala Ser Thr Lys Gly Pro Ser Val Phe Pro Leu Ala Pro Ser Ser Lys
130 135 140

Ser Thr Ser Gly Gly Thr Ala Ala Leu Gly Cys Leu Val Lys Asp Tyr
145 150 155 160

Phe Pro Glu Pro Val Thr Val Ser Trp Asn Ser Gly Ala Leu Thr Ser
165 170 175

Gly Val His Thr Phe Pro Ala Val Leu Gln Ser Ser Gly Leu Tyr Ser
180 185 190

Leu Ser Ser Val Val Thr Val Pro Ser Ser Ser Leu Gly Thr Gln Thr
195 200 205

Tyr Ile Cys Asn Val Asn His Lys Pro Ser Asn Thr Lys Val Asp Lys
    210                 215                 220

Lys Val Glu Pro Lys Ser Cys Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Asp Glu
        355                 360                 365

Leu Thr Lys Asn Gln Val Ser Leu Thr Cys Leu Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly Lys
    450                 455

<210> SEQ ID NO 236
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID251; BDG30.046; Human IgG1; L chain (VL+CL)

<400> SEQUENCE: 236

Asp Ile Val Met Thr Gln Ser Pro Ala Thr Leu Ser Val Ser Pro Gly
1               5                   10                  15

Glu Arg Ala Thr Leu Ser Cys Arg Ala Ser Glu Ser Val Ala Asn Asp
            20                  25                  30

Leu Ala Trp Tyr Gln Gln Lys Pro Gly Gln Val Pro Arg Leu Leu Ile
        35                  40                  45

Tyr Gly Ala Ser Thr Arg Ala Thr Gly Val Pro Ala Arg Phe Ser Gly
    50                  55                  60

Ser Gly Ser Gly Ala Glu Phe Thr Leu Thr Ile Ser Ser Leu Gln Ser
65                  70                  75                  80

Glu Asp Phe Ala Val Tyr Tyr Cys Gln Gln Tyr Ala Asn Trp Pro Pro
                85                  90                  95

Arg Glu Thr Phe Gly Gln Gly Thr Arg Leu Glu Ile Lys Arg Thr Val
100 105 110

Ala Ala Pro Ser Val Phe Ile Phe Pro Pro Ser Asp Glu Gln Leu Lys
115 120 125

Ser Gly Thr Ala Ser Val Val Cys Leu Leu Asn Asn Phe Tyr Pro Arg
130 135 140

Glu Ala Lys Val Gln Trp Lys Val Asp Asn Ala Leu Gln Ser Gly Asn
145 150 155 160

Ser Gln Glu Ser Val Thr Glu Gln Asp Ser Lys Asp Ser Thr Tyr Ser
165 170 175

Leu Ser Ser Thr Leu Thr Leu Ser Lys Ala Asp Tyr Glu Lys His Lys
180 185 190

Val Tyr Ala Cys Glu Val Thr His Gln Gly Leu Ser Ser Pro Val Thr
195 200 205

Lys Ser Phe Asn Arg Gly Glu Cys
210 215

<210> SEQ ID NO 237
<211> LENGTH: 128
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_272; BDG30.090; Human IgG1; protein sequence - VH

<400> SEQUENCE: 237

Glu Val Gln Leu Val Gln Ser Gly Ala Glu Val Lys Lys Pro Gly Ser
1 5 10 15

Ser Val Lys Val Ser Cys Lys Ala Ser Gly Asp Thr Phe Thr Ser Tyr
20 25 30

Ser Phe Asn Trp Val Arg Gln Ala Pro Gly Gln Gly Leu Glu Trp Met
35 40 45

Gly Arg Ile Ile Thr Ile Asp Asp Asp Thr Glu Tyr Ala Pro His Leu
50 55 60

Gln Gly Arg Val Thr Ile Thr Ala Asp Lys Ser Thr Ser Thr Val Tyr
65 70 75 80

Leu Glu Leu Arg Asn Leu Arg Ser Asp Asp Thr Ala Val Tyr Phe Cys
85 90 95

Ala Gly Val Tyr Glu Gly Pro Asn Ser Glu Gly Ser Tyr Asp Asp Tyr
100 105 110

Gly Phe Tyr Lys His Trp Gly Gln Gly Thr Leu Val Thr Val Ser Ser
115 120 125

<210> SEQ ID NO 238
<211> LENGTH: 109
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_272; BDG30.090; Human IgG1; protein sequence - VL

<400> SEQUENCE: 238

Asp Ile Val Met Thr Gln Ser Pro Ala Thr Leu Ser Val Ser Pro Gly
1 5 10 15

```
Glu Arg Ala Thr Leu Ser Cys Arg Ala Ser Glu Ser Val Gly Asn Asp
            20                  25                  30

Leu Ala Trp Tyr Gln Gln Lys Pro Gly Gln Val Pro Arg Leu Leu Ile
        35                  40                  45

Tyr Gly Ala Ser Thr Arg Ala Pro Gly Val Pro Ala Arg Phe Ser Gly
    50                  55                  60

Ser Gly Ser Gly Ala Glu Phe Thr Leu Thr Ile Ser Ser Leu Gln Ser
65                  70                  75                  80

Glu Asp Phe Ala Val Tyr Tyr Cys Gln Gln Tyr Ala Asn Trp Pro Pro
                85                  90                  95

Arg Glu Thr Phe Gly Gln Gly Thr Arg Leu Glu Ile Lys
            100                 105


<210> SEQ ID NO 239
<211> LENGTH: 458
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_272; BDG30.090; Human IgG1; H chain
      (VH+CH1+hinge+CH2+CH3)

<400> SEQUENCE: 239

Glu Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Thr Ser Tyr
            20                  25                  30

Ser Phe Asn Trp Val Arg Gln Ala Pro Gly Gln Gly Leu Glu Trp Met
        35                  40                  45

Gly Arg Ile Ile Thr Ile Asp Asp Asp Thr Glu Tyr Ala Pro His Leu
    50                  55                  60

Gln Gly Arg Val Thr Ile Thr Ala Asp Lys Ser Thr Ser Thr Val Tyr
65                  70                  75                  80

Leu Glu Leu Arg Asn Leu Arg Ser Asp Asp Thr Ala Val Tyr Phe Cys
                85                  90                  95

Ala Gly Val Tyr Glu Gly Pro Asn Ser Glu Gly Ser Tyr Asp Asp Tyr
            100                 105                 110

Gly Phe Tyr Lys His Trp Gly Gln Gly Thr Leu Val Thr Val Ser Ser
        115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
    210                 215                 220

Lys Val Glu Pro Lys Ser Cys Asp Lys Thr His Thr Cys Pro Pro Cys
225                 230                 235                 240

Pro Ala Pro Glu Leu Leu Gly Gly Pro Ser Val Phe Leu Phe Pro Pro
```

```
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Asp Glu
        355                 360                 365

Leu Thr Lys Asn Gln Val Ser Leu Thr Cys Leu Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly Lys
    450                 455
```

<210> SEQ ID NO 240
<211> LENGTH: 216
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_272; BDG30.090; Human IgG1; L chain (VL+CL)

<400> SEQUENCE: 240

```
Asp Ile Val Met Thr Gln Ser Pro Ala Thr Leu Ser Val Ser Pro Gly
1               5                   10                  15

Glu Arg Ala Thr Leu Ser Cys Arg Ala Ser Glu Ser Val Gly Asn Asp
            20                  25                  30

Leu Ala Trp Tyr Gln Gln Lys Pro Gly Gln Val Pro Arg Leu Leu Ile
        35                  40                  45

Tyr Gly Ala Ser Thr Arg Ala Pro Gly Val Pro Ala Arg Phe Ser Gly
    50                  55                  60

Ser Gly Ser Gly Ala Glu Phe Thr Leu Thr Ile Ser Ser Leu Gln Ser
65                  70                  75                  80

Glu Asp Phe Ala Val Tyr Tyr Cys Gln Gln Tyr Ala Asn Trp Pro Pro
                85                  90                  95

Arg Glu Thr Phe Gly Gln Gly Thr Arg Leu Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
```

```
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215


<210> SEQ ID NO 241
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_276; BDG30.092; Human IgG1; protein
      sequence - VH

<400> SEQUENCE: 241

Glu Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Thr Ser Tyr
            20                  25                  30

Ser Phe Asn Trp Val Arg Gln Ala Pro Gly Gln Gly Leu Glu Trp Met
        35                  40                  45

Gly Arg Ile Ile Thr Ile Tyr Asp Asp Thr Glu Tyr Ala Pro His Leu
    50                  55                  60

Gln Gly Arg Val Thr Ile Thr Ala Asp Lys Ser Thr Ser Thr Val Tyr
65                  70                  75                  80

Leu Glu Leu Arg Asn Leu Arg Ser Asp Asp Thr Ala Val Tyr Phe Cys
                85                  90                  95

Ala Gly Val Tyr Glu Gly Pro Asn Ser Glu Gly Ser Tyr Asp Asp Tyr
            100                 105                 110

Gly Phe Phe Lys His Trp Gly Gln Gly Thr Leu Val Thr Val Ser Ser
        115                 120                 125


<210> SEQ ID NO 242
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_276; BDG30.092; Human IgG1; protein
      sequence - VL

<400> SEQUENCE: 242

Asp Ile Val Met Thr Gln Ser Pro Ala Thr Leu Ser Val Ser Pro Gly
1               5                   10                  15

Glu Arg Ala Thr Leu Ser Cys Arg Ala Ser Glu Ser Val Ala Asn Asp
            20                  25                  30

Leu Ala Trp Tyr Gln Gln Lys Pro Gly Gln Val Pro Arg Leu Leu Ile
        35                  40                  45

Tyr Gly Ala Ser Thr Arg Ala Thr Gly Val Pro Ala Arg Phe Ser Gly
```

```
    50                  55                  60

Ser Gly Ser Gly Ala Glu Phe Thr Leu Thr Ile Ser Ser Leu Gln Ser
65                  70                  75                  80

Glu Asp Phe Ala Val Tyr Tyr Cys Gln Gln Tyr Ala Asn Trp Pro Pro
                85                  90                  95

Arg Glu Thr Phe Gly Gln Gly Thr Arg Leu Glu Ile Lys
            100                 105


<210> SEQ ID NO 243
<211> LENGTH: 458
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_276; BDG30.092; Human IgG1; H chain
      (VH+CH1+hinge+CH2+CH3)

<400> SEQUENCE: 243

Glu Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Thr Ser Tyr
            20                  25                  30

Ser Phe Asn Trp Val Arg Gln Ala Pro Gly Gln Gly Leu Glu Trp Met
        35                  40                  45

Gly Arg Ile Ile Thr Ile Tyr Asp Asp Thr Glu Tyr Ala Pro His Leu
    50                  55                  60

Gln Gly Arg Val Thr Ile Thr Ala Asp Lys Ser Thr Ser Thr Val Tyr
65                  70                  75                  80

Leu Glu Leu Arg Asn Leu Arg Ser Asp Asp Thr Ala Val Tyr Phe Cys
                85                  90                  95

Ala Gly Val Tyr Glu Gly Pro Asn Ser Glu Gly Ser Tyr Asp Asp Tyr
            100                 105                 110

Gly Phe Phe Lys His Trp Gly Gln Gly Thr Leu Val Thr Val Ser Ser
        115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
    210                 215                 220

Lys Val Glu Pro Lys Ser Cys Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285
```

Tyr Val Asp Gly Val Glu Val His Asn Ala Lys Thr Lys Pro Arg Glu
    290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Asp Glu
        355                 360                 365

Leu Thr Lys Asn Gln Val Ser Leu Thr Cys Leu Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly Lys
    450                 455

<210> SEQ ID NO 244
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_276; BDG30.092; Human IgG1; L chain (VL+CL)

<400> SEQUENCE: 244

Asp Ile Val Met Thr Gln Ser Pro Ala Thr Leu Ser Val Ser Pro Gly
1               5                   10                  15

Glu Arg Ala Thr Leu Ser Cys Arg Ala Ser Glu Ser Val Ala Asn Asp
            20                  25                  30

Leu Ala Trp Tyr Gln Gln Lys Pro Gly Gln Val Pro Arg Leu Leu Ile
        35                  40                  45

Tyr Gly Ala Ser Thr Arg Ala Thr Gly Val Pro Ala Arg Phe Ser Gly
    50                  55                  60

Ser Gly Ser Gly Ala Glu Phe Thr Leu Thr Ile Ser Ser Leu Gln Ser
65                  70                  75                  80

Glu Asp Phe Ala Val Tyr Tyr Cys Gln Gln Tyr Ala Asn Trp Pro Pro
                85                  90                  95

Arg Glu Thr Phe Gly Gln Gly Thr Arg Leu Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

```
Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215


<210> SEQ ID NO 245
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_277; BDG30.093; Human IgG1; protein
      sequence - VH

<400> SEQUENCE: 245

Glu Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Thr Ser Tyr
            20                  25                  30

Ser Phe Asn Trp Val Arg Gln Ala Pro Gly Gln Gly Leu Glu Trp Met
        35                  40                  45

Gly Arg Ile Ile Thr Ile Leu Asp Asp Thr Glu Tyr Ala Pro His Leu
    50                  55                  60

Gln Gly Arg Val Thr Ile Thr Ala Asp Lys Ser Thr Ser Thr Val Tyr
65                  70                  75                  80

Leu Glu Leu Arg Asn Leu Arg Ser Asp Asp Thr Ala Val Tyr Phe Cys
                85                  90                  95

Ala Gly Val Tyr Glu Gly Pro Asn Ser Glu Gly Ser Tyr Asp Asp Tyr
            100                 105                 110

Gly Phe Leu Lys Tyr Trp Gly Gln Gly Thr Leu Val Thr Val Ser Ser
        115                 120                 125


<210> SEQ ID NO 246
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_277; BDG30.093; Human IgG1; protein
      sequence - VL

<400> SEQUENCE: 246

Asp Ile Val Met Thr Gln Ser Pro Ala Thr Leu Ser Val Ser Pro Gly
1               5                   10                  15

Glu Arg Ala Thr Leu Ser Cys Arg Ala Ser Glu Ser Val Ala Val Asp
            20                  25                  30

Leu Ala Trp Tyr Gln Gln Lys Pro Gly Gln Val Pro Arg Leu Leu Ile
        35                  40                  45

Tyr Gly Ala Ser Thr Arg Ala Thr Gly Val Pro Ala Arg Phe Ser Gly
    50                  55                  60

Ser Gly Ser Gly Ala Glu Phe Thr Leu Thr Ile Ser Ser Leu Gln Ser
65                  70                  75                  80

Glu Asp Phe Ala Val Tyr Tyr Cys Gln Gln Tyr Ala Asn Lys Pro Pro
                85                  90                  95
```

Arg Glu Thr Phe Gly Gln Gly Thr Arg Leu Glu Ile Lys
100 105

<210> SEQ ID NO 247
<211> LENGTH: 458
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_277; BDG30.093; Human IgG1; H chain (VH+CH1+hinge+CH2+CH3)

<400> SEQUENCE: 247

Glu Val Gln Leu Val Gln Ser Gly Ala Glu Val Lys Lys Pro Gly Ser
1 5 10 15

Ser Val Lys Val Ser Cys Lys Ala Ser Gly Asp Thr Phe Thr Ser Tyr
20 25 30

Ser Phe Asn Trp Val Arg Gln Ala Pro Gly Gln Gly Leu Glu Trp Met
35 40 45

Gly Arg Ile Ile Thr Ile Leu Asp Asp Thr Glu Tyr Ala Pro His Leu
50 55 60

Gln Gly Arg Val Thr Ile Thr Ala Asp Lys Ser Thr Ser Thr Val Tyr
65 70 75 80

Leu Glu Leu Arg Asn Leu Arg Ser Asp Asp Thr Ala Val Tyr Phe Cys
85 90 95

Ala Gly Val Tyr Glu Gly Pro Asn Ser Glu Gly Ser Tyr Asp Asp Tyr
100 105 110

Gly Phe Leu Lys Tyr Trp Gly Gln Gly Thr Leu Val Thr Val Ser Ser
115 120 125

Ala Ser Thr Lys Gly Pro Ser Val Phe Pro Leu Ala Pro Ser Ser Lys
130 135 140

Ser Thr Ser Gly Gly Thr Ala Ala Leu Gly Cys Leu Val Lys Asp Tyr
145 150 155 160

Phe Pro Glu Pro Val Thr Val Ser Trp Asn Ser Gly Ala Leu Thr Ser
165 170 175

Gly Val His Thr Phe Pro Ala Val Leu Gln Ser Ser Gly Leu Tyr Ser
180 185 190

Leu Ser Ser Val Val Thr Val Pro Ser Ser Ser Leu Gly Thr Gln Thr
195 200 205

Tyr Ile Cys Asn Val Asn His Lys Pro Ser Asn Thr Lys Val Asp Lys
210 215 220

Lys Val Glu Pro Lys Ser Cys Asp Lys Thr His Thr Cys Pro Pro Cys
225 230 235 240

Pro Ala Pro Glu Leu Leu Gly Gly Pro Ser Val Phe Leu Phe Pro Pro
245 250 255

Lys Pro Lys Asp Thr Leu Met Ile Ser Arg Thr Pro Glu Val Thr Cys
260 265 270

Val Val Val Asp Val Ser His Glu Asp Pro Glu Val Lys Phe Asn Trp
275 280 285

Tyr Val Asp Gly Val Glu Val His Asn Ala Lys Thr Lys Pro Arg Glu
290 295 300

Glu Gln Tyr Asn Ser Thr Tyr Arg Val Val Ser Val Leu Thr Val Leu
305 310 315 320

His Gln Asp Trp Leu Asn Gly Lys Glu Tyr Lys Cys Lys Val Ser Asn
325 330 335

```
Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Asp Glu
        355                 360                 365

Leu Thr Lys Asn Gln Val Ser Leu Thr Cys Leu Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly Lys
    450                 455


<210> SEQ ID NO 248
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_277; BDG30.093; Human IgG1; L chain (VL+CL)

<400> SEQUENCE: 248

Asp Ile Val Met Thr Gln Ser Pro Ala Thr Leu Ser Val Ser Pro Gly
1               5                   10                  15

Glu Arg Ala Thr Leu Ser Cys Arg Ala Ser Glu Ser Val Ala Val Asp
            20                  25                  30

Leu Ala Trp Tyr Gln Gln Lys Pro Gly Gln Val Pro Arg Leu Leu Ile
        35                  40                  45

Tyr Gly Ala Ser Thr Arg Ala Thr Gly Val Pro Ala Arg Phe Ser Gly
    50                  55                  60

Ser Gly Ser Gly Ala Glu Phe Thr Leu Thr Ile Ser Ser Leu Gln Ser
65                  70                  75                  80

Glu Asp Phe Ala Val Tyr Tyr Cys Gln Gln Tyr Ala Asn Lys Pro Pro
                85                  90                  95

Arg Glu Thr Phe Gly Gln Gly Thr Arg Leu Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215
```

<210> SEQ ID NO 249
<211> LENGTH: 128
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: CID_280; BDG30.094; Human IgG1; protein
sequence - VH

<400> SEQUENCE: 249

Glu Val Gln Leu Val Gln Ser Gly Ala Glu Val Lys Lys Pro Gly Ser
1 5 10 15

Ser Val Lys Val Ser Cys Lys Ala Ser Gly Asp Thr Phe Thr Ser Tyr
20 25 30

Ser Phe Asn Trp Val Arg Gln Ala Pro Gly Gln Gly Leu Glu Trp Met
35 40 45

Gly Arg Ile Ile Thr Asp Leu Asp Asp Thr Glu Tyr Ala Pro His Leu
50 55 60

Gln Gly Arg Val Thr Ile Thr Ala Asp Lys Ser Thr Ser Thr Val Tyr
65 70 75 80

Leu Glu Leu Arg Asn Leu Arg Ser Asp Asp Thr Ala Val Tyr Phe Cys
85 90 95

Ala Gly Val Tyr Glu Gly Pro Asn Ser Glu Gly Ser Tyr Asp Asp Tyr
100 105 110

Gly Gln Leu Lys His Trp Gly Gln Gly Thr Leu Val Thr Val Ser Ser
115 120 125

<210> SEQ ID NO 250
<211> LENGTH: 109
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: CID_280; BDG30.094; Human IgG1; protein
sequence - VL

<400> SEQUENCE: 250

Asp Ile Val Met Thr Gln Ser Pro Ala Thr Leu Ser Val Ser Pro Gly
1 5 10 15

Glu Arg Ala Thr Leu Ser Cys Arg Ala Ser Glu Ser Val Ala Asn Asp
20 25 30

Leu Ala Trp Tyr Gln Gln Lys Pro Gly Gln Val Pro Arg Leu Leu Ile
35 40 45

Tyr Gly Ala Ser Thr Arg Ala Thr Gly Val Pro Ala Arg Phe Ser Gly
50 55 60

Ser Gly Ser Gly Ala Glu Phe Thr Leu Thr Ile Ser Ser Leu Gln Ser
65 70 75 80

Glu Asp Phe Ala Val Tyr Tyr Cys Gln Gln Tyr Ala Asn Trp Pro Pro
85 90 95

Arg Glu Thr Phe Gly Gln Gly Thr Arg Leu Glu Ile Lys
100 105

<210> SEQ ID NO 251
<211> LENGTH: 458
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: CID_280; BDG30.094; Human IgG1; H chain
(VH+CH1+hinge+CH2+CH3)

<400> SEQUENCE: 251

```
Glu Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Thr Ser Tyr
            20                  25                  30

Ser Phe Asn Trp Val Arg Gln Ala Pro Gly Gln Gly Leu Glu Trp Met
        35                  40                  45

Gly Arg Ile Ile Thr Asp Leu Asp Asp Thr Glu Tyr Ala Pro His Leu
    50                  55                  60

Gln Gly Arg Val Thr Ile Thr Ala Asp Lys Ser Thr Ser Thr Val Tyr
65                  70                  75                  80

Leu Glu Leu Arg Asn Leu Arg Ser Asp Asp Thr Ala Val Tyr Phe Cys
                85                  90                  95

Ala Gly Val Tyr Glu Gly Pro Asn Ser Glu Gly Ser Tyr Asp Asp Tyr
            100                 105                 110

Gly Gln Leu Lys His Trp Gly Gln Gly Thr Leu Val Thr Val Ser Ser
        115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
    210                 215                 220

Lys Val Glu Pro Lys Ser Cys Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Asp Glu
        355                 360                 365

Leu Thr Lys Asn Gln Val Ser Leu Thr Cys Leu Val Lys Gly Phe Tyr
```

```
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly Lys
    450                 455


<210> SEQ ID NO 252
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_280; BDG30.094; Human IgG1; L chain (VL+CL)

<400> SEQUENCE: 252

Asp Ile Val Met Thr Gln Ser Pro Ala Thr Leu Ser Val Ser Pro Gly
1               5                   10                  15

Glu Arg Ala Thr Leu Ser Cys Arg Ala Ser Glu Ser Val Ala Asn Asp
            20                  25                  30

Leu Ala Trp Tyr Gln Gln Lys Pro Gly Gln Val Pro Arg Leu Leu Ile
        35                  40                  45

Tyr Gly Ala Ser Thr Arg Ala Thr Gly Val Pro Ala Arg Phe Ser Gly
    50                  55                  60

Ser Gly Ser Gly Ala Glu Phe Thr Leu Thr Ile Ser Ser Leu Gln Ser
65                  70                  75                  80

Glu Asp Phe Ala Val Tyr Tyr Cys Gln Gln Tyr Ala Asn Trp Pro Pro
                85                  90                  95

Arg Glu Thr Phe Gly Gln Gly Thr Arg Leu Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215


<210> SEQ ID NO 253
<211> LENGTH: 128
<212> TYPE: PRT
<213> ORGANISM: Artificial Sequence
<220> FEATURE:
<223> OTHER INFORMATION: Description of Artificial Sequence: Synthetic
```

polypeptide
<220> FEATURE:
<223> OTHER INFORMATION: CID_284; BDG30.095; Human IgG1; protein
sequence - VH

<400> SEQUENCE: 253

```
Glu Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Thr Ser Tyr
            20                  25                  30

Ser Phe Asn Trp Val Arg Gln Ala Pro Gly Gln Gly Leu Glu Trp Met
        35                  40                  45

Gly Arg Ile Ile Thr Ile Asp Asp Asp Thr Glu Tyr Ala Pro His Leu
    50                  55                  60

Gln Gly Arg Val Thr Ile Thr Ala Asp Lys Ser Thr Ser Thr Val Tyr
65                  70                  75                  80

Leu Glu Leu Arg Asn Leu Arg Ser Asp Asp Thr Ala Val Tyr Phe Cys
                85                  90                  95

Ala Gly Val Tyr Glu Gly Pro Asn Ser Glu Gly Ser Tyr Asp Asp Tyr
            100                 105                 110

Gly Gln Leu Lys His Trp Gly Gln Gly Thr Leu Val Thr Val Ser Ser
        115                 120                 125
```

<210> SEQ ID NO 254
<211> LENGTH: 109
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: CID_284; BDG30.095; Human IgG1; protein
sequence - VL

<400> SEQUENCE: 254

```
Asp Ile Val Met Thr Gln Ser Pro Ala Thr Leu Ser Val Ser Pro Gly
1               5                   10                  15

Glu Arg Ala Thr Leu Ser Cys Arg Ala Ser Glu Ser Val Gly Asn Asp
            20                  25                  30

Leu Ala Trp Tyr Gln Gln Lys Pro Gly Gln Val Pro Arg Leu Leu Ile
        35                  40                  45

Tyr Gly Ala Ser Thr Arg Ala Thr Gly Val Pro Ala Arg Phe Ser Gly
    50                  55                  60

Ser Gly Ser Gly Ala Glu Phe Thr Leu Thr Ile Ser Ser Leu Gln Ser
65                  70                  75                  80

Glu Asp Phe Ala Val Tyr Tyr Cys Gln Gln Tyr Ala Asn Val Pro Pro
                85                  90                  95

Arg Glu Thr Phe Gly Gln Gly Thr Arg Leu Glu Ile Lys
            100                 105
```

<210> SEQ ID NO 255
<211> LENGTH: 458
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: CID_284; BDG30.095; Human IgG1; H chain
(VH+CH1+hinge+CH2+CH3)

<400> SEQUENCE: 255

```
Glu Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Thr Ser Tyr
            20                  25                  30

Ser Phe Asn Trp Val Arg Gln Ala Pro Gly Gln Gly Leu Glu Trp Met
        35                  40                  45

Gly Arg Ile Ile Thr Ile Asp Asp Asp Thr Glu Tyr Ala Pro His Leu
    50                  55                  60

Gln Gly Arg Val Thr Ile Thr Ala Asp Lys Ser Thr Ser Thr Val Tyr
65                  70                  75                  80

Leu Glu Leu Arg Asn Leu Arg Ser Asp Asp Thr Ala Val Tyr Phe Cys
                85                  90                  95

Ala Gly Val Tyr Glu Gly Pro Asn Ser Glu Gly Ser Tyr Asp Asp Tyr
            100                 105                 110

Gly Gln Leu Lys His Trp Gly Gln Gly Thr Leu Val Thr Val Ser Ser
        115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
    210                 215                 220

Lys Val Glu Pro Lys Ser Cys Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Asp Glu
        355                 360                 365

Leu Thr Lys Asn Gln Val Ser Leu Thr Cys Leu Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415
```

```
Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly Lys
    450                 455


<210> SEQ ID NO 256
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_284; BDG30.095; Human IgG1; L chain (VL+CL)

<400> SEQUENCE: 256

Asp Ile Val Met Thr Gln Ser Pro Ala Thr Leu Ser Val Ser Pro Gly
1               5                   10                  15

Glu Arg Ala Thr Leu Ser Cys Arg Ala Ser Glu Ser Val Gly Asn Asp
            20                  25                  30

Leu Ala Trp Tyr Gln Gln Lys Pro Gly Gln Val Pro Arg Leu Leu Ile
        35                  40                  45

Tyr Gly Ala Ser Thr Arg Ala Thr Gly Val Pro Ala Arg Phe Ser Gly
    50                  55                  60

Ser Gly Ser Gly Ala Glu Phe Thr Leu Thr Ile Ser Ser Leu Gln Ser
65                  70                  75                  80

Glu Asp Phe Ala Val Tyr Tyr Cys Gln Gln Tyr Ala Asn Val Pro Pro
                85                  90                  95

Arg Glu Thr Phe Gly Gln Gly Thr Arg Leu Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215


<210> SEQ ID NO 257
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_436; BDG30.032; Human IgG1; protein
      sequence - VH

<400> SEQUENCE: 257

Glu Val Gln Leu Val Glu Ser Gly Gly Gly Leu Val Gln Pro Gly Gly
```

1 5 10 15

Ser Leu Arg Leu Ser Cys Ala Ala Ser Gly Phe Asn Ile Arg Asp Thr
20 25 30

Tyr Ile His Trp Val Arg Gln Ser Pro Gly Lys Gly Leu Glu Trp Val
35 40 45

Ala Asp Ile Asp Pro Asp Asn Gly Asp Thr Arg Tyr Ala Asp Ser Val
50 55 60

Lys Gly Arg Phe Thr Ile Ser Ala Asp Thr Ser Lys Asn Thr Ala Tyr
65 70 75 80

Leu Gln Met Asn Ser Leu Arg Ala Glu Asp Thr Ala Ile Tyr Tyr Cys
85 90 95

Ser Arg Asp Leu Ala Asp Gly Tyr Asn Ala Phe Asp Arg Trp Gly Gln
100 105 110

Gly Thr Leu Val Thr Val Ser Ser
115 120

<210> SEQ ID NO 258
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_436; BDG30.032; Human IgG1; protein sequence - VL

<400> SEQUENCE: 258

Asp Ile Gln Met Thr Gln Ser Pro Ile Leu Leu Ser Ala Ser Val Gly
1 5 10 15

Asp Arg Val Thr Ile Thr Cys Arg Ala Ser Gln Asp Val Ser Thr Ala
20 25 30

Val Ala Trp Ser Gln Gln Arg Thr Asn Gly Ser Pro Arg Leu Leu Ile
35 40 45

Tyr Ser Ala Ser Ser Leu Tyr Ser Gly Val Pro Ser Arg Phe Ser Gly
50 55 60

Ser Arg Ser Gly Thr Asp Phe Thr Leu Thr Ile Ser Ser Leu Gln Pro
65 70 75 80

Glu Asp Ile Ala Asp Tyr Tyr Cys Gln Gln Pro Thr Tyr Thr Pro Pro
85 90 95

Thr Phe Gly Ala Gly Thr Lys Val Glu Ile Lys
100 105

<210> SEQ ID NO 259
<211> LENGTH: 450
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_436; BDG30.032; Human IgG1; H chain (VH+CH1+hinge+CH2+CH3)

<400> SEQUENCE: 259

Glu Val Gln Leu Val Glu Ser Gly Gly Gly Leu Val Gln Pro Gly Gly
1 5 10 15

Ser Leu Arg Leu Ser Cys Ala Ala Ser Gly Phe Asn Ile Arg Asp Thr
20 25 30

Tyr Ile His Trp Val Arg Gln Ser Pro Gly Lys Gly Leu Glu Trp Val

```
        35                  40                  45

Ala Asp Ile Asp Pro Asp Asn Gly Asp Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Ile Tyr Tyr Cys
                85                  90                  95

Ser Arg Asp Leu Ala Asp Gly Tyr Asn Ala Phe Asp Arg Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450
```

<210> SEQ ID NO 260
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_436; BDG30.032; Human IgG1; L chain (VL+CL)

<400> SEQUENCE: 260

```
Asp Ile Gln Met Thr Gln Ser Pro Ile Leu Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Ser Gln Gln Arg Thr Asn Gly Ser Pro Arg Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Ile Ala Asp Tyr Tyr Cys Gln Gln Pro Thr Tyr Thr Pro Pro
                85                  90                  95

Thr Phe Gly Ala Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 261
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_437; BDG30.033; Human IgG1; protein sequence - VH

<400> SEQUENCE: 261

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Arg Asp Thr
            20                  25                  30

Phe Ile His Trp Val Arg Gln Ser Pro Gly Lys Gly Leu Glu Trp Val
        35                  40                  45
```

```
Ala Asp Ile Asp Pro Asp Asn Gly Asp Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Ile Tyr Tyr Cys
                85                  90                  95

Ser Arg Glu Gly Glu Asp Gly Tyr Asn Ala Trp Asp Leu Trp Gly Gln
            100                 105                 110

Gly Thr Leu Val Thr Val Ser Ser
        115                 120


<210> SEQ ID NO 262
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_437; BDG30.033; Human IgG1; protein
      sequence - VL

<400> SEQUENCE: 262

Asp Ile Gln Met Thr Gln Ser Pro Ile Leu Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Ser Gln Gln Arg Thr Asn Gly Ser Pro Arg Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Ile Ala Asp Tyr Tyr Cys Gln Gln Pro Pro Tyr Thr Pro Pro
                85                  90                  95

Thr Phe Gly Ala Gly Thr Lys Val Glu Ile Lys
            100                 105


<210> SEQ ID NO 263
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_437; BDG30.033; Human IgG1; H chain
      (VH+CH1+hinge+CH2+CH3)

<400> SEQUENCE: 263

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Arg Asp Thr
            20                  25                  30

Phe Ile His Trp Val Arg Gln Ser Pro Gly Lys Gly Leu Glu Trp Val
        35                  40                  45

Ala Asp Ile Asp Pro Asp Asn Gly Asp Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80
```

```
Leu Gln Met Asn Ser Leu Arg Ala Glu Asp Thr Ala Ile Tyr Tyr Cys
                85                  90                  95

Ser Arg Glu Gly Glu Asp Gly Tyr Asn Ala Trp Asp Leu Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450
```

<210> SEQ ID NO 264
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_437; BDG30.033; Human IgG1; L chain (VL+CL)

<400> SEQUENCE: 264

Asp Ile Gln Met Thr Gln Ser Pro Ile Leu Leu Ser Ala Ser Val Gly
1 5 10 15

Asp Arg Val Thr Ile Thr Cys Arg Ala Ser Gln Asp Val Ser Thr Ala
20 25 30

Val Ala Trp Ser Gln Gln Arg Thr Asn Gly Ser Pro Arg Leu Leu Ile
35 40 45

Tyr Ser Ala Ser Ser Leu Tyr Ser Gly Val Pro Ser Arg Phe Ser Gly
50 55 60

Ser Arg Ser Gly Thr Asp Phe Thr Leu Thr Ile Ser Ser Leu Gln Pro
65 70 75 80

Glu Asp Ile Ala Asp Tyr Tyr Cys Gln Gln Pro Pro Tyr Thr Pro Pro
85 90 95

Thr Phe Gly Ala Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 265
<211> LENGTH: 120
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: CID_229; BDG30.080; Human IgG1; protein
sequence - VH

<400> SEQUENCE: 265

Glu Val Gln Leu Val Glu Ser Gly Gly Gly Leu Val Gln Pro Gly Gly
1 5 10 15

Ser Leu Arg Leu Ser Cys Ala Ala Ser Gly Phe Asn Ile Arg Ala Met
20 25 30

Tyr Ile His Trp Val Arg Gln Ser Pro Gly Lys Gly Leu Glu Trp Val
35 40 45

Ala Asp Ile Asp Pro Thr Asn Gly Asp Thr Arg Tyr Ala Asp Ser Val
50 55 60

Lys Gly Arg Phe Thr Ile Ser Ala Asp Thr Ser Lys Asn Thr Ala Tyr
65 70 75 80

Leu Gln Met Asn Ser Leu Arg Ala Glu Asp Thr Ala Ile Tyr Tyr Cys
85 90 95

```
Thr Arg Glu Gly Gln Asp Gly Tyr Asn Ala Phe Asp Lys Trp Gly Gln
            100                 105                 110

Gly Thr Leu Val Thr Val Ser Ser
        115                 120


<210> SEQ ID NO 266
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_229; BDG30.080; Human IgG1; protein
      sequence - VL

<400> SEQUENCE: 266

Asp Ile Gln Met Thr Gln Ser Pro Ile Leu Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Ser Gln Gln Arg Thr Asn Gly Ser Pro Arg Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Ile Ala Asp Tyr Tyr Cys Gln Gln His Arg Tyr Thr Pro Pro
                85                  90                  95

Thr Phe Gly Ala Gly Thr Lys Val Glu Ile Lys
            100                 105


<210> SEQ ID NO 267
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_229; BDG30.080; Human IgG1; H chain
      (VH+CH1+hinge+CH2+CH3)

<400> SEQUENCE: 267

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Arg Ala Met
            20                  25                  30

Tyr Ile His Trp Val Arg Gln Ser Pro Gly Lys Gly Leu Glu Trp Val
        35                  40                  45

Ala Asp Ile Asp Pro Thr Asn Gly Asp Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Ile Tyr Tyr Cys
                85                  90                  95

Thr Arg Glu Gly Gln Asp Gly Tyr Asn Ala Phe Asp Lys Trp Gly Gln
            100                 105                 110

Gly Thr Leu Val Thr Val Ser Ser Ala Ser Thr Lys Gly Pro Ser Val
        115                 120                 125
```

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 268
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_229; BDG30.080; Human IgG1; L chain (VL+CL)

<400> SEQUENCE: 268

Asp Ile Gln Met Thr Gln Ser Pro Ile Leu Leu Ser Ala Ser Val Gly
1               5                   10                  15

```
Asp Arg Val Thr Ile Thr Cys Arg Ala Ser Gln Asp Val Ser Thr Ala
            20                  25                  30

Val Ala Trp Ser Gln Gln Arg Thr Asn Gly Ser Pro Arg Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Ile Ala Asp Tyr Tyr Cys Gln Gln His Arg Tyr Thr Pro Pro
                85                  90                  95

Thr Phe Gly Ala Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 269
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_231; BDG30.081; Human IgG1; protein sequence - VH

<400> SEQUENCE: 269

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Arg Ala Thr
            20                  25                  30

Tyr Ile His Trp Val Arg Gln Ser Pro Gly Lys Gly Leu Glu Trp Val
        35                  40                  45

Ala Asp Ile Ser Pro Asp Asn Gly Asp Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Ile Tyr Tyr Cys
                85                  90                  95

Ser Arg Asp Leu Ala Asp Gly Tyr Asn Ala Phe Asp Leu Trp Gly Gln
            100                 105                 110

Gly Thr Leu Val Thr Val Ser Ser
        115                 120
```

<210> SEQ ID NO 270
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_231; BDG30.081; Human IgG1; protein sequence - VL

<400> SEQUENCE: 270

```
Asp Ile Gln Met Thr Gln Ser Pro Ile Leu Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Ser Gln Gln Arg Thr Asn Gly Ser Pro Arg Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Ile Ala Asp Tyr Tyr Cys Gln Gln His Gly Tyr Thr Pro Pro
                85                  90                  95

Thr Phe Gly Ala Gly Thr Lys Val Glu Ile Lys
            100                 105
```

<210> SEQ ID NO 271
<211> LENGTH: 450
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_231; BDG30.081; Human IgG1; H chain (VH+CH1+hinge+CH2+CH3)

<400> SEQUENCE: 271

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Arg Ala Thr
            20                  25                  30

Tyr Ile His Trp Val Arg Gln Ser Pro Gly Lys Gly Leu Glu Trp Val
        35                  40                  45

Ala Asp Ile Ser Pro Asp Asn Gly Asp Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Ile Tyr Tyr Cys
                85                  90                  95

Ser Arg Asp Leu Ala Asp Gly Tyr Asn Ala Phe Asp Leu Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
```

```
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 272
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_231; BDG30.081; Human IgG1; L chain (VL+CL)

<400> SEQUENCE: 272

Asp Ile Gln Met Thr Gln Ser Pro Ile Leu Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Ser Gln Gln Arg Thr Asn Gly Ser Pro Arg Leu Leu Ile
        35                  40                  45

Tyr Ser Ala Ser Ser Leu Tyr Ser Gly Val Pro Ser Arg Phe Ser Gly
```

```
    50                  55                  60

Ser Arg Ser Gly Thr Asp Phe Thr Leu Thr Ile Ser Ser Leu Gln Pro
65                  70                  75                  80

Glu Asp Ile Ala Asp Tyr Tyr Cys Gln Gln His Gly Tyr Thr Pro Pro
                85                  90                  95

Thr Phe Gly Ala Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 273
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_232; BDG30.082; Human IgG1; protein
      sequence - VH

<400> SEQUENCE: 273

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Arg Asp Thr
            20                  25                  30

Tyr Ile His Trp Val Arg Gln Ser Pro Gly Lys Gly Leu Glu Trp Val
        35                  40                  45

Ala Asp Ile Asp Pro Asp Asn Gly Asp Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Ile Tyr Tyr Cys
                85                  90                  95

Thr Arg Glu Gly Ala Asp Gly Tyr Asn Ala Phe Asp Leu Trp Gly Gln
            100                 105                 110

Gly Thr Leu Val Thr Val Ser Ser
        115                 120


<210> SEQ ID NO 274
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
```

<223> OTHER INFORMATION: CID_232; BDG30.082; Human IgG1; protein
sequence - VL

<400> SEQUENCE: 274

Asp Ile Gln Met Thr Gln Ser Pro Ile Leu Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Ser Gln Gln Arg Thr Asn Gly Ser Pro Arg Leu Leu Ile
        35                  40                  45

Tyr Pro Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Ile Ala Asp Tyr Tyr Cys Gln Gln Pro Asp Tyr Thr Pro Pro
                85                  90                  95

Thr Phe Gly Ala Gly Thr Lys Val Glu Ile Lys
            100                 105

<210> SEQ ID NO 275
<211> LENGTH: 450
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: CID_232; BDG30.082; Human IgG1; H chain
(VH+CH1+hinge+CH2+CH3)

<400> SEQUENCE: 275

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Arg Asp Thr
            20                  25                  30

Tyr Ile His Trp Val Arg Gln Ser Pro Gly Lys Gly Leu Glu Trp Val
        35                  40                  45

Ala Asp Ile Asp Pro Asp Asn Gly Asp Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Ile Tyr Tyr Cys
                85                  90                  95

Thr Arg Glu Gly Ala Asp Gly Tyr Asn Ala Phe Asp Leu Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

```
Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 276
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_232; BDG30.082; Human IgG1; L chain (VL+CL)

<400> SEQUENCE: 276

Asp Ile Gln Met Thr Gln Ser Pro Ile Leu Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Ser Gln Gln Arg Thr Asn Gly Ser Pro Arg Leu Leu Ile
        35                  40                  45

Tyr Pro Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Ile Ala Asp Tyr Tyr Cys Gln Gln Pro Asp Tyr Thr Pro Pro
                85                  90                  95
```

```
Thr Phe Gly Ala Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 277
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_234; BDG30.084; Human IgG1; protein
      sequence - VH

<400> SEQUENCE: 277

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Arg Ala Phe
            20                  25                  30

Tyr Ile His Trp Val Arg Gln Ser Pro Gly Lys Gly Leu Glu Trp Val
        35                  40                  45

Ala Asp Ile Asp Pro Thr Asn Gly Asp Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Ile Tyr Tyr Cys
                85                  90                  95

Thr Arg Glu Gly Glu Asp Gly Tyr Asn Ala Phe Asp Gln Trp Gly Gln
            100                 105                 110

Gly Thr Leu Val Thr Val Ser Ser
        115                 120


<210> SEQ ID NO 278
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_234; BDG30.084; Human IgG1; protein
      sequence - VL

<400> SEQUENCE: 278

Asp Ile Gln Met Thr Gln Ser Pro Ile Leu Leu Ser Ala Ser Val Gly
1               5                   10                  15
```

```
Asp Arg Val Thr Ile Thr Cys Arg Ala Ser Gln Asp Val Ser Thr Ala
            20                  25                  30

Val Ala Trp Tyr Gln Gln Arg Thr Asn Gly Ser Pro Arg Leu Leu Ile
        35                  40                  45

Tyr Pro Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Ile Ala Asp Tyr Tyr Cys Gln Gln Pro Arg Tyr Thr Pro Pro
                85                  90                  95

Thr Phe Gly Ala Gly Thr Lys Val Glu Ile Lys
            100                 105


<210> SEQ ID NO 279
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_234; BDG30.084; Human IgG1; H chain
      (VH+CH1+hinge+CH2+CH3)

<400> SEQUENCE: 279

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Arg Ala Phe
            20                  25                  30

Tyr Ile His Trp Val Arg Gln Ser Pro Gly Lys Gly Leu Glu Trp Val
        35                  40                  45

Ala Asp Ile Asp Pro Thr Asn Gly Asp Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Ile Tyr Tyr Cys
                85                  90                  95

Thr Arg Glu Gly Glu Asp Gly Tyr Asn Ala Phe Asp Gln Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255
```

```
Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 280
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_234; BDG30.084; Human IgG1; L chain (VL+CL)

<400> SEQUENCE: 280

Asp Ile Gln Met Thr Gln Ser Pro Ile Leu Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Arg Thr Asn Gly Ser Pro Arg Leu Leu Ile
        35                  40                  45

Tyr Pro Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Ile Ala Asp Tyr Tyr Cys Gln Gln Pro Arg Tyr Thr Pro Pro
                85                  90                  95

Thr Phe Gly Ala Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140
```

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 281
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_261; BDG30.085; Human IgG1; protein sequence - VH

<400> SEQUENCE: 281

Glu Val Gln Leu Val Glu Ser Gly Gly Gly Leu Val Gln Pro Gly Gly
1 5 10 15

Ser Leu Arg Leu Ser Cys Ala Ala Ser Gly Phe Asn Ile Lys Asp Phe
20 25 30

Phe Ile His Trp Val Arg Gln Ala Pro Gly Lys Gly Leu Glu Trp Val
35 40 45

Ala Asp Ile Asp Pro Thr Asn Gly Asp Thr Arg Tyr Ala Asp Ser Val
50 55 60

Lys Gly Arg Phe Thr Ile Ser Ala Asp Thr Ser Lys Asn Thr Ala Tyr
65 70 75 80

Leu Gln Met Asn Ser Leu Arg Ala Glu Asp Thr Ala Val Tyr Tyr Cys
85 90 95

Ser Arg Glu Gly Gln Asp Gly Tyr Asn Ala Trp Asp Leu Trp Gly Gln
100 105 110

Gly Thr Leu Val Thr Val Ser Ser
115 120

<210> SEQ ID NO 282
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_261; BDG30.085; Human IgG1; protein sequence - VL

<400> SEQUENCE: 282

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asp Ile Ser Thr Ala
20 25 30

Val Ala Trp Ser Gln Gln Lys Pro Gly Lys Ala Pro Lys Leu Leu Ile
35 40 45

Tyr Ser Ala Ser Ser Leu Tyr Ser Gly Val Pro Ser Arg Phe Ser Gly
50 55 60

Ser Arg Ser Gly Thr Asp Phe Thr Leu Thr Ile Ser Ser Leu Gln Pro
65 70 75 80

Glu Asp Phe Ala Thr Tyr Tyr Cys Gln Gln Pro Ser Leu Thr Pro Pro
85 90 95

Thr Phe Gly Gln Gly Thr Lys Val Glu Ile Lys
100 105

<210> SEQ ID NO 283
<211> LENGTH: 450
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_261; BDG30.085; Human IgG1; H chain (VH+CH1+hinge+CH2+CH3)

<400> SEQUENCE: 283

Glu Val Gln Leu Val Glu Ser Gly Gly Gly Leu Val Gln Pro Gly Gly
1 5 10 15

Ser Leu Arg Leu Ser Cys Ala Ala Ser Gly Phe Asn Ile Lys Asp Phe
20 25 30

Phe Ile His Trp Val Arg Gln Ala Pro Gly Lys Gly Leu Glu Trp Val
35 40 45

Ala Asp Ile Asp Pro Thr Asn Gly Asp Thr Arg Tyr Ala Asp Ser Val
50 55 60

Lys Gly Arg Phe Thr Ile Ser Ala Asp Thr Ser Lys Asn Thr Ala Tyr
65 70 75 80

Leu Gln Met Asn Ser Leu Arg Ala Glu Asp Thr Ala Val Tyr Tyr Cys
85 90 95

Ser Arg Glu Gly Gln Asp Gly Tyr Asn Ala Trp Asp Leu Trp Gly Gln
100 105 110

Gly Thr Leu Val Thr Val Ser Ser Ala Ser Thr Lys Gly Pro Ser Val
115 120 125

Phe Pro Leu Ala Pro Ser Ser Lys Ser Thr Ser Gly Gly Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Gln Thr Tyr Ile Cys Asn Val Asn His Lys
195 200 205

Pro Ser Asn Thr Lys Val Asp Lys Lys Val Glu Pro Lys Ser Cys Asp
210 215 220

Lys Thr His Thr Cys Pro Pro Cys Pro Ala Pro Glu Leu Leu Gly Gly
225 230 235 240

Pro Ser Val Phe Leu Phe Pro Pro Lys Pro Lys Asp Thr Leu Met Ile
245 250 255

Ser Arg Thr Pro Glu Val Thr Cys Val Val Val Asp Val Ser His Glu
260 265 270

Asp Pro Glu Val Lys Phe Asn Trp Tyr Val Asp Gly Val Glu Val His
275 280 285

Asn Ala Lys Thr Lys Pro Arg Glu Glu Gln Tyr Asn Ser Thr Tyr Arg

```
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 284
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_261; BDG30.085; Human IgG1; L chain (VL+CL)

<400> SEQUENCE: 284

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Thr Ala
            20                  25                  30

Val Ala Trp Ser Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Pro Ser Leu Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
```

```
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 285
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_262; BDG30.086; Human IgG1; protein
      sequence - VH

<400> SEQUENCE: 285

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Tyr
            20                  25                  30

Phe Ile His Trp Val Arg Gln Ala Pro Gly Lys Gly Leu Glu Trp Val
        35                  40                  45

Ala Asp Ile Asp Pro Thr Asn Gly Asp Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Glu Gly Gln Asp Gly Tyr Asn Ala Trp Asp Gln Trp Gly Gln
            100                 105                 110

Gly Thr Leu Val Thr Val Ser Ser
        115                 120


<210> SEQ ID NO 286
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_262; BDG30.086; Human IgG1; protein
      sequence - VL

<400> SEQUENCE: 286

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Thr Ala
            20                  25                  30

Val Ala Trp Ser Gln Gln Lys Pro Gly Lys Ala Pro Lys Leu Leu Ile
        35                  40                  45

Tyr Pro Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Pro Tyr Thr Pro Pro
                85                  90                  95

Thr Phe Gly Gln Gly Thr Lys Val Glu Ile Lys
```

```
            100                 105


<210> SEQ ID NO 287
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_262; BDG30.086; Human IgG1; H chain
      (VH+CH1+hinge+CH2+CH3)

<400> SEQUENCE: 287

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Tyr
            20                  25                  30

Phe Ile His Trp Val Arg Gln Ala Pro Gly Lys Gly Leu Glu Trp Val
        35                  40                  45

Ala Asp Ile Asp Pro Thr Asn Gly Asp Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Glu Gly Gln Asp Gly Tyr Asn Ala Trp Asp Gln Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335
```

```
Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 288
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_262; BDG30.086; Human IgG1; L chain (VL+CL)

<400> SEQUENCE: 288

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Thr Ala
            20                  25                  30

Val Ala Trp Ser Gln Gln Lys Pro Gly Lys Ala Pro Lys Leu Leu Ile
        35                  40                  45

Tyr Pro Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Pro Tyr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 289
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_264; BDG30.087; Human IgG1; protein sequence - VH

<400> SEQUENCE: 289

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Ala Tyr
            20                  25                  30

Tyr Ile His Trp Val Arg Gln Ala Pro Gly Lys Gly Leu Glu Trp Val
        35                  40                  45

Ala Asp Ile Asp Pro Asp Asn Gly Asp Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Glu Gly Gln Asp Gly Tyr Asn Ala Trp Asp Gln Trp Gly Gln
            100                 105                 110

Gly Thr Leu Val Thr Val Ser Ser
        115                 120
```

<210> SEQ ID NO 290
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_264; BDG30.087; Human IgG1; protein sequence - VL

<400> SEQUENCE: 290

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Ser Gln Gln Lys Pro Gly Lys Ala Pro Lys Leu Leu Ile
        35                  40                  45

Tyr Pro Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Pro Thr Leu Thr Pro Pro
                85                  90                  95

Thr Phe Gly Gln Gly Thr Lys Val Glu Ile Lys
            100                 105
```

<210> SEQ ID NO 291
<211> LENGTH: 450
<212> TYPE: PRT
<213> ORGANISM: Artificial Sequence
<220> FEATURE:

<223> OTHER INFORMATION: Description of Artificial Sequence: Synthetic
polypeptide
<220> FEATURE:
<223> OTHER INFORMATION: CID_264; BDG30.087; Human IgG1; H chain
(VH+CH1+hinge+CH2+CH3)

<400> SEQUENCE: 291

Glu Val Gln Leu Val Glu Ser Gly Gly Gly Leu Val Gln Pro Gly Gly
1 5 10 15

Ser Leu Arg Leu Ser Cys Ala Ala Ser Gly Phe Asn Ile Lys Ala Tyr
20 25 30

Tyr Ile His Trp Val Arg Gln Ala Pro Gly Lys Gly Leu Glu Trp Val
35 40 45

Ala Asp Ile Asp Pro Asp Asn Gly Asp Thr Arg Tyr Ala Asp Ser Val
50 55 60

Lys Gly Arg Phe Thr Ile Ser Ala Asp Thr Ser Lys Asn Thr Ala Tyr
65 70 75 80

Leu Gln Met Asn Ser Leu Arg Ala Glu Asp Thr Ala Val Tyr Tyr Cys
85 90 95

Ser Arg Glu Gly Gln Asp Gly Tyr Asn Ala Trp Asp Gln Trp Gly Gln
100 105 110

Gly Thr Leu Val Thr Val Ser Ser Ala Ser Thr Lys Gly Pro Ser Val
115 120 125

Phe Pro Leu Ala Pro Ser Ser Lys Ser Thr Ser Gly Gly Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Gln Thr Tyr Ile Cys Asn Val Asn His Lys
195 200 205

Pro Ser Asn Thr Lys Val Asp Lys Lys Val Glu Pro Lys Ser Cys Asp
210 215 220

Lys Thr His Thr Cys Pro Pro Cys Pro Ala Pro Glu Leu Leu Gly Gly
225 230 235 240

Pro Ser Val Phe Leu Phe Pro Pro Lys Pro Lys Asp Thr Leu Met Ile
245 250 255

Ser Arg Thr Pro Glu Val Thr Cys Val Val Val Asp Val Ser His Glu
260 265 270

Asp Pro Glu Val Lys Phe Asn Trp Tyr Val Asp Gly Val Glu Val His
275 280 285

Asn Ala Lys Thr Lys Pro Arg Glu Glu Gln Tyr Asn Ser Thr Tyr Arg
290 295 300

Val Val Ser Val Leu Thr Val Leu His Gln Asp Trp Leu Asn Gly Lys
305 310 315 320

Glu Tyr Lys Cys Lys Val Ser Asn Lys Ala Leu Pro Ala Pro Ile Glu
325 330 335

Lys Thr Ile Ser Lys Ala Lys Gly Gln Pro Arg Glu Pro Gln Val Tyr
340 345 350

Thr Leu Pro Pro Ser Arg Asp Glu Leu Thr Lys Asn Gln Val Ser Leu
355 360 365

Thr Cys Leu Val Lys Gly Phe Tyr Pro Ser Asp Ile Ala Val Glu Trp
370 375 380

```
Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 292
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_264; BDG30.087; Human IgG1; L chain (VL+CL)

<400> SEQUENCE: 292

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Ser Gln Gln Lys Pro Gly Lys Ala Pro Lys Leu Leu Ile
        35                  40                  45

Tyr Pro Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Pro Thr Leu Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 293
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
```

<220> FEATURE:
<223> OTHER INFORMATION: CID_266; BDG30.088; Human IgG1; protein
sequence - VH

<400> SEQUENCE: 293

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Arg Ala Tyr
            20                  25                  30

Tyr Ile His Trp Val Arg Gln Ala Pro Gly Lys Gly Leu Glu Trp Val
        35                  40                  45

Ala Asp Ile Asp Pro Thr Asn Gly Asp Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Glu Gly Gln Asp Gly Tyr Asn Ala Trp Asp Leu Trp Gly Gln
            100                 105                 110

Gly Thr Leu Val Thr Val Ser Ser
        115                 120
```

<210> SEQ ID NO 294
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: CID_266; BDG30.088; Human IgG1; protein
sequence - VL

<400> SEQUENCE: 294

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Pro Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Pro Gly Tyr Thr Pro Pro
                85                  90                  95

Thr Phe Gly Gln Gly Thr Lys Val Glu Ile Lys
            100                 105
```

<210> SEQ ID NO 295
<211> LENGTH: 450
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: CID_266; BDG30.088; Human IgG1; H chain
(VH+CH1+hinge+CH2+CH3)

<400> SEQUENCE: 295

-continued

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Arg Ala Tyr
            20                  25                  30

Tyr Ile His Trp Val Arg Gln Ala Pro Gly Lys Gly Leu Glu Trp Val
        35                  40                  45

Ala Asp Ile Asp Pro Thr Asn Gly Asp Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Glu Gly Gln Asp Gly Tyr Asn Ala Trp Asp Leu Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
```

```
            420                 425                 430

Glu Ala Leu His Asn His Tyr Thr Gln Lys Ser Leu Ser Leu Ser Pro
        435                 440                 445

Gly Lys
    450
```

<210> SEQ ID NO 296
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_266; BDG30.088; Human IgG1; L chain (VL+CL)

<400> SEQUENCE: 296

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Pro Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Pro Gly Tyr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 297
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_267; BDG30.089; Human IgG1; protein sequence - VH

<400> SEQUENCE: 297

```
Glu Val Gln Leu Val Glu Ser Gly Gly Gly Leu Val Gln Pro Gly Gly
1               5                   10                  15
```

Ser Leu Arg Leu Ser Cys Ala Ala Ser Gly Phe Asn Ile Arg Asp Tyr
20 25 30

Tyr Ile His Trp Val Arg Gln Ala Pro Gly Lys Gly Leu Glu Trp Val
35 40 45

Ala Asp Ile Asp Pro Thr Asn Gly Asp Thr Arg Tyr Ala Asp Ser Val
50 55 60

Lys Gly Arg Phe Thr Ile Ser Ala Asp Thr Ser Lys Asn Thr Ala Tyr
65 70 75 80

Leu Gln Met Asn Ser Leu Arg Ala Glu Asp Thr Ala Val Tyr Tyr Cys
85 90 95

Ser Arg Glu Gly Gln Asp Gly Tyr Asn Ala Trp Asp Leu Trp Gly Gln
100 105 110

Gly Thr Leu Val Thr Val Ser Ser
115 120

<210> SEQ ID NO 298
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_267; BDG30.089; Human IgG1; protein sequence - VL

<400> SEQUENCE: 298

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asp Val Ser Thr Ala
20 25 30

Val Ala Trp Tyr Gln Gln Lys Pro Gly Lys Ala Pro Lys Leu Leu Ile
35 40 45

Tyr Pro Ala Ser Ser Leu Tyr Ser Gly Val Pro Ser Arg Phe Ser Gly
50 55 60

Ser Arg Ser Gly Thr Asp Phe Thr Leu Thr Ile Ser Ser Leu Gln Pro
65 70 75 80

Glu Asp Phe Ala Thr Tyr Tyr Cys Gln Gln His Pro Tyr Thr Pro Pro
85 90 95

Thr Phe Gly Gln Gly Thr Lys Val Glu Ile Lys
100 105

<210> SEQ ID NO 299
<211> LENGTH: 450
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_267; BDG30.089; Human IgG1; H chain (VH+CH1+hinge+CH2+CH3)

<400> SEQUENCE: 299

Glu Val Gln Leu Val Glu Ser Gly Gly Gly Leu Val Gln Pro Gly Gly
1 5 10 15

Ser Leu Arg Leu Ser Cys Ala Ala Ser Gly Phe Asn Ile Arg Asp Tyr
20 25 30

Tyr Ile His Trp Val Arg Gln Ala Pro Gly Lys Gly Leu Glu Trp Val
35 40 45

```
Ala Asp Ile Asp Pro Thr Asn Gly Asp Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Glu Gly Gln Asp Gly Tyr Asn Ala Trp Asp Leu Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450
```

<210> SEQ ID NO 300
<211> LENGTH: 214
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: CID_267; BDG30.089; Human IgG1; L chain (VL+CL)

<400> SEQUENCE: 300

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Pro Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Pro Tyr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 301
<211> LENGTH: 117
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: CID_332; BDG30.109; Human IgG1; protein
sequence - VH

<400> SEQUENCE: 301

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Leu
            20                  25                  30

Gly Ile Gly Trp Val Arg Gln Ala Pro Gly Gln Gly Leu Glu Trp Met
        35                  40                  45

Gly Trp Ile Asn Thr His Thr Gly Glu Pro Tyr Asp Asn Pro Lys Phe 50 55 60

Lys Gly Arg Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Thr Arg Asp His Pro Leu Gly Leu Asp Tyr Trp Gly Gln Gly Thr Thr
100 105 110

Val Thr Val Ser Ser
115

<210> SEQ ID NO 302
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_332; BDG30.109; Human IgG1; protein sequence - VL

<400> SEQUENCE: 302

Asp Ile Val Met Thr Gln Ser Pro Asp Ser Leu Ala Val Ser Leu Gly
1 5 10 15

Glu Arg Ala Thr Ile Asn Cys Arg Ser Ser Gln Ser Val Asp Val Asn
20 25 30

Gly Val Ser Tyr Leu Asp Trp Tyr Gln Gln Lys Pro Gly Gln Pro Pro
35 40 45

Lys Leu Leu Ile Thr Lys Ala Ser Asn Arg Glu Ser Gly Val Pro Asp
50 55 60

Arg Phe Ser Gly Ser Gly Ser Gly Thr Asp Phe Thr Leu Thr Ile Ser
65 70 75 80

Ser Leu Gln Ala Glu Asp Val Ala Val Tyr Tyr Cys Gln Gln Asn Arg
85 90 95

Glu Asp Pro Tyr Thr Phe Gly Gly Gly Thr Lys Val Glu Ile Lys
100 105 110

<210> SEQ ID NO 303
<211> LENGTH: 447
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_332; BDG30.109; Human IgG1; H chain (VH+CH1+hinge+CH2+CH3)

<400> SEQUENCE: 303

Gln Val Gln Leu Val Gln Ser Gly Ala Glu Val Lys Lys Pro Gly Ser
1 5 10 15

Ser Val Lys Val Ser Cys Lys Ala Ser Gly Tyr Thr Phe Thr Asp Leu
20 25 30

Gly Ile Gly Trp Val Arg Gln Ala Pro Gly Gln Gly Leu Glu Trp Met
35 40 45

Gly Trp Ile Asn Thr His Thr Gly Glu Pro Tyr Asp Asn Pro Lys Phe
50 55 60

Lys Gly Arg Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys

```
                85                  90                  95

Thr Arg Asp His Pro Leu Gly Leu Asp Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445
```

<210> SEQ ID NO 304
<211> LENGTH: 218
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_332; BDG30.109; Human IgG1; L chain (VL+CL)

<400> SEQUENCE: 304

Asp Ile Val Met Thr Gln Ser Pro Asp Ser Leu Ala Val Ser Leu Gly
1 5 10 15

Glu Arg Ala Thr Ile Asn Cys Arg Ser Ser Gln Ser Val Asp Val Asn
20 25 30

Gly Val Ser Tyr Leu Asp Trp Tyr Gln Gln Lys Pro Gly Gln Pro Pro
35 40 45

Lys Leu Leu Ile Thr Lys Ala Ser Asn Arg Glu Ser Gly Val Pro Asp
50 55 60

Arg Phe Ser Gly Ser Gly Ser Gly Thr Asp Phe Thr Leu Thr Ile Ser
65 70 75 80

Ser Leu Gln Ala Glu Asp Val Ala Val Tyr Tyr Cys Gln Gln Asn Arg
85 90 95

Glu Asp Pro Tyr Thr Phe Gly Gly Gly Thr Lys Val Glu Ile Lys Arg
100 105 110

Thr Val Ala Ala Pro Ser Val Phe Ile Phe Pro Pro Ser Asp Glu Gln
115 120 125

Leu Lys Ser Gly Thr Ala Ser Val Val Cys Leu Leu Asn Asn Phe Tyr
130 135 140

Pro Arg Glu Ala Lys Val Gln Trp Lys Val Asp Asn Ala Leu Gln Ser
145 150 155 160

Gly Asn Ser Gln Glu Ser Val Thr Glu Gln Asp Ser Lys Asp Ser Thr
165 170 175

Tyr Ser Leu Ser Ser Thr Leu Thr Leu Ser Lys Ala Asp Tyr Glu Lys
180 185 190

His Lys Val Tyr Ala Cys Glu Val Thr His Gln Gly Leu Ser Ser Pro
195 200 205

Val Thr Lys Ser Phe Asn Arg Gly Glu Cys
210 215

<210> SEQ ID NO 305
<211> LENGTH: 117
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_350; BDG30.111; Human IgG1; protein sequence - VH

<400> SEQUENCE: 305

Gln Val Gln Leu Val Gln Ser Gly Ala Glu Val Lys Lys Pro Gly Ser
1 5 10 15

Ser Val Lys Val Ser Cys Lys Gly Ser Gly Tyr Thr Phe Thr Asp Leu
20 25 30

Gly Ile Gly Trp Val Arg Gln Ala Pro Gly Gln Gly Leu Glu Trp Met
35 40 45

Gly Trp Ile Asn Thr His Thr Gly Glu Pro Phe Tyr Asn Pro Lys Phe
50 55 60

Lys Gly Arg Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Thr Arg Asp His Pro Leu Gly Leu Asp Tyr Trp Gly Gln Gly Thr Thr
100 105 110

```
Val Thr Val Ser Ser
        115


<210> SEQ ID NO 306
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_350; BDG30.111; Human IgG1; protein
      sequence - VL

<400> SEQUENCE: 306

Asp Ile Val Met Thr Gln Ser Pro Asp Ser Leu Ala Val Ser Leu Gly
1               5                   10                  15

Glu Arg Ala Thr Ile Asn Cys Arg Ser Ser Gln Ser Val Asp Val Asn
            20                  25                  30

Gly Val Ser Tyr Leu Asn Trp Tyr Gln Gln Lys Pro Gly Gln Pro Pro
        35                  40                  45

Lys Phe Leu Ile Tyr Lys Ala Ser Asn Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ala Arg
                85                  90                  95

Glu Asp Pro Tyr Thr Phe Gly Gly Gly Thr Lys Val Glu Ile Lys
            100                 105                 110


<210> SEQ ID NO 307
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_350; BDG30.111; Human IgG1; H chain
      (VH+CH1+hinge+CH2+CH3)

<400> SEQUENCE: 307

Gln Val Gln Leu Val Gln Ser Gly Ala Glu Val Lys Lys Pro Gly Ser
1               5                   10                  15

Ser Val Lys Val Ser Cys Lys Gly Ser Gly Tyr Thr Phe Thr Asp Leu
            20                  25                  30

Gly Ile Gly Trp Val Arg Gln Ala Pro Gly Gln Gly Leu Glu Trp Met
        35                  40                  45

Gly Trp Ile Asn Thr His Thr Gly Glu Pro Phe Tyr Asn Pro Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Asp His Pro Leu Gly Leu Asp Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140
```

Leu Val Lys Asp Tyr Phe Pro Glu Pro Val Thr Val Ser Trp Asn Ser
145 150 155 160

Gly Ala Leu Thr Ser Gly Val His Thr Phe Pro Ala Val Leu Gln Ser
165 170 175

Ser Gly Leu Tyr Ser Leu Ser Ser Val Val Thr Val Pro Ser Ser Ser
180 185 190

Leu Gly Thr Gln Thr Tyr Ile Cys Asn Val Asn His Lys Pro Ser Asn
195 200 205

Thr Lys Val Asp Lys Lys Val Glu Pro Lys Ser Cys Asp Lys Thr His
210 215 220

Thr Cys Pro Pro Cys Pro Ala Pro Glu Leu Leu Gly Gly Pro Ser Val
225 230 235 240

Phe Leu Phe Pro Pro Lys Pro Lys Asp Thr Leu Met Ile Ser Arg Thr
245 250 255

Pro Glu Val Thr Cys Val Val Val Asp Val Ser His Glu Asp Pro Glu
260 265 270

Val Lys Phe Asn Trp Tyr Val Asp Gly Val Glu Val His Asn Ala Lys
275 280 285

Thr Lys Pro Arg Glu Glu Gln Tyr Asn Ser Thr Tyr Arg Val Val Ser
290 295 300

Val Leu Thr Val Leu His Gln Asp Trp Leu Asn Gly Lys Glu Tyr Lys
305 310 315 320

Cys Lys Val Ser Asn Lys Ala Leu Pro Ala Pro Ile Glu Lys Thr Ile
325 330 335

Ser Lys Ala Lys Gly Gln Pro Arg Glu Pro Gln Val Tyr Thr Leu Pro
340 345 350

Pro Ser Arg Asp Glu Leu Thr Lys Asn Gln Val Ser Leu Thr Cys Leu
355 360 365

Val Lys Gly Phe Tyr Pro Ser Asp Ile Ala Val Glu Trp Glu Ser Asn
370 375 380

Gly Gln Pro Glu Asn Asn Tyr Lys Thr Thr Pro Pro Val Leu Asp Ser
385 390 395 400

Asp Gly Ser Phe Phe Leu Tyr Ser Lys Leu Thr Val Asp Lys Ser Arg
405 410 415

Trp Gln Gln Gly Asn Val Phe Ser Cys Ser Val Met His Glu Ala Leu
420 425 430

His Asn His Tyr Thr Gln Lys Ser Leu Ser Leu Ser Pro Gly Lys
435 440 445

<210> SEQ ID NO 308
<211> LENGTH: 218
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_350; BDG30.111; Human IgG1; L chain (VL+CL)

<400> SEQUENCE: 308

Asp Ile Val Met Thr Gln Ser Pro Asp Ser Leu Ala Val Ser Leu Gly
1 5 10 15

Glu Arg Ala Thr Ile Asn Cys Arg Ser Ser Gln Ser Val Asp Val Asn
20 25 30

Gly Val Ser Tyr Leu Asn Trp Tyr Gln Gln Lys Pro Gly Gln Pro Pro
35 40 45

```
Lys Phe Leu Ile Tyr Lys Ala Ser Asn Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ala Arg
                85                  90                  95

Glu Asp Pro Tyr Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215


<210> SEQ ID NO 309
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_327; BDG30.113; Human IgG1(L234A/L235A);
      protein sequence - VH

<400> SEQUENCE: 309

Glu Val Gln Leu Val Gln Ser Gly Pro Glu Leu Lys Lys Pro Gly Ala
1               5                   10                  15

Ser Val Lys Val Ser Cys Lys Gly Ser Gly Tyr Thr Phe Thr Asp Leu
            20                  25                  30

Gly Met Gly Trp Val Arg Gln Ala Pro Gly Gln Gly Leu Glu Trp Met
        35                  40                  45

Gly Trp Ile Asn Thr Gln Thr Gly Glu Pro Phe Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Thr Arg Asp His Pro Leu Gly Leu Asp Tyr Trp Gly Gln Gly Thr Leu
            100                 105                 110

Val Thr Val Ser Ser
        115


<210> SEQ ID NO 310
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
```

<220> FEATURE:
<223> OTHER INFORMATION: CID_327; BDG30.113; Human IgG1(L234A/L235A); protein sequence - VL

<400> SEQUENCE: 310

```
Asp Ile Gln Val Thr Gln Ser Pro Ser Ser Leu Ser Ala Ser Val Gly
1               5                   10                  15

Asp Arg Val Thr Ile Thr Cys Ile Thr Ser Gln Ser Val Asp Val Ala
            20                  25                  30

Gly Val Ser Tyr Leu Asn Trp Tyr Gln Gln Lys Pro Gly Lys Val Pro
        35                  40                  45

Lys Phe Leu Ile His Lys Ala Ser Asn Leu Arg Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Val Ala Thr Tyr Tyr Cys Gln Gln Ala Arg
                85                  90                  95

Glu Asp Pro Tyr Thr Phe Gly Gln Gly Thr Lys Val Glu Ile Lys
            100                 105                 110
```

<210> SEQ ID NO 311
<211> LENGTH: 447
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_327; BDG30.113; Human IgG1(L234A/L235A); H chain (VH+CH1+hinge+CH2+CH3)

<400> SEQUENCE: 311

```
Glu Val Gln Leu Val Gln Ser Gly Pro Glu Leu Lys Lys Pro Gly Ala
1               5                   10                  15

Ser Val Lys Val Ser Cys Lys Gly Ser Gly Tyr Thr Phe Thr Asp Leu
            20                  25                  30

Gly Met Gly Trp Val Arg Gln Ala Pro Gly Gln Gly Leu Glu Trp Met
        35                  40                  45

Gly Trp Ile Asn Thr Gln Thr Gly Glu Pro Phe Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Thr Arg Asp His Pro Leu Gly Leu Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205
```

```
Thr Lys Val Asp Lys Lys Val Glu Pro Lys Ser Cys Asp Lys Thr His
    210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445


<210> SEQ ID NO 312
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_327; BDG30.113; Human IgG1(L234A/L235A); L
      chain (VL+CL)

<400> SEQUENCE: 312

Asp Ile Gln Val Thr Gln Ser Pro Ser Ser Leu Ser Ala Ser Val Gly
1               5                   10                  15

Asp Arg Val Thr Ile Thr Cys Ile Thr Ser Gln Ser Val Asp Val Ala
            20                  25                  30

Gly Val Ser Tyr Leu Asn Trp Tyr Gln Gln Lys Pro Gly Lys Val Pro
        35                  40                  45

Lys Phe Leu Ile His Lys Ala Ser Asn Leu Arg Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Val Ala Thr Tyr Tyr Cys Gln Gln Ala Arg
                85                  90                  95

Glu Asp Pro Tyr Thr Phe Gly Gln Gly Thr Lys Val Glu Ile Lys Arg
```

```
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 313
<211> LENGTH: 117
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_328; BDG30.114; Human IgG1(L234A/L235A); protein sequence - VH

<400> SEQUENCE: 313

```
Glu Val Gln Leu Val Gln Ser Gly Pro Glu Leu Lys Lys Pro Gly Ala
1               5                   10                  15

Ser Val Lys Val Ser Cys Lys Gly Ser Gly Tyr Thr Phe Thr Asp Leu
            20                  25                  30

Gly Met Asn Trp Val Arg Gln Ala Pro Gly Gln Gly Leu Glu Trp Met
        35                  40                  45

Gly Trp Ile Asn Thr Gln Thr Gly Glu Pro Phe Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Phe Cys
                85                  90                  95

Ala Arg Asp His Pro Leu Gly Leu Asp Tyr Trp Gly Gln Gly Thr Leu
            100                 105                 110

Val Thr Val Ser Ser
        115
```

<210> SEQ ID NO 314
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_328; BDG30.114; Human IgG1(L234A/L235A); protein sequence - VL

<400> SEQUENCE: 314

```
Asp Ile Gln Val Thr Gln Ser Pro Ser Ser Leu Ser Ala Ser Val Gly
1               5                   10                  15

Asp Arg Val Thr Ile Thr Cys Ile Thr Ser Gln Ser Val Asp Val Asn
```

```
            20                  25                  30

Gly Val Ser Tyr Leu Asn Trp Tyr Gln Gln Lys Pro Gly Lys Val Pro
        35                  40                  45

Lys Phe Leu Ile Tyr Lys Ala Ser Ile Leu Arg Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Val Ala Thr Tyr Tyr Cys Gln Gln Ser Arg
                85                  90                  95

Glu Asp Pro Tyr Thr Phe Gly Gln Gly Thr Lys Val Glu Ile Lys
            100                 105                 110


<210> SEQ ID NO 315
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_328; BDG30.114; Human IgG1(L234A/L235A); H
      chain (VH+CH1+hinge+CH2+CH3)

<400> SEQUENCE: 315

Glu Val Gln Leu Val Gln Ser Gly Pro Glu Leu Lys Lys Pro Gly Ala
1               5                   10                  15

Ser Val Lys Val Ser Cys Lys Gly Ser Gly Tyr Thr Phe Thr Asp Leu
            20                  25                  30

Gly Met Asn Trp Val Arg Gln Ala Pro Gly Gln Gly Leu Glu Trp Met
        35                  40                  45

Gly Trp Ile Asn Thr Gln Thr Gly Glu Pro Phe Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Phe Cys
                85                  90                  95

Ala Arg Asp His Pro Leu Gly Leu Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255
```

Pro Glu Val Thr Cys Val Val Val Asp Val Ser His Glu Asp Pro Glu
260 265 270

Val Lys Phe Asn Trp Tyr Val Asp Gly Val Glu Val His Asn Ala Lys
275 280 285

Thr Lys Pro Arg Glu Glu Gln Tyr Asn Ser Thr Tyr Arg Val Val Ser
290 295 300

Val Leu Thr Val Leu His Gln Asp Trp Leu Asn Gly Lys Glu Tyr Lys
305 310 315 320

Cys Lys Val Ser Asn Lys Ala Leu Pro Ala Pro Ile Glu Lys Thr Ile
325 330 335

Ser Lys Ala Lys Gly Gln Pro Arg Glu Pro Gln Val Tyr Thr Leu Pro
340 345 350

Pro Ser Arg Asp Glu Leu Thr Lys Asn Gln Val Ser Leu Thr Cys Leu
355 360 365

Val Lys Gly Phe Tyr Pro Ser Asp Ile Ala Val Glu Trp Glu Ser Asn
370 375 380

Gly Gln Pro Glu Asn Asn Tyr Lys Thr Thr Pro Pro Val Leu Asp Ser
385 390 395 400

Asp Gly Ser Phe Phe Leu Tyr Ser Lys Leu Thr Val Asp Lys Ser Arg
405 410 415

Trp Gln Gln Gly Asn Val Phe Ser Cys Ser Val Met His Glu Ala Leu
420 425 430

His Asn His Tyr Thr Gln Lys Ser Leu Ser Leu Ser Pro Gly Lys
435 440 445

<210> SEQ ID NO 316
<211> LENGTH: 218
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_328; BDG30.114; Human IgG1(L234A/L235A); L chain (VL+CL)

<400> SEQUENCE: 316

Asp Ile Gln Val Thr Gln Ser Pro Ser Ser Leu Ser Ala Ser Val Gly
1 5 10 15

Asp Arg Val Thr Ile Thr Cys Ile Thr Ser Gln Ser Val Asp Val Asn
20 25 30

Gly Val Ser Tyr Leu Asn Trp Tyr Gln Gln Lys Pro Gly Lys Val Pro
35 40 45

Lys Phe Leu Ile Tyr Lys Ala Ser Ile Leu Arg Ser Gly Val Pro Ser
50 55 60

Arg Phe Ser Gly Ser Gly Ser Gly Thr Asp Phe Thr Leu Thr Ile Ser
65 70 75 80

Ser Leu Gln Pro Glu Asp Val Ala Thr Tyr Tyr Cys Gln Gln Ser Arg
85 90 95

Glu Asp Pro Tyr Thr Phe Gly Gln Gly Thr Lys Val Glu Ile Lys Arg
100 105 110

Thr Val Ala Ala Pro Ser Val Phe Ile Phe Pro Pro Ser Asp Glu Gln
115 120 125

Leu Lys Ser Gly Thr Ala Ser Val Val Cys Leu Leu Asn Asn Phe Tyr
130 135 140

Pro Arg Glu Ala Lys Val Gln Trp Lys Val Asp Asn Ala Leu Gln Ser
145 150 155 160

Gly Asn Ser Gln Glu Ser Val Thr Glu Gln Asp Ser Lys Asp Ser Thr
165 170 175

Tyr Ser Leu Ser Ser Thr Leu Thr Leu Ser Lys Ala Asp Tyr Glu Lys
180 185 190

His Lys Val Tyr Ala Cys Glu Val Thr His Gln Gly Leu Ser Ser Pro
195 200 205

Val Thr Lys Ser Phe Asn Arg Gly Glu Cys
210 215

<210> SEQ ID NO 317
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_262; BDG30.116; Human IgG1(L234A/L235A); protein sequence - VH

<400> SEQUENCE: 317

Glu Val Gln Leu Val Glu Ser Gly Gly Gly Leu Val Gln Pro Gly Gly
1 5 10 15

Ser Leu Arg Leu Ser Cys Ala Ala Ser Gly Phe Asn Ile Lys Asp Tyr
20 25 30

Phe Ile His Trp Val Arg Gln Ala Pro Gly Lys Gly Leu Glu Trp Val
35 40 45

Ala Asp Ile Asp Pro Thr Asn Gly Asp Thr Arg Tyr Ala Asp Ser Val
50 55 60

Lys Gly Arg Phe Thr Ile Ser Ala Asp Thr Ser Lys Asn Thr Ala Tyr
65 70 75 80

Leu Gln Met Asn Ser Leu Arg Ala Glu Asp Thr Ala Val Tyr Tyr Cys
85 90 95

Ser Arg Glu Gly Gln Asp Gly Tyr Asn Ala Trp Asp Gln Trp Gly Gln
100 105 110

Gly Thr Leu Val Thr Val Ser Ser
115 120

<210> SEQ ID NO 318
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_262; BDG30.116; Human IgG1(L234A/L235A); protein sequence - VL

<400> SEQUENCE: 318

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asp Ile Ser Thr Ala
20 25 30

Val Ala Trp Ser Gln Gln Lys Pro Gly Lys Ala Pro Lys Leu Leu Ile
35 40 45

Tyr Pro Ala Ser Ser Leu Tyr Ser Gly Val Pro Ser Arg Phe Ser Gly
50 55 60

Ser Arg Ser Gly Thr Asp Phe Thr Leu Thr Ile Ser Ser Leu Gln Pro
65 70 75 80

Glu Asp Phe Ala Thr Tyr Tyr Cys Gln Gln His Pro Tyr Thr Pro Pro
85 90 95

Thr Phe Gly Gln Gly Thr Lys Val Glu Ile Lys
100 105

<210> SEQ ID NO 319
<211> LENGTH: 450
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_262; BDG30.116; Human IgG1(L234A/L235A); H chain (VH+CH1+hinge+CH2+CH3)

<400> SEQUENCE: 319

Glu Val Gln Leu Val Glu Ser Gly Gly Gly Leu Val Gln Pro Gly Gly
1 5 10 15

Ser Leu Arg Leu Ser Cys Ala Ala Ser Gly Phe Asn Ile Lys Asp Tyr
20 25 30

Phe Ile His Trp Val Arg Gln Ala Pro Gly Lys Gly Leu Glu Trp Val
35 40 45

Ala Asp Ile Asp Pro Thr Asn Gly Asp Thr Arg Tyr Ala Asp Ser Val
50 55 60

Lys Gly Arg Phe Thr Ile Ser Ala Asp Thr Ser Lys Asn Thr Ala Tyr
65 70 75 80

Leu Gln Met Asn Ser Leu Arg Ala Glu Asp Thr Ala Val Tyr Tyr Cys
85 90 95

Ser Arg Glu Gly Gln Asp Gly Tyr Asn Ala Trp Asp Gln Trp Gly Gln
100 105 110

Gly Thr Leu Val Thr Val Ser Ser Ala Ser Thr Lys Gly Pro Ser Val
115 120 125

Phe Pro Leu Ala Pro Ser Ser Lys Ser Thr Ser Gly Gly Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Gln Thr Tyr Ile Cys Asn Val Asn His Lys
195 200 205

Pro Ser Asn Thr Lys Val Asp Lys Lys Val Glu Pro Lys Ser Cys Asp
210 215 220

Lys Thr His Thr Cys Pro Pro Cys Pro Ala Pro Glu Ala Ala Gly Gly
225 230 235 240

Pro Ser Val Phe Leu Phe Pro Pro Lys Pro Lys Asp Thr Leu Met Ile
245 250 255

Ser Arg Thr Pro Glu Val Thr Cys Val Val Val Asp Val Ser His Glu
260 265 270

Asp Pro Glu Val Lys Phe Asn Trp Tyr Val Asp Gly Val Glu Val His
275 280 285

Asn Ala Lys Thr Lys Pro Arg Glu Glu Gln Tyr Asn Ser Thr Tyr Arg
290 295 300

Val Val Ser Val Leu Thr Val Leu His Gln Asp Trp Leu Asn Gly Lys

```
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 320
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_262; BDG30.116; Human IgG1(L234A/L235A); L
      chain (VL+CL)

<400> SEQUENCE: 320

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Thr Ala
            20                  25                  30

Val Ala Trp Ser Gln Gln Lys Pro Gly Lys Ala Pro Lys Leu Leu Ile
        35                  40                  45

Tyr Pro Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Pro Tyr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

```
Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 321
<211> LENGTH: 128
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_277; BDG30.117; Human IgG1(L234A/L235A); protein sequence - VH

<400> SEQUENCE: 321

```
Glu Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Thr Ser Tyr
            20                  25                  30

Ser Phe Asn Trp Val Arg Gln Ala Pro Gly Gln Gly Leu Glu Trp Met
        35                  40                  45

Gly Arg Ile Ile Thr Ile Leu Asp Asp Thr Glu Tyr Ala Pro His Leu
    50                  55                  60

Gln Gly Arg Val Thr Ile Thr Ala Asp Lys Ser Thr Ser Thr Val Tyr
65                  70                  75                  80

Leu Glu Leu Arg Asn Leu Arg Ser Asp Asp Thr Ala Val Tyr Phe Cys
                85                  90                  95

Ala Gly Val Tyr Glu Gly Pro Asn Ser Glu Gly Ser Tyr Asp Asp Tyr
            100                 105                 110

Gly Phe Leu Lys Tyr Trp Gly Gln Gly Thr Leu Val Thr Val Ser Ser
        115                 120                 125
```

<210> SEQ ID NO 322
<211> LENGTH: 109
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_277; BDG30.117; Human IgG1(L234A/L235A); protein sequence - VL

<400> SEQUENCE: 322

```
Asp Ile Val Met Thr Gln Ser Pro Ala Thr Leu Ser Val Ser Pro Gly
1               5                   10                  15

Glu Arg Ala Thr Leu Ser Cys Arg Ala Ser Glu Ser Val Ala Val Asp
            20                  25                  30

Leu Ala Trp Tyr Gln Gln Lys Pro Gly Gln Val Pro Arg Leu Leu Ile
        35                  40                  45

Tyr Gly Ala Ser Thr Arg Ala Thr Gly Val Pro Ala Arg Phe Ser Gly
    50                  55                  60

Ser Gly Ser Gly Ala Glu Phe Thr Leu Thr Ile Ser Ser Leu Gln Ser
65                  70                  75                  80

Glu Asp Phe Ala Val Tyr Tyr Cys Gln Gln Tyr Ala Asn Lys Pro Pro
                85                  90                  95

Arg Glu Thr Phe Gly Gln Gly Thr Arg Leu Glu Ile Lys
            100                 105
```

<210> SEQ ID NO 323
<211> LENGTH: 458
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_277; BDG30.117; Human IgG1(L234A/L235A); H chain (VH+CH1+hinge+CH2+CH3)

<400> SEQUENCE: 323

```
Glu Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Thr Ser Tyr
            20                  25                  30

Ser Phe Asn Trp Val Arg Gln Ala Pro Gly Gln Gly Leu Glu Trp Met
        35                  40                  45

Gly Arg Ile Ile Thr Ile Leu Asp Asp Thr Glu Tyr Ala Pro His Leu
    50                  55                  60

Gln Gly Arg Val Thr Ile Thr Ala Asp Lys Ser Thr Ser Thr Val Tyr
65                  70                  75                  80

Leu Glu Leu Arg Asn Leu Arg Ser Asp Asp Thr Ala Val Tyr Phe Cys
                85                  90                  95

Ala Gly Val Tyr Glu Gly Pro Asn Ser Glu Gly Ser Tyr Asp Asp Tyr
            100                 105                 110

Gly Phe Leu Lys Tyr Trp Gly Gln Gly Thr Leu Val Thr Val Ser Ser
        115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
    210                 215                 220

Lys Val Glu Pro Lys Ser Cys Asp Lys Thr His Thr Cys Pro Pro Cys
225                 230                 235                 240

Pro Ala Pro Glu Ala Ala Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350
```

```
Gln Pro Arg Glu Pro Gln Val Tyr Thr Leu Pro Pro Ser Arg Asp Glu
        355                 360                 365

Leu Thr Lys Asn Gln Val Ser Leu Thr Cys Leu Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly Lys
    450                 455


<210> SEQ ID NO 324
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_277; BDG30.117; Human IgG1(L234A/L235A); L
      chain (VL+CL)

<400> SEQUENCE: 324

Asp Ile Val Met Thr Gln Ser Pro Ala Thr Leu Ser Val Ser Pro Gly
1               5                   10                  15

Glu Arg Ala Thr Leu Ser Cys Arg Ala Ser Glu Ser Val Ala Val Asp
            20                  25                  30

Leu Ala Trp Tyr Gln Gln Lys Pro Gly Gln Val Pro Arg Leu Leu Ile
        35                  40                  45

Tyr Gly Ala Ser Thr Arg Ala Thr Gly Val Pro Ala Arg Phe Ser Gly
    50                  55                  60

Ser Gly Ser Gly Ala Glu Phe Thr Leu Thr Ile Ser Ser Leu Gln Ser
65                  70                  75                  80

Glu Asp Phe Ala Val Tyr Tyr Cys Gln Gln Tyr Ala Asn Lys Pro Pro
                85                  90                  95

Arg Glu Thr Phe Gly Gln Gly Thr Arg Leu Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215
```

<210> SEQ ID NO 325
<211> LENGTH: 128
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: CID_280; BDG30.118; Human IgG1(L234A/L235A);
protein sequence - VH

<400> SEQUENCE: 325

Glu Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Thr Ser Tyr
            20                  25                  30

Ser Phe Asn Trp Val Arg Gln Ala Pro Gly Gln Gly Leu Glu Trp Met
        35                  40                  45

Gly Arg Ile Ile Thr Asp Leu Asp Asp Thr Glu Tyr Ala Pro His Leu
    50                  55                  60

Gln Gly Arg Val Thr Ile Thr Ala Asp Lys Ser Thr Ser Thr Val Tyr
65                  70                  75                  80

Leu Glu Leu Arg Asn Leu Arg Ser Asp Asp Thr Ala Val Tyr Phe Cys
                85                  90                  95

Ala Gly Val Tyr Glu Gly Pro Asn Ser Glu Gly Ser Tyr Asp Asp Tyr
            100                 105                 110

Gly Gln Leu Lys His Trp Gly Gln Gly Thr Leu Val Thr Val Ser Ser
        115                 120                 125

<210> SEQ ID NO 326
<211> LENGTH: 109
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: CID_280; BDG30.118; Human IgG1(L234A/L235A);
protein sequence - VL

<400> SEQUENCE: 326

Asp Ile Val Met Thr Gln Ser Pro Ala Thr Leu Ser Val Ser Pro Gly
1               5                   10                  15

Glu Arg Ala Thr Leu Ser Cys Arg Ala Ser Glu Ser Val Ala Asn Asp
            20                  25                  30

Leu Ala Trp Tyr Gln Gln Lys Pro Gly Gln Val Pro Arg Leu Leu Ile
        35                  40                  45

Tyr Gly Ala Ser Thr Arg Ala Thr Gly Val Pro Ala Arg Phe Ser Gly
    50                  55                  60

Ser Gly Ser Gly Ala Glu Phe Thr Leu Thr Ile Ser Ser Leu Gln Ser
65                  70                  75                  80

Glu Asp Phe Ala Val Tyr Tyr Cys Gln Gln Tyr Ala Asn Trp Pro Pro
                85                  90                  95

Arg Glu Thr Phe Gly Gln Gly Thr Arg Leu Glu Ile Lys
            100                 105

<210> SEQ ID NO 327
<211> LENGTH: 458
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_280; BDG30.118; Human IgG1(L234A/L235A); H
chain (VH+CH1+hinge+CH2+CH3)

<400> SEQUENCE: 327

Glu Val Gln Leu Val Gln Ser Gly Ala Glu Val Lys Lys Pro Gly Ser
1 5 10 15

Ser Val Lys Val Ser Cys Lys Ala Ser Gly Asp Thr Phe Thr Ser Tyr
20 25 30

Ser Phe Asn Trp Val Arg Gln Ala Pro Gly Gln Gly Leu Glu Trp Met
35 40 45

Gly Arg Ile Ile Thr Asp Leu Asp Asp Thr Glu Tyr Ala Pro His Leu
50 55 60

Gln Gly Arg Val Thr Ile Thr Ala Asp Lys Ser Thr Ser Thr Val Tyr
65 70 75 80

Leu Glu Leu Arg Asn Leu Arg Ser Asp Asp Thr Ala Val Tyr Phe Cys
85 90 95

Ala Gly Val Tyr Glu Gly Pro Asn Ser Glu Gly Ser Tyr Asp Asp Tyr
100 105 110

Gly Gln Leu Lys His Trp Gly Gln Gly Thr Leu Val Thr Val Ser Ser
115 120 125

Ala Ser Thr Lys Gly Pro Ser Val Phe Pro Leu Ala Pro Ser Ser Lys
130 135 140

Ser Thr Ser Gly Gly Thr Ala Ala Leu Gly Cys Leu Val Lys Asp Tyr
145 150 155 160

Phe Pro Glu Pro Val Thr Val Ser Trp Asn Ser Gly Ala Leu Thr Ser
165 170 175

Gly Val His Thr Phe Pro Ala Val Leu Gln Ser Ser Gly Leu Tyr Ser
180 185 190

Leu Ser Ser Val Val Thr Val Pro Ser Ser Ser Leu Gly Thr Gln Thr
195 200 205

Tyr Ile Cys Asn Val Asn His Lys Pro Ser Asn Thr Lys Val Asp Lys
210 215 220

Lys Val Glu Pro Lys Ser Cys Asp Lys Thr His Thr Cys Pro Pro Cys
225 230 235 240

Pro Ala Pro Glu Ala Ala Gly Gly Pro Ser Val Phe Leu Phe Pro Pro
245 250 255

Lys Pro Lys Asp Thr Leu Met Ile Ser Arg Thr Pro Glu Val Thr Cys
260 265 270

Val Val Val Asp Val Ser His Glu Asp Pro Glu Val Lys Phe Asn Trp
275 280 285

Tyr Val Asp Gly Val Glu Val His Asn Ala Lys Thr Lys Pro Arg Glu
290 295 300

Glu Gln Tyr Asn Ser Thr Tyr Arg Val Val Ser Val Leu Thr Val Leu
305 310 315 320

His Gln Asp Trp Leu Asn Gly Lys Glu Tyr Lys Cys Lys Val Ser Asn
325 330 335

Lys Ala Leu Pro Ala Pro Ile Glu Lys Thr Ile Ser Lys Ala Lys Gly
340 345 350

Gln Pro Arg Glu Pro Gln Val Tyr Thr Leu Pro Pro Ser Arg Asp Glu
355 360 365

Leu Thr Lys Asn Gln Val Ser Leu Thr Cys Leu Val Lys Gly Phe Tyr
370 375 380

```
Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly Lys
    450                 455


<210> SEQ ID NO 328
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_280; BDG30.118; Human IgG1(L234A/L235A); L
      chain (VL+CL)

<400> SEQUENCE: 328

Asp Ile Val Met Thr Gln Ser Pro Ala Thr Leu Ser Val Ser Pro Gly
1               5                   10                  15

Glu Arg Ala Thr Leu Ser Cys Arg Ala Ser Glu Ser Val Ala Asn Asp
            20                  25                  30

Leu Ala Trp Tyr Gln Gln Lys Pro Gly Gln Val Pro Arg Leu Leu Ile
        35                  40                  45

Tyr Gly Ala Ser Thr Arg Ala Thr Gly Val Pro Ala Arg Phe Ser Gly
    50                  55                  60

Ser Gly Ser Gly Ala Glu Phe Thr Leu Thr Ile Ser Ser Leu Gln Ser
65                  70                  75                  80

Glu Asp Phe Ala Val Tyr Tyr Cys Gln Gln Tyr Ala Asn Trp Pro Pro
                85                  90                  95

Arg Glu Thr Phe Gly Gln Gly Thr Arg Leu Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215


<210> SEQ ID NO 329
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide
```

<220> FEATURE:
<223> OTHER INFORMATION: CID_284; BDG30.119; Human IgG1(L234A/L235A); protein sequence - VH

<400> SEQUENCE: 329

```
Glu Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Thr Ser Tyr
            20                  25                  30

Ser Phe Asn Trp Val Arg Gln Ala Pro Gly Gln Gly Leu Glu Trp Met
        35                  40                  45

Gly Arg Ile Ile Thr Ile Asp Asp Asp Thr Glu Tyr Ala Pro His Leu
    50                  55                  60

Gln Gly Arg Val Thr Ile Thr Ala Asp Lys Ser Thr Ser Thr Val Tyr
65                  70                  75                  80

Leu Glu Leu Arg Asn Leu Arg Ser Asp Asp Thr Ala Val Tyr Phe Cys
                85                  90                  95

Ala Gly Val Tyr Glu Gly Pro Asn Ser Glu Gly Ser Tyr Asp Asp Tyr
            100                 105                 110

Gly Gln Leu Lys His Trp Gly Gln Gly Thr Leu Val Thr Val Ser Ser
        115                 120                 125
```

<210> SEQ ID NO 330
<211> LENGTH: 109
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_284; BDG30.119; Human IgG1(L234A/L235A); protein sequence - VL

<400> SEQUENCE: 330

```
Asp Ile Val Met Thr Gln Ser Pro Ala Thr Leu Ser Val Ser Pro Gly
1               5                   10                  15

Glu Arg Ala Thr Leu Ser Cys Arg Ala Ser Glu Ser Val Gly Asn Asp
            20                  25                  30

Leu Ala Trp Tyr Gln Gln Lys Pro Gly Gln Val Pro Arg Leu Leu Ile
        35                  40                  45

Tyr Gly Ala Ser Thr Arg Ala Thr Gly Val Pro Ala Arg Phe Ser Gly
    50                  55                  60

Ser Gly Ser Gly Ala Glu Phe Thr Leu Thr Ile Ser Ser Leu Gln Ser
65                  70                  75                  80

Glu Asp Phe Ala Val Tyr Tyr Cys Gln Gln Tyr Ala Asn Val Pro Pro
                85                  90                  95

Arg Glu Thr Phe Gly Gln Gly Thr Arg Leu Glu Ile Lys
            100                 105
```

<210> SEQ ID NO 331
<211> LENGTH: 458
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_284; BDG30.119; Human IgG1(L234A/L235A); H chain (VH+CH1+hinge+CH2+CH3)

<400> SEQUENCE: 331

-continued

```
Glu Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Thr Ser Tyr
            20                  25                  30

Ser Phe Asn Trp Val Arg Gln Ala Pro Gly Gln Gly Leu Glu Trp Met
        35                  40                  45

Gly Arg Ile Ile Thr Ile Asp Asp Asp Thr Glu Tyr Ala Pro His Leu
    50                  55                  60

Gln Gly Arg Val Thr Ile Thr Ala Asp Lys Ser Thr Ser Thr Val Tyr
65                  70                  75                  80

Leu Glu Leu Arg Asn Leu Arg Ser Asp Asp Thr Ala Val Tyr Phe Cys
                85                  90                  95

Ala Gly Val Tyr Glu Gly Pro Asn Ser Glu Gly Ser Tyr Asp Asp Tyr
            100                 105                 110

Gly Gln Leu Lys His Trp Gly Gln Gly Thr Leu Val Thr Val Ser Ser
        115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
    210                 215                 220

Lys Val Glu Pro Lys Ser Cys Asp Lys Thr His Thr Cys Pro Pro Cys
225                 230                 235                 240

Pro Ala Pro Glu Ala Ala Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Asp Glu
        355                 360                 365

Leu Thr Lys Asn Gln Val Ser Leu Thr Cys Leu Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
```

```
            420                 425                 430

Val Phe Ser Cys Ser Val Met His Glu Ala Leu His Asn His Tyr Thr
        435                 440                 445

Gln Lys Ser Leu Ser Leu Ser Pro Gly Lys
    450                 455


<210> SEQ ID NO 332
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_284; BDG30.119; Human IgG1(L234A/L235A); L
      chain (VL+CL)

<400> SEQUENCE: 332

Asp Ile Val Met Thr Gln Ser Pro Ala Thr Leu Ser Val Ser Pro Gly
1               5                   10                  15

Glu Arg Ala Thr Leu Ser Cys Arg Ala Ser Glu Ser Val Gly Asn Asp
            20                  25                  30

Leu Ala Trp Tyr Gln Gln Lys Pro Gly Gln Val Pro Arg Leu Leu Ile
        35                  40                  45

Tyr Gly Ala Ser Thr Arg Ala Thr Gly Val Pro Ala Arg Phe Ser Gly
    50                  55                  60

Ser Gly Ser Gly Ala Glu Phe Thr Leu Thr Ile Ser Ser Leu Gln Ser
65                  70                  75                  80

Glu Asp Phe Ala Val Tyr Tyr Cys Gln Gln Tyr Ala Asn Val Pro Pro
                85                  90                  95

Arg Glu Thr Phe Gly Gln Gly Thr Arg Leu Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215


<210> SEQ ID NO 333
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Flexible linker

<400> SEQUENCE: 333

Gly Gly Gly Gly Ser
1               5
```

<210> SEQ ID NO 334
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDRH2

<400> SEQUENCE: 334

Ile Ile Thr Asp Leu Asp Asp Thr
1               5

<210> SEQ ID NO 335
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDRH2

<400> SEQUENCE: 335

Ile Ile Thr Ile Pro Asp Asp Thr
1               5

<210> SEQ ID NO 336
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDRH2

<400> SEQUENCE: 336

Ile Ile Thr Ile Asp Asp Asp Thr
1               5

<210> SEQ ID NO 337
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDRH2

<400> SEQUENCE: 337

Ile Ile Thr Ile Leu Asp Asp Ser
1               5

<210> SEQ ID NO 338
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDRH2

<400> SEQUENCE: 338

Ile Ile Thr Ile Asp Asp Asp Thr 1 5

<210> SEQ ID NO 339
<211> LENGTH: 8
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: CDRH2

<400> SEQUENCE: 339

Ile Ile Thr Ile Tyr Asp Asp Thr
1 5

<210> SEQ ID NO 340
<211> LENGTH: 8
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: CDRH2

<400> SEQUENCE: 340

Ile Asn Thr His Thr Gly Met Pro
1 5

<210> SEQ ID NO 341
<211> LENGTH: 8
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: CDRH2

<400> SEQUENCE: 341

Ile Asn Thr His Thr Gly Glu Pro
1 5

<210> SEQ ID NO 342
<211> LENGTH: 8
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: CDRH2

<400> SEQUENCE: 342

Ile Asn Thr His Thr Gly Lys Pro
1 5

<210> SEQ ID NO 343
<211> LENGTH: 8
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: CDRH2

<400> SEQUENCE: 343

Ile Asn Thr Gln Thr Gly Glu Pro
1 5

<210> SEQ ID NO 344
<211> LENGTH: 8
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: CDRH2

<400> SEQUENCE: 344

Ile Asn Thr Ile Thr Gly Glu Pro
1 5

<210> SEQ ID NO 345
<211> LENGTH: 8
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: CDRH2

<400> SEQUENCE: 345

Ile Asp Pro Asp Asn Gly Asp Thr
1 5

<210> SEQ ID NO 346
<211> LENGTH: 8
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: CDRH2

<400> SEQUENCE: 346

Ile Asp Pro Thr Asn Gly Asp Thr
1 5

<210> SEQ ID NO 347
<211> LENGTH: 21
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: CDRH3

<400> SEQUENCE: 347

Ala Gly Val Tyr Glu Gly Pro Asn Ser Glu Gly Ser Tyr Asp Asp Tyr
1 5 10 15

Gly Phe Leu Lys His
20

<210> SEQ ID NO 348
<211> LENGTH: 21
<212> TYPE: PRT
<213> ORGANISM: Artificial Sequence
<220> FEATURE:
<223> OTHER INFORMATION: Description of Artificial Sequence: Synthetic peptide
<220> FEATURE:

<223> OTHER INFORMATION: CDRH3

<400> SEQUENCE: 348

Ala Gly Val Tyr Glu Gly Pro Asn Ser Glu Gly Ser Tyr Asp Asp Tyr
1 5 10 15

Gly Phe Tyr Lys His
20

<210> SEQ ID NO 349
<211> LENGTH: 21
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: CDRH3

<400> SEQUENCE: 349

Ala Gly Val Tyr Glu Gly Pro Asn Ser Glu Gly Ser Tyr Asp Asp Tyr
1 5 10 15

Gly Phe Phe Lys His
20

<210> SEQ ID NO 350
<211> LENGTH: 21
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: CDRH3

<400> SEQUENCE: 350

Ala Gly Val Tyr Glu Gly Pro Asn Ser Glu Gly Ser Tyr Asp Asp Tyr
1 5 10 15

Gly Phe Leu Lys Tyr
20

<210> SEQ ID NO 351
<211> LENGTH: 21
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: CDRH3

<400> SEQUENCE: 351

Ala Gly Val Tyr Glu Gly Pro Asn Ser Glu Gly Ser Tyr Asp Asp Tyr
1 5 10 15

Gly Ala Leu Lys His
20

<210> SEQ ID NO 352
<211> LENGTH: 21
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: CDRH3

<400> SEQUENCE: 352

Ala Gly Val Tyr Glu Gly Pro Asn Ser Glu Gly Ser Tyr Asp Asp Tyr
1 5 10 15

Gly Gln Leu Lys His
20

<210> SEQ ID NO 353
<211> LENGTH: 10
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: CDRH3

<400> SEQUENCE: 353

Ala Arg Asp His Pro Leu Gly Leu Asp Tyr
1 5 10

<210> SEQ ID NO 354
<211> LENGTH: 10
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: CDRH3

<400> SEQUENCE: 354

Thr Arg Asp His Pro Leu Gly Leu Asp Tyr
1 5 10

<210> SEQ ID NO 355
<211> LENGTH: 10
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: CDRH3

<400> SEQUENCE: 355

Ala Arg Asp His Pro Leu Gly Leu Asp Tyr
1 5 10

<210> SEQ ID NO 356
<211> LENGTH: 13
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: CDRH3

<400> SEQUENCE: 356

Ser Arg Asp Leu Ala Asp Gly Tyr Asn Ala Phe Asp Arg
1 5 10

<210> SEQ ID NO 357
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<220> FEATURE:
<223> OTHER INFORMATION: CDRH3

<400> SEQUENCE: 357

Ser Arg Glu Gly Glu Asp Gly Tyr Asn Ala Trp Asp Leu
1               5                   10

<210> SEQ ID NO 358
<211> LENGTH: 13
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: CDRH3

<400> SEQUENCE: 358

Thr Arg Glu Gly Asp Asp Gly Tyr Asn Ala Trp Asp Lys
1               5                   10

<210> SEQ ID NO 359
<211> LENGTH: 6
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: CDRL1

<400> SEQUENCE: 359

Glu Ser Val Ala Asn Asp
1               5

<210> SEQ ID NO 360
<211> LENGTH: 6
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: CDRL1

<400> SEQUENCE: 360

Glu Ser Gly Ala Asn Asp
1               5

<210> SEQ ID NO 361
<211> LENGTH: 6
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: CDRL1

<400> SEQUENCE: 361

Arg Ser Val Ala Asn Asp
1               5

<210> SEQ ID NO 362
<211> LENGTH: 6
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: CDRL1

<400> SEQUENCE: 362

Glu Ser Val Ala Asn Asn
1 5

<210> SEQ ID NO 363
<211> LENGTH: 6
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: CDRL1

<400> SEQUENCE: 363

Glu Ser Val Ala Thr Asp
1 5

<210> SEQ ID NO 364
<211> LENGTH: 6
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: CDRL1

<400> SEQUENCE: 364

Glu Ser Val Arg Asn Asp
1 5

<210> SEQ ID NO 365
<211> LENGTH: 6
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: CDRL1

<400> SEQUENCE: 365

Glu Ser Val Gly Asn Asp
1 5

<210> SEQ ID NO 366
<211> LENGTH: 6
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: CDRL1

<400> SEQUENCE: 366

Glu Ser Val Ala Val Asp
1 5

<210> SEQ ID NO 367
<211> LENGTH: 10
<212> TYPE: PRT
<213> ORGANISM: Artificial Sequence
<220> FEATURE:

<223> OTHER INFORMATION: Description of Artificial Sequence: Synthetic
peptide
<220> FEATURE:
<223> OTHER INFORMATION: CDRL1

<400> SEQUENCE: 367

Gln Ser Val Asp Val Asn Gly Val Ser Tyr
1 5 10

<210> SEQ ID NO 368
<211> LENGTH: 10
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: CDRL1

<400> SEQUENCE: 368

Gln Ser Val Asp Val Asn Gly Leu Ser Tyr
1 5 10

<210> SEQ ID NO 369
<211> LENGTH: 10
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: CDRL1

<400> SEQUENCE: 369

Gln Ser Val Asp Val Ala Gly Val Ser Tyr
1 5 10

<210> SEQ ID NO 370
<211> LENGTH: 10
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: CDRL1

<400> SEQUENCE: 370

Gln Ser Leu Asp Val Asn Gly Val Ser Tyr
1 5 10

<210> SEQ ID NO 371
<211> LENGTH: 6
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: CDRL1

<400> SEQUENCE: 371

Gln Asp Val Ser Thr Ala
1 5

<210> SEQ ID NO 372
<211> LENGTH: 3
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: CDRL2

<400> SEQUENCE: 372

Gly Ala Ser
1

<210> SEQ ID NO 373
<211> LENGTH: 3
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: CDRL2

<400> SEQUENCE: 373

Asp Ala Ser
1

<210> SEQ ID NO 374
<211> LENGTH: 3
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: CDRL2

<400> SEQUENCE: 374

Gly Ile Ser
1

<210> SEQ ID NO 375
<211> LENGTH: 3
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: CDRL2

<400> SEQUENCE: 375

Lys Ala Ser
1

<210> SEQ ID NO 376
<211> LENGTH: 3
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: CDRL2

<400> SEQUENCE: 376

Lys Ala Val
1

<210> SEQ ID NO 377
<211> LENGTH: 3
<212> TYPE: PRT

<213> ORGANISM: Artificial Sequence
<220> FEATURE:
<223> OTHER INFORMATION: Description of Artificial Sequence: Synthetic
peptide
<220> FEATURE:
<223> OTHER INFORMATION: CDRL2

<400> SEQUENCE: 377

Ser Ala Ser
1

<210> SEQ ID NO 378
<211> LENGTH: 11
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: CDRL3

<400> SEQUENCE: 378

Gln Gln Tyr Ala Asn Trp Pro Pro Arg Glu Thr
1 5 10

<210> SEQ ID NO 379
<211> LENGTH: 11
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: CDRL3

<400> SEQUENCE: 379

Gln Gln Tyr Ala Asn Trp Pro Pro Arg Gly Thr
1 5 10

<210> SEQ ID NO 380
<211> LENGTH: 11
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: CDRL3

<400> SEQUENCE: 380

Gln Gln Tyr Thr Asn Trp Pro Pro Arg Glu Thr
1 5 10

<210> SEQ ID NO 381
<211> LENGTH: 11
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: CDRL3

<400> SEQUENCE: 381

Gln Gln Tyr Ala Ile Trp Pro Pro Arg Glu Thr
1 5 10

<210> SEQ ID NO 382
<211> LENGTH: 11

<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: CDRL3

<400> SEQUENCE: 382

Gln Gln Tyr Ala Arg Trp Pro Pro Thr Glu Thr
1 5 10

<210> SEQ ID NO 383
<211> LENGTH: 11
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: CDRL3

<400> SEQUENCE: 383

Gln Gln Tyr Asp Asn Trp Pro Pro Arg Glu Thr
1 5 10

<210> SEQ ID NO 384
<211> LENGTH: 11
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: CDRL3

<400> SEQUENCE: 384

Gln Gln Tyr Ala Asn Trp Pro Pro His Glu Thr
1 5 10

<210> SEQ ID NO 385
<211> LENGTH: 11
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: CDRL3

<400> SEQUENCE: 385

Gln Gln Tyr Ala Asn Trp Pro Trp Arg Glu Thr
1 5 10

<210> SEQ ID NO 386
<211> LENGTH: 11
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: CDRL3

<400> SEQUENCE: 386

Gln Gln Gly Ala Asn Trp Pro Pro Arg Glu Thr
1 5 10

<210> SEQ ID NO 387

<211> LENGTH: 11
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: CDRL3

<400> SEQUENCE: 387

Gln Gln Tyr Ala Asn Lys Pro Pro Arg Glu Thr
1 5 10

<210> SEQ ID NO 388
<211> LENGTH: 11
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: CDRL3

<400> SEQUENCE: 388

Gln Gln Tyr Ala Asn Trp Pro Pro Arg Gly Thr
1 5 10

<210> SEQ ID NO 389
<211> LENGTH: 11
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: CDRL3

<400> SEQUENCE: 389

Gln Gln Tyr Ala Asn Thr Pro Pro Arg Glu Thr
1 5 10

<210> SEQ ID NO 390
<211> LENGTH: 11
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: CDRL3

<400> SEQUENCE: 390

Gln Gln Tyr Ala Asn Val Pro Pro Arg Glu Thr
1 5 10

<210> SEQ ID NO 391
<211> LENGTH: 11
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: CDRL3

<400> SEQUENCE: 391

Gln Gln Tyr Ala Asn Asp Pro Pro Arg Glu Thr
1 5 10

<210> SEQ ID NO 392
<211> LENGTH: 9
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: CDRL3

<400> SEQUENCE: 392

Gln Gln Ser Arg Glu Asp Pro Tyr Thr
1 5

<210> SEQ ID NO 393
<211> LENGTH: 9
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: CDRL3

<400> SEQUENCE: 393

Gln Gln Ala Arg Glu Asp Pro Tyr Thr
1 5

<210> SEQ ID NO 394
<211> LENGTH: 9
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: CDRL3

<400> SEQUENCE: 394

Gln Gln Asn Arg Glu Asp Pro Tyr Thr
1 5

<210> SEQ ID NO 395
<211> LENGTH: 9
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: CDRL3

<400> SEQUENCE: 395

Gln Gln Pro Thr Tyr Thr Pro Pro Thr
1 5

<210> SEQ ID NO 396
<211> LENGTH: 9
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: CDRL3

<400> SEQUENCE: 396

Gln Gln Pro Pro Tyr Thr Pro Pro Thr
1 5

<210> SEQ ID NO 397
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDRL3

<400> SEQUENCE: 397

Gln Gln Pro Ser Tyr Thr Pro Pro Thr
1               5

<210> SEQ ID NO 398
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDRH1

<400> SEQUENCE: 398

Gly Phe Asn Ile Arg Ala Met Tyr
1               5

<210> SEQ ID NO 399
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDRH1

<400> SEQUENCE: 399

Gly Phe Asn Ile Arg Ala Phe Tyr
1               5

<210> SEQ ID NO 400
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDRH1

<400> SEQUENCE: 400

Gly Phe Asn Ile Lys Asp Phe Phe
1               5

<210> SEQ ID NO 401
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDRH1

<400> SEQUENCE: 401

Gly Phe Asn Ile Lys Asp Tyr Phe
1               5

<210> SEQ ID NO 402
<211> LENGTH: 8
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: CDRH1

<400> SEQUENCE: 402

Gly Phe Asn Ile Lys Ala Tyr Tyr
1 5

<210> SEQ ID NO 403
<211> LENGTH: 8
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: CDRH1

<400> SEQUENCE: 403

Gly Phe Asn Ile Arg Ala Tyr Tyr
1 5

<210> SEQ ID NO 404
<211> LENGTH: 8
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: CDRH1

<400> SEQUENCE: 404

Gly Phe Asn Ile Arg Asp Tyr Tyr
1 5

<210> SEQ ID NO 405
<211> LENGTH: 8
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: CDRH1

<400> SEQUENCE: 405

Gly Phe Asn Ile Arg Asp Met Phe
1 5

<210> SEQ ID NO 406
<211> LENGTH: 8
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: CDRH2

<400> SEQUENCE: 406

Ile Ser Pro Asp Asn Gly Asp Thr 1 5

<210> SEQ ID NO 407
<211> LENGTH: 13
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: CDRH3

<400> SEQUENCE: 407

Thr Arg Glu Gly Gln Asp Gly Tyr Asn Ala Phe Asp Lys
1 5 10

<210> SEQ ID NO 408
<211> LENGTH: 13
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: CDRH3

<400> SEQUENCE: 408

Ser Arg Glu Met Ala Asp Gly Tyr Asn Ala Phe Asp Leu
1 5 10

<210> SEQ ID NO 409
<211> LENGTH: 13
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: CDRH3

<400> SEQUENCE: 409

Ser Arg Asp Leu Ala Asp Gly Tyr Asn Ala Phe Asp Leu
1 5 10

<210> SEQ ID NO 410
<211> LENGTH: 13
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: CDRH3

<400> SEQUENCE: 410

Thr Arg Glu Gly Ala Asp Gly Tyr Asn Ala Phe Asp Leu
1 5 10

<210> SEQ ID NO 411
<211> LENGTH: 13
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: CDRH3

<400> SEQUENCE: 411

Thr Arg Glu Gly Glu Asp Gly Tyr Asn Ala Phe Asp Gln
1 5 10

<210> SEQ ID NO 412
<211> LENGTH: 13
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: CDRH3

<400> SEQUENCE: 412

Ser Arg Glu Gly Gln Asp Gly Tyr Asn Ala Trp Asp Leu
1 5 10

<210> SEQ ID NO 413
<211> LENGTH: 13
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: CDRH3

<400> SEQUENCE: 413

Ser Arg Glu Gly Gln Asp Gly Tyr Asn Ala Trp Asp Gln
1 5 10

<210> SEQ ID NO 414
<211> LENGTH: 13
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: CDRH3

<400> SEQUENCE: 414

Ser Arg Glu Gly Gln Asp Gly Tyr Asn Ala Trp Asp Met
1 5 10

<210> SEQ ID NO 415
<211> LENGTH: 13
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: CDRH3

<400> SEQUENCE: 415

Thr Arg Glu Gly Gln Asp Gly Tyr Asn Ala Phe Asp Met
1 5 10

<210> SEQ ID NO 416
<211> LENGTH: 13
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: CDRH3

<400> SEQUENCE: 416

Thr Arg Glu Gly Glu Asp Gly Tyr Asn Ala Phe Asp Met
1 5 10

<210> SEQ ID NO 417
<211> LENGTH: 6
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: CDRL1

<400> SEQUENCE: 417

Gln Asp Ile Ser Thr Ala
1 5

<210> SEQ ID NO 418
<211> LENGTH: 3
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: CDRL2

<400> SEQUENCE: 418

Pro Ala Ser
1

<210> SEQ ID NO 419
<211> LENGTH: 9
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: CDRL3

<400> SEQUENCE: 419

Gln Gln His Arg Tyr Thr Pro Pro Thr
1 5

<210> SEQ ID NO 420
<211> LENGTH: 9
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: CDRL3

<400> SEQUENCE: 420

Gln Gln Pro Asn Tyr Thr Pro Pro Thr
1 5

<210> SEQ ID NO 421
<211> LENGTH: 9
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: CDRL3

<400> SEQUENCE: 421

Gln Gln His Gly Tyr Thr Pro Pro Thr
1               5

<210> SEQ ID NO 422
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDRL3

<400> SEQUENCE: 422

Gln Gln Pro Asp Tyr Thr Pro Pro Thr
1               5

<210> SEQ ID NO 423
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDRL3

<400> SEQUENCE: 423

Gln Gln Pro Arg Tyr Thr Pro Pro Thr
1               5

<210> SEQ ID NO 424
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDRL3

<400> SEQUENCE: 424

Gln Gln Pro Ser Leu Thr Pro Pro Thr
1               5

<210> SEQ ID NO 425
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDRL3

<400> SEQUENCE: 425

Gln Gln His Pro Tyr Thr Pro Pro Thr
1               5

<210> SEQ ID NO 426
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDRL3

<400> SEQUENCE: 426

Gln Gln His Gly Tyr Thr Pro Pro Thr
1 5

<210> SEQ ID NO 427
<211> LENGTH: 9
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: CDRL3

<400> SEQUENCE: 427

Gln Gln Pro Thr Leu Thr Pro Pro Thr
1 5

<210> SEQ ID NO 428
<211> LENGTH: 9
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: CDRL3

<400> SEQUENCE: 428

Gln Gln Pro Asn Leu Thr Pro Pro Thr
1 5

<210> SEQ ID NO 429
<211> LENGTH: 9
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: CDRL3

<400> SEQUENCE: 429

Gln Gln Pro Gly Tyr Thr Pro Pro Thr
1 5

<210> SEQ ID NO 430
<211> LENGTH: 9
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: CDRL3

<400> SEQUENCE: 430

Gln Gln Pro Leu Tyr Thr Pro Pro Thr
1 5

<210> SEQ ID NO 431
<211> LENGTH: 9
<212> TYPE: PRT
<213> ORGANISM: Artificial Sequence
<220> FEATURE:
<223> OTHER INFORMATION: Description of Artificial Sequence: Synthetic peptide
<220> FEATURE:

<223> OTHER INFORMATION: CDRL3

<400> SEQUENCE: 431

Gln Gln His Ala Tyr Thr Pro Pro Thr
1 5

<210> SEQ ID NO 432
<211> LENGTH: 450
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_436; BDG30.115; Human IgG1; H chain (VH+CH1+hinge+CH2+CH3)

<400> SEQUENCE: 432

Glu Val Gln Leu Val Glu Ser Gly Gly Gly Leu Val Gln Pro Gly Gly
1 5 10 15

Ser Leu Arg Leu Ser Cys Ala Ala Ser Gly Phe Asn Ile Arg Asp Thr
20 25 30

Tyr Ile His Trp Val Arg Gln Ser Pro Gly Lys Gly Leu Glu Trp Val
35 40 45

Ala Asp Ile Asp Pro Asp Asn Gly Asp Thr Arg Tyr Ala Asp Ser Val
50 55 60

Lys Gly Arg Phe Thr Ile Ser Ala Asp Thr Ser Lys Asn Thr Ala Tyr
65 70 75 80

Leu Gln Met Asn Ser Leu Arg Ala Glu Asp Thr Ala Ile Tyr Tyr Cys
85 90 95

Ser Arg Asp Leu Ala Asp Gly Tyr Asn Ala Phe Asp Arg Trp Gly Gln
100 105 110

Gly Thr Leu Val Thr Val Ser Ser Ala Ser Thr Lys Gly Pro Ser Val
115 120 125

Phe Pro Leu Ala Pro Ser Ser Lys Ser Thr Ser Gly Gly Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Gln Thr Tyr Ile Cys Asn Val Asn His Lys
195 200 205

Pro Ser Asn Thr Lys Val Asp Lys Lys Val Glu Pro Lys Ser Cys Asp
210 215 220

Lys Thr His Thr Cys Pro Pro Cys Pro Ala Pro Glu Ala Ala Gly Gly
225 230 235 240

Pro Ser Val Phe Leu Phe Pro Pro Lys Pro Lys Asp Thr Leu Met Ile
245 250 255

Ser Arg Thr Pro Glu Val Thr Cys Val Val Val Asp Val Ser His Glu
260 265 270

Asp Pro Glu Val Lys Phe Asn Trp Tyr Val Asp Gly Val Glu Val His
275 280 285

Asn Ala Lys Thr Lys Pro Arg Glu Glu Gln Tyr Asn Ser Thr Tyr Arg
290 295 300

Val Val Ser Val Leu Thr Val Leu His Gln Asp Trp Leu Asn Gly Lys 305 310 315 320

Glu Tyr Lys Cys Lys Val Ser Asn Lys Ala Leu Pro Ala Pro Ile Glu
325 330 335

Lys Thr Ile Ser Lys Ala Lys Gly Gln Pro Arg Glu Pro Gln Val Tyr
340 345 350

Thr Leu Pro Pro Ser Arg Asp Glu Leu Thr Lys Asn Gln Val Ser Leu
355 360 365

Thr Cys Leu Val Lys Gly Phe Tyr Pro Ser Asp Ile Ala Val Glu Trp
370 375 380

Glu Ser Asn Gly Gln Pro Glu Asn Asn Tyr Lys Thr Thr Pro Pro Val
385 390 395 400

Leu Asp Ser Asp Gly Ser Phe Phe Leu Tyr Ser Lys Leu Thr Val Asp
405 410 415

Lys Ser Arg Trp Gln Gln Gly Asn Val Phe Ser Cys Ser Val Met His
420 425 430

Glu Ala Leu His Asn His Tyr Thr Gln Lys Ser Leu Ser Leu Ser Pro
435 440 445

Gly Lys
450

<210> SEQ ID NO 433
<211> LENGTH: 447
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_332; BDG30.122; Human IgG1; H chain (VH+CH1+hinge+CH2+CH3)

<400> SEQUENCE: 433

Gln Val Gln Leu Val Gln Ser Gly Ala Glu Val Lys Lys Pro Gly Ser
1 5 10 15

Ser Val Lys Val Ser Cys Lys Ala Ser Gly Tyr Thr Phe Thr Asp Leu
20 25 30

Gly Ile Gly Trp Val Arg Gln Ala Pro Gly Gln Gly Leu Glu Trp Met
35 40 45

Gly Trp Ile Asn Thr His Thr Gly Glu Pro Tyr Asp Asn Pro Lys Phe
50 55 60

Lys Gly Arg Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Thr Arg Asp His Pro Leu Gly Leu Asp Tyr Trp Gly Gln Gly Thr Thr
100 105 110

Val Thr Val Ser Ser Ala Ser Thr Lys Gly Pro Ser Val Phe Pro Leu
115 120 125

Ala Pro Ser Ser Lys Ser Thr Ser Gly Gly Thr Ala Ala Leu Gly Cys
130 135 140

Leu Val Lys Asp Tyr Phe Pro Glu Pro Val Thr Val Ser Trp Asn Ser
145 150 155 160

Gly Ala Leu Thr Ser Gly Val His Thr Phe Pro Ala Val Leu Gln Ser
165 170 175

Ser Gly Leu Tyr Ser Leu Ser Ser Val Val Thr Val Pro Ser Ser Ser
180 185 190

```
Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445


<210> SEQ ID NO 434
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_350; BDG30.123; Human IgG1; H chain
      (VH+CH1+hinge+CH2+CH3)

<400> SEQUENCE: 434

Gln Val Gln Leu Val Gln Ser Gly Ala Glu Val Lys Lys Pro Gly Ser
1               5                   10                  15

Ser Val Lys Val Ser Cys Lys Gly Ser Gly Tyr Thr Phe Thr Asp Leu
            20                  25                  30

Gly Ile Gly Trp Val Arg Gln Ala Pro Gly Gln Gly Leu Glu Trp Met
        35                  40                  45

Gly Trp Ile Asn Thr His Thr Gly Glu Pro Phe Tyr Asn Pro Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

```
Thr Arg Asp His Pro Leu Gly Leu Asp Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445


<210> SEQ ID NO 435
<211> LENGTH: 458
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID251; BDG30.200; Human IgG1; H chain
      (VH+CH1+hinge+CH2+CH3)
```

<400> SEQUENCE: 435

Glu Val Gln Leu Val Gln Ser Gly Ala Glu Val Lys Lys Pro Gly Ser
1 5 10 15

Ser Val Lys Val Ser Cys Lys Ala Ser Gly Asp Thr Phe Thr Ser Tyr
20 25 30

Ser Phe Asn Trp Val Arg Gln Ala Pro Gly Gln Gly Leu Glu Trp Met
35 40 45

Gly Arg Ile Ile Thr Ile Leu Asp Asp Thr Glu Tyr Ala Pro His Leu
50 55 60

Gln Gly Arg Val Thr Ile Thr Ala Asp Lys Ser Thr Ser Thr Val Tyr
65 70 75 80

Leu Glu Leu Arg Asn Leu Arg Ser Asp Asp Thr Ala Val Tyr Phe Cys
85 90 95

Ala Gly Val Tyr Glu Gly Pro Asn Ser Glu Gly Ser Tyr Asp Asp Tyr
100 105 110

Gly Phe Leu Lys His Trp Gly Gln Gly Thr Leu Val Thr Val Ser Ser
115 120 125

Ala Ser Thr Lys Gly Pro Ser Val Phe Pro Leu Ala Pro Ser Ser Lys
130 135 140

Ser Thr Ser Gly Gly Thr Ala Ala Leu Gly Cys Leu Val Lys Asp Tyr
145 150 155 160

Phe Pro Glu Pro Val Thr Val Ser Trp Asn Ser Gly Ala Leu Thr Ser
165 170 175

Gly Val His Thr Phe Pro Ala Val Leu Gln Ser Ser Gly Leu Tyr Ser
180 185 190

Leu Ser Ser Val Val Thr Val Pro Ser Ser Ser Leu Gly Thr Gln Thr
195 200 205

Tyr Ile Cys Asn Val Asn His Lys Pro Ser Asn Thr Lys Val Asp Lys
210 215 220

Lys Val Glu Pro Lys Ser Cys Asp Lys Thr His Thr Cys Pro Pro Cys
225 230 235 240

Pro Ala Pro Glu Ala Ala Gly Gly Pro Ser Val Phe Leu Phe Pro Pro
245 250 255

Lys Pro Lys Asp Thr Leu Met Ile Ser Arg Thr Pro Glu Val Thr Cys
260 265 270

Val Val Val Asp Val Ser His Glu Asp Pro Glu Val Lys Phe Asn Trp
275 280 285

Tyr Val Asp Gly Val Glu Val His Asn Ala Lys Thr Lys Pro Arg Glu
290 295 300

Glu Gln Tyr Asn Ser Thr Tyr Arg Val Val Ser Val Leu Thr Val Leu
305 310 315 320

His Gln Asp Trp Leu Asn Gly Lys Glu Tyr Lys Cys Lys Val Ser Asn
325 330 335

Lys Ala Leu Pro Ala Pro Ile Glu Lys Thr Ile Ser Lys Ala Lys Gly
340 345 350

Gln Pro Arg Glu Pro Gln Val Tyr Thr Leu Pro Pro Ser Arg Asp Glu
355 360 365

Leu Thr Lys Asn Gln Val Ser Leu Thr Cys Leu Val Lys Gly Phe Tyr
370 375 380

Pro Ser Asp Ile Ala Val Glu Trp Glu Ser Asn Gly Gln Pro Glu Asn
385 390 395 400

Asn Tyr Lys Thr Thr Pro Pro Val Leu Asp Ser Asp Gly Ser Phe Phe
405 410 415

Leu Tyr Ser Lys Leu Thr Val Asp Lys Ser Arg Trp Gln Gln Gly Asn
420 425 430

Val Phe Ser Cys Ser Val Met His Glu Ala Leu His Asn His Tyr Thr
435 440 445

Gln Lys Ser Leu Ser Leu Ser Pro Gly Lys
450 455

<210> SEQ ID NO 436
<211> LENGTH: 458
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_276; BDG30.201; Human IgG1; H chain (VH+CH1+hinge+CH2+CH3)

<400> SEQUENCE: 436

Glu Val Gln Leu Val Gln Ser Gly Ala Glu Val Lys Lys Pro Gly Ser
1 5 10 15

Ser Val Lys Val Ser Cys Lys Ala Ser Gly Asp Thr Phe Thr Ser Tyr
20 25 30

Ser Phe Asn Trp Val Arg Gln Ala Pro Gly Gln Gly Leu Glu Trp Met
35 40 45

Gly Arg Ile Ile Thr Ile Tyr Asp Asp Thr Glu Tyr Ala Pro His Leu
50 55 60

Gln Gly Arg Val Thr Ile Thr Ala Asp Lys Ser Thr Ser Thr Val Tyr
65 70 75 80

Leu Glu Leu Arg Asn Leu Arg Ser Asp Asp Thr Ala Val Tyr Phe Cys
85 90 95

Ala Gly Val Tyr Glu Gly Pro Asn Ser Glu Gly Ser Tyr Asp Asp Tyr
100 105 110

Gly Phe Phe Lys His Trp Gly Gln Gly Thr Leu Val Thr Val Ser Ser
115 120 125

Ala Ser Thr Lys Gly Pro Ser Val Phe Pro Leu Ala Pro Ser Ser Lys
130 135 140

Ser Thr Ser Gly Gly Thr Ala Ala Leu Gly Cys Leu Val Lys Asp Tyr
145 150 155 160

Phe Pro Glu Pro Val Thr Val Ser Trp Asn Ser Gly Ala Leu Thr Ser
165 170 175

Gly Val His Thr Phe Pro Ala Val Leu Gln Ser Ser Gly Leu Tyr Ser
180 185 190

Leu Ser Ser Val Val Thr Val Pro Ser Ser Ser Leu Gly Thr Gln Thr
195 200 205

Tyr Ile Cys Asn Val Asn His Lys Pro Ser Asn Thr Lys Val Asp Lys
210 215 220

Lys Val Glu Pro Lys Ser Cys Asp Lys Thr His Thr Cys Pro Pro Cys
225 230 235 240

Pro Ala Pro Glu Ala Ala Gly Gly Pro Ser Val Phe Leu Phe Pro Pro
245 250 255

Lys Pro Lys Asp Thr Leu Met Ile Ser Arg Thr Pro Glu Val Thr Cys
260 265 270

Val Val Val Asp Val Ser His Glu Asp Pro Glu Val Lys Phe Asn Trp
275 280 285

Tyr Val Asp Gly Val Glu Val His Asn Ala Lys Thr Lys Pro Arg Glu

```
    290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Asp Glu
        355                 360                 365

Leu Thr Lys Asn Gln Val Ser Leu Thr Cys Leu Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly Lys
    450                 455


<210> SEQ ID NO 437
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CID_261; BDG30.202; Human IgG1; H chain
      (VH+CH1+hinge+CH2+CH3)

<400> SEQUENCE: 437

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Phe
            20                  25                  30

Phe Ile His Trp Val Arg Gln Ala Pro Gly Lys Gly Leu Glu Trp Val
        35                  40                  45

Ala Asp Ile Asp Pro Thr Asn Gly Asp Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Glu Gly Gln Asp Gly Tyr Asn Ala Trp Asp Leu Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175
```

Leu Gln Ser Ser Gly Leu Tyr Ser Leu Ser Ser Val Val Thr Val Pro
180 185 190

Ser Ser Ser Leu Gly Thr Gln Thr Tyr Ile Cys Asn Val Asn His Lys
195 200 205

Pro Ser Asn Thr Lys Val Asp Lys Lys Val Glu Pro Lys Ser Cys Asp
210 215 220

Lys Thr His Thr Cys Pro Pro Cys Pro Ala Pro Glu Ala Ala Gly Gly
225 230 235 240

Pro Ser Val Phe Leu Phe Pro Pro Lys Pro Lys Asp Thr Leu Met Ile
245 250 255

Ser Arg Thr Pro Glu Val Thr Cys Val Val Val Asp Val Ser His Glu
260 265 270

Asp Pro Glu Val Lys Phe Asn Trp Tyr Val Asp Gly Val Glu Val His
275 280 285

Asn Ala Lys Thr Lys Pro Arg Glu Glu Gln Tyr Asn Ser Thr Tyr Arg
290 295 300

Val Val Ser Val Leu Thr Val Leu His Gln Asp Trp Leu Asn Gly Lys
305 310 315 320

Glu Tyr Lys Cys Lys Val Ser Asn Lys Ala Leu Pro Ala Pro Ile Glu
325 330 335

Lys Thr Ile Ser Lys Ala Lys Gly Gln Pro Arg Glu Pro Gln Val Tyr
340 345 350

Thr Leu Pro Pro Ser Arg Asp Glu Leu Thr Lys Asn Gln Val Ser Leu
355 360 365

Thr Cys Leu Val Lys Gly Phe Tyr Pro Ser Asp Ile Ala Val Glu Trp
370 375 380

Glu Ser Asn Gly Gln Pro Glu Asn Asn Tyr Lys Thr Thr Pro Pro Val
385 390 395 400

Leu Asp Ser Asp Gly Ser Phe Phe Leu Tyr Ser Lys Leu Thr Val Asp
405 410 415

Lys Ser Arg Trp Gln Gln Gly Asn Val Phe Ser Cys Ser Val Met His
420 425 430

Glu Ala Leu His Asn His Tyr Thr Gln Lys Ser Leu Ser Leu Ser Pro
435 440 445

Gly Lys
450

<210> SEQ ID NO 438
<211> LENGTH: 450
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_264; BDG30.203; Human IgG1; H chain (VH+CH1+hinge+CH2+CH3)

<400> SEQUENCE: 438

Glu Val Gln Leu Val Glu Ser Gly Gly Gly Leu Val Gln Pro Gly Gly
1 5 10 15

Ser Leu Arg Leu Ser Cys Ala Ala Ser Gly Phe Asn Ile Lys Ala Tyr
20 25 30

Tyr Ile His Trp Val Arg Gln Ala Pro Gly Lys Gly Leu Glu Trp Val
35 40 45

Ala Asp Ile Asp Pro Asp Asn Gly Asp Thr Arg Tyr Ala Asp Ser Val
50 55 60

```
Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Glu Gly Gln Asp Gly Tyr Asn Ala Trp Asp Gln Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450
```

<210> SEQ ID NO 439
<211> LENGTH: 450

<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CID_266; BDG30.204; Human IgG1; H chain (VH+CH1+hinge+CH2+CH3)

<400> SEQUENCE: 439

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Arg Ala Tyr
            20                  25                  30

Tyr Ile His Trp Val Arg Gln Ala Pro Gly Lys Gly Leu Glu Trp Val
        35                  40                  45

Ala Asp Ile Asp Pro Thr Asn Gly Asp Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Glu Gly Gln Asp Gly Tyr Asn Ala Trp Asp Leu Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365
```

-continued

```
Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450
```

ANTI-TUMOR NECROSIS FACTOR RECEPTOR (TNFR2) ANTIBODIES AND USES THEREOF

CROSS-REFERENCE TO RELATED APPLICATIONS

This application is a National Phase Application of PCT International Application No. PCT/IL2021/050807, International Filing Date Jul. 1, 2022, claiming the benefit of U.S. Provisional Application Ser. No. 63/047,490 filed Jul. 2, 2020, which are hereby incorporated by reference in their entirety.

SEQUENCE LISTING STATEMENT

The instant application contains a Sequence Listing, which has been submitted electronically in ASCII format and is hereby incorporated by reference in its entirety. Said ASCII copy, created on Jun. 28, 2021, is named P-597451-PC_SL.txt and is 573,679 bytes in size.

FIELD OF THE INVENTION

The present disclosure relates in general to engineered antibodies. In one or more embodiments, the present disclosure describes the making and uses of antibodies against tumor necrosis factor receptor 2 (TNFR2).

BACKGROUND OF THE INVENTION

Tumor necrosis factor-alpha (TNFα) is an extremely pleiotropic cytokine. It is not only produced by immune cells which include activated macrophages, T cells, and natural killer (NK) cells, but can also be produced in endothelial cells, microglia, cardiac myocytes, and fibroblasts. Upon production, TNFα is presented as a membrane bound form (mTNFα), which is a 26 kDa transmembrane protein that can be cleaved by TNF-converting enzyme (TACE) to form a soluble form of TNFα (sTNFα) that is released from the membrane.

TNFα interacts with two receptors, tumor necrosis factor receptor superfamily member 1A (TNFR1) and tumor necrosis factor receptor superfamily member 1B (TNFR2). The extracellular domains of the two TNF receptors share a common structure composed of four cysteine-rich domains (CRDs) that are responsible for binding TNFα.

TNFR1 is constitutively expressed on virtually all nuclear cell types. It has been reported to bind sTNFα and mTNFα and is activated by both. One of TNFR1's main function is to mediate TNF-induced apoptosis via the NF-kB pathway; however, in certain situations, activation of the NF-kB pathway may result in production of anti-apoptotic proteins and pro-inflammatory cytokines such as IL-1 and IL-6.

TNFR2, which was discovered and characterized more recently, is mostly expressed on activated T cells, myeloid cells and glial cells. It is a 75 kDa trans-membrane receptor with an extracellular domain consisting of four cysteine rich domains (CRD), a single transmembrane domain and a cytoplasmic domain that interacts with TNF receptor-associated factor 2 (TRAF2). Recruitment of TRAF2 promotes a cascade of events resulting in activation of an alternative NF-kB pathway. Although TNFR2 can bind tightly to both sTNFα and mTNFα, it is mainly activated through mTNFα and not sTNFα.

It has been shown that TNFR2 is expressed at high levels on the surface of $CD4^{+}CD25^{+}Foxp3^{+}$ regulatory T cells (Tregs) and myeloid-derived suppressor cells (MDSCs). Activation of TNFR2 in these cells promotes their immunosuppressive activity and is crucial for Treg and MDSC proliferation and survival. Additionally, TNFR2 has a dual role on $CD8^{+}$ effector T cells (Teffs): on one hand, TNFR2 mediates an activation signal to $CD8^{+}$ Teffs during early immune response, while on the other hand, signals for apoptosis in these cells to terminate the immune response.

The key role of TNFR2 in regulation of the immune system is reflected in several pathogenic conditions. In cancer, TNFR2 is highly expressed in the tumor microenvironment (TME) on infiltrating Tregs, MDSC and on the tumor cells themselves. Activation of the TNFR2 receptor on Tregs and MDSC results in suppression of the immune system in the TME. Additionally, blocking of TNFR2 on cancer cell lines in vitro has been shown to have a dose dependent killing effect.

In autoimmune diseases, abnormalities in the TNFα signaling pathway have been reported in various autoimmune diseases including rheumatoid arthritis (RA), Crohn's disease (CD), multiple sclerosis (MS) and Type I diabetes. In many of these pathological conditions where TNFR1 is more dominant, blocking of TNFα mostly in its soluble form is sufficient to have an efficacious effect. TNFα blockers like infliximab and adalimumab have been applied successfully in rheumatoid arthritis (RA), Crohn's disease (CD), and ulcerative colitis (UC). However, there are other conditions such as type 1 diabetes (T1D) and multiple sclerosis where the foregoing approach has been shown to be not particularly effective.

In certain instances, specific inhibition or activation of the TNFR2 pathway may prove beneficial, for example, in murine cancer models, specific inhibition of TNFR2 shows a robust effect both directly on cancer cells as well as on immune system activation. TNFR2 has been strongly implicated as a driving force in some autoimmune diseases where Tregs and MDCS play a major role. In an experimental autoimmune encephalomyelitis (EAE) mice model of MS, deletion of the TNFR2 gene was shown to have a deleterious effect. Agonizing TNFR2 in graft versus host disease (GvHD) models has been shown to reduce severity of GvHD. TNFR2 activation has also been implicated with *Bacillus* Calmette-Guerin (BCG) novel treatment of type 1 diabetes (T1D).

In view of the important roles of TNFR2 in the regulation of immune responses in various disease conditions, there is a need to develop improved targeting of TNFR2 by either antagonists or agonists as a strategy for improved therapies for treating diseases, such as, for example, cancer and autoimmune diseases.

SUMMARY OF THE INVENTION

The present disclosure provides a number of anti-TNFR2 (tumor necrosis factor receptor 2) antibodies. In one embodiment, each of the anti-TNFR2 antibodies comprises a set of three complementarity determining regions (CDRs) on a heavy chain (HCDR1, HCDR2, and HCDR3) and a set of three CDRs on a light chain (LCDR1, LCDR2, and LCDR3). In one embodiment, the set of HCDR1, HCDR2, and HCDR3 comprises a combination of the amino acid sequences as shown in Table 7, and the set of LCDR1, LCDR2, and LCDR3 on a corresponding light chain comprises a combination of the amino acid sequences as shown in Table 8. In another embodiment, the set of HCDR1, HCDR2, HCDR3, and the set of LCDR1, LCDR2, LCDR3 on a corresponding light chain comprise the combination of amino acid sequences as shown in Table 9.

In one embodiment, each of the anti-TNFR2 antibodies comprises a heavy chain variable region and a light chain variable region, wherein the amino acid sequences for the heavy chain variable region and the light chain variable region can be one of the following pairs: SEQ ID NOs:289-290, SEQ ID NOs:3-4, SEQ ID NOs:7-8, SEQ ID NOs:11-12, SEQ ID NOs:15-16, SEQ ID NOs:19-20, SEQ ID NOs:23-24, SEQ ID NOs:27-28, SEQ ID NOs:31-32, SEQ ID NOs:35-36, SEQ ID NOs:39-40, SEQ ID NOs:43-44, SEQ ID NOs:47-48, SEQ ID NOs:51-52, SEQ ID NOs:55-56, SEQ ID NOs:59-60, SEQ ID NOs:63-64, SEQ ID NOs:67-68, SEQ ID NOs:71-72, SEQ ID NOs:75-76, SEQ ID NOs:79-80, SEQ ID NOs:83-84, SEQ ID NOs:87-88, SEQ ID NOs:91-92, SEQ ID NOs:95-96, SEQ ID NOs:99-100, SEQ ID NOs:103-104, SEQ ID NOs:107-108, SEQ ID NOs:111-112, SEQ ID NOs:115-116, SEQ ID NOs:119-120, SEQ ID NOs:123-124, SEQ ID NOs:127-128, SEQ ID NOs:131-132, SEQ ID NOs:135-136, SEQ ID NOs:139-140, SEQ ID NOs:143-144, SEQ ID NOs:147-148, SEQ ID NOs:151-152, SEQ ID NOs:157-158, SEQ ID NOs:163-164, SEQ ID NOs:169-170, SEQ ID NOs:175-176, SEQ ID NOs:181-182, SEQ ID NOs:193-194, SEQ ID NOs:199-200, SEQ ID NOs:205-206, SEQ ID NOs:211-212, SEQ ID NOs:217-218, SEQ ID NOs:223-224, SEQ ID NOs:229-230, SEQ ID NOs:233-234, SEQ ID NOs:237-238, SEQ ID NOs:241-242, SEQ ID NOs:245-246, SEQ ID NOs:249-250, SEQ ID NOs:253-254, SEQ ID NOs:257-258, SEQ ID NOs:261-262, SEQ ID NOs:265-266, SEQ ID NOs:269-270, SEQ ID NOs:273-274, SEQ ID NOs:277-278, SEQ ID NOs:281-282, SEQ ID NOs:285-286, SEQ ID NOs:293-294, SEQ ID NOs:297-298, SEQ ID NOs:301-302, SEQ ID NOs:305-306, SEQ ID NOs:309-310, SEQ ID NOs:313-314, SEQ ID NOs:317-318, SEQ ID NOs:321-322, SEQ ID NOs:325-326, or SEQ ID NOs:329-330.

In another embodiment, each of the anti-TNFR2 antibodies comprises a heavy chain and a light chain, wherein the amino acid sequences for the heavy chain and the light chain can be one of the following pairs: SEQ ID NOs:438 and 292, SEQ ID NO: 291-292, SEQ ID NOs:235-236, SEQ ID NOs:239-240, SEQ ID NOs:243-244, SEQ ID NOs:247-248, SEQ ID NOs:251-252, SEQ ID NOs:255-256, SEQ ID NOs:259-260, SEQ ID NOs:263-264, SEQ ID NOs:267-268, SEQ ID NOs:271-272, SEQ ID NOs:275-276, SEQ ID NOs:279-280, SEQ ID NOs:283-284, SEQ ID NOs:287-288, SEQ ID NOs:295-296, SEQ ID NOs:299-300, SEQ ID NOs:303-304, SEQ ID NOs:307-308, SEQ ID NOs:311-312, SEQ ID NOs:315-316, SEQ ID NOs:319-320, SEQ ID NOs:323-324, SEQ ID NOs:327-328, SEQ ID NOs:331-332, SEQ ID NOs: 432 and 260, SEQ ID NOs: 433 and 304, SEQ ID NOs: 434 and 308, SEQ ID NOs: 435 and 236, SEQ ID NOs: 436 and 244, SEQ ID NOs: 437 and 284, or SEQ ID NOs: 439 and 296.

In yet another embodiment, the present disclosure provides a composition comprising a pharmaceutically acceptable carrier and an anti-TNFR2 antibody disclosed herein.

The present disclosure also provides polynucleotide sequences encoding the anti-TNFR2 antibodies disclosed herein, as well as vectors and host cells comprising such polynucleotide sequences.

In a further embodiment, the anti-TNFR2 antibodies disclosed herein can be used to modulate the proliferation and/or functions of regulatory T cells. In another embodiment, the anti-TNFR2 antibodies disclosed herein can be used to modulate the proliferation and/or functions of myeloid-derived suppressor cells.

In one or more additional embodiments, the anti-TNFR2 antibodies disclosed herein can be used to treat diseases such as cancer, autoimmune diseases, GvHD, viral infections or bacterial infections.

These and other embodiments of the anti-TNFR2 antibodies will be appreciated from the ensuing descriptions of the figures and detailed description of the anti-TNFR2 antibodies which follow.

BRIEF DESCRIPTION OF THE DRAWINGS

Some embodiments of the anti-TNFR2 antibodies and uses thereof are herein described, by way of example only, with reference to the accompanying drawings. With specific reference now to the drawings in detail, it is stressed that the particulars shown are by way of example and for purposes of illustrative discussion of embodiments of the anti-TNFR2 antibodies and uses thereof. In this regard, the description taken with the drawings makes apparent to those skilled in the art how embodiments of the anti-TNFR2 antibodies and uses thereof may be practiced.

FIG. 1B shows the results for CID_251, FIG. 1C shows the results for CID_436, and FIG. 1D shows the results for CID_437.

(FIG. 3A: presents data for clones 30.092, 30.085, and 30.089; FIG. 3B present data for clones 30.086, 30.116, 30.093, 30.117, 30.094, 30.118, 30.095, 30.119, 30.109, 30.111, 30.113, and 30.114). Wells were coated with 50 ng/well IgG and tested for binding of 100 nM TNFR1 or TNFR2 (FIG. 3A). N.C.: negative control, human anti IL-2 IgG1 (50 ng/well) does not bind either TNFR1 or TNFR2. LALA_N.C.: negative control, human anti IL-2 IgG1 (50 ng/well) with a LALA mutation in the Fc region does not bind either TNFR1 or TNFR2. P.C.: TNFR1 and TNFR2 positive control, TNFα-Fc (50 ng/well) were coated to the well and 100 nM TNFR2 or TNFR1 were tested for binding to TNFα (FIG. 3B).

Figure 4A:
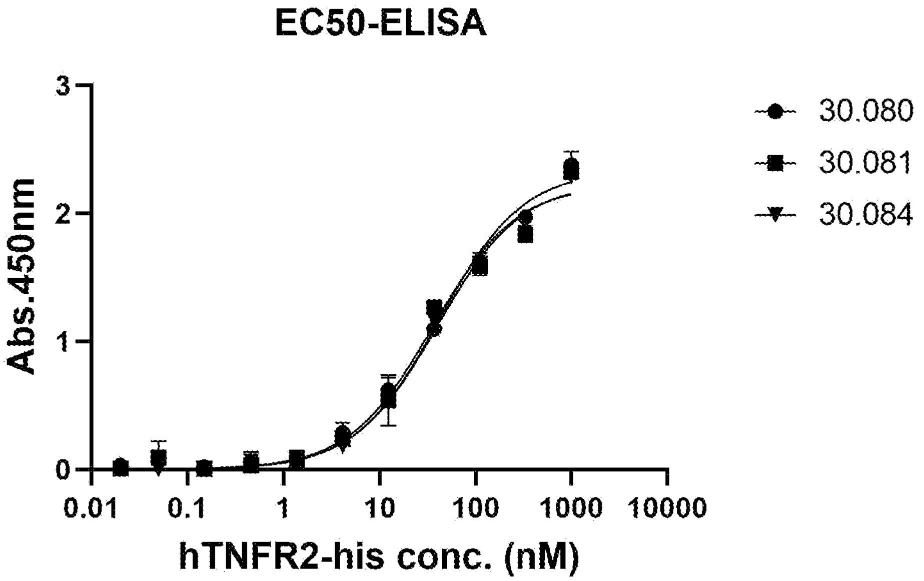
FIGS. 4A-4F show ELISA $EC_{50}$ binding of selected IgG1 to TNFR2. IgG clones 30.080 (circle), 30.081 (square), and 30.084 (downward triangle) (FIG. 4A), IgG clones 30.085 (circle), 30.087 (upward triangle), 30.088 (downward triangle), 30.089 (diamond), and 30.032 (square) (FIG. 4B), IgG clones 30.092 (square) and 30.046 (circle) (FIG. 4C), IgG 30.086 (square), 30.116 (triangle), and isotype control antibody (I.C.; circle) (FIG. 4D), IgG clones 30.093
Figure 4B:
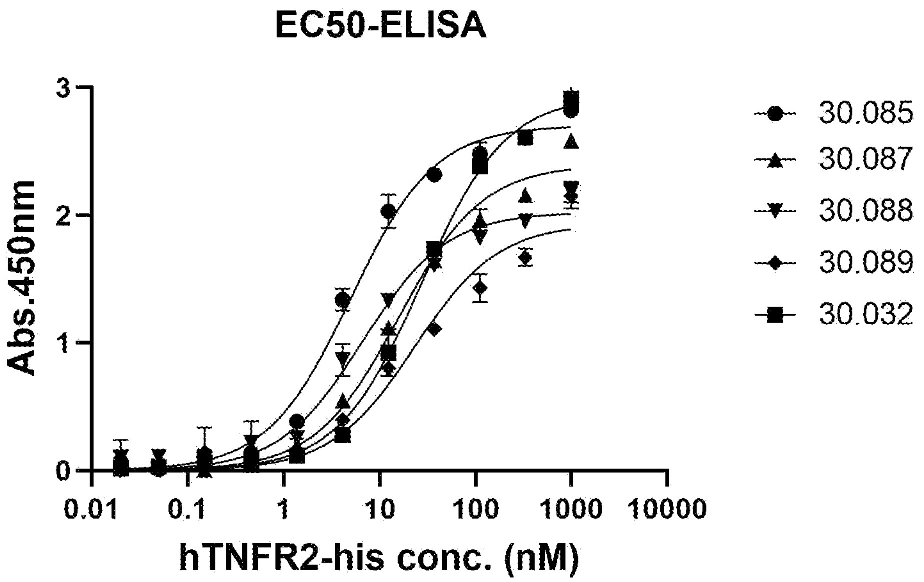
Figure 4C:
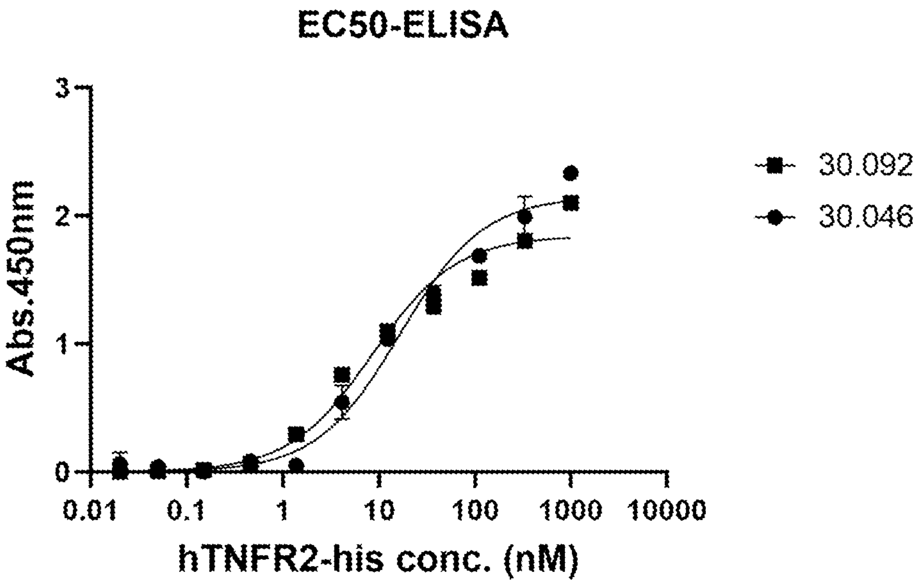
Figure 4D:
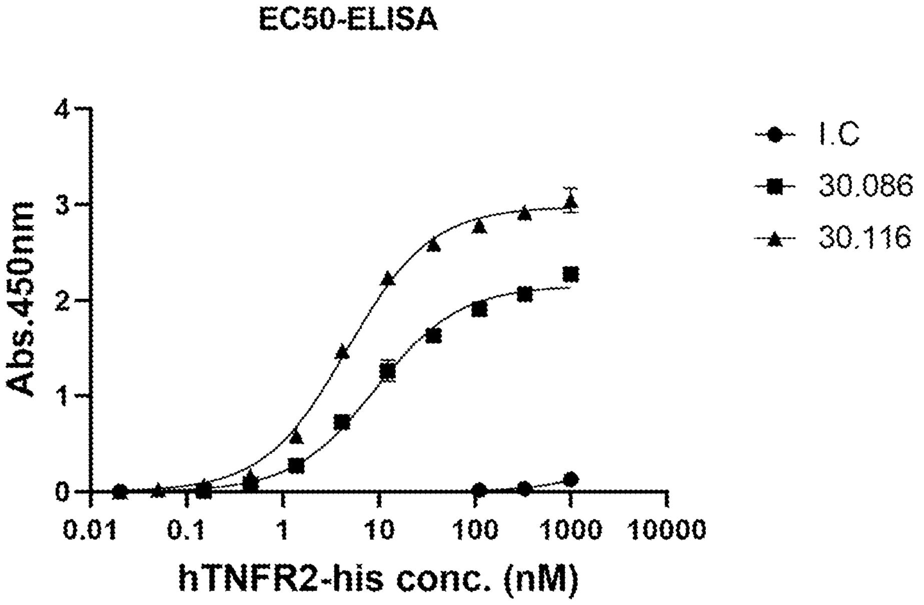
Figure 4E:
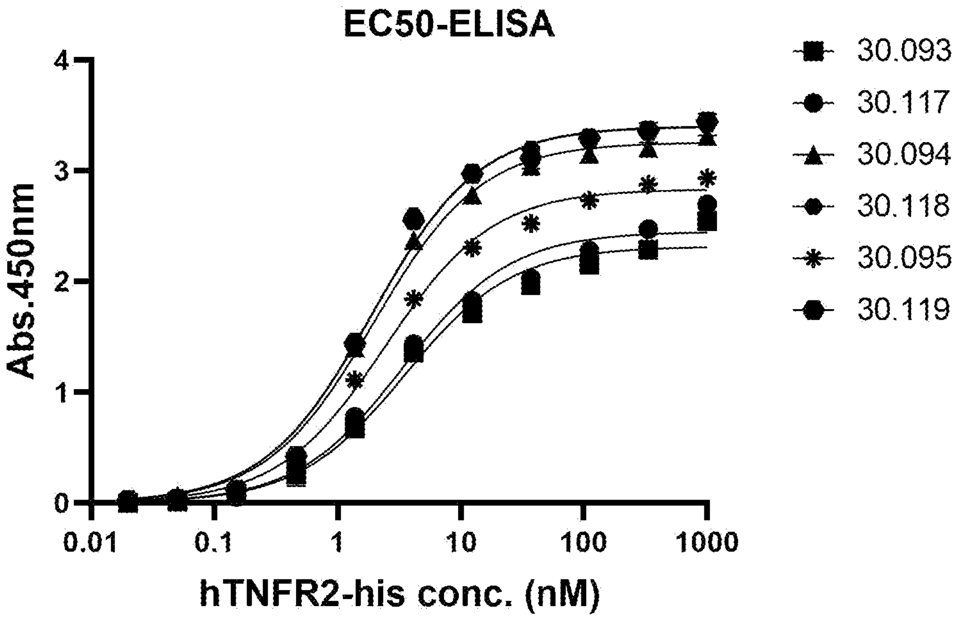
Figure 4F:
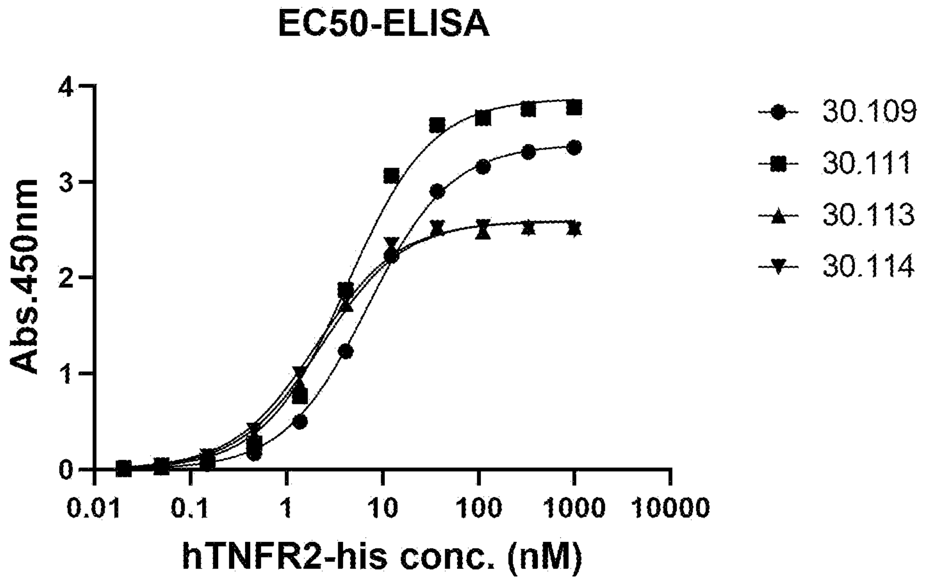

(square), 30.117 (circle), 30.094 (upward triangle), 30.118 (small hexagon), 30.095 (asterisk), and 30.119 (large hexagon) (FIG. 4E), and IgG clones 30.109 (circle), 30.111 (square), 30.113 (upward triangle), and 30.114 (downward triangle) (FIG. 4F).

Figure 5:
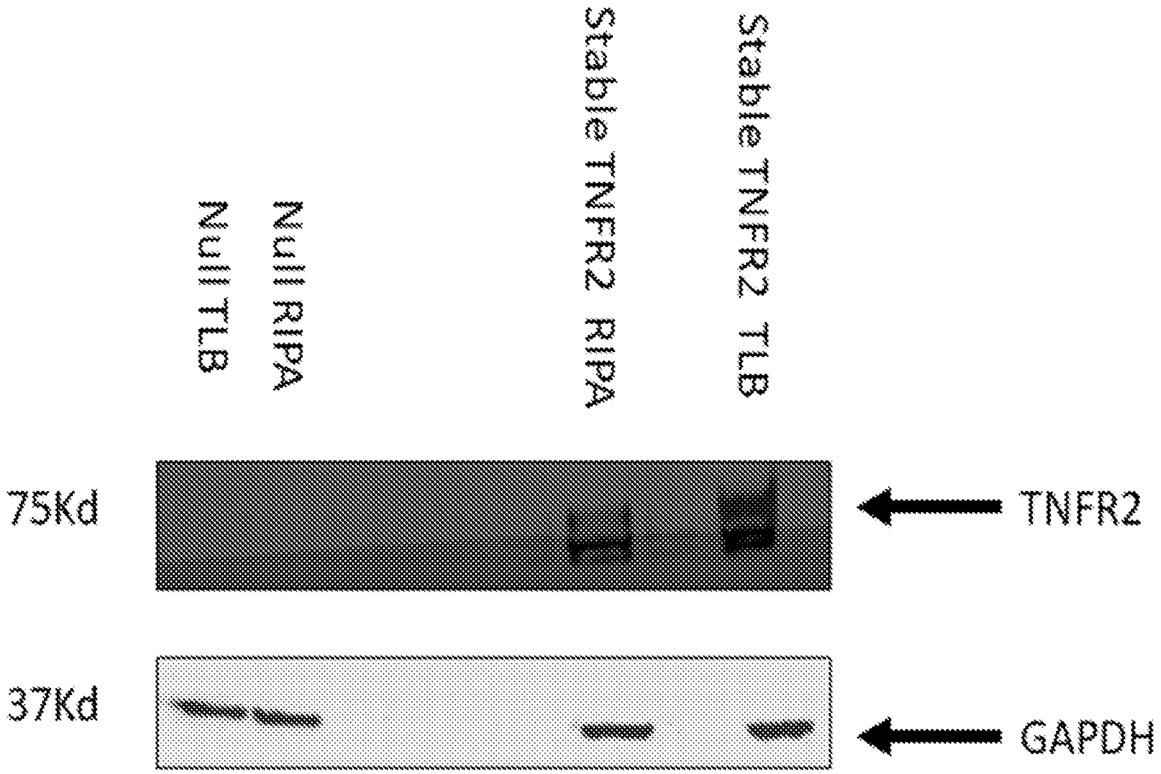

FIG. 5 shows the expression of human TNFR2 by HEK-TNFR2 cells. $1\times10^6$ cells were harvested and lysed with either Tris Lysis Buffer (TLB) or with RIPA lysis buffer. Protein concentration was determined by the Bradford method, and 22 ug protein cell lysate was subjected to western blot, detecting TNFR2 and GAPDH as control. Left 2 lanes: Untransfected HEK-Blue™ Null cells, right 2 lanes: HEK-Blue™ Null cells transfected with pCDNA3.1 plasmid encoding human TNFR2.

Figure 6A:
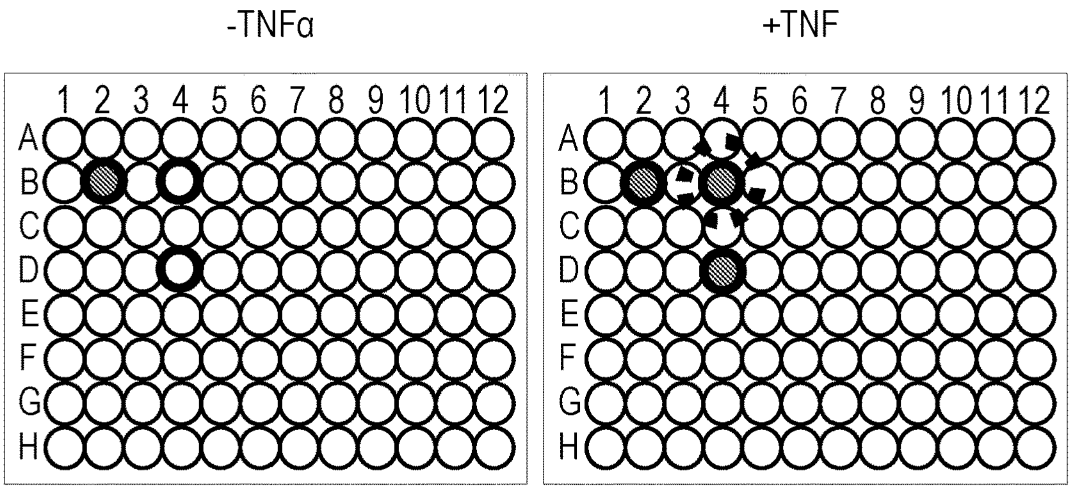
Figure 6B:
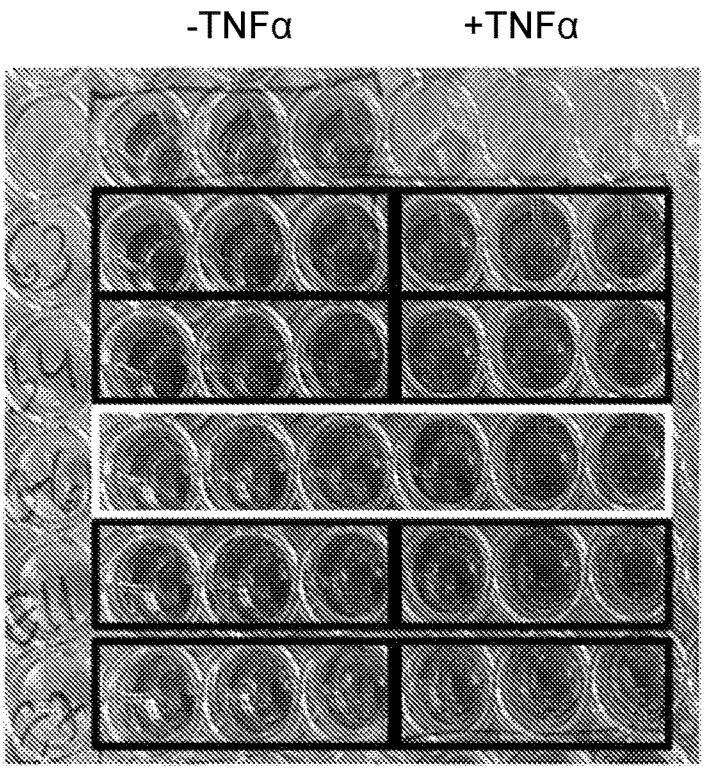
Figure 6C:
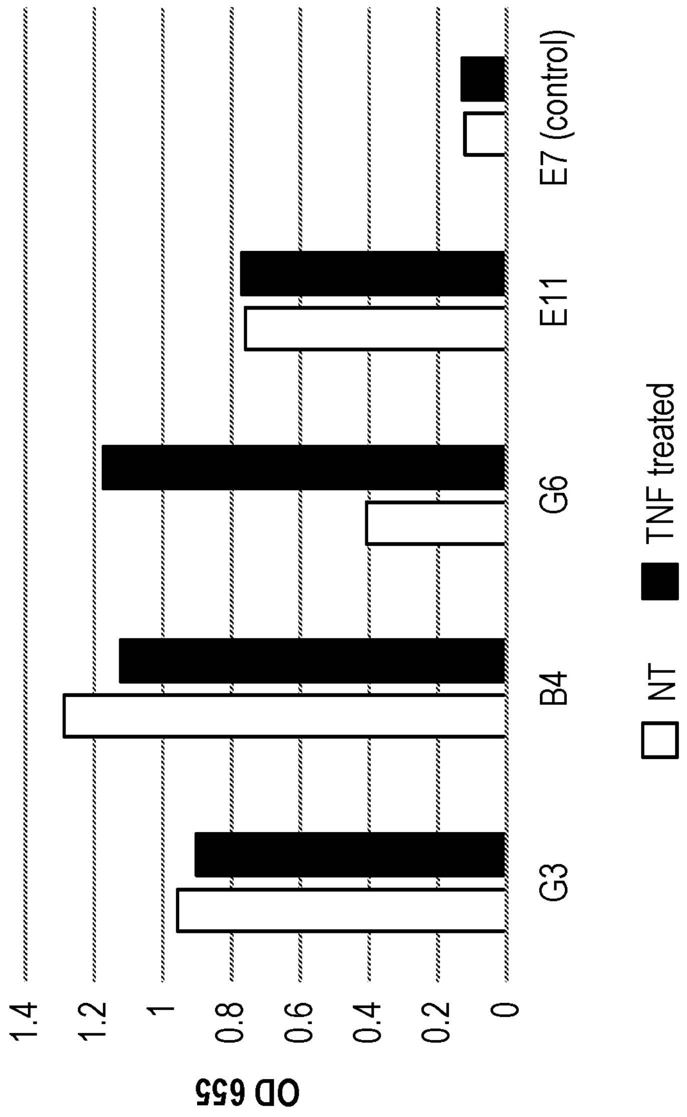

FIGS. 6A-6C show identification of TNFα responsive clones. FIG. 6A shows a schematic representation of the selection process. Briefly, a parental plate of single clones was replicated and TNFα-Fc was added to the replica plate; soluble embryonic alkaline phosphatase (SEAP) activity was measured in both plates using QB reagent. Cells that exhibited a SEAP signal only in response to TNFα addition were selected. FIG. 6B shows a photo of SEAP activity colors of selected clones with or without TNFα. FIG. 6C shows quantification of the colorimetric reaction of QB at OD 655 of selected clones.

Figure 7A:
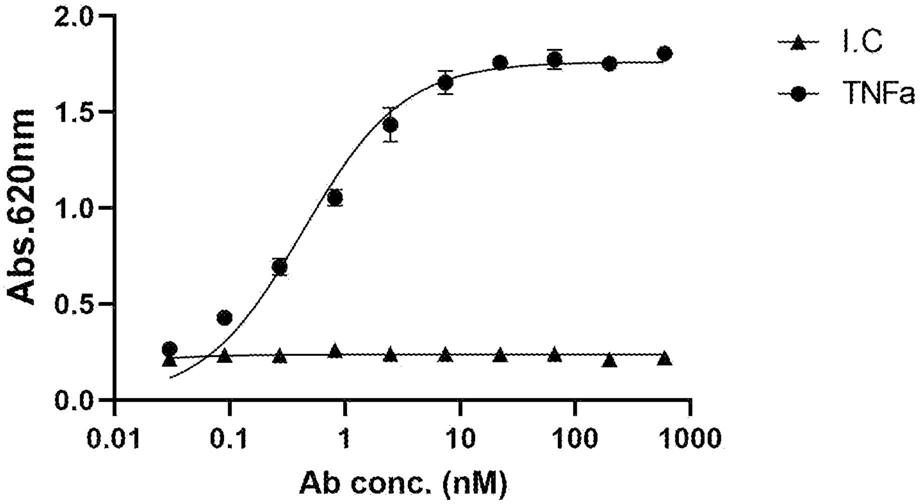
Figure 7B:
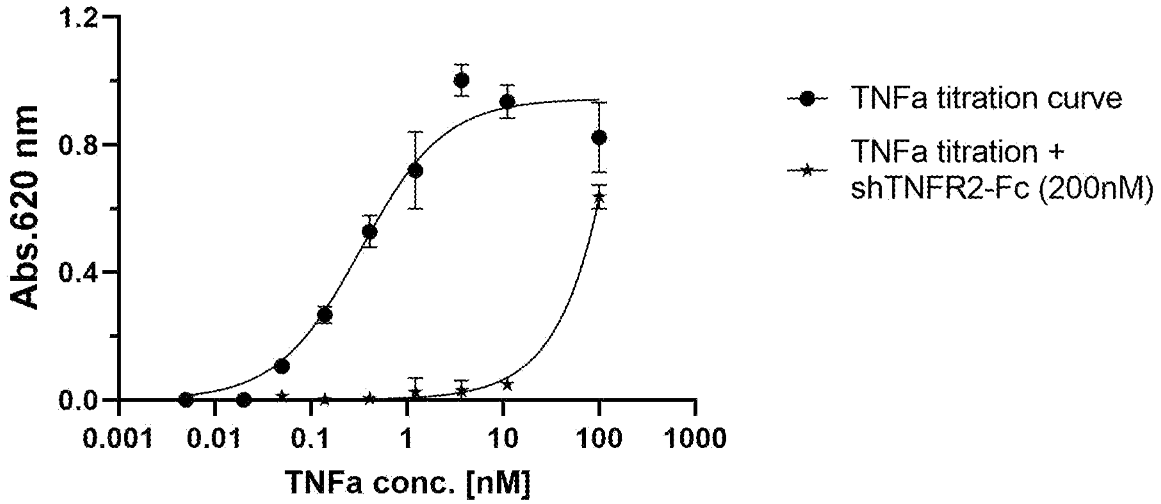

FIGS. 7A-7B show TNFR2-TNF dependent activation of the NFκB pathway. FIG. 7A shows the dose response of clone G6 to TNFα-Fc (circles). I.C is an isotype control antibody (upward triangles). FIG. 7B shows that activation of TNFα (circles) is inhibited by the addition of soluble TNFR2-Fc (asterisks). OD 620 values are presented.

Figure 8A:
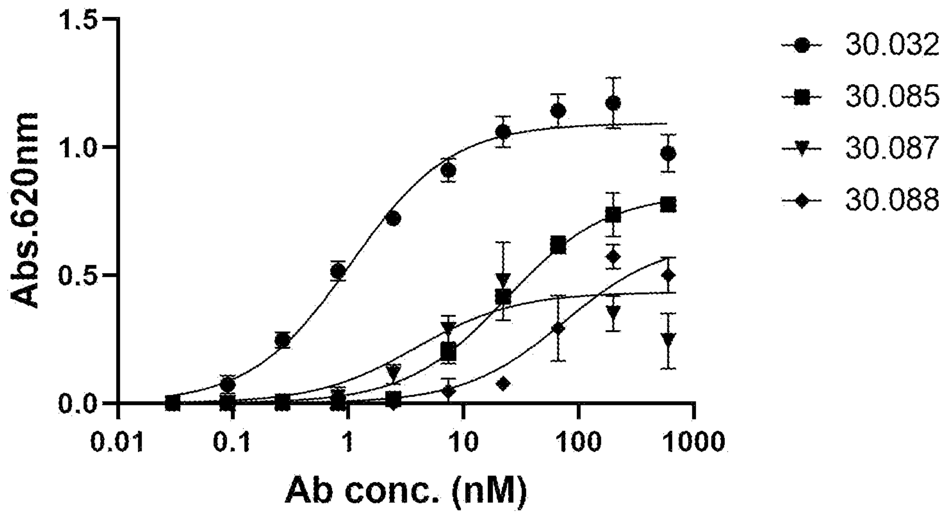
Figure 8B:
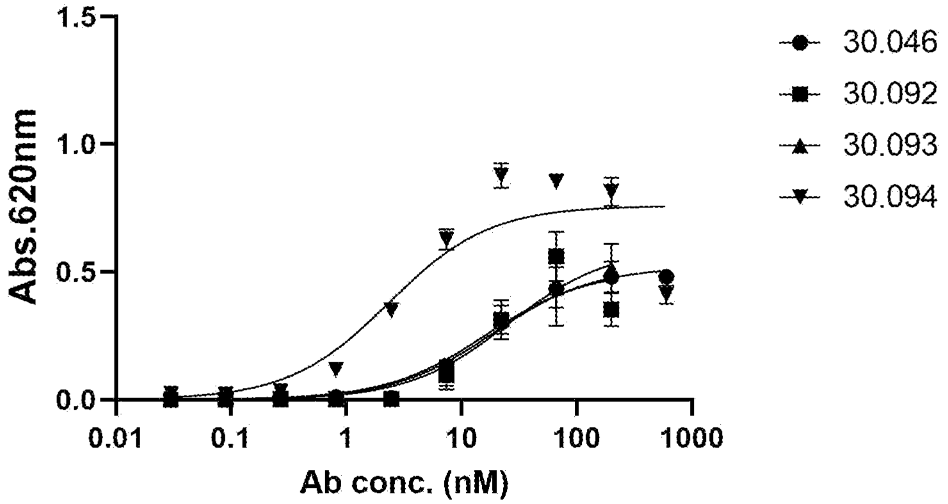
Figure 8C:
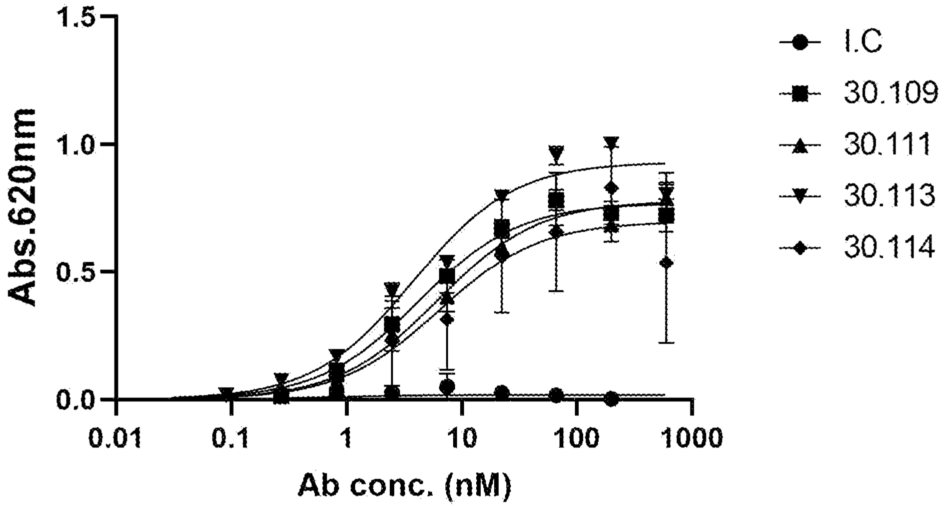
Figure 8D:
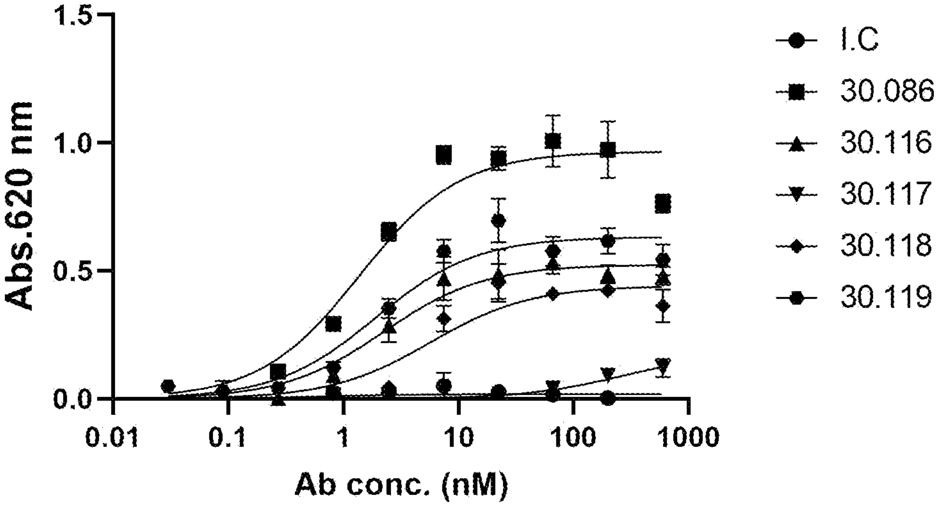
Figure 8E:
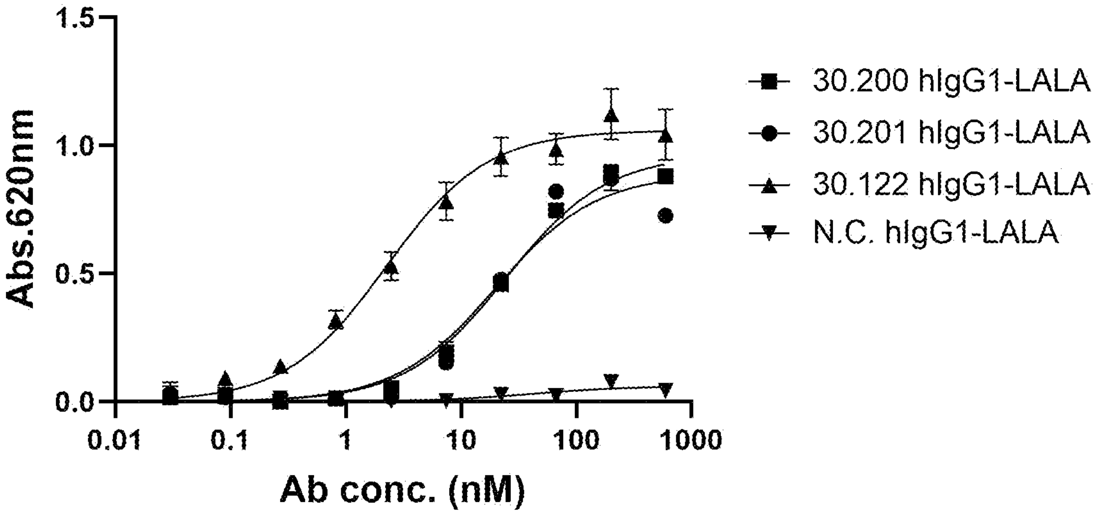
Figure 8F:
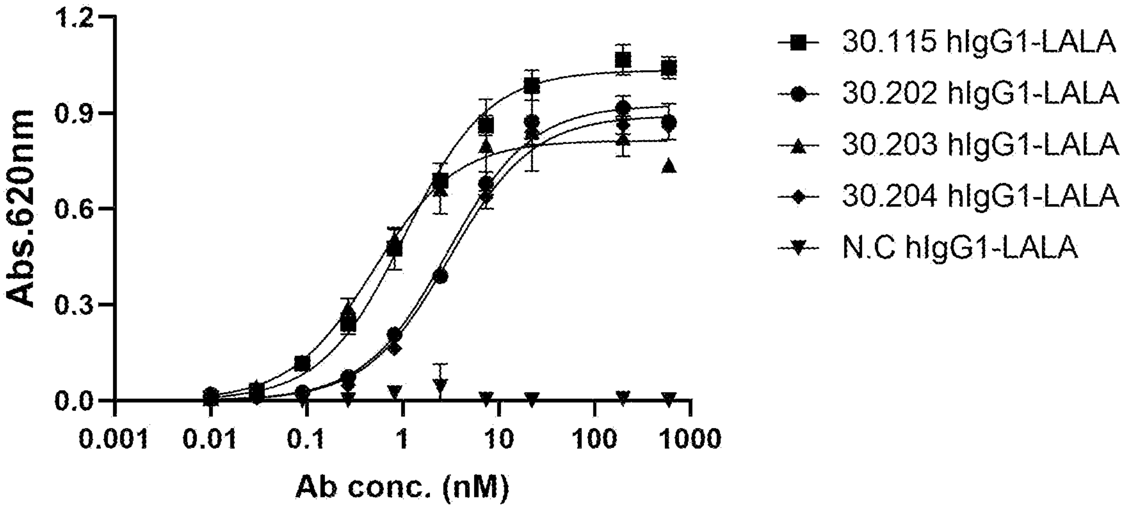
Figure 8G:
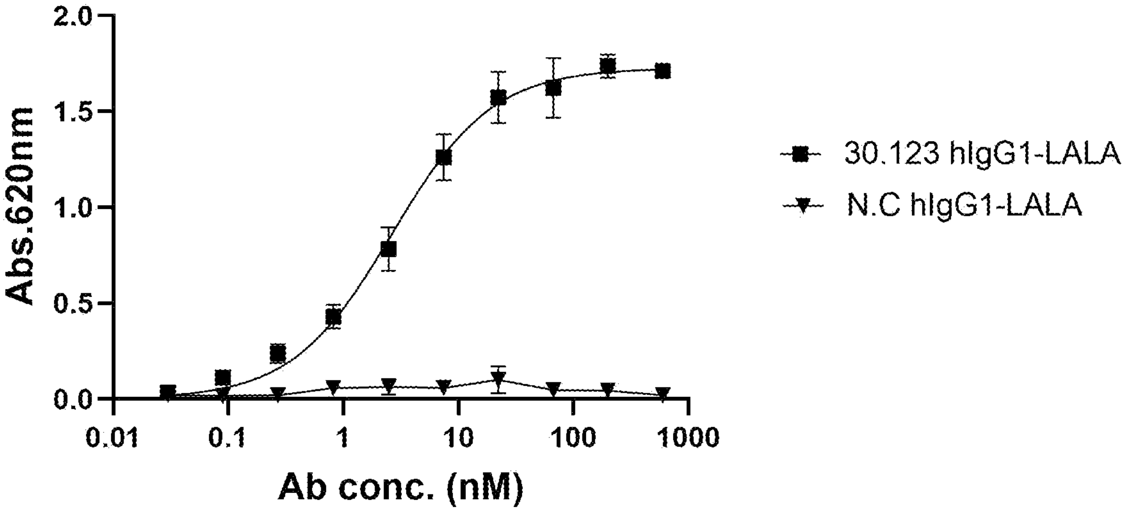

FIGS. 8A-8G show the $EC_{50}$ of functional agonism of TNFR2 by the indicated antibodies incubated with the HEK293-TNFR2 cell line, which harbors soluble embryonic alkaline phosphatase (SEAP) under the control of a NFkB-controlled promoter. I.C. and N.C. are IgG and IgG-LALA isotype control antibodies, respectively. IgG clones 30.032 (circles), 30.085 (squares), 30.087 (downward triangles), and 30.088 (diamonds) (FIG. 8A); IgG clones 30.046 (circles), 30.092 (squares), 30.093 (upward triangles), and 30.094 (downward triangles) (FIG. 8B); I. C. (circles) and IgG clones 30.109 (squares), 30.111 (upward triangles), 30.113 (downward triangles), and 30.114 (diamonds) (FIG. 8C); I.C. (circles) and IgG clones 30.086 (squares), 30.116 (upward triangles), 30.117 (downward triangles), 30.118 (diamonds), and 30.119 (hexagon) (FIG. 8D); IgG clones 30.200 (squares), 30.201 (circles), and 30.122 (upward triangles), N.C. (downward triangles) (FIG. 8E); IgG clones 30.115 (squares), 30.202 (circles), 30.203 (upward triangles), 30.204 (diamonds) and N.C. (downward triangles) (FIG. 8F); and IgG clone 30.123 (squares) and N.C.—negative control (downward triangles) (FIG. 8G).

Figure 9A:
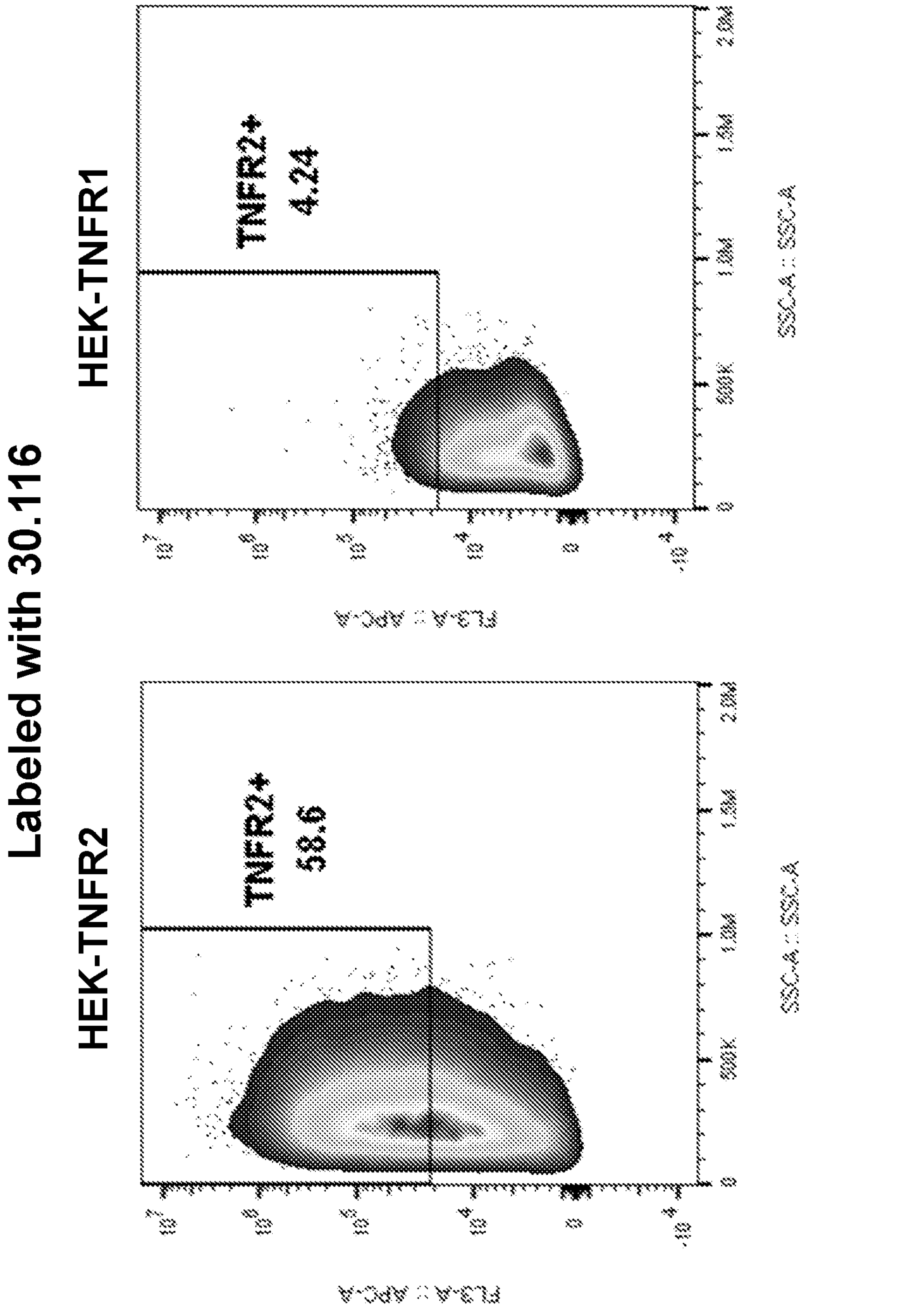
Figure 9B:
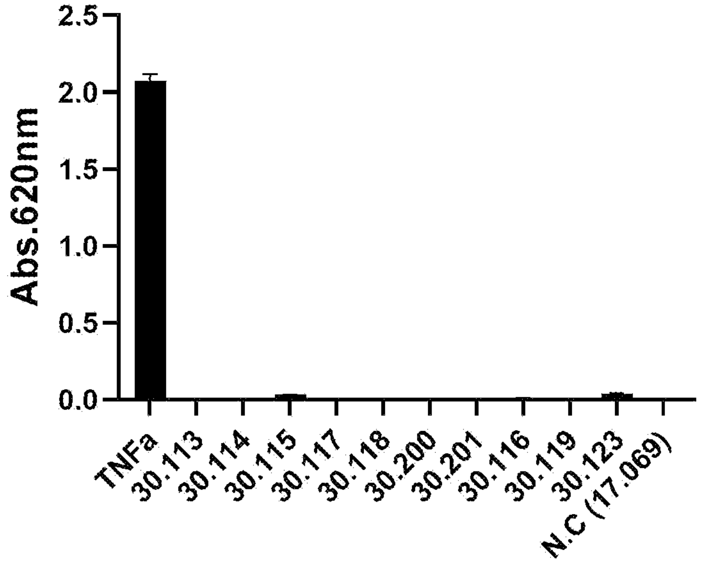
Figure 9C:
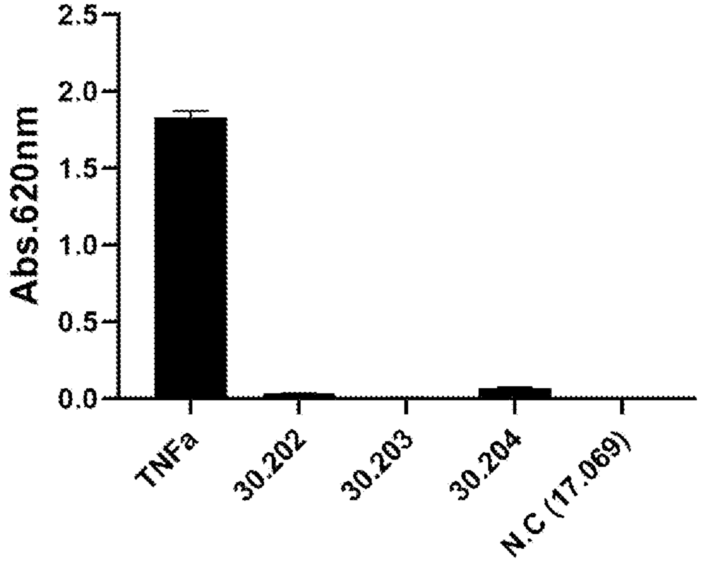
Figure 10A:
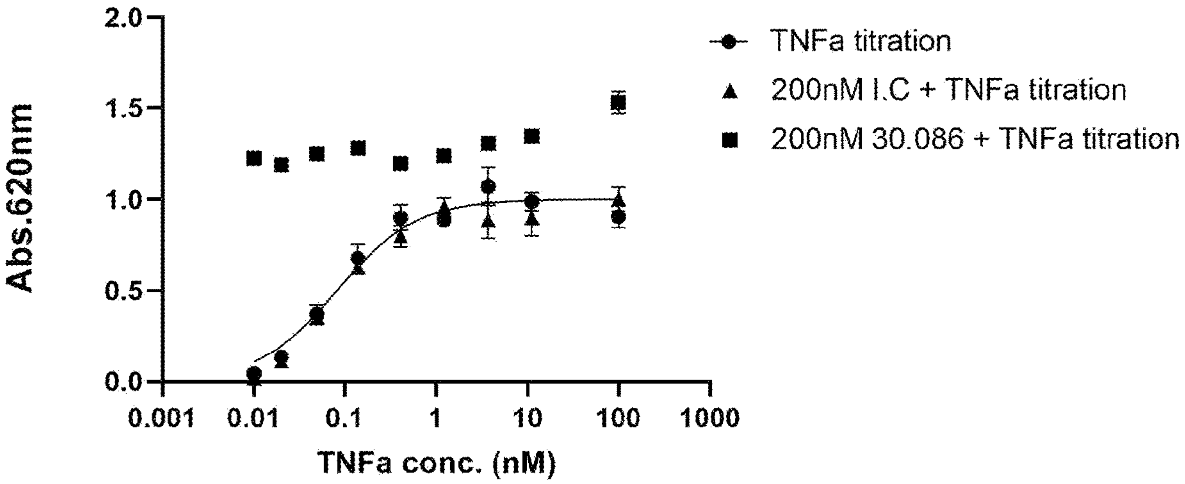
Figure 10B:
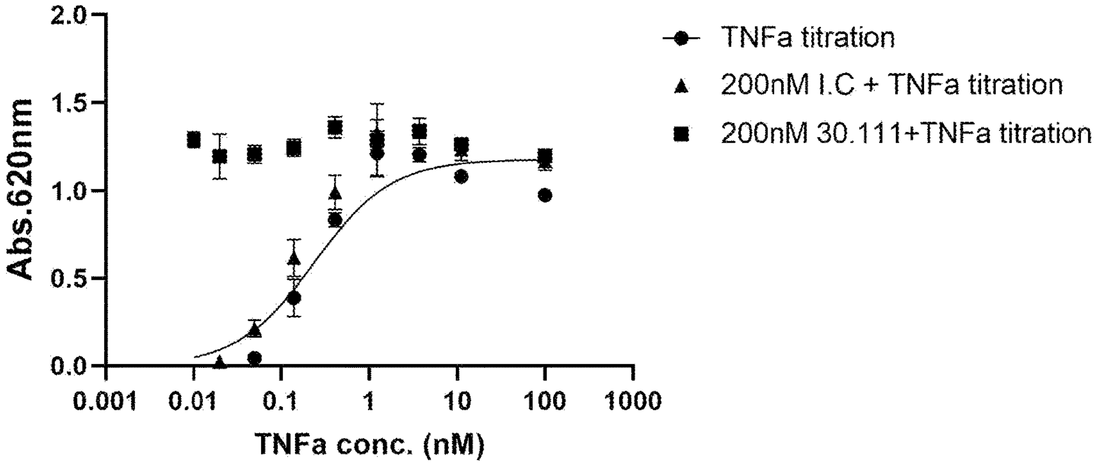
Figure 10C:
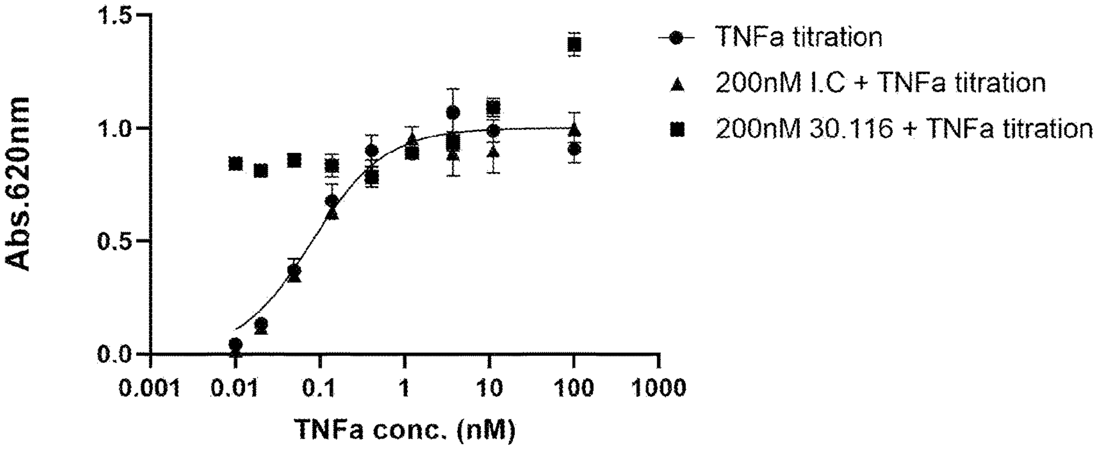
Figure 10D:
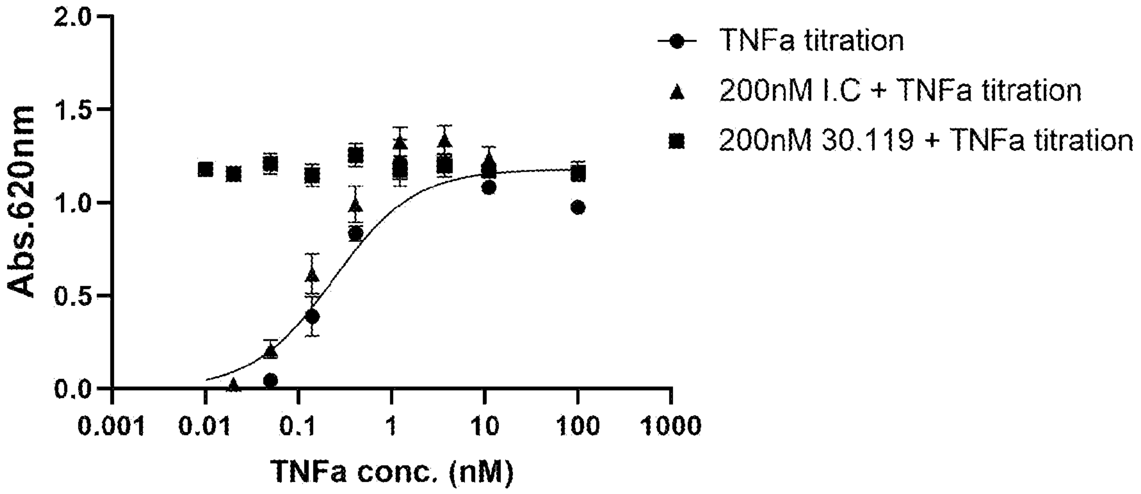

FIGS. 9A-9C show that antibody dependent activation of the NFkB controlled promoter is specific to TNFR2, and TNFR1 is not agonized by the TNFR2 specific antibodies. Representative flow cytometry labeling of HEK-TNFR2 and HEK-TNFR1 cell lines show that only HEK-TNFR2 is labeled by the 30.116 anti-TNFR2 antibody (FIG. 9A). For the results presented in FIGS. 9B-9C, 1 mM of antibody clones 30.113, 30.114, 30.115, 30.116, 30.117, 30.118, 30.200, 30.201, 30.116, 30.119, 30.123, 30.202, 30.203, 30.204, or IgG-LALA isotype control N.C. 17069, did not activate the TNFR1 dependent NFkB pathway, although 11 nM of human TNFa does activate the TNFR1 dependent NFκB pathway.

FIGS. 10A-10D show the effects of TNFα on antibody-dependent TNFR2 activation of selected clones. HEK-TNFR2 reporter cells were incubated with 200 nM soluble anti-TNFR2 antibodies (squares) for one hour, followed by subsequent addition of 0.05 nM to 100 nM TNFα (circles). Isotype control antibody (I.C.; upward triangle).

DETAILED DESCRIPTION OF THE INVENTION

The present disclosure presents a panel of high affinity antibody agonists that can agonize the TNFR2 receptor in an Fc independent manner, which could potentially be used for treatment of patients having a medical condition that requires (or could benefit from) activation of the TNFR2 pathway. As used herein, an "agonist antibody" of the TNFR2 receptor refers to an antibody that can essentially mimic the activity of the native ligand. The agonist activity can occur when the antibody binds the TNF receptor in a manner that mimics the binding of the physiological ligand, thereby resulting in antibody-mediated agonism. As used herein, the terms "native ligand" and "normal ligand" may be used interchangeably, having all the same meanings and qualities.

In some embodiments, an agonist antibody described herein mimics the activity of the native ligand. In some embodiments, an agonist antibody described herein replaces the activity of the normal ligand completely. In some embodiments, an agonist antibody described herein specifically activates the TNFR2 receptor. In some embodiments, an agonist antibody described herein replaces the activity of the normal ligand completely. In some embodiments, an agonist antibody described herein replaces the activity of the normal ligand and specifically activates the TNFR2 receptor.

In some embodiments, 100% of the activity of the normal ligand is replaced, as compared with the activity in the presence of the native ligand. In some embodiments, 50%-100% of the activity of the normal ligand is replaced, as compared with the activity in the presence of the native ligand. In some embodiments, 75%-100% of the activity of the normal ligand is replaced, as compared with the activity in the presence of the native ligand.

As used herein, the terms "comprise", "comprises", "comprising", "includes", "including", "having" and their conjugates mean "including but not limited to".

As used herein, the singular forms "a", "an" and "the" include plural references unless the context clearly dictates otherwise. For example, the term "an antibody" or "at least one antibody" may include a plurality of antibodies.

Throughout this application, various embodiments of the present disclosure may be presented in a range format. It should be understood that the description in range format is merely for convenience and brevity and should not be construed as an inflexible limitation on the scope of the anti-TNFR2 antibodies and uses thereof. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

When values are expressed as approximations, by use of the antecedent "about," it is understood that the particular value forms another embodiment. All ranges are inclusive and combinable. In one embodiment, the term "about" refers to a deviance of between 0.1-5% from the indicated number or range of numbers. In another embodiment, the term "about" refers to a deviance of between 1-10% from the indicated number or range of numbers. In another embodiment, the term "about" refers to a deviance of up to 20% from the indicated number or range of numbers. In one embodiment, the term "about" refers to a deviance of ±10% from the indicated number or range of numbers. In another embodiment, the term "about" refers to a deviance of ±5% from the indicated number or range of numbers.

Unless otherwise defined, all technical and/or scientific terms used herein have the same meaning as commonly understood by one of ordinary skill in the art to which the anti-TNFR2 antibodies and uses thereof pertains. Although methods and materials similar or equivalent to those described herein can be used in the practice or testing of embodiments of the anti-TNFR2 antibodies and uses thereof, methods and/or materials are described below. In case of conflict, the patent specification, including definitions, will control. In addition, the materials, methods, and examples are illustrative only and are not intended to be necessarily limiting. Each literature reference or other citation referred to herein is incorporated herein by reference in its entirety.

In the description presented herein, each of the steps of making and using the anti-TNFR2 antibodies and variations thereof are described. This description is not intended to be limiting and changes in the components, sequence of steps, and other variations would be understood to be within the scope of the present anti-TNFR2 antibodies, methods of making, and uses thereof.

It is appreciated that certain features of the anti-TNFR2 antibodies and uses thereof, which are, for clarity, described in the context of separate embodiments, may also be provided in combination in a single embodiment. Conversely, various features of the anti-TNFR2 antibodies and uses thereof, which are, for brevity, described in the context of a single embodiment, may also be provided separately or in any suitable subcombination or as suitable in any other described embodiment of the anti-TNFR2 antibodies and uses thereof. Certain features described in the context of various embodiments are not to be considered essential features of those embodiments, unless the embodiment is inoperative without those elements.

As used herein, the term "antibody" may be used interchangeably with the term "immunoglobulin", having all the same qualities and meanings. An antibody binding domain or an antigen binding site can be a fragment of an antibody or a genetically engineered product of one or more fragments of the antibody, which fragment is involved in specifically binding with a target antigen. By "specifically binding" is meant that the binding is selective for the antigen of interest and can be discriminated from unwanted or nonspecific interactions. For example, an antibody is said to specifically bind a TNFR2 epitope when the equilibrium dissociation constant is $\leq 10^{-5}$, $10^{-6}$, or $10^{-7}$ M. In some embodiments, the equilibrium dissociation constant may be $\leq 10^{-8}$ M or $10^{-9}$ M. In some further embodiments, the equilibrium dissociation constant may be $\leq 10^{-10}$ M, $10^{-11}$ M, or $10^{-12}$M. In some embodiments, the equilibrium dissociation constant may be in the range of $\leq 10^{-5}$ M to $10^{-12}$M.

Half maximal effective concentration ($EC_{50}$) refers to the concentration of a drug, antibody or toxicant which induces a response halfway between the baseline and maximum responses after a specified exposure time. In some embodiments, the response comprises a binding affinity. In some embodiments, the response comprises a functional response for example an agonistic response. A skilled artisan would appreciate that as used herein in certain embodiments, the $EC_{50}$ measurement of an anti-TNFR2 antibody disclosed herein provides a measure of a half-maximal binding of the anti-TNFR2 antibody to the TNFR2 antigen ($EC_{50}$ binding). Measure of $EC_{50}$ binding affinity comprises measuring the binding of an anti-TNFR2 antibody described herein to the TNFR2 antigen, as exemplified in Table 2 and Table 5 in the Examples. The skilled artisan would appreciate that as used herein in certain embodiments, the $EC_{50}$ measurement of an anti-TNFR2 antibody disclosed herein provides a measure of a half-maximal effective concentration of the anti-TNFR2 antibody to induce an agonist response ($EC_{50}$ functional agonism). Measure of $EC_{50}$ functional agonism comprises measuring the effects of the anti-TNFR2 antibodies described herein on cellular signaling of TNFR2, as exemplified in Table 6 in the Examples.

In some embodiments, $EC_{50}$ comprises the concentration of antibody required to obtain a 50% agonist response that would be observed upon binding of TNFα. In certain embodiments, a measure of $EC_{50}$ is commonly used as a measure of a drug's potency and may in some embodiments, reflect the binding of the antibody to the receptor. In some embodiments, anti-TNFR2 antibodies having nanomolar $EC_{50}$ binding concentration measurements, encompass tight binding anti-TNFR2 antibodies. In some embodiments, anti-TNFR2 antibodies having nanomolar $EC_{50}$ functional agonism concentration measurements encompass functionally effective agonistic antibodies. In certain embodiments, an anti-TNFR2 antibody disclosed herein comprises tight binding to the TNFR2 receptor. In certain embodiments, an anti-TNFR2 antibody disclosed herein comprises an agonist for the TNFR2 receptor. In certain embodiments, an anti-TNFR2 antibody disclosed herein comprises a tight binding agonist for the TNFR2 receptor.

In some embodiments, the binding $EC_{50}$ of an anti-TNFR2 antibody is in the nanomolar range. In some embodiments, the binding $EC_{50}$ of an anti-TNFR2 antibody is comprised within a range of about 0.05-100 nM. In some embodiments, the binding $EC_{50}$ of an anti-TNFR2 antibody is comprised within a range of about 0.05-50 nM. In some embodiments, the binding $EC_{50}$ of an anti-TNFR2 antibody is comprised within a range of about 0.05-20 nM. In some embodiments, the binding $EC_{50}$ of an anti-TNFR2 antibody is comprised within a range of about 0.05-10 nM. In some embodiments, the binding $EC_{50}$ of an anti-TNFR2 antibody is comprised within a range of about 0.1-100 nM. In some embodiments, the binding $EC_{50}$ of an anti-TNFR2 antibody is comprised within a range of about 0.1-50 nM. In some embodiments, the binding $EC_{50}$ of an anti-TNFR2 antibody is comprised within a range of about 0.1-20 nM. In some embodiments, the binding $EC_{50}$ of an anti-TNFR2 antibody is comprised within a range of about 0.1-10 nM. In some embodiments, the binding $EC_{50}$ of an anti-TNFR2 antibody is comprised within a range of about 1-100 nM. In some embodiments, the binding $EC_{50}$ of an anti-TNFR2 antibody is comprised within a range of about 1-20 nM. In some embodiments, the binding $EC_{50}$ of an anti-TNFR2 antibody is comprised within a range of about 20-40 nM. In some embodiments, the binding $EC_{50}$ of an anti-TNFR2 antibody is comprised within a range of about 40-60 nM. In some embodiments, the binding $EC_{50}$ of an anti-TNFR2 antibody is comprised within a range of about 60-80 nM. In some embodiments, the binding $EC_{50}$ of an anti-TNFR2 antibody is comprised within a range of about 80-100 nM. In some embodiments, the binding $EC_{50}$ of an anti-TNFR2 antibody is comprised within a range of about 1-40 nM. In some embodiments, the binding $EC_{50}$ of an anti-TNFR2 antibody is comprised within a range of about 1-60 nM. In some embodiments, the binding $EC_{50}$ of an anti-TNFR2 antibody is comprised within a range of about 1-80 nM. In some embodiments, the binding $EC_{50}$ of an anti-TNFR2 antibody is comprised within a range of about 1-50 nM. In some embodiments, the binding $EC_{50}$ of an anti-TNFR2 antibody is comprised within a range of about 0.05-5 nM. In some embodiments, the binding $EC_{50}$ of an anti-TNFR2 antibody is comprised within a range of about 0.1-5 nM. In some embodiments, the binding $EC_{50}$ of an anti-TNFR2 antibody is comprised within a range of about 0.05-20 nM.

In some embodiments, the binding $EC_{50}$ of an anti-TNFR2 antibody is comprised within a range of about 0.05-5 nM. In some embodiments, the binding $EC_{50}$ of an anti-TNFR2 antibody is comprised within a range of about 0.1-5 nM. In some embodiments, the binding $EC_{50}$ of an anti-TNFR2 antibody is comprised within a range of about 1-5 nM. In some embodiments, the binding $EC_{50}$ of an anti-TNFR2 antibody is comprised within a range of about 0.05-10 nM. In some embodiments, the binding $EC_{50}$ of an anti-TNFR2 antibody is comprised within a range of about 0.1-10 nM. In some embodiments, the binding $EC_{50}$ of an anti-TNFR2 antibody is comprised within a range of about 1-10 nM. In some embodiments, the binding $EC_{50}$ of an anti-TNFR2 antibody is comprised within a range of about 5-10 nM. In some embodiments, the binding $EC_{50}$ of an anti-TNFR2 antibody is comprised within a range of about 0.05-15 nM. In some embodiments, the binding $EC_{50}$ of an anti-TNFR2 antibody is comprised within a range of about 0.01-15 nM. In some embodiments, the binding $EC_{50}$ of an anti-TNFR2 antibody is comprised within a range of about 1-15 nM.

In some embodiments, the $EC_{50}$ measuring functional agonism is referred to herein as the functional $EC_{50}$, having all the same qualities. In some embodiments, the functional $EC_{50}$ of an anti-TNFR2 antibody is in the nanomolar range. In some embodiments, the functional $EC_{50}$ of an anti-TNFR2 antibody is comprised within a range of about 0.05-100 nM. In some embodiments, the functional $EC_{50}$ of an anti-TNFR2 antibody is comprised within a range of about 0.05-50 nM. In some embodiments, the functional $EC_{50}$ of an anti-TNFR2 antibody is comprised within a range of about 0.05-20 nM. In some embodiments, the functional $EC_{50}$ of an anti-TNFR2 antibody is comprised within a range of about 0.05-10 nM. In some embodiments, the functional $EC_{50}$ of an anti-TNFR2 antibody is comprised within a range of about 0.1-100 nM. In some embodiments, the functional $EC_{50}$ of an anti-TNFR2 antibody is comprised within a range of about 0.1-50 nM. In some embodiments, the functional $EC_{50}$ of an anti-TNFR2 antibody is comprised within a range of about 0.1-20 nM. In some embodiments, the functional $EC_{50}$ of an anti-TNFR2 antibody is comprised within a range of about 0.1-10 nM. In some embodiments, the functional $EC_{50}$ of an anti-TNFR2 antibody is comprised within a range of about 1-100 nM. In some embodiments, the functional $EC_{50}$ of an anti-TNFR2 antibody is comprised within a range of about 1-20 nM. In some embodiments, the functional $EC_{50}$ of an anti-TNFR2 antibody is comprised within a range of about 20-40 nM. In some embodiments, the functional $EC_{50}$ of an anti-TNFR2 antibody is comprised within a range of about 40-60 nM. In some embodiments, the functional $EC_{50}$ of an anti-TNFR2 antibody is comprised within a range of about 60-80 nM. In some embodiments, the functional $EC_{50}$ of an anti-TNFR2 antibody is comprised within a range of about 80-100 nM. In some embodiments, the functional $EC_{50}$ of an anti-TNFR2 antibody is comprised within a range of about 1-40 nM. In some embodiments, the functional $EC_{50}$ of an anti-TNFR2 antibody is comprised within a range of about 1-60 nM. In some embodiments, the functional $EC_{50}$ of an anti-TNFR2 antibody is comprised within a range of about 1-80 nM. In some embodiments, the functional $EC_{50}$ of an anti-TNFR2 antibody is comprised within a range of about 1-50 nM. In some embodiments, the functional $EC_{50}$ of an anti-TNFR2 antibody is comprised within a range of about 0.05-5 nM. In some embodiments, the functional $EC_{50}$ of an anti-TNFR2 antibody is comprised within a range of about 0.1-5 nM. In some embodiments, the functional $EC_{50}$ of an anti-TNFR2 antibody is comprised within a range of about 0.05-20 nM.

In some embodiments, the functional $EC_{50}$ of an anti-TNFR2 antibody is comprised within a range of about 0.05-5 nM. In some embodiments, the functional $EC_{50}$ of an anti-TNFR2 antibody is comprised within a range of about 0.1-5 nM. In some embodiments, the functional $EC_{50}$ of an anti-TNFR2 antibody is comprised within a range of about 1-5 nM. In some embodiments, the functional $EC_{50}$ of an anti-TNFR2 antibody is comprised within a range of about 0.05-10 nM. In some embodiments, the functional $EC_{50}$ of an anti-TNFR2 antibody is comprised within a range of about 0.1-10 nM. In some embodiments, the functional $EC_{50}$ of an anti-TNFR2 antibody is comprised within a range of about 1-10 nM. In some embodiments, the functional $EC_{50}$ of an anti-TNFR2 antibody is comprised within a range of about 5-10 nM. In some embodiments, the functional $EC_{50}$ of an anti-TNFR2 antibody is comprised within a range of about 0.05-15 nM. In some embodiments, the functional $EC_{50}$ of an anti-TNFR2 antibody is comprised within a range of about 0.01-15 nM. In some embodiments, the functional $EC_{50}$ of an anti-TNFR2 antibody is comprised within a range of about 1-15 nM.

As used herein, the term "antibody" encompasses an antibody fragment or fragments that retain binding specificity including, but not limited to, IgG, heavy chain variable regions (VH), light chain variable regions (VL), Fab fragments, $F(ab)_2$ fragments, scFv fragments, Fv fragments, a nanobody, minibodies, diabodies, triabodies, tetrabodies, and single domain antibodies (see, e.g., Hudson and Souriau, Nature Med. 9: 129-134 (2003)). Also encompassed are humanized, primatized, and chimeric antibodies as these terms are generally understood in the art.

As used herein, the term "heavy chain variable region" may be used interchangeably with the term "VH domain" or the term "VH", having all the same meanings and qualities. As used herein, the term "light chain variable region" may be used interchangeably with the term "VL domain" or the term "VL", having all the same meanings and qualities. A skilled artisan would recognize that a "heavy chain variable region" or "VH" with regard to an antibody encompasses the fragment of the heavy chain that contains three complementarity determining regions (CDRs) interposed between flanking stretches known as framework regions. The framework regions are more highly conserved than the CDRs, and form a scaffold to support the CDRs. Similarly, a skilled artisan would also recognize that a "light chain variable region" or "VL" with regard to an antibody encompasses the fragment of the light chain that contains three CDRs interposed between framework regions.

As used herein, the term "complementarity determining region" or "CDR" refers to the hypervariable region(s) of a heavy or light chain variable region. Proceeding from the N-terminus, each of a heavy or light chain polypeptide has three CDRs denoted as "CDR1," "CDR2," and "CDR3". Crystallographic analysis of a number of antigen-antibody complexes has demonstrated that the amino acid residues of CDRs form extensive contact with a bound antigen, wherein the most extensive antigen contact is with the heavy chain CDR3. Thus, the CDR regions are primarily responsible for the specificity of an antigen-binding site. In one embodiment, an antigen-binding site includes six CDRs, comprising the CDRs from each of a heavy and a light chain variable region.

As used herein, the term "framework region" or "FR" refers to the four flanking amino acid sequences which frame the CDRs of a heavy or light chain variable region. Some FR residues may contact bound antigen, however, FR residues are primarily responsible for folding the variable region into the antigen-binding site. In some embodiments, the FR residues responsible for folding the variable regions comprise residues directly adjacent to the CDRs. Within FRs, certain amino residues and certain structural features are very highly conserved. In this regard, all variable region sequences contain an internal disulfide loop of around 90 amino acid residues. When a variable region folds into an antigen binding site, the CDRs are displayed as projecting loop motifs that form an antigen-binding surface. It is generally recognized that there are conserved structural regions of FRs that influence the folded shape of the CDR loops into certain "canonical" structures regardless of the precise CDR amino acid sequence. Furthermore, certain FR residues are known to participate in non-covalent interdomain contacts which stabilize the interaction of the antibody heavy and light chains.

Wu and Kabat (Wu and Kabat, "An analysis of the sequences of the variable regions of Bence Jones proteins and myeloma light chains and their implications for antibody complementarity", Journal of Experimental Medicine, 132 (2): 211-250 (1970); Kabat et al., "Sequence of proteins of immunological interest", Bethesda: National Institutes of Health; 323 (1983)) pioneered the alignment of antibody peptide sequences, and their contributions in this area were several-fold. Firstly, through study of sequence similarities between variable domains, they identified correspondent residues that to a greater or lesser extent were homologous across all antibodies in all vertebrate species, inasmuch as they adopted similar three-dimensional structure, played similar functional roles, interacted similarly with neighboring residues, and existed in similar chemical environments. Secondly, they devised a peptide sequence numbering system in which homologous immunoglobulin residues were assigned the same position number. One skilled in the art can unambiguously assign to any variable domain sequence what is now commonly called Kabat numbering without reliance on any experimental data beyond the sequence itself. Thirdly, Kabat and Wu calculated variability for each Kabat-numbered sequence position, which is the finding of few or many possible amino acids when variable domain sequences are aligned. They identified three contiguous regions of high variability embedded within four less variable contiguous regions. Kabat and Wu formally demarcated residues constituting these variable tracts, and designated these "complementarity determining regions" (CDRs), referring to chemical complementarity between antibody and antigen. A role in three-dimensional folding of the variable domain, but not in antigen recognition, was ascribed to the remaining less-variable regions, which are now termed "framework regions". Fourthly, Kabat and Wu established a public database of antibody peptide and nucleic acid sequences, which continues to be maintained and is well known to those skilled in the art.

Chothia and coworkers (Cyrus Chothia, Arthur M. Lesk (1987), Journal of Molecular Biology. 196(4): 901-917) found that certain sub-portions within Kabat CDRs adopt nearly identical peptide backbone conformations, despite having great diversity at the level of amino acid sequence. These sub-portions were designated as L1, L2 and L3 or H1, H2 and H3, where the "L" and the "H" designates the light chain and the heavy chains regions, respectively. These regions may be referred to as Chothia CDRs, which have boundaries that overlap with Kabat CDRs.

More recent studies have shown that virtually all antibody binding residues fall within regions of structural consensus. (Kunik, V., et al., PloS Computational Biology 8(2): e1002388 (February 2012)). In some embodiments, these regions are referred to as antibody binding regions. It was shown that these regions can be identified from the antibody sequence as well. "Paratome", an implementation of a structural approach for the identification of structural consensus in antibodies, was used for this purpose. (Ofran, Y. et al., J. Immunol. 757:6230-6235 (2008)). While residues identified by Paratome cover virtually all the antibody binding sites, the CDRs (as identified by the commonly used CDR identification tools) miss significant portions of them. Antibody binding residues which were identified by Paratome but were not identified by any of the common CDR identification methods are referred to as Paratome-unique residues. Similarly, antibody binding residues that are identified by any of the common CDR identification methods but are not identified by Paratome are referred to as CDR-unique residues. Paratome-unique residues make crucial energetic contribution to antibody-antigen interactions, while CDRs-unique residues have a rather minor contribution. These results allow for better identification of antigen binding sites.

IMGT® is the international ImMunoGeneTics information System®, (See, Nucleic Acids Res. 2015 January; 43 (Database issue):D413-22. doi: 10.1093/nar/gku1056. Epub 2014 Nov. 5 Free article. PMID: 25378316 LIGM:441 and Dev Comp Immunol. 2003 January; 27(1):55-77). IMGT is a unique numbering system for immunoglobulin and T cell receptor variable domains and Ig superfamily V-like domains (Lefranc et al., Dev Comp Immunol. 27: 55-77 (2003)). IMGT® presents a uniform numbering system for these IG and TcR variable domain sequences, based on aligning 5 or more IG and TcR variable region sequences, taking into account and combining the Kabat definition of FRs and CDRs, structural data, and Chothia's characterization of the hypervariable loops. IMGT is considered well known in the art as a universal numbering scheme for antibodies.

In describing variant amino acid positions present in the VH and VL domains, in some embodiments any common CDR definition may be used to describe the CDR regions, for example but not limited to the approaches used by IMGT®, KABAT, or Chothia and Paratome.

An antibody may exist in various forms or having various domains including, without limitation, a complementarity determining region (CDR), a variable region (Fv), a VH domain, a VL domain, a single chain variable region (scFv), and a Fab fragment.

A person of ordinary skill in the art would appreciate that a scFv is a fusion polypeptide comprising the variable heavy chain (VH) and variable light chain (VL) regions of an immunoglobulin, connected by a short linker peptide. The linker may have, for example, 10 to about 25 amino acids.

A skilled artisan would also appreciate that the term “Fab” with regard to an antibody generally encompasses that portion of the antibody consisting of a single light chain (both variable and constant regions) bound to the variable region and first constant region of a single heavy chain by a disulfide bond, whereas $F(ab')_2$ comprises a fragment of a heavy chain comprising a VH domain and a light chain comprising a VL domain.

In some embodiments, an antibody encompasses whole antibody molecules, including monoclonal and polyclonal antibodies. In some embodiments, an antibody encompasses an antibody fragment or fragments that retain binding specificity including, but not limited to, variable heavy chain (VH) fragments, variable light chain (VL) fragments, Fab fragments, $F(ab')_2$ fragments, scFv fragments, Fv fragments, minibodies, diabodies, triabodies, and tetrabodies.

In one embodiment, the anti-TNFR2 antibodies disclosed herein can be incorporated as part of a bispecific antibody. As it is generally known in the art, a bispecific antibody is a recombinant protein that includes antigen-binding fragments of two different monoclonal antibodies, and is thereby capable of binding two different antigens. In some embodiments, bispecific antibodies are used for cancer immunotherapy by simultaneously targeting, for example, both CTLs (such as a CTL receptor component such as CD3) or effector natural killer (NK) cells, and a tumor antigen. Similarly, a multi-specific antibody is a recombinant protein that includes antigen-binding fragments of at least two different monoclonal antibodies, such as two, three or four different monoclonal antibodies.

Anti-TNFR2 Antibodies

The present disclosure provides a number of anti-TNFR2 (tumor necrosis factor receptor 2) antibodies. In one embodiment, each of the anti-TNFR2 antibodies comprises a set of three complementarity determining regions (CDRs) on a heavy chain (HCDR1, HCDR2, and HCDR3) and a set of three CDRs on a light chain (LCDR1, LCDR2, and LCDR3). In one embodiment, the set of HCDR1, HCDR2, and HCDR3 comprises a combination of the amino acid sequences as shown in Table 7, and the set of LCDR1, LCDR2, and LCDR3 on a corresponding light chain comprises a combination of the amino acid sequences as shown in Table 8. For the purpose of illustration, take clone CID251 as an example (see Table 7), the set of HCDR1, HCDR2, and HCDR3 for this antibody comprises the amino acid sequences of SEQ ID NO:185, SEQ ID NO:190 and SEQ ID NO:347 respectively (see Table 7), whereas the set of LCDR1, LCDR2, and LCDR3 for the same antibody comprises the amino acid sequences of SEQ ID NO:359, SEQ ID NO:372 and SEQ ID NO:378 respectively (see Table 8).

In some embodiments, the set of HCDR1, HCDR2, and HCDR3 comprises the amino acid sequences set forth in SEQ ID NOs: 185, 190, and 347, respectively, and the set of LCDR1, LCDR2, and LCDR3 for the same antibody comprises the amino acid sequences set forth in SEQ ID NOs: 359, 372, and 378, respectively. In some embodiments, the set of HCDR1, HCDR2, and HCDR3 comprises the amino acid sequences set forth in SEQ ID NOs: 185, 190, and 347, respectively, and the set of LCDR1, LCDR2, and LCDR3 for the same antibody comprises the amino acid sequences set forth in SEQ ID NOs: 359, 372, and 378, respectively. In some embodiments, the set of HCDR1, HCDR2, and HCDR3 comprises the amino acid sequences set forth in SEQ ID NOs: 185, 334, 347, respectively, and the set of LCDR1, LCDR2, and LCDR3 for the same antibody comprises the amino acid sequences set forth in SEQ ID NOs: 360, 372, and 379, respectively. In some embodiments, the set of HCDR1, HCDR2, and HCDR3 comprises the amino acid sequences set forth in SEQ ID NOs: 185, 190, and 347, respectively, and the set of LCDR1, LCDR2, and LCDR3 for the same antibody comprises the amino acid sequences set forth in SEQ ID NOs: 359, 372, and 380, respectively. In some embodiments, the set of HCDR1, HCDR2, and HCDR3 comprises the amino acid sequences set forth in SEQ ID NOs: 185, 190, and 347, respectively, and the set of LCDR1, LCDR2, and LCDR3 for the same antibody comprises the amino acid sequences set forth in SEQ ID NOs: 359, 372, and 381, respectively. In some embodiments, the set of HCDR1, HCDR2, and HCDR3 comprises the amino acid sequences set forth in SEQ ID NOs: 185, 190, and 347, respectively, and the set of LCDR1, LCDR2, and LCDR3 for the same antibody comprises the amino acid sequences set forth in SEQ ID NOs: 361, 372, and 381, respectively. In some embodiments, the set of HCDR1, HCDR2, and HCDR3 comprises the amino acid sequences set forth in SEQ ID NOs: 185, 190, and 347, respectively, and the set of LCDR1, LCDR2, and LCDR3 for the same antibody comprises the amino acid sequences set forth in SEQ ID NOs: 362, 372, and 382, respectively. In some embodiments, the set of HCDR1, HCDR2, and HCDR3 comprises the amino acid sequences set forth in SEQ ID NOs: 185, 335, and 347, respectively, and the set of LCDR1, LCDR2, and LCDR3 for the same antibody comprises the amino acid sequences set forth in SEQ ID NOs: 363, 372, and 383, respectively. In some embodiments, the set of HCDR1, HCDR2, and HCDR3 comprises the amino acid sequences set forth in SEQ ID NOs: 185, 190, 347, respectively, and the set of LCDR1, LCDR2, and LCDR3 for the same antibody comprises the amine acid sequences set forth in SEQ ID NOs: 364, 372, and 384, respectively. In some embodiments, the set of HCDR1, HCDR2, and HCDR3 comprises the amino acid sequences set forth in SEQ ID NOs: 185, 336, and 348, respectively, and the set of LCDR1, LCDR2, and LCDR3 for the same antibody comprises the amino acid sequences set forth in SEQ ID NOs: 365, 372, and 378, respectively. In some embodiments, the set of HCDR1, HCDR2, and HCDR3 comprises the amino acid sequences set forth in SEQ ID NOs: 185, 337, and 347, respectively, and the set of LCDR1, LCDR2, and LCDR3 for the same antibody comprises the amino acid sequences set forth in SEQ ID NOs: 359, 373, and 385, respectively. In some embodiments, the set of HCDR1, HCDR2, and HCDR3 comprises the amino acid sequences set forth in SEQ ID NOs: 185, 338, and 348, respectively, and the set of LCDR1, LCDR2, and LCDR3 for the same antibody comprises the amino acid sequences set forth in SEQ ID NOs: 359, 372, and 386, respectively. In some embodiments, the set of HCDR1, HCDR2, and HCDR3 comprises the amino acid sequences set forth in SEQ ID NOs: 185, 339, and 349, respectively, and the set of LCDR1, LCDR2, and LCDR3 for the same antibody comprises the amino acid sequences set forth in SEQ ID NOs: 359, 372, and 378, respectively. In some embodiments, the set of HCDR1, HCDR2, and HCDR3 comprises the amino acid sequences set forth in SEQ ID NOs: 185, 190, and 350, respectively, and the set of LCDR1, LCDR2, and LCDR3 for the same antibody comprises the amino acid sequences set forth in SEQ ID NOs: 366, 372, and 387, respectively. In some embodiments, the set of HCDR1, HCDR2, and HCDR3 comprises the amino acid sequences set forth in SEQ ID NOs: 185, 190, and 351, respectively, and the set of LCDR1, LCDR2, and LCDR3 for the same antibody comprises the amino acid sequences set forth in SEQ ID NOs: 359, 372, and 378, respectively. In some embodiments, the set of HCDR1, HCDR2, and HCDR3 comprises the amino acid sequences set forth in SEQ ID NOs: 185, 334, and 347, respectively, and the set of LCDR1, LCDR2, and LCDR3 for the same antibody comprises the amino acid sequences set forth in SEQ ID NOs: 360, 372, and 388, respectively. In some embodiments, the set of HCDR1, HCDR2, and HCDR3 comprises the amino acid sequences set forth in SEQ ID NOs: 185, 334, and 352, respectively, and the set of LCDR1, LCDR2, and LCDR3 for the same antibody comprises the amino acid sequences set forth in SEQ ID NOs: 359, 372, and 378, respectively. In some embodiments, the set of HCDR1, HCDR2, and HCDR3 comprises the amino acid sequences set forth in SEQ ID NOs: 185, 190, and 352, respectively, and the set of LCDR1, LCDR2, and LCDR3 for the same antibody comprises the amino acid sequences set forth in SEQ ID NOs: 359, 372, and 389, respectively. In some embodiments, the set of HCDR1, HCDR2, and HCDR3 comprises the amino acid sequences set forth in SEQ ID NOs: 185, 334, and 347, respectively, and the set of LCDR1, LCDR2, and LCDR3 for the same antibody comprises the amino acid sequences set forth in SEQ ID NOs: 359, 372, and 378, respectively. In some embodiments, the set of HCDR1, HCDR2, and HCDR3 comprises the amino acid sequences set forth in SEQ ID NOs: 185, 190, and 347, respectively, and the set of LCDR1, LCDR2, and LCDR3 for the same antibody comprises the amino acid sequences set forth in SEQ ID NOs: 365, 372, and 378, respectively. In some embodiments, the set of HCDR1, HCDR2, and HCDR3 comprises the amino acid sequences set forth in SEQ ID NOs: 185, 336, and 352, respectively, and the set of LCDR1, LCDR2, and LCDR3 for the same antibody comprises the amino acid sequences set forth in SEQ ID NOs: 365, 372, and 390, respectively. In some embodiments, the set of HCDR1, HCDR2, and HCDR3 comprises the amino acid sequences set forth in SEQ ID NOs: 185, 336, and 352, respectively, and the set of LCDR1, LCDR2, and LCDR3 for the same antibody comprises the amino acid sequences set forth in SEQ ID NOs: 365, 374, and 391, respectively. In some embodiments, the set of HCDR1, HCDR2, and HCDR3 comprises the amino acid sequences set forth in SEQ ID NOs: 186, 340, and 353, respectively, and the set of LCDR1, LCDR2, and LCDR3 for the same antibody comprises the amino acid sequences set forth in SEQ ID NOs: 367, 375, and 392, respectively. In some embodiments, the set of HCDR1, HCDR2, and HCDR3 comprises the amino acid sequences set forth in SEQ ID NOs: 186, 341, and 354, respectively, and the set of LCDR1, LCDR2, and LCDR3 for the same antibody comprises the amino acid sequences set forth in SEQ ID NOs: 367, 375, 392, respectively. In some embodiments, the set of HCDR1, HCDR2, and HCDR3 comprises the amino acid sequences set forth in SEQ ID NOs: 186, 341, and 354, respectively, and the set of LCDR1, LCDR2, and LCDR3 for the same antibody comprises the amino acid sequences set forth in SEQ ID NOs: 368, 375, and 392, respectively. In some embodiments, the set of HCDR1, HCDR2, and HCDR3 comprises the amino acid sequences set forth in SEQ ID NOs: 186, 342, and 354, respectively, and the set of LCDR1, LCDR2, and LCDR3 for the same antibody comprises the amino acid sequences set forth in SEQ ID NOs: 367, 375 and 392, respectively. In some embodiments, the set of HCDR1, HCDR2, and HCDR3 comprises the amino acid sequences set forth in SEQ ID NOs: 186, 343, and 354, respectively, and the set of LCDR1, LCDR2, and LCDR3 for the same antibody comprises the amino acid sequences set forth in SEQ ID NOs: 369, 375, and 393, respectively. In some embodiments, the set of HCDR1, HCDR2, and HCDR3 comprises the amino acid sequences set forth in SEQ ID NOs: 186, 343, and 355, respectively, and the set of LCDR1, LCDR2, and LCDR3 for the same antibody comprises the amino acid sequences set forth in SEQ ID NOs: 367, 375, and 392, respectively. In some embodiments, the set of HCDR1, HCDR2, and HCDR3 comprises the amino acid sequences set forth in SEQ ID NOs: 186, 341, and 354, respectively, and the set of LCDR1, LCDR2, and LCDR3 for the same antibody comprises the amino acid sequences set forth in SEQ ID NOs: 367, 375, and 392, respectively. In some embodiments, the set of HCDR1, HCDR2, and HCDR3 comprises the amino acid sequences set forth in SEQ ID NOs: 186, 341, and 355, respectively, and the set of LCDR1, LCDR2, and LCDR3 for the same antibody comprises the amino acid sequences set forth in SEQ ID NOs: 367, 376, and 392, respectively. In some embodiments, the set of HCDR1, HCDR2, and HCDR3 comprises the amino acid sequences set forth in SEQ ID NOs: 186, 344, and 354, respectively, and the set of LCDR1, LCDR2, and LCDR3 for the same antibody comprises the amino acid sequences set forth in SEQ ID NOs: 370, 375, and 392, respectively. In some embodiments, the set of HCDR1, HCDR2, and HCDR3 comprises the amino acid sequences set forth in SEQ ID NOs: 186, 341, and 354, respectively, and the set of LCDR1, LCDR2, and LCDR3 for the same antibody comprises the amino acid sequences set forth in SEQ ID NOs: 367, 375, and 394, respectively. In some embodiments, the set of HCDR1, HCDR2, and HCDR3 comprises the amino acid sequences set forth in SEQ ID NOs: 186, 344, and 354, respectively, and the set of LCDR1, LCDR2, and LCDR3 for the same antibody comprises the amino acid sequences set forth in SEQ ID NOs: 367, 375, and 392, respectively. In some embodiments, the set of HCDR1, HCDR2, and HCDR3 comprises the amino acid sequences set forth in SEQ ID NOs: 186, 341, and 359, respectively, and the set of LCDR1, LCDR2, and LCDR3 for the same antibody comprises the amino acid sequences set forth in SEQ ID NOs: 367, 375, and 393, respectively. In some embodiments, the set of HCDR1, HCDR2, and HCDR3 comprises the amino acid sequences set forth in SEQ ID NOs: 187, 345, and 356, respectively, and the set of LCDR1, LCDR2, and LCDR3 for the same antibody comprises the amino acid sequences set forth in SEQ ID NOs: 371, 377, and 395, respectively. In some embodiments, the set of HCDR1, HCDR2, and HCDR3 comprises the amino acid sequences set forth in SEQ ID NOs: 188, 345, and 357, respectively, and the set of LCDR1, LCDR2, and LCDR3 for the same antibody comprises the amino acid sequences set forth in SEQ ID NOs: 371, 377, and 396, respectively. In some embodiments, the set of HCDR1, HCDR2, and HCDR3 comprises the amino acid sequences set forth in SEQ ID NOs: 189, 346, and 358, respectively, and the set of LCDR1, LCDR2, and LCDR3 for the same antibody comprises the amino acid sequences set forth in SEQ ID NOs: 371, 377, and 397, respectively.

In another embodiment, the anti-TNFR2 antibodies comprises heavy chain and light chain CDR sequences that are at least 80% (e.g., at least 85%, 90%, 95%, 96%, 97%, 98%, or 99%) identical to the amino acid sequences set forth above, for example but not limited to identity as determined using BlastP software of the National Center of Biotechnology Information (NCBI) using default parameters.

A skilled artisan would appreciate that percent identity (% identity) provides a number that describes how similar the query sequence is to the target sequence (i.e., how many amino acids in each sequence are identical). The higher the percent identity is, the more significant the match.

When used in relation to polypeptide (or protein) sequences, the term "identity" refers to the degree of identity between two or more polypeptide (or protein) sequences or fragments thereof. Typically, the degree of similarity between two or more polypeptide (or protein) sequences refers to the degree of similarity of the composition, order, or arrangement of two or more amino acids of the two or more polypeptides (or proteins).

In yet some further embodiments, the set of HCDR1, HCDR2, HCDR3 on a heavy chain, and the set of LCDR1, LCDR2, LCDR3 on a corresponding light chain comprise the amino acid sequences as shown in Table 9. For the purpose of illustration, taking clone CID_264 as an example (see Table 9), the set of HCDR1, HCDR2, and HCDR3 for this antibody comprises the amino acid sequences of SEQ ID NO:402, SEQ ID NO:345, and SEQ ID NO:413, respectively (see Table 9), whereas the set of LCDR1, LCDR2, and LCDR3 for the same antibody comprises the amino acid sequences of SEQ ID NO:371, SEQ ID NO:418, and SEQ ID NO:427, respectively (see Table 9).

In some embodiments, the set of HCDR1, HCDR2, and HCDR3 comprises the amino acid sequences set forth in SEQ ID NOs: 402, 345, and 413, respectively, and the set of LCDR1, LCDR2, and LCDR3 for the same antibody comprises the amino acid sequences set forth in SEQ ID NOs: 371, 418, and 427, respectively. In some embodiments, the set of HCDR1, HCDR2, and HCDR3 comprises the amino acid sequences set forth in SEQ ID NOs: 398, 346, and 407, respectively, and the set of LCDR1, LCDR2, and LCDR3 for the same antibody comprises the amino acid sequences set forth in SEQ ID NOs: 371, 377, and 419, respectively. In some embodiments, the set of HCDR1, HCDR2, and HCDR3 comprises the amino acid sequences set forth in SEQ ID NOs: 187, 346, and 408, respectively, and the set of LCDR1, LCDR2, and LCDR3 for the same antibody comprises the amino acid sequences set forth in SEQ ID NOs: 371, 377, and 420, respectively. In some embodiments, the set of HCDR1, HCDR2, and HCDR3 comprises the amino acid sequences set forth in SEQ ID NOs: 189, 406, and 409, respectively, and the set of LCDR1, LCDR2, and LCDR3 for the same antibody comprises the amino acid sequences set forth in SEQ ID NOs: 371, 377, and 421, respectively. In some embodiments, the set of HCDR1, HCDR2, and HCDR3 comprises the amino acid sequences set forth in SEQ ID NOs: 187, 345, and 410, respectively, and the set of LCDR1, LCDR2, and LCDR3 for the same antibody comprises the amino acid sequences set forth in SEQ ID NOs: 371, 418, and 422, respectively. In some embodiments, the set of HCDR1, HCDR2, and HCDR3 comprises the amino acid sequences set forth in SEQ ID NOs: 399, 346, and 411, respectively, and the set of LCDR1, LCDR2, and LCDR3 for the same antibody comprises the amino acid sequences set forth in SEQ ID NOs: 371, 418, and 423, respectively. In some embodiments, the set of HCDR1, HCDR2, and HCDR3 comprises the amino acid sequences set forth in SEQ ID NOs: 400, 346, and 412, respectively, and the set of LCDR1, LCDR2, and LCDR3 for the same antibody comprises the amino acid sequences set forth in SEQ ID NOs: 417, 377, and 424, respectively. In some embodiments, the set of HCDR1, HCDR2, and HCDR3 comprises the amino acid sequences set forth in SEQ ID NOs: 401, 346, and 413, respectively, and the set of LCDR1, LCDR2, and LCDR3 for the same antibody comprises the amino acid sequences set forth in SEQ ID NOs: 417, 418, and 425, respectively. In some embodiments, the set of HCDR1, HCDR2, and HCDR3 comprises the amino acid sequences set forth in SEQ ID NOs: 401, 346, and 414, respectively, and the set of LCDR1, LCDR2, and LCDR3 for the same antibody comprises the amino acid sequences set forth in SEQ ID NOs: 417, 418, and 426, respectively. In some embodiments, the set of HCDR1, HCDR2, and HCDR3 comprises the amino acid sequences set forth in SEQ ID NOs: 398, 346, and 415, respectively, and the set of LCDR1, LCDR2, and LCDR3 for the same antibody comprises the amino acid sequences set forth in SEQ ID NOs: 417, 377, and 428, respectively. In some embodiments, the set of HCDR1, HCDR2, and HCDR3 comprises the amino acid sequences set forth in SEQ ID NOs: 403, 346, and 412, respectively, and the set of LCDR1, LCDR2, and LCDR3 for the same antibody comprises the amino acid sequences set forth in SEQ ID NOs: 371, 418, and 429, respectively. In some embodiments, the set of HCDR1, HCDR2, and HCDR3 comprises the amino acid sequences set forth in SEQ ID NOs: 404, 346, and 412, respectively, and the set of LCDR1, LCDR2, and LCDR3 for the same antibody comprises the amino acid sequences set forth in SEQ ID NOs: 371, 418, and 425, respectively. In some embodiments, the set of HCDR1, HCDR2, and HCDR3 comprises the amino acid sequences set forth in SEQ ID NOs: 401, 346, and 414, respectively, and the set of LCDR1, LCDR2, and LCDR3 for the same antibody comprises the amino acid sequences set forth in SEQ ID NOs: 417, 418, and 430, respectively. In some embodiments, the set of HCDR1, HCDR2, and HCDR3 comprises the amino acid sequences set forth in SEQ ID NOs: 405, 406, and 416, respectively, and the set of LCDR1, LCDR2, and LCDR3 for the same antibody comprises the amino acid sequences set forth in SEQ ID NOs: 371, 377, and 431, respectively.

In another embodiment, the anti-TNFR2 antibodies comprises heavy chain and light chain CDR sequences that are at least 80% (e.g., at least 85%, 90%, 95%, 96%, 97%, 98%, or 99%) identical to the amino acid sequences set forth above, for example but not limited to as determined using BlastP software of the National Center of Biotechnology Information (NCBI) using default parameters.

In one embodiment, each of the anti-TNFR2 antibodies presented herein comprises a heavy chain variable region (VH) and a light chain variable region (VL), wherein the amino acid sequences for the heavy chain variable region and the light chain variable region can be one of the following pairs: SEQ ID NOs:289-290, SEQ ID NOs:3-4, SEQ ID NOs:7-8, SEQ ID NOs:11-12, SEQ ID NOs:15-16, SEQ ID NOs:19-20, SEQ ID NOs:23-24, SEQ ID NOs:27-28, SEQ ID NOs:31-32, SEQ ID NOs:35-36, SEQ ID NOs:39-40, SEQ ID NOs:43-44, SEQ ID NOs:47-48, SEQ ID NOs:51-52, SEQ ID NOs:55-56, SEQ ID NOs:59-60, SEQ ID NOs:63-64, SEQ ID NOs:67-68, SEQ ID NOs:71-72, SEQ ID NOs:75-76, SEQ ID NOs:79-80, SEQ ID NOs:83-84, SEQ ID NOs:87-88, SEQ ID NOs:91-92, SEQ ID NOs:95-96, SEQ ID NOs:99-100, SEQ ID NOs:103-104, SEQ ID NOs:107-108, SEQ ID NOs:111-112, SEQ ID NOs:115-116, SEQ ID NOs:119-120, SEQ ID NOs:123-124, SEQ ID NOs:127-128, SEQ ID NOs:131-132, SEQ ID NOs:135-136, SEQ ID NOs:139-140, SEQ ID NOs:143-144, SEQ ID NOs:147-148, SEQ ID NOs:151-152, SEQ ID NOs:157-158, SEQ ID NOs:163-164, SEQ ID NOs:169-170, SEQ ID NOs:175-176, SEQ ID NOs:181-182, SEQ ID NOs:193-194, SEQ ID NOs:199-200, SEQ ID NOs:205-

206, SEQ ID NOs:211-212, SEQ ID NOs:217-218, SEQ ID NOs:223-224, SEQ ID NOs:229-230, SEQ ID NOs:233-234, SEQ ID NOs:237-238, SEQ ID NOs:241-242, SEQ ID NOs:245-246, SEQ ID NOs:249-250, SEQ ID NOs:253-254, SEQ ID NOs:257-258, SEQ ID NOs:261-262, SEQ ID NOs:265-266, SEQ ID NOs:269-270, SEQ ID NOs:273-274, SEQ ID NOs:277-278, SEQ ID NOs:281-282, SEQ ID NOs:285-286, SEQ ID NOs:293-294, SEQ ID NOs:297-298, SEQ ID NOs:301-302, SEQ ID NOs:305-306, SEQ ID NOs:309-310, SEQ ID NOs:313-314, SEQ ID NOs:317-318, SEQ ID NOs:321-322, SEQ ID NOs:325-326, or SEQ ID NOs:329-330.

In some embodiments, the amino acid sequences for the heavy chain variable region and the light chain variable region of an anti-TNFR2 antibody disclosed herein is set forth in SEQ ID NOs:289-290. In some embodiments, the amino acid sequences for the heavy chain variable region and the light chain variable region of an anti-TNFR2 antibody disclosed herein is set forth in SEQ ID NOs:3-4. In some embodiments, the amino acid sequences for the heavy chain variable region and the light chain variable region of an anti-TNFR2 antibody disclosed herein is set forth in SEQ ID NOs:7-8. In some embodiments, the amino acid sequences for the heavy chain variable region and the light chain variable region of an anti-TNFR2 antibody disclosed herein is set forth in SEQ ID NOs:11-12. In some embodiments, the amino acid sequences for the heavy chain variable region and the light chain variable region of an anti-TNFR2 antibody disclosed herein is set forth in SEQ ID NOs:15-16. In some embodiments, the amino acid sequences for the heavy chain variable region and the light chain variable region of an anti-TNFR2 antibody disclosed herein is set forth in SEQ ID NOs:19-20. In some embodiments, the amino acid sequences for the heavy chain variable region and the light chain variable region of an anti-TNFR2 antibody disclosed herein is set forth in SEQ ID NOs:23-24. In some embodiments, the amino acid sequences for the heavy chain variable region and the light chain variable region of an anti-TNFR2 antibody disclosed herein is set forth in SEQ ID NOs:27-28. In some embodiments, the amino acid sequences for the heavy chain variable region and the light chain variable region of an anti-TNFR2 antibody disclosed herein is set forth in SEQ ID NOs:31-32. In some embodiments, the amino acid sequences for the heavy chain variable region and the light chain variable region of an anti-TNFR2 antibody disclosed herein is set forth in SEQ ID NOs:35-36. In some embodiments, the amino acid sequences for the heavy chain variable region and the light chain variable region of an anti-TNFR2 antibody disclosed herein is set forth in SEQ ID NOs:39-40. In some embodiments, the amino acid sequences for the heavy chain variable region and the light chain variable region of an anti-TNFR2 antibody disclosed herein is set forth in SEQ ID NOs:43-44. In some embodiments, the amino acid sequences for the heavy chain variable region and the light chain variable region of an anti-TNFR2 antibody disclosed herein is set forth in SEQ ID NOs:47-48. In some embodiments, the amino acid sequences for the heavy chain variable region and the light chain variable region of an anti-TNFR2 antibody disclosed herein is set forth in SEQ ID NOs:51-52. In some embodiments, the amino acid sequences for the heavy chain variable region and the light chain variable region of an anti-TNFR2 antibody disclosed herein is set forth in SEQ ID NOs:55-56. In some embodiments, the amino acid sequences for the heavy chain variable region and the light chain variable region of an anti-TNFR2 antibody disclosed herein is set forth in SEQ ID NOs:59-60. In some embodiments, the amino acid sequences for the heavy chain variable region and the light chain variable region of an anti-TNFR2 antibody disclosed herein is set forth in SEQ ID NOs:63-64. In some embodiments, the amino acid sequences for the heavy chain variable region and the light chain variable region of an anti-TNFR2 antibody disclosed herein is set forth in SEQ ID NOs:67-68. In some embodiments, the amino acid sequences for the heavy chain variable region and the light chain variable region of an anti-TNFR2 antibody disclosed herein is set forth in SEQ ID NOs:71-72. In some embodiments, the amino acid sequences for the heavy chain variable region and the light chain variable region of an anti-TNFR2 antibody disclosed herein is set forth in SEQ ID NOs:75-76. In some embodiments, the amino acid sequences for the heavy chain variable region and the light chain variable region of an anti-TNFR2 antibody disclosed herein is set forth in SEQ ID NOs:79-80. In some embodiments, the amino acid sequences for the heavy chain variable region and the light chain variable region of an anti-TNFR2 antibody disclosed herein is set forth in SEQ ID NOs:83-84. In some embodiments, the amino acid sequences for the heavy chain variable region and the light chain variable region of an anti-TNFR2 antibody disclosed herein is set forth in SEQ ID NOs:87-88. In some embodiments, the amino acid sequences for the heavy chain variable region and the light chain variable region of an anti-TNFR2 antibody disclosed herein is set forth in SEQ ID NOs:91-92. In some embodiments, the amino acid sequences for the heavy chain variable region and the light chain variable region of an anti-TNFR2 antibody disclosed herein is set forth in SEQ ID NOs:95-96. In some embodiments, the amino acid sequences for the heavy chain variable region and the light chain variable region of an anti-TNFR2 antibody disclosed herein is set forth in SEQ ID NOs:99-100. In some embodiments, the amino acid sequences for the heavy chain variable region and the light chain variable region of an anti-TNFR2 antibody disclosed herein is set forth in SEQ ID NOs:103-104. In some embodiments, the amino acid sequences for the heavy chain variable region and the light chain variable region of an anti-TNFR2 antibody disclosed herein is set forth in SEQ ID NOs:107-108. In some embodiments, the amino acid sequences for the heavy chain variable region and the light chain variable region of an anti-TNFR2 antibody disclosed herein is set forth in SEQ ID NOs:111-112. In some embodiments, the amino acid sequences for the heavy chain variable region and the light chain variable region of an anti-TNFR2 antibody disclosed herein is set forth in SEQ ID NOs:115-116. In some embodiments, the amino acid sequences for the heavy chain variable region and the light chain variable region of an anti-TNFR2 antibody disclosed herein is set forth in SEQ ID NOs:119-120. In some embodiments, the amino acid sequences for the heavy chain variable region and the light chain variable region of an anti-TNFR2 antibody disclosed herein is set forth in SEQ ID NOs:123-124. In some embodiments, the amino acid sequences for the heavy chain variable region and the light chain variable region of an anti-TNFR2 antibody disclosed herein is set forth in SEQ ID NOs:127-128. In some embodiments, the amino acid sequences for the heavy chain variable region and the light chain variable region of an anti-TNFR2 antibody disclosed herein is set forth in SEQ ID NOs:131-132. In some embodiments, the amino acid sequences for the heavy chain variable region and the light chain variable region of an anti-TNFR2 antibody disclosed herein is set forth in SEQ ID NOs:135-136. In some embodiments, the amino acid sequences for the heavy chain variable region and the light chain variable region of an anti-TNFR2 antibody disclosed herein is set forth in SEQ ID NOs:139-140. In some embodiments, the amino acid sequences for the heavy chain variable region and the light chain variable region of an anti-TNFR2 antibody disclosed herein is set forth in SEQ ID NOs:143-144. In some embodiments, the amino acid sequences for the heavy chain variable region and the light chain variable region of an anti-TNFR2 antibody disclosed herein is set forth in SEQ ID NOs:147-148. In some embodiments, the amino acid sequences for the heavy chain variable region and the light chain variable region of an anti-TNFR2 antibody disclosed herein is set forth in SEQ ID NOs:151-152. In some embodiments, the amino acid sequences for the heavy chain variable region and the light chain variable region of an anti-TNFR2 antibody disclosed herein is set forth in SEQ ID NOs:157-158. In some embodiments, the amino acid sequences for the heavy chain variable region and the light chain variable region of an anti-TNFR2 antibody disclosed herein is set forth in SEQ ID NOs:163-164. In some embodiments, the amino acid sequences for the heavy chain variable region and the light chain variable region of an anti-TNFR2 antibody disclosed herein is set forth in SEQ ID NOs:169-170. In some embodiments, the amino acid sequences for the heavy chain variable region and the light chain variable region of an anti-TNFR2 antibody disclosed herein is set forth in SEQ ID NOs:175-176. In some embodiments, the amino acid sequences for the heavy chain variable region and the light chain variable region of an anti-TNFR2 antibody disclosed herein is set forth in SEQ ID NOs:181-182. In some embodiments, the amino acid sequences for the heavy chain variable region and the light chain variable region of an anti-TNFR2 antibody disclosed herein is set forth in SEQ ID NOs:193-194. In some embodiments, the amino acid sequences for the heavy chain variable region and the light chain variable region of an anti-TNFR2 antibody disclosed herein is set forth in SEQ ID NOs:199-200. In some embodiments, the amino acid sequences for the heavy chain variable region and the light chain variable region of an anti-TNFR2 antibody disclosed herein is set forth in SEQ ID NOs:205-206. In some embodiments, the amino acid sequences for the heavy chain variable region and the light chain variable region of an anti-TNFR2 antibody disclosed herein is set forth in SEQ ID NOs:211-212. In some embodiments, the amino acid sequences for the heavy chain variable region and the light chain variable region of an anti-TNFR2 antibody disclosed herein is set forth in SEQ ID NOs:217-218. In some embodiments, the amino acid sequences for the heavy chain variable region and the light chain variable region of an anti-TNFR2 antibody disclosed herein is set forth in SEQ ID NOs:223-224. In some embodiments, the amino acid sequences for the heavy chain variable region and the light chain variable region of an anti-TNFR2 antibody disclosed herein is set forth in SEQ ID NOs:229-230. In some embodiments, the amino acid sequences for the heavy chain variable region and the light chain variable region of an anti-TNFR2 antibody disclosed herein is set forth in SEQ ID NOs:233-234. In some embodiments, the amino acid sequences for the heavy chain variable region and the light chain variable region of an anti-TNFR2 antibody disclosed herein is set forth in SEQ ID NOs:237-238. In some embodiments, the amino acid sequences for the heavy chain variable region and the light chain variable region of an anti-TNFR2 antibody disclosed herein is set forth in SEQ ID NOs:241-242. In some embodiments, the amino acid sequences for the heavy chain variable region and the light chain variable region of an anti-TNFR2 antibody disclosed herein is set forth in SEQ ID NOs:245-246. In some embodiments, the amino acid sequences for the heavy chain variable region and the light chain variable region of an anti-TNFR2 antibody disclosed herein is set forth in SEQ ID NOs:249-250. In some embodiments, the amino acid sequences for the heavy chain variable region and the light chain variable region of an anti-TNFR2 antibody disclosed herein is set forth in SEQ ID NOs:253-254. In some embodiments, the amino acid sequences for the heavy chain variable region and the light chain variable region of an anti-TNFR2 antibody disclosed herein is set forth in SEQ ID NOs:257-258. In some embodiments, the amino acid sequences for the heavy chain variable region and the light chain variable region of an anti-TNFR2 antibody disclosed herein is set forth in SEQ ID NOs:261-262. In some embodiments, the amino acid sequences for the heavy chain variable region and the light chain variable region of an anti-TNFR2 antibody disclosed herein is set forth in SEQ ID NOs:265-266. In some embodiments, the amino acid sequences for the heavy chain variable region and the light chain variable region of an anti-TNFR2 antibody disclosed herein is set forth in SEQ ID NOs:269-270. In some embodiments, the amino acid sequences for the heavy chain variable region and the light chain variable region of an anti-TNFR2 antibody disclosed herein is set forth in SEQ ID NOs:273-274. In some embodiments, the amino acid sequences for the heavy chain variable region and the light chain variable region of an anti-TNFR2 antibody disclosed herein is set forth in SEQ ID NOs:277-278. In some embodiments, the amino acid sequences for the heavy chain variable region and the light chain variable region of an anti-TNFR2 antibody disclosed herein is set forth in SEQ ID NOs:281-282. In some embodiments, the amino acid sequences for the heavy chain variable region and the light chain variable region of an anti-TNFR2 antibody disclosed herein is set forth in SEQ ID NOs:285-286. In some embodiments, the amino acid sequences for the heavy chain variable region and the light chain variable region of an anti-TNFR2 antibody disclosed herein is set forth in SEQ ID NOs:293-294. In some embodiments, the amino acid sequences for the heavy chain variable region and the light chain variable region of an anti-TNFR2 antibody disclosed herein is set forth in SEQ ID NOs:297-298. In some embodiments, the amino acid sequences for the heavy chain variable region and the light chain variable region of an anti-TNFR2 antibody disclosed herein is set forth in SEQ ID NOs:301-302. In some embodiments, the amino acid sequences for the heavy chain variable region and the light chain variable region of an anti-TNFR2 antibody disclosed herein is set forth in SEQ ID NOs:305-306. In some embodiments, the amino acid sequences for the heavy chain variable region and the light chain variable region of an anti-TNFR2 antibody disclosed herein is set forth in SEQ ID NOs:309-310. In some embodiments, the amino acid sequences for the heavy chain variable region and the light chain variable region of an anti-TNFR2 antibody disclosed herein is set forth in SEQ ID NOs:313-314. In some embodiments, the amino acid sequences for the heavy chain variable region and the light chain variable region of an anti-TNFR2 antibody disclosed herein is set forth in SEQ ID NOs:317-318. In some embodiments, the amino acid sequences for the heavy chain variable region and the light chain variable region of an anti-TNFR2 antibody disclosed herein is set forth in SEQ ID NOs:321-322. In some embodiments, the amino acid sequences for the heavy chain variable region and the light chain variable region of an anti-TNFR2 antibody disclosed herein is set forth in SEQ ID NOs:325-326. In some embodiments, the amino acid sequences for the heavy chain variable region and the light chain variable region of an anti-TNFR2 antibody disclosed herein is set forth in or SEQ ID NOs:329-330.

In another embodiment, the anti-TNFR2 antibodies comprise VH and VL sequences that are at least 80% (e.g., at least 85%, 90%, 95%, 96%, 97%, 98%, or 99%) identical to the amino acid sequences set forth above, for example but not limited to as determined using BlastP software of the National Center of Biotechnology Information (NCBI) using default parameters.

In a further embodiment, provided herein is an anti-TNFR2 scFv. In view of the sequences for the heavy chain variable regions and light chain variable regions disclosed herein, one of ordinary skill in the art could readily construct an anti-TNFR2 scFv using standard techniques known in the art.

In certain embodiments, the present disclosure provides polypeptides comprising the VH and VL domains which can be dimerized under suitable conditions. For example, the VH and VL domains may be combined in a suitable buffer and dimerized through appropriate interactions such as hydrophobic interactions. Alternatively, the VH and VL domains may be combined in a suitable buffer containing an enzyme and/or a cofactor which can promote dimerization of the VH and VL domains. In yet a another approach, the VH and VL domains may be combined in a suitable vehicle that allows them to react with each other in the presence of a suitable reagent and/or catalyst.

In certain embodiments, the VH and VL domains may be contained within longer polypeptide sequences that may include for example, but are not limited to, constant regions, hinge regions, linker regions, Fc regions, or disulfide binding regions, or any combination thereof. A constant domain is an immunoglobulin fold unit of the constant part of an immunoglobulin molecule, also referred to as a domain of the constant region (e.g. CH1, CH2, CH3, CH4, Ck, Cl). In some embodiments, the longer polypeptides may comprise multiple copies of one or both of the VH and VL domains generated according to the methods disclosed herein; for example, when the polypeptides generated herein are used to form a diabody or a triabody.

In another embodiment, each of the anti-TNFR2 antibodies presented herein comprises a heavy chain and a light chain, wherein the amino acid sequences for the heavy chain and the light chain can be one of the following pairs: SEQ ID NOs: 438 and 292, SEQ ID NOs:291-292, SEQ ID NOs:235-236, SEQ ID NOs:239-240, SEQ ID NOs:243-244, SEQ ID NOs:247-248, SEQ ID NOs:251-252, SEQ ID NOs:255-256, SEQ ID NOs:259-260, SEQ ID NOs:263-264, SEQ ID NOs:267-268, SEQ ID NOs:271-272, SEQ ID NOs:275-276, SEQ ID NOs:279-280, SEQ ID NOs:283-284, SEQ ID NOs:287-288, SEQ ID NOs:295-296, SEQ ID NOs:299-300, SEQ ID NOs:303-304, SEQ ID NOs:307-308, SEQ ID NOs:311-312, SEQ ID NOs:315-316, SEQ ID NOs:319-320, SEQ ID NOs:323-324, SEQ ID NOs:327-328, SEQ ID NOs:331-332, SEQ ID NOs: 432 and 260, SEQ ID NOs: 433 and 304, SEQ ID NOs: 434 and 308, SEQ ID NOs: 435 and 236, SEQ ID NOs: 436 and 244, SEQ ID NOs: 437 and 284, or SEQ ID NOs: 439 and 296.

In some embodiments, an anti-TNFR2 antibody comprises a heavy chain and a light chain, wherein the amino acid sequences for the heavy chain and the light chain are set forth in SEQ ID NOs: 438 and 292. In some embodiments, an anti-TNFR2 antibody comprises a heavy chain and a light chain, wherein the amino acid sequences for the heavy chain and the light chain are set forth in SEQ ID NOs:291-292. In some embodiments, an anti-TNFR2 antibody comprises a heavy chain and a light chain, wherein the amino acid sequences for the heavy chain and the light chain are set forth in SEQ ID NOs:235-236. In some embodiments, an anti-TNFR2 antibody comprises a heavy chain and a light chain, wherein the amino acid sequences for the heavy chain and the light chain are set forth in SEQ ID NOs:239-240. In some embodiments, an anti-TNFR2 antibody comprises a heavy chain and a light chain, wherein the amino acid sequences for the heavy chain and the light chain are set forth in SEQ ID NOs:243-244. In some embodiments, an anti-TNFR2 antibody comprises a heavy chain and a light chain, wherein the amino acid sequences for the heavy chain and the light chain are set forth in SEQ ID NOs:247-248. In some embodiments, an anti-TNFR2 antibody comprises a heavy chain and a light chain, wherein the amino acid sequences for the heavy chain and the light chain are set forth in SEQ ID NOs:251-252. In some embodiments, an anti-TNFR2 antibody comprises a heavy chain and a light chain, wherein the amino acid sequences for the heavy chain and the light chain are set forth in SEQ ID NOs:255-256. In some embodiments, an anti-TNFR2 antibody comprises a heavy chain and a light chain, wherein the amino acid sequences for the heavy chain and the light chain are set forth in SEQ ID NOs:259-260. In some embodiments, an anti-TNFR2 antibody comprises a heavy chain and a light chain, wherein the amino acid sequences for the heavy chain and the light chain are set forth in SEQ ID NOs:263-264. In some embodiments, an anti-TNFR2 antibody comprises a heavy chain and a light chain, wherein the amino acid sequences for the heavy chain and the light chain are set forth in SEQ ID NOs:267-268. In some embodiments, an anti-TNFR2 antibody comprises a heavy chain and a light chain, wherein the amino acid sequences for the heavy chain and the light chain are set forth in SEQ ID NOs:271-272. In some embodiments, an anti-TNFR2 antibody comprises a heavy chain and a light chain, wherein the amino acid sequences for the heavy chain and the light chain are set forth in SEQ ID NOs:275-276. In some embodiments, an anti-TNFR2 antibody comprises a heavy chain and a light chain, wherein the amino acid sequences for the heavy chain and the light chain are set forth in SEQ ID NOs:279-280. In some embodiments, an anti-TNFR2 antibody comprises a heavy chain and a light chain, wherein the amino acid sequences for the heavy chain and the light chain are set forth in SEQ ID NOs:283-284. In some embodiments, an anti-TNFR2 antibody comprises a heavy chain and a light chain, wherein the amino acid sequences for the heavy chain and the light chain are set forth in SEQ ID NOs:287-288. In some embodiments, an anti-TNFR2 antibody comprises a heavy chain and a light chain, wherein the amino acid sequences for the heavy chain and the light chain are set forth in SEQ ID NOs:295-296. In some embodiments, an anti-TNFR2 antibody comprises a heavy chain and a light chain, wherein the amino acid sequences for the heavy chain and the light chain are set forth in SEQ ID NOs:299-300. In some embodiments, an anti-TNFR2 antibody comprises a heavy chain and a light chain, wherein the amino acid sequences for the heavy chain and the light chain are set forth in SEQ ID NOs:303-304. In some embodiments, an anti-TNFR2 antibody comprises a heavy chain and a light chain, wherein the amino acid sequences for the heavy chain and the light chain are set forth in SEQ ID NOs:307-308. In some embodiments, an anti-TNFR2 antibody comprises a heavy chain and a light chain, wherein the amino acid sequences for the heavy chain and the light chain are set forth in SEQ ID NOs:311-312. In some embodiments, an anti-TNFR2 antibody comprises a heavy chain and a light chain, wherein the amino acid sequences for the heavy chain and the light chain are set forth in SEQ ID NOs:315-316. In some embodiments, an anti-TNFR2 antibody comprises a heavy chain and a light chain, wherein the amino acid sequences for the heavy chain and the light chain are set forth in SEQ ID NOs:319-320. In some embodiments, an anti-TNFR2 antibody comprises a heavy chain and a light chain, wherein the amino acid sequences for the heavy chain and the light chain are set forth in SEQ ID NOs:323-324. In some embodiments, an anti-TNFR2 antibody comprises a heavy chain and a light chain, wherein the amino acid sequences for the heavy chain and the light chain are set forth in SEQ ID NOs:327-328. In some embodiments, an anti-TNFR2 antibody comprises a heavy chain and a light chain, wherein the amino acid sequences for the heavy chain and the light chain are set forth in SEQ ID NOs:331-332. In some embodiments, an anti-TNFR2 antibody comprises a heavy chain and a light chain, wherein the amino acid sequences for the heavy chain and the light chain are set forth in SEQ ID NOs: 432 and 260. In some embodiments, an anti-TNFR2 antibody comprises a heavy chain and a light chain, wherein the amino acid sequences for the heavy chain and the light chain are set forth in SEQ ID NOs: 433 and 304. In some embodiments, an anti-TNFR2 antibody comprises a heavy chain and a light chain, wherein the amino acid sequences for the heavy chain and the light chain are set forth in SEQ ID NOs: 434 and 308. In some embodiments, an anti-TNFR2 antibody comprises a heavy chain and a light chain, wherein the amino acid sequences for the heavy chain and the light chain are set forth in SEQ ID NOs: 435 and 236. In some embodiments, an anti-TNFR2 antibody comprises a heavy chain and a light chain, wherein the amino acid sequences for the heavy chain and the light chain are set forth in SEQ ID NOs: 436 and 244. In some embodiments, an anti-TNFR2 antibody comprises a heavy chain and a light chain, wherein the amino acid sequences for the heavy chain and the light chain are set forth in SEQ ID NOs: 437 and 284. In some embodiments, an anti-TNFR2 antibody comprises a heavy chain and a light chain, wherein the amino acid sequences for the heavy chain and the light chain are set forth in or SEQ ID NOs: 439 and 296.

In another embodiment, the anti-TNFR2 antibodies comprises heavy chain and light chain amino acid sequences that are at least 80% (e.g., at least 85%, 90%, 95%, 96%, 97%, 98%, or 99%) identical to the amino acid sequences set forth above, for example but not limited to as determined using BlastP software of the National Center of Biotechnology Information (NCBI) using default parameters.

In one embodiment, the anti-TNFR2 antibody presented herein can be an IgG, a Fv, a scFv, a Fab, a F(ab')2, a minibody, a diabody, a triabody, a nanobody, a bispecific antibody, or a single domain antibody. For example, the anti-TNFR2 antibody can be an IgG antibody such as an IgG1, IgG2, IgG3, or IgG4 antibody. In some embodiments, the anti-TNFR2 antibody is an IgG1 antibody. In some other embodiments, the anti-TNFR2 antibody is an IgG2 antibody. In yet some other embodiments, the anti-TNFR2 antibody is an IgG3 antibody. In some further embodiments, the anti-TNFR2 antibody is an IgG4 antibody.

In some embodiments, the anti-TNFR2 antibody presented herein can agonize TNFR2. In some embodiments, the anti-TNFR2 antibody presented herein can agonize TNFR2 in an Fc independent manner.

In one embodiment, the present disclosure provides antibodies that bind with high affinity to TNFR2. In one embodiment, binding affinity is calculated by a modification of the Scatchard method as described by Frankel et al. (Mol. Immunol., 16:101-106, 1979). In another embodiment, binding affinity is measured by an antigen/antibody dissociation rate. In another embodiment, binding affinity is measured by a competition radioimmunoassay. In another embodiment, binding affinity is measured by ELISA. In another embodiment, antibody affinity is measured by flow cytometry.

In one embodiment, the anti-TNFR2 antibody presented herein activates signaling through TNFR2 at a level of at least 80% as compared to signaling activated by TNF. In another embodiment, the anti-TNFR2 antibody presented herein activates signaling through TNFR2 at a level of at least 85%, at least 90%, at least 95%, at least 99%, or at least 100% as compared to signaling activated by TNF.

In one embodiment, the present disclosure also provides isolated polynucleotide sequences encoding the heavy chain and light chain CDRs as described herein. In another embodiment, the present disclosure provides a vector comprising such polynucleotide sequences. In view of the amino acid sequences disclosed herein, one of ordinary skill in the art would be able to readily construct a vector or plasmid encoding the amino acid sequences. In another embodiment, the present disclosure also provides a host cell comprising such vector as provided herein. Depending on the uses and experimental conditions, one of skill in the art would readily employ a suitable host cell to carry and/or express the above-mentioned polynucleotide sequences. In some embodiments, a host cell comprises a mammalian host cell, such as for example but not limited to ExpiCHO™ and Expi293F™ (ThermoFisher, USA)

In one embodiment, the present disclosure also provides isolated polynucleotide sequences encoding the heavy chain and light chain variable regions as described herein. In another embodiment, the present disclosure also provides a vector comprising such polynucleotide sequences. In view of the amino acid sequences disclosed herein, one of ordinary skill in the art would readily construct a vector or plasmid to encode for the amino acid sequences. In another embodiment, the present disclosure also provides a host cell comprising the vector provided herein. Depending on the uses and experimental conditions, one of skill in the art would readily employ a suitable host cell to carry and/or express the above-mentioned polynucleotide sequences.

In one embodiment, the present disclosure also provides isolated polynucleotide sequence encoding the heavy chains and light chains as described herein. In another embodiment, the present disclosure also provides a vector comprising such polynucleotide sequences. In view of the amino acid sequences disclosed herein, one of ordinary skill in the art would readily construct a vector or plasmid to encode for the amino acid sequences. In another embodiment, the present disclosure also provides a host cell comprising the vector provided herein. Depending on the uses and experimental conditions, one of skill in the art would readily employ a suitable host cell to carry and/or express the above-mentioned polynucleotide sequences.

Compositions of Use

In one embodiment, the present disclosure also provides a composition comprising the anti-TNFR2 antibody disclosed herein and a pharmaceutically acceptable carrier. Pharmaceutically acceptable carriers of use are well-known in the art. For example, Remington's Pharmaceutical Sciences, by E.W. Martin, Mack Publishing Co., Easton, PA, 23rd Edition, 2020, describes compositions and formulations suitable for pharmaceutical delivery of the antibodies disclosed herein.

A composition comprising an anti-TNFR2 antibody or an antigen-binding fragment thereof, disclosed herein, can be administered to a subject (e.g. a human or an animal) alone, or in combination with a carrier, i.e., a pharmaceutically acceptable carrier. By pharmaceutically acceptable is meant a material that is not biologically or otherwise undesirable, i.e., the material can be administered to a subject without causing any undesirable biological effects or interacting in a deleterious manner with any of the other components of the pharmaceutical composition in which it is contained. As would be well-known to one of ordinary skill in the art, the carrier is selected to minimize any degradation of the polypeptides disclosed herein and to minimize any adverse side effects in the subject. The pharmaceutical compositions may be prepared by methodologies well known in the pharmaceutical art.

In one embodiment, the composition comprises anti-TNFR2 antibodies that comprise a set of three complementarity determining regions (CDRs) on a heavy chain (HCDR1, HCDR2, and HCDR3) and a set of three CDRs on a light chain (LCDR1, LCDR2, and LCDR3). In one embodiment, the set of HCDR1, HCDR2, and HCDR3 comprises the amino acid sequences as shown in Table 7, and the set of LCDR1, LCDR2, and LCDR3 on a corresponding light chain comprises the amino acid sequences as shown in Table 8, as described above.

In some embodiments, the composition comprises an anti-TNFR2 antibody comprising HCDR1, HCDR2, and HCDR3 amino acid sequences as set forth in SEQ ID NOs: 185, 190, and 347, respectively, and LCDR1, LCDR2, and LCDR3 amino acid sequences as set forth in SEQ ID NOs: 359, 372, and 378, respectively. In some embodiments, the composition comprises an anti-TNFR2 antibody comprising HCDR1, HCDR2, and HCDR3 amino acid sequences as set forth in SEQ ID NOs: 185, 190, and 347, respectively, and LCDR1, LCDR2, and LCDR3 amino acid sequences as set forth in SEQ ID NOs: 359, 372, and 378, respectively. In some embodiments, the composition comprises an anti-TNFR2 antibody comprising HCDR1, HCDR2, and HCDR3 amino acid sequences as set forth in SEQ ID NOs: 185, 334, 347, respectively, and LCDR1, LCDR2, and LCDR3 amino acid sequences as set forth in SEQ ID NOs: 360, 372, and 379, respectively. In some embodiments, the composition comprises an anti-TNFR2 antibody comprising HCDR1, HCDR2, and HCDR3 amino acid sequences as set forth in SEQ ID NOs: 185, 190, and 347, respectively, and LCDR1, LCDR2, and LCDR3 amino acid sequences as set forth in SEQ ID NOs: 359, 372, and 380, respectively. In some embodiments, the composition comprises an anti-TNFR2 antibody comprising HCDR1, HCDR2, and HCDR3 amino acid sequences as set forth in SEQ ID NOs: 185, 190, and 347, respectively, and LCDR1, LCDR2, and LCDR3 amino acid sequences as set forth in SEQ ID NOs: 359, 372, and 381, respectively. In some embodiments, the composition comprises an anti-TNFR2 antibody comprising HCDR1, HCDR2, and HCDR3 amino acid sequences as set forth in SEQ ID NOs: 185, 190, and 347, respectively, and LCDR1, LCDR2, and LCDR3 amino acid sequences as set forth in SEQ ID NOs: 361, 372, and 381, respectively. In some embodiments, the composition comprises an anti-TNFR2 antibody comprising HCDR1, HCDR2, and HCDR3 amino acid sequences as set forth in SEQ ID NOs: 185, 190, and 347, respectively, and LCDR1, LCDR2, and LCDR3 amino acid sequences as set forth in SEQ ID NOs: 362, 372, and 382, respectively. In some embodiments, the composition comprises an anti-TNFR2 antibody comprising HCDR1, HCDR2, and HCDR3 amino acid sequences as set forth in SEQ ID NOs: 185, 335, and 347, respectively, and LCDR1, LCDR2, and LCDR3 amino acid sequences as set forth in SEQ ID NOs: 363, 372, and 383, respectively. In some embodiments, the composition comprises an anti-TNFR2 antibody comprising HCDR1, HCDR2, and HCDR3 amino acid sequences as set forth in SEQ ID NOs: 185, 190, 347, respectively, and the set of LCDR1, LCDR2, and LCDR3 for the same antibody comprises the amine acid sequences set forth in SEQ ID NOs: 364, 372, and 384, respectively. In some embodiments, the composition comprises an anti-TNFR2 antibody comprising HCDR1, HCDR2, and HCDR3 amino acid sequences as set forth in SEQ ID NOs: 185, 336, and 348, respectively, and LCDR1, LCDR2, and LCDR3 amino acid sequences as set forth in SEQ ID NOs: 365, 372, and 378, respectively. In some embodiments, the composition comprises an anti-TNFR2 antibody comprising HCDR1, HCDR2, and HCDR3 amino acid sequences as set forth in SEQ ID NOs: 185, 337, and 347, respectively, and LCDR1, LCDR2, and LCDR3 amino acid sequences as set forth in SEQ ID NOs: 359, 373, and 385, respectively. In some embodiments, the composition comprises an anti-TNFR2 antibody comprising HCDR1, HCDR2, and HCDR3 amino acid sequences as set forth in SEQ ID NOs: 185, 338, and 348, respectively, and LCDR1, LCDR2, and LCDR3 amino acid sequences as set forth in SEQ ID NOs: 359, 372, and 386, respectively. In some embodiments, the composition comprises an anti-TNFR2 antibody comprising HCDR1, HCDR2, and HCDR3 amino acid sequences as set forth in SEQ ID NOs: 185, 339, and 349, respectively, and LCDR1, LCDR2, and LCDR3 amino acid sequences as set forth in SEQ ID NOs: 359, 372, and 378, respectively. In some embodiments, the composition comprises an anti-TNFR2 antibody comprising HCDR1, HCDR2, and HCDR3 amino acid sequences as set forth in SEQ ID NOs: 185, 190, and 350, respectively, and LCDR1, LCDR2, and LCDR3 amino acid sequences as set forth in SEQ ID NOs: 366, 372, and 387, respectively. In some embodiments, the composition comprises an anti-TNFR2 antibody comprising HCDR1, HCDR2, and HCDR3 amino acid sequences as set forth in SEQ ID NOs: 185, 190, and 351, respectively, and LCDR1, LCDR2, and LCDR3 amino acid sequences as set forth in SEQ ID NOs: 359, 372, and 378, respectively. In some embodiments, the composition comprises an anti-TNFR2 antibody comprising HCDR1, HCDR2, and HCDR3 amino acid sequences as set forth in SEQ ID NOs: 185, 334, and 347, respectively, and LCDR1, LCDR2, and LCDR3 amino acid sequences as set forth in SEQ ID NOs: 360, 372, and 388, respectively. In some embodiments, the composition comprises an anti-TNFR2 antibody comprising HCDR1, HCDR2, and HCDR3 amino acid sequences as set forth in SEQ ID NOs: 185, 334, and 352, respectively, and LCDR1, LCDR2, and LCDR3 amino acid sequences as set forth in SEQ ID NOs: 359, 372, and 378, respectively. In some embodiments, the composition comprises an anti-TNFR2 antibody comprising HCDR1, HCDR2, and HCDR3 amino acid sequences as set forth in SEQ ID NOs: 185, 190, and 352, respectively, and LCDR1, LCDR2, and LCDR3 amino acid sequences as set forth in SEQ ID NOs: 359, 372, and 389, respectively. In some embodiments, the composition comprises an anti-TNFR2 antibody comprising HCDR1, HCDR2, and HCDR3 amino acid sequences as set forth in SEQ ID NOs: 185, 334, and 347, respectively, and LCDR1, LCDR2, and LCDR3 amino acid sequences as set forth in SEQ ID NOs: 359, 372, and 378, respectively. In some embodiments, the composition comprises an anti-TNFR2 antibody comprising HCDR1, HCDR2, and HCDR3 amino acid sequences as set forth in SEQ ID NOs: 185, 190, and 347, respectively, and LCDR1, LCDR2, and LCDR3 amino acid sequences as set forth in SEQ ID NOs: 365, 372, and 378, respectively. In some embodiments, the composition comprises an anti-TNFR2 antibody comprising HCDR1, HCDR2, and HCDR3 amino acid sequences as set forth in SEQ ID NOs: 185, 336, and 352, respectively, and LCDR1, LCDR2, and LCDR3 amino acid sequences as set forth in SEQ ID NOs: 365, 372, and 390, respectively. In some embodiments, the composition comprises an anti-TNFR2 antibody comprising HCDR1, HCDR2, and HCDR3 amino acid sequences as set forth in SEQ ID NOs: 185, 336, and 352, respectively, and LCDR1, LCDR2, and LCDR3 amino acid sequences as set forth in SEQ ID NOs: 365, 374, and 391, respectively. In some embodiments, the composition comprises an anti-TNFR2 antibody comprising HCDR1, HCDR2, and HCDR3 amino acid sequences as set forth in SEQ ID NOs: 186, 340, and 353, respectively, and LCDR1, LCDR2, and LCDR3 amino acid sequences as set forth in SEQ ID NOs: 367, 375, and 392, respectively. In some embodiments, the composition comprises an anti-TNFR2 antibody comprising HCDR1, HCDR2, and HCDR3 amino acid sequences as set forth in SEQ ID NOs: 186, 341, and 354, respectively, and LCDR1, LCDR2, and LCDR3 amino acid sequences as set forth in SEQ ID NOs: 367, 375, 392, respectively. In some embodiments, the composition comprises an anti-TNFR2 antibody comprising HCDR1, HCDR2, and HCDR3 amino acid sequences as set forth in SEQ ID NOs: 186, 341, and 354, respectively, and LCDR1, LCDR2, and LCDR3 amino acid sequences as set forth in SEQ ID NOs: 368, 375, and 392, respectively. In some embodiments, the composition comprises an anti-TNFR2 antibody comprising HCDR1, HCDR2, and HCDR3 amino acid sequences as set forth in SEQ ID NOs: 186, 342, and 354, respectively, and LCDR1, LCDR2, and LCDR3 amino acid sequences as set forth in SEQ ID NOs: 367, 375 and 392, respectively. In some embodiments, the composition comprises an anti-TNFR2 antibody comprising HCDR1, HCDR2, and HCDR3 amino acid sequences as set forth in SEQ ID NOs: 186, 343, and 354, respectively, and LCDR1, LCDR2, and LCDR3 amino acid sequences as set forth in SEQ ID NOs: 369, 375, and 393, respectively. In some embodiments, the composition comprises an anti-TNFR2 antibody comprising HCDR1, HCDR2, and HCDR3 amino acid sequences as set forth in SEQ ID NOs: 186, 343, and 355, respectively, and LCDR1, LCDR2, and LCDR3 amino acid sequences as set forth in SEQ ID NOs: 367, 375, and 392, respectively. In some embodiments, the composition comprises an anti-TNFR2 antibody comprising HCDR1, HCDR2, and HCDR3 amino acid sequences as set forth in SEQ ID NOs: 186, 341, and 354, respectively, and LCDR1, LCDR2, and LCDR3 amino acid sequences as set forth in SEQ ID NOs: 367, 375, and 392, respectively. In some embodiments, the composition comprises an anti-TNFR2 antibody comprising HCDR1, HCDR2, and HCDR3 amino acid sequences as set forth in SEQ ID NOs: 186, 341, and 355, respectively, and LCDR1, LCDR2, and LCDR3 amino acid sequences as set forth in SEQ ID NOs: 367, 376, and 392, respectively. In some embodiments, the composition comprises an anti-TNFR2 antibody comprising HCDR1, HCDR2, and HCDR3 amino acid sequences as set forth in SEQ ID NOs: 186, 344, and 354, respectively, and LCDR1, LCDR2, and LCDR3 amino acid sequences as set forth in SEQ ID NOs: 370, 375, and 392, respectively. In some embodiments, the composition comprises an anti-TNFR2 antibody comprising HCDR1, HCDR2, and HCDR3 amino acid sequences as set forth in SEQ ID NOs: 186, 341, and 354, respectively, and LCDR1, LCDR2, and LCDR3 amino acid sequences as set forth in SEQ ID NOs: 367, 375, and 394, respectively. In some embodiments, the composition comprises an anti-TNFR2 antibody comprising HCDR1, HCDR2, and HCDR3 amino acid sequences as set forth in SEQ ID NOs: 186, 344, and 354, respectively, and LCDR1, LCDR2, and LCDR3 amino acid sequences as set forth in SEQ ID NOs: 367, 375, and 392, respectively. In some embodiments, the composition comprises an anti-TNFR2 antibody comprising HCDR1, HCDR2, and HCDR3 amino acid sequences as set forth in SEQ ID NOs: 186, 341, and 359, respectively, and LCDR1, LCDR2, and LCDR3 amino acid sequences as set forth in SEQ ID NOs: 367, 375, and 393, respectively. In some embodiments, the composition comprises an anti-TNFR2 antibody comprising HCDR1, HCDR2, and HCDR3 amino acid sequences as set forth in SEQ ID NOs: 187, 345, and 356, respectively, and LCDR1, LCDR2, and LCDR3 amino acid sequences as set forth in SEQ ID NOs: 371, 377, and 395, respectively. In some embodiments, the composition comprises an anti-TNFR2 antibody comprising HCDR1, HCDR2, and HCDR3 amino acid sequences as set forth in SEQ ID NOs: 188, 345, and 357, respectively, and LCDR1, LCDR2, and LCDR3 amino acid sequences as set forth in SEQ ID NOs: 371, 377, and 396, respectively. In some embodiments, the composition comprises an anti-TNFR2 antibody comprising HCDR1, HCDR2, and HCDR3 amino acid sequences as set forth in SEQ ID NOs: 189, 346, and 358, respectively, and LCDR1, LCDR2, and LCDR3 amino acid sequences as set forth in SEQ ID NOs: 371, 377, and 397, respectively.

In another embodiment, the set of HCDR1, HCDR2, HCDR3, and the set of LCDR1, LCDR2, LCDR3 on a corresponding light chain comprise the amino acid sequences as shown in Table 9, as described above.

In some embodiments, the composition comprises an anti-TNFR2 antibody comprising HCDR1, HCDR2, and HCDR3 amino acid sequences as set forth in SEQ ID NOs: 402, 345, and 413, respectively, and LCDR1, LCDR2, and LCDR3 amino acid sequences as set forth in SEQ ID NOs: 371, 418, and 427, respectively In some embodiments, the composition comprises an anti-TNFR2 antibody comprising HCDR1, HCDR2, and HCDR3 amino acid sequences as set forth in SEQ ID NOs: 398, 346, and 407, respectively, and LCDR1, LCDR2, and LCDR3 amino acid sequences as set forth in SEQ ID NOs: 371, 377, and 419, respectively. In some embodiments, the composition comprises an anti-TNFR2 antibody comprising HCDR1, HCDR2, and HCDR3 amino acid sequences as set forth in SEQ ID NOs: 187, 346, and 408, respectively, and LCDR1, LCDR2, and LCDR3 amino acid sequences as set forth in SEQ ID NOs: 371, 377, and 420, respectively. In some embodiments, the composition comprises an anti-TNFR2 antibody comprising HCDR1, HCDR2, and HCDR3 amino acid sequences as set forth in SEQ ID NOs: 189, 406, and 409, respectively, and LCDR1, LCDR2, and LCDR3 amino acid sequences as set forth in SEQ ID NOs: 371, 377, and 421, respectively. In some embodiments, the composition comprises an anti-TNFR2 antibody comprising HCDR1, HCDR2, and HCDR3 amino acid sequences as set forth in SEQ ID NOs: 187, 345, and 410, respectively, and LCDR1, LCDR2, and LCDR3 amino acid sequences as set forth in SEQ ID NOs: 371, 418, and 422, respectively. In some embodiments, the composition comprises an anti-TNFR2 antibody comprising HCDR1, HCDR2, and HCDR3 amino acid sequences as set forth in SEQ ID NOs: 399, 346, and 411, respectively, and LCDR1, LCDR2, and LCDR3 amino acid sequences as set forth in SEQ ID NOs: 371, 418, and 423, respectively. In some embodiments, the composition comprises an anti-TNFR2 antibody comprising HCDR1, HCDR2, and HCDR3 amino acid sequences as set forth in SEQ ID NOs: 400, 346, and 412, respectively, and LCDR1, LCDR2, and LCDR3 amino acid sequences as set forth in SEQ ID NOs: 417, 377, and 424, respectively. In some embodiments, the composition comprises an anti-TNFR2 antibody comprising HCDR1, HCDR2, and HCDR3 amino acid sequences as set forth in SEQ ID NOs: 401, 346, and 413, respectively, and LCDR1, LCDR2, and LCDR3 amino acid sequences as set forth in SEQ ID NOs: 417, 418, and 425, respectively In some embodiments, the composition comprises an anti-TNFR2 antibody comprising HCDR1, HCDR2, and HCDR3 amino acid sequences as set forth in SEQ ID NOs: 401, 346, and 414, respectively, and LCDR1, LCDR2, and LCDR3 amino acid sequences as set forth in SEQ ID NOs: 417, 418, and 426, respectively. In some embodiments, the composition comprises an anti-TNFR2 antibody comprising HCDR1, HCDR2, and HCDR3 amino acid sequences as set forth in SEQ ID NOs: 398, 346, and 415, respectively, and LCDR1, LCDR2, and LCDR3 amino acid sequences as set forth in SEQ ID NOs: 417, 377, and 428, respectively. In some embodiments, the composition comprises an anti-TNFR2 antibody comprising HCDR1, HCDR2, and HCDR3 amino acid sequences as set forth in SEQ ID NOs: 403, 346, and 412, respectively, and LCDR1, LCDR2, and LCDR3 amino acid sequences as set forth in SEQ ID NOs: 371, 418, and 429, respectively. In some embodiments, the composition comprises an anti-TNFR2 antibody comprising HCDR1, HCDR2, and HCDR3 amino acid sequences as set forth in SEQ ID NOs: 404, 346, and 412, respectively, and LCDR1, LCDR2, and LCDR3 amino acid sequences as set forth in SEQ ID NOs: 371, 418, and 425, respectively. In some embodiments, the composition comprises an anti-TNFR2 antibody comprising HCDR1, HCDR2, and HCDR3 amino acid sequences as set forth in SEQ ID NOs: 401, 346, and 414, respectively, and LCDR1, LCDR2, and LCDR3 amino acid sequences as set forth in SEQ ID NOs: 417, 418, and 430, respectively. In some embodiments, the composition comprises an anti-TNFR2 antibody comprising HCDR1, HCDR2, and HCDR3 amino acid sequences as set forth in SEQ ID NOs: 405, 406, and 416, respectively, and LCDR1, LCDR2, and LCDR3 amino acid sequences as set forth in SEQ ID NOs: 371, 377, and 431, respectively.

In another embodiment, the composition comprises anti-TNFR2 antibodies having heavy chain and light chain CDR sequences that are at least 80% (e.g., at least 85%, 90%, 95%, 96%, 97%, 98%, or 99%) identical to the amino acid sequences set forth above, for example but not limited to identity as determined using BlastP software of the National Center of Biotechnology Information (NCBI) using default parameters.

In another embodiment, the composition comprises anti-TNFR2 antibodies having one of the following pairs of heavy chain variable region and light chain variable region: SEQ ID NOs:289-290, SEQ ID NOs:3-4, SEQ ID NOs:7-8, SEQ ID NOs:11-12, SEQ ID NOs:15-16, SEQ ID NOs:19-20, SEQ ID NOs:23-24, SEQ ID NOs:27-28, SEQ ID NOs:31-32, SEQ ID NOs:35-36, SEQ ID NOs:39-40, SEQ ID NOs:43-44, SEQ ID NOs:47-48, SEQ ID NOs:51-52, SEQ ID NOs:55-56, SEQ ID NOs:59-60, SEQ ID NOs:63-64, SEQ ID NOs:67-68, SEQ ID NOs:71-72, SEQ ID NOs:75-76, SEQ ID NOs:79-80, SEQ ID NOs:83-84, SEQ ID NOs:87-88, SEQ ID NOs:91-92, SEQ ID NOs:95-96, SEQ ID NOs:99-100, SEQ ID NOs:103-104, SEQ ID NOs:107-108, SEQ ID NOs:111-112, SEQ ID NOs:115-116, SEQ ID NOs:119-120, SEQ ID NOs:123-124, SEQ ID NOs:127-128, SEQ ID NOs:131-132, SEQ ID NOs:135-136, SEQ ID NOs:139-140, SEQ ID NOs:143-144, SEQ ID NOs:147-148, SEQ ID NOs:151-152, SEQ ID NOs:157-158, SEQ ID NOs:163-164, SEQ ID NOs:169-170, SEQ ID NOs:175-176, SEQ ID NOs:181-182, SEQ ID NOs:193-194, SEQ ID NOs:199-200, SEQ ID NOs:205-206, SEQ ID NOs:211-212, SEQ ID NOs:217-218, SEQ ID NOs:223-224, SEQ ID NOs:229-230, SEQ ID NOs:233-234, SEQ ID NOs:237-238, SEQ ID NOs:241-242, SEQ ID NOs:245-246, SEQ ID NOs:249-250, SEQ ID NOs:253-254, SEQ ID NOs:257-258, SEQ ID NOs:261-262, SEQ ID NOs:265-266, SEQ ID NOs:269-270, SEQ ID NOs:273-274, SEQ ID NOs:277-278, SEQ ID NOs:281-282, SEQ ID NOs:285-286, SEQ ID NOs:293-294, SEQ ID NOs:297-298, SEQ ID NOs:301-302, SEQ ID NOs:305-306, SEQ ID NOs:309-310, SEQ ID NOs:313-314, SEQ ID NOs:317-318, SEQ ID NOs:321-322, SEQ ID NOs:325-326, or SEQ ID NOs:329-330.

In certain embodiments, the composition comprises an anti-TNFR2 antibody comprising the heavy chain variable region and light chain variable region as set forth in SEQ ID NOs:289-290. In certain embodiments, the composition comprises an anti-TNFR2 antibody comprising the heavy chain variable region and light chain variable region as set forth in SEQ ID NOs:3-4. In certain embodiments, the composition comprises an anti-TNFR2 antibody comprising the heavy chain variable region and light chain variable region as set forth in SEQ ID NOs:7-8. In certain embodiments, the composition comprises an anti-TNFR2 antibody comprising the heavy chain variable region and light chain variable region as set forth in SEQ ID NOs:11-12. In certain embodiments, the composition comprises an anti-TNFR2 antibody comprising the heavy chain variable region and light chain variable region as set forth in SEQ ID NOs:15-16. In certain embodiments, the composition comprises an anti-TNFR2 antibody comprising the heavy chain variable region and light chain variable region as set forth in SEQ ID NOs:19-20. In certain embodiments, the composition comprises an anti-TNFR2 antibody comprising the heavy chain variable region and light chain variable region as set forth in SEQ ID NOs:23-24. In certain embodiments, the composition comprises an anti-TNFR2 antibody comprising the heavy chain variable region and light chain variable region as set forth in SEQ ID NOs:27-28. In certain embodiments, the composition comprises an anti-TNFR2 antibody comprising the heavy chain variable region and light chain variable region as set forth in SEQ ID NOs:31-32. In certain embodiments, the composition comprises an anti-TNFR2 antibody comprising the heavy chain variable region and light chain variable region as set forth in SEQ ID NOs:35-36. In certain embodiments, the composition comprises an anti-TNFR2 antibody comprising the heavy chain variable region and light chain variable region as set forth in SEQ ID NOs:39-40. In certain embodiments, the composition comprises an anti-TNFR2 antibody comprising the heavy chain variable region and light chain variable region as set forth in SEQ ID NOs:43-44. In certain embodiments, the composition comprises an anti-TNFR2 antibody comprising the heavy chain variable region and light chain variable region as set forth in SEQ ID NOs:47-48. In certain embodiments, the composition comprises an anti-TNFR2 antibody comprising the heavy chain variable region and light chain variable region as set forth in SEQ ID NOs:51-52. In certain embodiments, the composition comprises an anti-TNFR2 antibody comprising the heavy chain variable region and light chain variable region as set forth in SEQ ID NOs:55-56. In certain embodiments, the composition comprises an anti-TNFR2 antibody comprising the heavy chain variable region and light chain variable region as set forth in SEQ ID NOs:59-60. In certain embodiments, the composition comprises an anti-TNFR2 antibody comprising the heavy chain variable region and light chain variable region as set forth in SEQ ID NOs:63-64. In certain embodiments, the composition comprises an anti-TNFR2 antibody comprising the heavy chain variable region and light chain variable region as set forth in SEQ ID NOs:67-68. In certain embodiments, the composition comprises an anti-TNFR2 antibody comprising the heavy chain variable region and light chain variable region as set forth in SEQ ID NOs:71-72. In certain embodiments, the composition comprises an anti-TNFR2 antibody comprising the heavy chain variable region and light chain variable region as set forth in SEQ ID NOs:75-76. In certain embodiments, the composition comprises an anti-TNFR2 antibody comprising the heavy chain variable region and light chain variable region as set forth in SEQ ID NOs:79-80. In certain embodiments, the composition comprises an anti-TNFR2 antibody comprising the heavy chain variable region and light chain variable region as set forth in SEQ ID NOs:83-84. In certain embodiments, the composition comprises an anti-TNFR2 antibody comprising the heavy chain variable region and light chain variable region as set forth in SEQ ID NOs:87-88. In certain embodiments, the composition comprises an anti-TNFR2 antibody comprising the heavy chain variable region and light chain variable region as set forth in SEQ ID NOs:91-92. In certain embodiments, the composition comprises an anti-TNFR2 antibody comprising the heavy chain variable region and light chain variable region as set forth in SEQ ID NOs:95-96. In certain embodiments, the composition comprises an anti-TNFR2 antibody comprising the heavy chain variable region and light chain variable region as set forth in SEQ ID NOs:99-100. In certain embodiments, the composition comprises an anti-TNFR2 antibody comprising the heavy chain variable region and light chain variable region as set forth in SEQ ID NOs:103-104. In certain embodiments, the composition comprises an anti-TNFR2 antibody comprising the heavy chain variable region and light chain variable region as set forth in SEQ ID NOs:107-108. In certain embodiments, the composition comprises an anti-TNFR2 antibody comprising the heavy chain variable region and light chain variable region as set forth in SEQ ID NOs:111-112. In certain embodiments, the composition comprises an anti-TNFR2 antibody comprising the heavy chain variable region and light chain variable region as set forth in SEQ ID NOs:115-116. In certain embodiments, the composition comprises an anti-TNFR2 antibody comprising the heavy chain variable region and light chain variable region as set forth in SEQ ID NOs:119-120. In certain embodiments, the composition comprises an anti-TNFR2 antibody comprising the heavy chain variable region and light chain variable region as set forth in SEQ ID NOs:123-124. In certain embodiments, the composition comprises an anti-TNFR2 antibody comprising the heavy chain variable region and light chain variable region as set forth in SEQ ID NOs:127-128. In certain embodiments, the composition comprises an anti-TNFR2 antibody comprising the heavy chain variable region and light chain variable region as set forth in SEQ ID NOs:131-132. In certain embodiments, the composition comprises an anti-TNFR2 antibody comprising the heavy chain variable region and light chain variable region as set forth in SEQ ID NOs:135-136. In certain embodiments, the composition comprises an anti-TNFR2 antibody comprising the heavy chain variable region and light chain variable region as set forth in SEQ ID NOs:139-140. In certain embodiments, the composition comprises an anti-TNFR2 antibody comprising the heavy chain variable region and light chain variable region as set forth in SEQ ID NOs:143-144. In certain embodiments, the composition comprises an anti-TNFR2 antibody comprising the heavy chain variable region and light chain variable region as set forth in SEQ ID NOs:147-148. In certain embodiments, the composition comprises an anti-TNFR2 antibody comprising the heavy chain variable region and light chain variable region as set forth in SEQ ID NOs:151-152. In certain embodiments, the composition comprises an anti-TNFR2 antibody comprising the heavy chain variable region and light chain variable region as set forth in SEQ ID NOs:157-158. In certain embodiments, the composition comprises an anti-TNFR2 antibody comprising the heavy chain variable region and light chain variable region as set forth in SEQ ID NOs:163-164. In certain embodiments, the composition comprises an anti-TNFR2 antibody comprising the heavy chain variable region and light chain variable region as set forth in SEQ ID NOs:169-170. In certain embodiments, the composition comprises an anti-TNFR2 antibody comprising the heavy chain variable region and light chain variable region as set forth in SEQ ID NOs:175-176. In certain embodiments, the composition comprises an anti-TNFR2 antibody comprising the heavy chain variable region and light chain variable region as set forth in SEQ ID NOs:181-182. In certain embodiments, the composition comprises an anti-TNFR2 antibody comprising the heavy chain variable region and light chain variable region as set forth in SEQ ID NOs:193-194. In certain embodiments, the composition comprises an anti-TNFR2 antibody comprising the heavy chain variable region and light chain variable region as set forth in SEQ ID NOs:199-200. In certain embodiments, the composition comprises an anti-TNFR2 antibody comprising the heavy chain variable region and light chain variable region as set forth in SEQ ID NOs:205-206. In certain embodiments, the composition comprises an anti-TNFR2 antibody comprising the heavy chain variable region and light chain variable region as set forth in SEQ ID NOs:211-212. In certain embodiments, the composition comprises an anti-TNFR2 antibody comprising the heavy chain variable region and light chain variable region as set forth in SEQ ID NOs:217-218. In certain embodiments, the composition comprises an anti-TNFR2 antibody comprising the heavy chain variable region and light chain variable region as set forth in SEQ ID NOs:223-224. In certain embodiments, the composition comprises an anti-TNFR2 antibody comprising the heavy chain variable region and light chain variable region as set forth in SEQ ID NOs:229-230. In certain embodiments, the composition comprises an anti-TNFR2 antibody comprising the heavy chain variable region and light chain variable region as set forth in SEQ ID NOs:233-234. In certain embodiments, the composition comprises an anti-TNFR2 antibody comprising the heavy chain variable region and light chain variable region as set forth in SEQ ID NOs:237-238. In certain embodiments, the composition comprises an anti-TNFR2 antibody comprising the heavy chain variable region and light chain variable region as set forth in SEQ ID NOs:241-242. In certain embodiments, the composition comprises an anti-TNFR2 antibody comprising the heavy chain variable region and light chain variable region as set forth in SEQ ID NOs:245-246. In certain embodiments, the composition comprises an anti-TNFR2 antibody comprising the heavy chain variable region and light chain variable region as set forth in SEQ ID NOs:249-250. In certain embodiments, the composition comprises an anti-TNFR2 antibody comprising the heavy chain variable region and light chain variable region as set forth in SEQ ID NOs:253-254. In certain embodiments, the composition comprises an anti-TNFR2 antibody comprising the heavy chain variable region and light chain variable region as set forth in SEQ ID NOs:257-258. In certain embodiments, the composition comprises an anti-TNFR2 antibody comprising the heavy chain variable region and light chain variable region as set forth in SEQ ID NOs:261-262. In certain embodiments, the composition comprises an anti-TNFR2 antibody comprising the heavy chain variable region and light chain variable region as set forth in SEQ ID NOs:265-266. In certain embodiments, the composition comprises an anti-TNFR2 antibody comprising the heavy chain variable region and light chain variable region as set forth in SEQ ID NOs:269-270. In certain embodiments, the composition comprises an anti-TNFR2 antibody comprising the heavy chain variable region and light chain variable region as set forth in SEQ ID NOs:273-274. In certain embodiments, the composition comprises an anti-TNFR2 antibody comprising the heavy chain variable region and light chain variable region as set forth in SEQ ID NOs:277-278. In certain embodiments, the composition comprises an anti-TNFR2 antibody comprising the heavy chain variable region and light chain variable region as set forth in SEQ ID NOs:281-282. In certain embodiments, the composition comprises an anti-TNFR2 antibody comprising the heavy chain variable region and light chain variable region as set forth in SEQ ID NOs:285-286. In certain embodiments, the composition comprises an anti-TNFR2 antibody comprising the heavy chain variable region and light chain variable region as set forth in SEQ ID NOs:293-294. In certain embodiments, the composition comprises an anti-TNFR2 antibody comprising the heavy chain variable region and light chain variable region as set forth in SEQ ID NOs:297-298. In certain embodiments, the composition comprises an anti-TNFR2 antibody comprising the heavy chain variable region and light chain variable region as set forth in SEQ ID NOs:301-302. In certain embodiments, the composition comprises an anti-TNFR2 antibody comprising the heavy chain variable region and light chain variable region as set forth in SEQ ID NOs:305-306. In certain embodiments, the composition comprises an anti-TNFR2 antibody comprising the heavy chain variable region and light chain variable region as set forth in SEQ ID NOs:309-310. In certain embodiments, the composition comprises an anti-TNFR2 antibody comprising the heavy chain variable region and light chain variable region as set forth in SEQ ID NOs:313-314. In certain embodiments, the composition comprises an anti-TNFR2 antibody comprising the heavy chain variable region and light chain variable region as set forth in SEQ ID NOs:317-318. In certain embodiments, the composition comprises an anti-TNFR2 antibody comprising the heavy chain variable region and light chain variable region as set forth in SEQ ID NOs:321-322. In certain embodiments, the composition comprises an anti-TNFR2 antibody comprising the heavy chain variable region and light chain variable region as set forth in SEQ ID NOs:325-326. In certain embodiments, the composition comprises an anti-TNFR2 antibody comprising the heavy chain variable region and light chain variable region as set forth in or SEQ ID NOs:329-330.

In another embodiment, the composition comprises anti-TNFR2 antibodies having VH and VL sequences that are at least 80% (e.g., at least 85%, 90%, 95%, 96%, 97%, 98%, or 99%) identical to the amino acid sequences set forth above, for example but not limited to identity as determined using BlastP software of the National Center of Biotechnology Information (NCBI) using default parameters.

In yet another embodiment, the composition comprises anti-TNFR2 antibodies having one of the following pairs of heavy chain and light chain: SEQ ID NOs: 438 and 292, SEQ ID NOs:291-292, SEQ ID NOs:235-236, SEQ ID NOs:239-240, SEQ ID NOs:243-244, SEQ ID NOs:247-248, SEQ ID NOs:251-252, SEQ ID NOs:255-256, SEQ ID NOs:259-260, SEQ ID NOs:263-264, SEQ ID NOs:267-268, SEQ ID NOs:271-272, SEQ ID NOs:275-276, SEQ ID NOs:279-280, SEQ ID NOs:283-284, SEQ ID NOs:287-288, SEQ ID NOs:295-296, SEQ ID NOs:299-300, SEQ ID NOs:303-304, SEQ ID NOs:307-308, SEQ ID NOs:311-312, SEQ ID NOs:315-316, SEQ ID NOs:319-320, SEQ ID NOs:323-324, SEQ ID NOs:327-328, SEQ ID NOs:331-332, SEQ ID NOs: 432 and 260, SEQ ID NOs: 433 and 304, SEQ ID NOs: 434 and 308, SEQ ID NOs: 435 and 236, SEQ ID NOs: 436 and 244, SEQ ID NOs: 437 and 284, or SEQ ID NOs: 439 and 296.

In some embodiments, the composition comprises an anti-TNFR2 antibody comprising a heavy chain and a light chain as set forth in SEQ ID NOs: 438 and 292. In some embodiments, the composition comprises an anti-TNFR2 antibody comprising a heavy chain and a light chain as set forth in SEQ ID NOs:291-292. In some embodiments, the composition comprises an anti-TNFR2 antibody comprising a heavy chain and a light chain as set forth in SEQ ID NOs:235-236. In some embodiments, the composition comprises an anti-TNFR2 antibody comprising a heavy chain and a light chain as set forth in SEQ ID NOs:239-240. In some embodiments, the composition comprises an anti-TNFR2 antibody comprising a heavy chain and a light chain as set forth in SEQ ID NOs:243-244. In some embodiments, the composition comprises an anti-TNFR2 antibody comprising a heavy chain and a light chain as set forth in SEQ ID NOs:247-248. In some embodiments, the composition comprises an anti-TNFR2 antibody comprising a heavy chain and a light chain as set forth in SEQ ID NOs:251-252. In some embodiments, the composition comprises an anti-TNFR2 antibody comprising a heavy chain and a light chain as set forth in SEQ ID NOs:255-256. In some embodiments, the composition comprises an anti-TNFR2 antibody comprising a heavy chain and a light chain as set forth in SEQ ID NOs:259-260. In some embodiments, the composition comprises an anti-TNFR2 antibody comprising a heavy chain and a light chain as set forth in SEQ ID NOs:263-264. In some embodiments, the composition comprises an anti-TNFR2 antibody comprising a heavy chain and a light chain as set forth in SEQ ID NOs:267-268. In some embodiments, the composition comprises an anti-TNFR2 antibody comprising a heavy chain and a light chain as set forth in SEQ ID NOs:271-272. In some embodiments, the composition comprises an anti-TNFR2 antibody comprising a heavy chain and a light chain as set forth in SEQ ID NOs:275-276. In some embodiments, the composition comprises an anti-TNFR2 antibody comprising a heavy chain and a light chain as set forth in SEQ ID NOs:279-280. In some embodiments, the composition comprises an anti-TNFR2 antibody comprising a heavy chain and a light chain as set forth in SEQ ID NOs:283-284. In some embodiments, the composition comprises an anti-TNFR2 antibody comprising a heavy chain and a light chain as set forth in SEQ ID NOs:287-288. In some embodiments, the composition comprises an anti-TNFR2 antibody comprising a heavy chain and a light chain as set forth in SEQ ID NOs:295-296. In some embodiments, the composition comprises an anti-TNFR2 antibody comprising a heavy chain and a light chain as set forth in SEQ ID NOs:299-300. In some embodiments, the composition comprises an anti-TNFR2 antibody comprising a heavy chain and a light chain as set forth in SEQ ID NOs:303-304. In some embodiments, the composition comprises an anti-TNFR2 antibody comprising a heavy chain and a light chain as set forth in SEQ ID NOs:307-308. In some embodiments, the composition comprises an anti-TNFR2 antibody comprising a heavy chain and a light chain as set forth in SEQ ID NOs:311-312. In some embodiments, the composition comprises an anti-TNFR2 antibody comprising a heavy chain and a light chain as set forth in SEQ ID NOs:315-316. In some embodiments, the composition comprises an anti-TNFR2 antibody comprising a heavy chain and a light chain as set forth in SEQ ID NOs:319-320. In some embodiments, the composition comprises an anti-TNFR2 antibody comprising a heavy chain and a light chain as set forth in SEQ ID NOs:323-324. In some embodiments, the composition comprises an anti-TNFR2 antibody comprising a heavy chain and a light chain as set forth in SEQ ID NOs:327-328. In some embodiments, the composition comprises an anti-TNFR2 antibody comprising a heavy chain and a light chain as set forth in SEQ ID NOs:331-332. In some embodiments, the composition comprises an anti-TNFR2 antibody comprising a heavy chain and a light chain as set forth in SEQ ID NOs: 432 and 260. In some embodiments, the composition comprises an anti-TNFR2 antibody comprising a heavy chain and a light chain as set forth in SEQ ID NOs: 433 and 304. In some embodiments, the composition comprises an anti-TNFR2 antibody comprising a heavy chain and a light chain as set forth in SEQ ID NOs: 434 and 308. In some embodiments, the composition comprises an anti-TNFR2 antibody comprising a heavy chain and a light chain as set forth in SEQ ID NOs: 435 and 236. In some embodiments, the composition comprises an anti-TNFR2 antibody comprising a heavy chain and a light chain as set forth in SEQ ID NOs: 436 and 244. In some embodiments, the composition comprises an anti-TNFR2 antibody comprising a heavy chain and a light chain as set forth in SEQ ID NOs: 437 and 284. In some embodiments, the composition comprises an anti-TNFR2 antibody comprising a heavy chain and a light chain as set forth in or SEQ ID NOs: 439 and 296.

In another embodiment, the composition comprises anti-TNFR2 antibodies having heavy chains and light chains that are at least 80% (e.g., at least 85%, 90%, 95%, 96%, 97%, 98%, or 99%) identical to the amino acid sequences set forth above, for example but not limited to identity as determined using BlastP software of the National Center of Biotechnology Information (NCBI) using default parameters.

In one embodiment, the antibodies disclosed herein can be in the form of a conjugate. As used herein, a "conjugate" is an antibody or antibody fragment (such as an antigen-binding fragment) covalently linked to an effector molecule or a second protein (such as a second antibody). The effector molecule can be, for example, a drug, toxin, therapeutic agent, detectable label, protein, nucleic acid, lipid, nanoparticle, carbohydrate or recombinant virus. An antibody conjugate can also be referred to as an "immunoconjugate." When the conjugate comprises an antibody linked to a drug (e.g., a cytotoxic agent), the conjugate can be referred to as an "antibody-drug conjugate". Other antibody conjugates include, for example, multi-specific (such as bispecific or trispecific) antibodies and chimeric antigen receptors (CARs).

The pharmaceutical compositions comprising the antibodies or antigen-binding fragments thereof disclosed herein can be administered (e.g., to a mammal, a cell, or a tissue) in any suitable manner depending on whether local or systemic treatment is desired. For example, the composition can be administered topically (e.g. ophthalmically, vaginally, rectally, intranasally, transdermally, and the like), orally, by inhalation, or parenterally (including by intravenous drip or subcutaneous, intracavity, intraperitoneal, intradermal, or intramuscular injection). Topical intranasal administration refers to delivery of the compositions into the nose and nasal passages through one or both of the nares. The composition can be delivered by a spraying mechanism or droplet mechanism, or through aerosolization. Alternatively, administration can be intratumoral, e.g. local or intravenous injection.

If the composition is to be administered parenterally, the administration is generally by injection. Injectables can be prepared in conventional forms, either as liquid solutions or suspensions, solid forms suitable for suspension in liquid prior to injection, or as emulsions. Additionally, parental administration can involve preparation of a slow-release or sustained-release system so as to maintain a constant dosage.

Methods of Use

In one embodiment, the anti-TNFR2 antibodies disclosed herein can be used to modulate the proliferation and/or functions of regulatory T cells (T-reg cells) or myeloid-derived suppressor cells.

T-reg cells represent a heterogeneous class of T cells that can be distinguished based on their unique surface protein presentation. The most studied T-reg cells include $CD4^+$, $CD25^+$, $FoxP3^+$ T-reg cells and $CD17^+$ T-reg cells. It has been shown that certain classes of T-reg cells inhibit production of the proliferation-inducing cytokine, interleukin-2 (IL-2), in target T cells and may additionally sequester IL-2 from autoreactive cells by virtue of the affinity of CD25 (a subdomain of the IL-2 receptor) for IL-2. Moreover, it has been shown that CD4+, CD25+, $FoxP3^+$ T-reg cells are also present in B cell-rich areas and are capable of directly suppressing immunoglobulin production independent of their ability to attenuate TH2-cell activity.

As used herein, the term "myeloid-derived suppressor cell" or "MDSC" refers to a cell of the immune system that can modulate the activity of a variety of effector cells and antigen-presenting cells, such as T cells, NK cells, dendritic cells, and macrophages, among others. Myeloid derived suppressor cells are distinguished by their gene expression profile.

In another embodiment, the anti-TNFR2 antibodies disclosed herein can be used to treat diseases such as cancer, autoimmune diseases, GvHd, viral infection or bacterial infection.

As used herein, the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the terms "treat", "treatment", or "therapy" (as well as different forms thereof) refer to therapeutic treatment, including prophylactic or preventative measures, wherein the object is to prevent or slow down (lessen) an undesired physiological change associated with a disease or condition. Beneficial or desired clinical results include, but are not limited to, alleviation of symptoms, diminishment of the extent of a disease or condition, stabilization of a disease or condition (i.e., where the disease or condition does not worsen), delay or slowing of the progression of a disease or condition, amelioration or palliation of the disease or condition, and remission (whether partial or total) of the disease or condition, whether detectable or undetectable. Those in need of treatment include those already with the disease or condition as well as those prone to having the disease or condition or those in which the disease or condition is to be prevented.

The terms "subject," "individual," and "patient" are used interchangeably herein, and refer to human or non-human animals to whom treatment with a composition or formulation in accordance with the present anti-TNFR2 antibodies is provided. The terms "non-human animals" and "non-human mammals" are used interchangeably herein and include all vertebrates, e.g., mammals, such as non-human primates (e.g. higher primates), sheep, dog, rodent (e.g. mouse or rat), guinea pig, goat, pig, cat, rabbits, cows, horses, or non-mammals such as reptiles, amphibians, chickens, and turkeys. The compositions described herein can be used to treat any suitable mammal, including primates, such as monkeys and humans, horses, cows, cats, dogs, rabbits, and rodents such as rats and mice. In one embodiment, the mammal to be treated is human. The human can be any human of any age. In one embodiment, the human is an adult. In another embodiment, the human is a child. The human can be male, female, pregnant, middle-aged, adolescent, or elderly.

Pharmaceutical compositions suitable for use in the methods disclosed herein include compositions wherein the active ingredients are contained in an amount effective to achieve the intended purpose. In one embodiment, a therapeutically effective amount means an amount of one or more active ingredients (e.g., an anti-TNFR2 antibody) effective to prevent, alleviate or ameliorate symptoms of disease or prolong the survival of the subject being treated. Determination of a therapeutically effective amount is well within the capability of those skilled in the art.

In one embodiment, the present disclosure provides a method of modulating activities or functions of regulatory T cells in a subject. As used herein, "modulating" refers to "stimulating" or "inhibiting" an activity of a molecular target or pathway. For example, a composition modulates the activity of a molecular target or pathway if it stimulates or inhibits the activity of the molecular target or pathway by at least 10%, by at least about 20%, by at least about 25%, by at least about 30%, by at least about 40%, by at least about 50%, by at least about 60%, by at least about 70%, by at least about 75%, by at least about 80%, by at least about 90%, by at least about 95%, by at least about 98%, or by about 99% or more relative to the activity of the molecular target or pathway under the same conditions but lacking only the presence of the composition. In another example, a composition modulates the activity of a molecular target or pathway if it stimulates or inhibits the activity of the molecular target or pathway by at least 2-fold, at least 5-fold, at least 10-fold, at least 20-fold, at least 50-fold, at least 100-fold relative to the activity of the molecular target or pathway under the same conditions but lacking only the presence of the composition. The activity of a molecular target or pathway may be measured by any reproducible means. The activity of a molecular target or pathway may be measured in vitro or in vivo. For example, the activity of a molecular target or pathway may be measured in vitro or in vivo by an appropriate assay known in the art measuring the activity. Control samples (untreated with the composition) can be assigned a relative activity value of 100%.

In one embodiment, the method comprises the step of administering to the subject a composition comprising an effective amount of the anti-TNFR2 antibody disclosed herein. In one embodiment, the composition comprises anti-TNFR2 antibodies having the heavy chain and light chain CDR sequences as described herein. In another embodiment, the composition comprises anti-TNFR2 antibodies having the VH and VL sequences as described herein. In yet another embodiment, the composition comprises anti-TNFR2 antibodies having the heavy chain and light chain sequences as described herein. In one embodiment, the regulatory T cells are CD4+CD25+Foxp3+ or alternatively CD4+CD25+C127$_{low}$. In one embodiment, the method stimulates proliferation of the regulatory T cells. In another embodiment, the method can activate the regulatory T cells. In another embodiment, the method can modulate immune responses mediated by said regulatory T cells.

One skilled in the art would appreciate that in some embodiments, activation of regulatory T cells suppresses proliferation of immune system effector cells including Teff and NK cells, or reduces cytotoxic activity of effector cells including Teff and NK cells, or encourages immune system effector cells including Teff and NK cells to produce less proinflammatory cytokines, or any combination thereof. In some embodiments, administration of an anti-TNFR2 antibody to a subject in a method of use as described herein, suppresses proliferation of immune system effector cells including Teff and NK cells. In some embodiments, administration of an anti-TNFR2 antibody to a subject in a method as described herein, reduces cytotoxic activity of immune system effector cells including Teff and NK cells. In some embodiments, use of an anti-TNFR2 antibody for administration to a subject in a method as described herein, encourages immune system effector cells including Teff and NK cells to produce fewer proinflammatory cytokines.

One skilled in the art would appreciate that in some embodiments, modulation of an immune response encompasses a reduction of inflammation or elimination of inflammation in a situation wherein the expected outcome without the use of an anti-TNFR2 antibody described herein, would have been inflammation.

In one embodiment, the present disclosure also provides uses of a composition comprising the subject anti-TNFR2 antibodies for modulating activities or functions of regulatory T cells in a subject. In one embodiment, the composition comprises anti-TNFR2 antibodies having the heavy chain and light chain CDR sequences as described herein. In another embodiment, the composition comprises anti-TNFR2 antibodies having the VH and VL sequences as described herein. In yet another embodiment, the composition comprises anti-TNFR2 antibodies having the heavy chain and light chain sequences as described herein.

In one embodiment, the present disclosure provides a method of modulating activities or functions of myeloid-derived suppressor cells (MDSCs) in a subject. In one embodiment, the method comprises the step of administering to the subject a composition comprising an effective amount of the anti-TNFR2 antibody disclosed herein. In one embodiment, the composition comprises anti-TNFR2 antibodies having the heavy chain and light chain CDR sequences as described herein. In another embodiment, the composition comprises anti-TNFR2 antibodies having the VH and VL sequences as described herein. In yet another embodiment, the composition comprises anti-TNFR2 antibodies having the heavy chain and light chain sequences as described herein. In one embodiment, the method stimulates proliferation of the MDSCs. In another embodiment, the method can activate the MDSCs.

One skilled in the art would appreciate that in some embodiments, activation of MDSCs suppresses proliferation of immune system effector cells including Teff and NK cells, or reduces cytotoxic activity of immune system effector cells including Teff and NK cells, or down-regulates the production of proinflammatory cytokines, or any combination thereof by immune system effector cells including Teff and NK cells. In some embodiments, administration of an anti-TNFR2 antibody to subject in need, in a method described herein, suppresses proliferation of Immune system effector cells including Teff and NK cells. In some embodiments, use of an anti-TNFR2 antibody for administration to subject in need in a method described herein, suppresses proliferation of Immune system effector cells including Teff and NK cells. In some embodiments, use of an anti-TNFR2 antibody to a subject in a method described herein, reduces cytotoxic activity of Immune system effector cells including Teff and NK cells. In some embodiments, use of an anti-TNFR2 antibody to a subject in a method described herein, encourages Immune system effector cells including Teff and NK cells to produce less proinflammatory cytokines.

In one embodiment, the present disclosure also provides uses of a composition comprising anti-TNFR2 antibodies for modulating activities or functions of MDSCs in a subject. In one embodiment, the composition comprises anti-TNFR2 antibodies having the heavy chain and light chain CDR sequences as described herein. In another embodiment, the composition comprises anti-TNFR2 antibodies having the VH and VL sequences as described herein. In yet another embodiment, the composition comprises anti-TNFR2 antibodies having the heavy chain and light chain sequences as described herein.

In another embodiment, the present disclosure provides a method of treating a disease in a subject, comprising the step of administering to the subject a composition comprising an effective amount of the anti-TNFR2 antibody disclosed herein. In one embodiment, the composition comprises anti-TNFR2 antibodies having the heavy chain and light chain CDR sequences as described herein. In another embodiment, the composition comprises anti-TNFR2 antibodies having the VH and VL sequences as described herein. In yet another embodiment, the composition comprises anti-TNFR2 antibodies having the heavy chain and light chain sequences as described herein.

In one embodiment, the present disclosure also provides uses of a composition comprising anti-TNFR2 antibodies for treating a disease in a subject. In one embodiment, the composition comprises anti-TNFR2 antibodies having the heavy chain and light chain CDR sequences as described herein. In another embodiment, the composition comprises anti-TNFR2 antibodies having the VH and VL sequences as described herein. In yet another embodiment, the composition comprises anti-TNFR2 antibodies having the heavy chain and light chain sequences as described herein.

In one embodiment, the exact amount of the present polypeptides or compositions thereof required to elicit the desired effects will vary from subject to subject, depending on the species, age, gender, weight, and general condition of the subject, the particular polypeptides, the route of administration, and whether other drugs are included in the regimen. Thus, it is not possible to specify an exact amount for every composition. However, an appropriate amount can be determined by one of ordinary skill in the art using routine experimentation. Dosages can vary, and the polypeptides can be administered in one or more (e.g., two or more, three or more, four or more, or five or more) doses daily, for one or more days. Guidance in selecting appropriate doses for antibodies can be readily found in the literature.

In one embodiment, the disease can be viral infection, bacterial infection, cancer, autoimmune disease or immune disorder. In one embodiment, the disease can be an upper respiratory viral infection, an early stage lung infection, or a late stage lung infection. A number of diseases and cancers are known to be caused by viruses. Examples of disease-causing viruses include, but are not limited to, norovirus; rotavirus; hepatitis virus A, B, C, D, or E; rabies virus, West Nile virus, enterovirus, echovirus, coxsackievirus, herpes simplex virus (HSV), HSV-2, varicella-zoster virus, mosquito-borne viruses, arbovirus, St. Louis encephalitis virus, California encephalitis virus, lymphocytic choriomeningitis virus, human immunodeficiency virus (HIV), poliovirus, zika virus, rubella virus, cytomegalovirus, human papillomavirus (HPV), enterovirus D68, severe acute respiratory syndrome (SARS) coronavirus, Middle East respiratory syndrome coronavirus, SARS coronavirus 2, Epstein-Barr virus, influenza virus, respiratory syncytial virus, polyoma viruses (such as JC virus, BK virus), Ebola virus, Dengue virus, or any combination thereof.

In another embodiment, the disease is a cancer that can be, but is not limited to, carcinoma, sarcoma, lymphoma, leukemia, germ cell tumor, blastoma, chondrosarcoma, Ewing's sarcoma, malignant fibrous histiocytoma of bone, osteosarcoma, rhabdomyosarcoma, heart cancer, brain cancer, astrocytoma, glioma, medulloblastoma, neuroblastoma, breast cancer, medullary carcinoma, adrenocortical carcinoma, thyroid cancer, Merkel cell carcinoma, eye cancer, gastrointestinal cancer, colon cancer, gallbladder cancer, gastric (stomach) cancer, gastrointestinal carcinoid tumor, hepatocellular cancer, pancreatic cancer, rectal cancer, bladder cancer, cervical cancer, endometrial cancer, ovarian cancer, renal cell carcinoma, prostate cancer, testicular cancer, urethral cancer, uterine sarcoma, vaginal cancer, head cancer, neck cancer, nasopharyngeal carcinoma, hematopoetic cancer, Non-hodgkin lymphoma, skin cancer, basal-cell carcinoma, melanoma, small cell lung cancer, non-small cell lung cancer, or any combination thereof.

In another embodiment, the disease is an autoimmune disease that can be, but is not limited to, achalasia, amyloidosis, ankylosing spondylitis, anti-gbm/anti-tbm nephritis, antiphospholipid syndrome, arthritis, autoimmune angioedema, autoimmune encephalomyelitis, autoimmune hepatitis, autoimmune myocarditis, autoimmune oophoritis, autoimmune orchitis, autoimmune pancreatitis, autoimmune retinopathy, autoimmune urticaria, Behcet's disease, celiac disease, chagas disease, chronic inflammatory demyelinating polyneuropathy, Cogan's syndrome, congenital heart block, Crohn's disease, dermatitis, dermatomyositis, discoid lupus, Dressler's syndrome, endometriosis, fibromyalgia, fibrosing alveolitis, granulomatosis with polyangiitis, Graves' disease, Guillain-Barre syndrome, herpes gestationis, immune thrombocytopenic purpura, interstitial cystitis, juvenile arthritis, juvenile diabetes (type 1 diabetes), juvenile myositis, Kawasaki disease, Lambert-Eaton syndrome, lichen planus, lupus, Lyme disease, multiple sclerosis, myasthenia gravis, myositis, neonatal lupus, neutropenia, palindromic rheumatism, peripheral neuropathy, polyarteritis nodosa, polymyalgia rheumatica, polymyositis, postmyocardial infarction syndrome, postpericardiotomy syndrome, primary biliary cirrhosis, primary sclerosing cholangitis, progesterone dermatitis, psoriasis, psoriatic arthritis, reactive arthritis, retroperitoneal fibrosis, rheumatic fever, rheumatoid arthritis, sarcoidosis, Schmidt syndrome, scleritis, scleroderma, Sjögren's syndrome, thrombocytopenic purpura, type 1 diabetes, ulcerative colitis, uveitis, vasculitis, and vitiligo.

In some embodiments, the disease is a transplantation-related disease such as graft-versus-host disease (GvHD). According to one embodiment, the GVHD is acute GVHD. According to another embodiment, the GVHD is chronic GVHD.

Agonistic anti-TNFR2 antibodies (or antigen-binding fragments thereof) as described herein can additionally be used to treat patients in need of organ repair or regeneration. For instance, agonistic TNFR2 antibodies or antigen-binding fragments thereof may be used to stimulate organ repair or regeneration, e.g., by binding TNFR2 on the surface of cells within damaged tissue so as to induce TRAF2/3- and/or NFκB-mediated cell proliferation. Examples of tissues and organs that may be induced to regenerate by administration of an agonistic TNFR2 antibody or antigen-binding fragment thereof include, but are not limited to, pancreas, salivary gland, pituitary gland, kidney, heart, lung, hematopoietic system, cranial nerves, heart, blood vessels including the aorta, olfactory gland, ear, nerves, structures of the head, eye, thymus, tongue, bone, liver, small intestine, large intestine, gut, lung, brain, skin, peripheral nervous system, central nervous system, spinal cord, breast, embryonic structures, embryos, and testes.

Agonistic anti-TNFR2 antibodies (or antigen-binding fragments thereof) as described herein can also be administered to a subject (e.g., a human) in order to treat a neurological disease or condition, such as brain tumor, brain metastasis, spinal cord injury, schizophrenia, epilepsy, Amyotrophic lateral sclerosis (ALS), Parkinson's disease, Alzheimer's disease, Huntington's disease, or stroke.

The agonistic TNFR2 antibodies (or antigen-binding fragments thereof) described herein may also be admixed, conjugated, or administered with, or administered separately from, another agent that promotes regulatory T cells proliferation. Additional agents that can be used to promote regulatory T cell expansion include, but are not limited to, IL-2 and TNFα, the cognate ligand for TNFR2.

In another embodiment, the present disclosure provides a method of using a polynucleotide to treat a disease or condition as described above, wherein the polynucleotide encodes an anti-TNFR2 antibody as described herein.

Various embodiments and embodiments of the present anti-TNFR2 antibodies as delineated hereinabove and as claimed in the claims section below find experimental support in the following examples. Exemplified herein is the generation of anti-TNFR2 agonist antibodies that present as non-aggregated species and migrated on the SEC columns as a typically folded IgG1. The anti-TNFR2 IgG1 agonist antibodies generated bound soluble TNFR2-His at about an EC50 range of 1.8 nM to 66 nM, indicating that these antibodies are tight binders. Further, the antibodies specifically bound TNFR2 and did not bind TNFR1. Anti-TNFR2 antibodies generated include high affinity functional agonists, which may agonize the TNFR2 receptor without the addition of other molecules with an EC50 range of 0.5 nM to 277 nM. Moreover, TNFR2 activation by anti-TNFR2 antibodies generated appears to be independent of IgG-Fc clustering. Examination of the effects of TNFα on the activation properties of the anti-TNFR2 antibodies generated, indicated that these antibodies activate the TNFR2 receptor to almost its full capacity, and most likely at an epitope that is not blocking the TNFα binding site.

EXAMPLES

Example 1

Generation of TNFR2 Agonists

Experimental Procedures
Library Generation
Library Construction

Libraries were constructed based on three template antibodies (PDB: 2I5Y, 4101 and 3E8U) by overlapping extension PCR with degenerate oligonucleotides. PCR used to introduce diversity was carried out using Phusion high fidelity DNA polymerase (New England Biolabs USA, Cat: M0530) according to manufacturer instructions in a 3-step reaction (98° C. for 30 sec, 65° C. for 20 sec, 72° C. for 30 sec, 30 cycles). The PCR products were gel purified using a gel purification kit and assembled in equimolar ratios in a 3-step PCR reaction, as above, but in the absence of primers. The assembled PCR product was reused as template for PCR amplifying the full scFv library, as above, using forward and reverse primers adding the yeast surface display (YSD) expression vector homology sequences at the 5' and 3' to the scFv library to efficiently perform homologous recombination in yeast cells.

scFv libraries were constructed with three repeats of flexible linkers of Gly-Gly-Gly-Gly-Ser (SEQ ID NO:333) between the VH and VL.

Fab display libraries were constructed in a similar fashion to the scFv libraries with the following modifications: the VL and VH were constructed separately and were cloned under two promoters. The VH was cloned in-frame under the Gal 10 promoter, between the aga2 gene and the constant heavy chain domain 1 (CH1). The VL was cloned in-frame under the Gall promoter between a signal peptide and a constant light domain (CL). The Fab fragments were combined using PCR into one fragment and cloned into the pFAB1 expression vector in a similar fashion to the scFv libraries.

Library Transformation

Library transformation was carried out as published (Benatuil et al., An improved yeast transformation method for the generation of very large human antibody libraries. *Protein Eng. Des. Sel.* 23, 155-159 (2010)). Four hundred μl of a yeast suspension (EBY100, ATCC, USA) per 0.2 cm cuvette (cell projects) was electroporated (BioRad, USA, GenePulser) with 4 μg linearized vector (pCTcon3 or pFAB1) and 12 μg DNA insert (either scFv fragment or assemble Fab) in a 1:3 vector to insert ratio (Chao, G. et al., Isolating and engineering human antibodies using yeast surface display. *Nat. Protoc.* 1, 755-768 (2006)). The average number of transformants in a library was determined to be ~$1\times10^8$ by serial dilutions of transformed cells.

Library Screening
Screening and Selection Using Yeast Surface Display

Yeast display libraries were grown in a SDCAA selective medium and induced for expression with 2% w/v galactose at 30° C. overnight according to established protocols (Chao, G. et al., (2006)). Briefly, the library was incubated with 1000 to 0.1 nM of recombinant human TNFR2 with 6×his tag or TNFR2-Fc fusion (Reprokine, Israel) in PBS 0.1% BSA for 1 hour, then washed three times with PBS 0.1% BSA and labeled with either: mouse anti c-Myc FITC (Miltenyi Biotec, cat #130-116-485), mouse anti c-Myc (Santa Cruze, USA cat #sc-40), and also fluorescently labeled goat anti-mouse IgG-FITC (Sigma-Aldrich, cat #F4143-1 ml), monoclonal anti His APC (Miltenyi Biotec, Germany. cat 0020130-119-782), or anti Fc APC (Jackson ImmunoResearch, USA. cat. 109-135-098).

When it was necessary to avoid non-specific binding, the fluorescent-labeled antibodies were alternated with rabbit anti c-Myc (Abcam, cat #ab9106), goat anti-rabbit APC (Abcam, Cat #ab130805), and anti-His Alexa488 (Qiagen, cat #20-35310).

Post labeling the library was selected on MACS beads, until the library size was reduced to $1\times10^6$ and then sorted on BioRad S3e or BD ARIA III Fluorescence Activated Cell Sorter (FACS) for high affinity binders of recombinant human TNFR2. Clones isolated from the final sort were sequenced by extraction of plasmid DNA from the yeast clones using a Zymoprep kit (Zymo Research, USA) and the DNA was sequenced.

When applicable yeast displaying Fab were labeled and selected under the same conditions mentioned for scFv selection with the addition of anti-FLAG-PE (Miltenyi Biotec, cat #130-101-576) for the detection of Fab light chain display.

Koff Selection

To select for binders with improved off rate, the yeast were incubated for 30 min with 10 nM to 1 nM TNFR2-His. Subsequently the yeast were washed three times with 1 ml PBS 0.1% BSA and incubated for 4 h, 6 h, and 24 h with 100 nM TNFR2-Fc. Alternatively, post wash, the cells were diluted 10-fold in PBS 0.1% BSA and incubated for the indicated time points. The yeast were then washed three times and labeled with anti-Myc-FITC (Santa Cruze, USA, Cat #9E10) and monoclonal anti-His/APC (Miltenyi Biotec, Germany. cat 0020130-119-782), and sorted on Se3 FACS as described above.

Furthermore, two rounds of Koff selections were done at the most suitable time point in which approximately 50%-70% of initial binding was lost.

Analysis of Clones by Yeast Surface Display $EC_{50}$

To determine the effective concentration$_{50}$ ($EC_{50}$) of TNFR2 binding to yeast scFv or Fab clones ($EC_{50}$—TNFR2 binding), specific clones were labeled at TNFR concentrations ranging from 0.1 nM to 1000 nM and analyzed on an FACS. Median fluorescence intensity (MFI) was determined for each TNFR2 concentration and $EC_{50}$ (TNFR2 binding) was calculated using Prisma 8 GraphPad (GraphPad, San Diego, USA) software.

IgG Production

Reformatting

Selected scFv and Fab clones were reformatted to human IgG1 format. The sequences of the light chain (LC) and heavy chain (HC) variable regions were optimized to mammalian codon usage and ordered as genblocks (GB) from IDT (Integrated DNA Technologies. Coralville, Iowa USA). The GB were cloned using standard cloning techniques into pSF-CMV-HuIgG1_HC (HC plasmid) and pSF-CMV-Hu-Lambda_LC (LC plasmid) (Oxford genetics, Oxford UK). When indicated, a pSF-CMV-HuIgG1_HC with L234A/L235A (LALA) mutation was used.

IgG Expression

Expi-CHO cells (Thermo Fisher Scientific, USA) were transfected with LC and HC plasmids at a ratio of 2:1 and expression was carried out according to the manufacturer's instructions. Briefly: 50 ml Expi-CHO cells were cultured at 37° C., 120 rpm, $CO_2$ 8% to a density of $6\times10^6$ cells/ml. Then, 50 μg of expression heavy chain and light chain plasmids at a ratio of 1:2 were transfected into the CHO cells. Post transfections, a booster and feed were added to the culture, and growth conditions were changed to 32° C., 120 rpm, 5% $CO_2$. The cells were harvested 10 days after transfection. The IgGs were purified from the supernatant using protein A beads (Tosoh Bioscience GmbH, Germany), followed by size exclusion chromatography (SEC) purification on SUPERDEX 200™ 10/300 increase column, with PBS as mobile phase (GE healthcare, USA).

Size Exclusion Chromatography

To analyze and purify the IgGs, samples were loaded on a SUPERDEX200™ 10/300 increase column (GE healthcare, USA) at a flow rate of 0.8 ml/min on a GE AKTA Explorer chromatography system (GE healthcare, USA). Alternatively, where indicated, up to 12 mg IgGs were loaded on a Waters ACQUITY arc HPLC, equipped with BioResolve™ SEC mAb column (Waters, USA), with a flow rate of 0.5 ml/min and run time of 20 minutes. PBS served as mobile phase and retention was monitored at 280 nM for both columns.

Ligand Binding ELISA

IgG binding affinity to TNFR2 was examined by ELISA. 96 well plates (Greiner Bio-One high binding) were coated with (50 ng/well) of the analyzed antibody and incubated overnight at 4° C. The plates were then washed three times with 300 μl PBS buffer containing 0.05% Tween 20 (PBS-T), blocked with 300μ PBS-T supplemented with 1% to 2% BSA, and incubated for 1 hour at room temperature. Antibodies-coated plates were washed three times with 300 μl PBS-T and incubated with serial dilutions of test ligand hTNFR2-His (Reprokine, Israel) in a final volume of 50 ml for 1-2 hours. Plates were then washed three times with 300 μl PBS-T and incubated with 50 μl anti-HIS-HRP (Santa Cruz Biotechnology, USA, SC-8036HRP) conjugate that was diluted 1:250 in PBS. After an additional wash step of six washes, the reaction was developed with 50 ml tetramethylbenzidine (TMB) reagent (Southern biotech, USA), and stopped with 50 ml 0.5N $H_2SO_4$. Detection was done on a Synergy LX BioTek (BioTek, USA) plate reader with an absorbance filter set to 450 nM. The binding affinity was determined by fitting the data to a specific binding non-linear regression model on Prisma 8 GraphPad software.

TNFR2/TNFR1 specificity ELISA was done in a similar manner to the $EC_{50}$ ELISA assay ($EC_{50}$-TNFR2 binding) but with a concentration of 100-1000 nM for both TNFR1 and TNFR2.

FACS Analysis

LALA mutated Fc format anti-TNFR2 antibody (30.116), was incubated with HEK-TNFR1 (HEK-Blue-TNFa (InvivoGen, Cat: hkb-tnfdmyd) and HEK-TNFR2 (described herein) cell lines for 15 min on ice (200 nM of Ab, 1,000,000 cells per well). Subsequently, the cells were stained with goat anti-human Fc-APC conjugated, for 30 min on ice according to manufacture instructions (Jackson immune research, cat. #109-135-098). Cell were analyzed on CytoFLEX flow cytometer (Beckman, USA). Gates were determined separately for each cell population, based on secondary only control.

Results

Library Design

In order to generate an antibody that binds TNFR2, a "re-epitoping" approach was applied to an existing antibody. The re-epitoping process allows for the introduction of new specificity to an existing antibody, and can allow for choosing a known antibody with favorable biophysical and biochemical properties as a template. Therefore, the re-epitoped antibody can have both a new specificity and desirable developability profile. The computational process of re-epitoping requires two steps: (i) using any computational analysis that identifies putative complementarity between existing antibody and a new epitope, and (ii) application of any computational analysis or tool that can suggest introduction of specific mutations predicted to enhance antibody binding to the new, desired epitope. Examples of such computational processes are presented in published U.S. Patent Application No. US20180068055, and Nimrod et al., *Cell Rep.* 25(8):2121-2131 (2018). In one embodiment, three libraries were designed using the sequences of the variable domains of re-epitoping template antibodies 2I5Y, 4IOI and 3E8U, which are predicted to be good candidates for introducing new specificity towards TNFR2. The sequences of some of these templates were further modified in later generation libraries to account for better developability or for humanization. The libraries for re-epitoping were constructed and introduced to yeast as described above.

YSD Screen for TNFR2 Binders

Following introduction of variations, the library was screened in a yeast surface display (YSD) format to identify clones that specifically bind to TNFR2. Initially, the libraries underwent MACS (magnetic beads) selection followed by FCAS selection. Clones from all three re-epitoping templates showed relative binding.

To further enhance affinity, affinity maturation libraries were constructed in a similar fashion to the construction of libraries described above. The affinity maturation libraries were passed through regular and specific Koff improvement selection as described above. Best binders were gated, yeast clones were isolated and sequenced. These clones are listed in Table 1.

TABLE 1

Sequences of TNFR2 Binders in scFv and Fab Format

| Clone_ID | Sequences | SEQ ID NO: |
|---|---|---|
| CID251 | DNA sequence | 1 |
| | Protein sequence, VH + VL | 2 |
| | protein sequence - VH | 3 |
| | protein sequence - VL | 4 |
| CID_252 | DNA sequence | 5 |
| | Protein sequence, VH + VL | 6 |
| | protein sequence - VH | 7 |
| | protein sequence - VL | 8 |
| CID_253 | DNA sequence | 9 |
| | Protein sequence, VH + VL | 10 |
| | protein sequence - VH | 11 |
| | protein sequence - VL | 12 |
| CID_254 | DNA sequence | 13 |
| | Protein sequence, VH + VL | 14 |
| | protein sequence - VH | 15 |
| | protein sequence - VL | 16 |
| CID_255 | DNA sequence | 17 |
| | Protein sequence, VH + VL | 18 |
| | protein sequence - VH | 19 |
| | protein sequence - VL | 20 |
| CID_256 | DNA sequence | 21 |
| | Protein sequence, VH + VL | 22 |
| | protein sequence - VH | 23 |
| | protein sequence - VL | 24 |
| CID_257 | DNA sequence | 25 |
| | Protein sequence, VH + VL | 26 |
| | protein sequence - VH | 27 |
| | protein sequence - VL | 28 |
| CID_258 | DNA sequence | 29 |
| | Protein sequence, VH + VL | 30 |
| | protein sequence - VH | 31 |
| | protein sequence - VL | 32 |

TABLE 1-continued

Sequences of TNFR2 Binders in scFv and Fab Format

| Clone_ID | Sequences | SEQ ID NO: |
|---|---|---|
| CID_259 | DNA sequence | 33 |
| | Protein sequence, VH + VL | 34 |
| | protein sequence - VH | 35 |
| | protein sequence - VL | 36 |
| CID_272 | DNA sequence | 37 |
| | Protein sequence, VH + VL | 38 |
| | protein sequence - VH | 39 |
| | protein sequence - VL | 40 |
| CID_274 | DNA sequence | 41 |
| | Protein sequence, VH + VL | 42 |
| | protein sequence - VH | 43 |
| | protein sequence - VL | 44 |
| CID_275 | DNA sequence | 45 |
| | Protein sequence, VH + VL | 46 |
| | protein sequence - VH | 47 |
| | protein sequence - VL | 48 |
| CID_276 | DNA sequence | 49 |
| | Protein sequence, VH + VL | 50 |
| | protein sequence - VH | 51 |
| | protein sequence - VL | 52 |
| CID_277 | DNA sequence | 53 |
| | Protein sequence, VH + VL | 54 |
| | protein sequence - VH | 55 |
| | protein sequence - VL | 56 |
| CID_278 | DNA sequence | 57 |
| | Protein sequence, VH + VL | 58 |
| | protein sequence - VH | 59 |
| | protein sequence - VL | 60 |
| CID_280 | DNA sequence | 61 |
| | Protein sequence, VH + VL | 62 |
| | protein sequence - VH | 63 |
| | protein sequence - VL | 64 |
| CID_281 | DNA sequence | 65 |
| | Protein sequence, VH + VL | 66 |
| | protein sequence - VH | 67 |
| | protein sequence - VL | 68 |
| CID_282 | DNA sequence | 69 |
| | Protein sequence, VH + VL | 70 |
| | protein sequence - VH | 71 |
| | protein sequence - VL | 72 |
| CID_283 | DNA sequence | 73 |
| | Protein sequence, VH + VL | 74 |
| | protein sequence - VH | 75 |
| | protein sequence - VL | 76 |
| CID_284 | DNA sequence | 77 |
| | Protein sequence, VH + VL | 78 |
| | protein sequence - VH | 79 |
| | protein sequence - VL | 80 |
| CID_285 | DNA sequence | 81 |
| | Protein sequence, VH + VL | 82 |
| | protein sequence - VH | 83 |
| | protein sequence - VL | 84 |
| CID_436 | DNA sequence | 85 |
| | Protein sequence, VH + VL | 86 |
| | protein sequence - VH | 87 |
| | protein sequence - VL | 88 |
| CID_437 | DNA sequence | 89 |
| | Protein sequence, VH + VL | 90 |
| | protein sequence - VH | 91 |
| | protein sequence - VL | 92 |
| CID_331 | DNA sequence | 93 |
| | Protein sequence, VH + VL | 94 |
| | protein sequence - VH | 95 |
| | protein sequence - VL | 96 |
| CID_332 | DNA sequence | 97 |
| | Protein sequence, VH + VL | 98 |
| | protein sequence - VH | 99 |
| | protein sequence - VL | 100 |
| CID_333 | DNA sequence | 101 |
| | Protein sequence, VH + VL | 102 |
| | protein sequence - VH | 103 |
| | protein sequence - VL | 104 |
| CID_323 | DNA sequence | 105 |
| | Protein sequence, VH + VL | 106 |
| | protein sequence - VH | 107 |
| | protein sequence - VL | 108 |

TABLE 1-continued

Sequences of TNFR2 Binders in scFv and Fab Format

| Clone_ID | Sequences | SEQ ID NO: |
|---|---|---|
| CID_324 | DNA sequence | 109 |
| | Protein sequence, VH + VL | 110 |
| | protein sequence - VH | 111 |
| | protein sequence - VL | 112 |
| CID_325 | DNA sequence | 113 |
| | Protein sequence, VH + VL | 114 |
| | protein sequence - VH | 115 |
| | protein sequence - VL | 116 |
| CID_326 | DNA sequence | 117 |
| | Protein sequence, VH + VL | 118 |
| | protein sequence - VH | 119 |
| | protein sequence - VL | 120 |
| CID_327 | DNA sequence | 121 |
| | Protein sequence, VH + VL | 122 |
| | protein sequence - VH | 123 |
| | protein sequence - VL | 124 |
| CID_328 | DNA sequence | 125 |
| | Protein sequence, VH + VL | 126 |
| | protein sequence - VH | 127 |
| | protein sequence - VL | 128 |
| CID_329 | DNA sequence | 129 |
| | Protein sequence, VH + VL | 130 |
| | protein sequence - VH | 131 |
| | protein sequence - VL | 132 |
| CID_330 | DNA sequence | 133 |
| | Protein sequence, VH + VL | 134 |
| | protein sequence - VH | 135 |
| | protein sequence - VL | 136 |
| CID_350 | DNA sequence | 137 |
| | Protein sequence, VH + VL | 138 |
| | protein sequence - VH | 139 |
| | protein sequence - VL | 140 |
| CID_279 | DNA sequence | 141 |
| | Protein sequence, VH + VL | 142 |
| | protein sequence - VH | 143 |
| | protein sequence - VL | 144 |
| CID_438 | DNA sequence | 145 |
| | Protein sequence, VH + VL | 146 |
| | protein sequence - VH | 147 |
| | protein sequence - VL | 148 |
| CID_229 | DNA - VH + CH1 | 149 |
| | DNA - VL + CL | 150 |
| | Amino acid sequence - VH | 151 |
| | Amino acid sequence - VL | 152 |
| | Amino acid sequence - CH1 | 153 |
| | Amino acid sequence - CL | 154 |
| CID_231 | DNA - VH + CH1 | 155 |
| | DNA - VL + CL | 156 |
| | Amino acid sequence - VH | 157 |
| | Amino acid sequence - VL | 158 |
| | Amino acid sequence - CH1 | 159 |
| | Amino acid sequence - CL | 160 |
| CID_232 | DNA - VH + CH1 | 161 |
| | DNA - VL + CL | 162 |
| | Amino acid sequence - VH | 163 |
| | Amino acid sequence - VL | 164 |
| | Amino acid sequence - CH1 | 165 |
| | Amino acid sequence - CL | 166 |
| CID_234 | DNA - VH + CH1 | 167 |
| | DNA - VL + CL | 168 |
| | Amino acid sequence - VH | 169 |
| | Amino acid sequence - VL | 170 |
| | Amino acid sequence - CH1 | 171 |
| | Amino acid sequence - CL | 172 |
| CID_261 | DNA - VH + CH1 | 173 |
| | DNA - VL + CL | 174 |
| | Amino acid sequence - VH | 175 |
| | Amino acid sequence - VL | 176 |
| | Amino acid sequence - CH1 | 177 |
| | Amino acid sequence - CL | 178 |
| CID_262 | DNA - VH + CH1 | 179 |
| | DNA - VL + CL | 180 |
| | Amino acid sequence - VH | 181 |
| | Amino acid sequence - VL | 182 |
| | Amino acid sequence - CH1 | 183 |
| | Amino acid sequence - CL | 184 |

TABLE 1-continued

Sequences of TNFR2 Binders in scFv and Fab Format

| Clone_ID | Sequences | SEQ ID NO: |
|---|---|---|
| CID_264 | DNA - VH + CH1 | 191 |
| | DNA - VL + CL | 192 |
| | Amino acid sequence - VH | 193 |
| | Amino acid sequence - VL | 194 |
| | Amino acid sequence - CH1 | 195 |
| | Amino acid sequence - CL | 196 |
| CID_266 | DNA - VH + CH1 | 197 |
| | DNA - VL + CL | 198 |
| | Amino acid sequence - VH | 199 |
| | Amino acid sequence - VL | 200 |
| | Amino acid sequence - CH1 | 201 |
| | Amino acid sequence - CL | 202 |
| CID_267 | DNA - VH + CH1 | 203 |
| | DNA - VL + CL | 204 |
| | Amino acid sequence - VH | 205 |
| | Amino acid sequence - VL | 206 |
| | Amino acid sequence - CH1 | 207 |
| | Amino acid sequence - CL | 208 |
| CID_268 | DNA - VH + CH1 | 209 |
| | DNA - VL + CL | 210 |
| | Amino acid sequence - VH | 211 |
| | Amino acid sequence - VL | 212 |
| | Amino acid sequence - CH1 | 213 |
| | Amino acid sequence - CL | 214 |
| CID_271 | DNA - VH + CH1 | 215 |
| | DNA - VL + CL | 216 |
| | Amino acid sequence - VH | 217 |
| | Amino acid sequence - VL | 218 |
| | Amino acid sequence - CH1 | 219 |
| | Amino acid sequence - CL | 220 |
| CID_230 | DNA - VH + CH1 | 221 |
| | DNA - VL + CL | 222 |
| | Amino acid sequence - VH | 223 |
| | Amino acid sequence - VL | 224 |
| | Amino acid sequence - CH1 | 225 |
| | Amino acid sequence - CL | 226 |
| CID_265 | DNA - VH + CH1 | 227 |
| | DNA - VL + CL | 228 |
| | Amino acid sequence - VH | 229 |
| | Amino acid sequence - VL | 230 |
| | Amino acid sequence - CH1 | 231 |
| | Amino acid sequence - CL | 232 |

Yeast Surface Display $EC_{50}$ Binding to TNFR2

To verify that the TNFR2 binding clones exhibit at least single to double digit nanomolar affinity to TNFR2, a limited set of clones were subjected to a yeast surface display (YSD) $EC_{50}$ binding assay as described above. As can be seen in FIGS. 1A-1D, these clones show affinity to TNFR2-His in the range of 1 nM to 20 nM, indicating that the yeast-displayed scFv and Fabs are tight binders of human TNFR2. A summary of the YSD-$EC_{50}$ values of these clones is presented in

TABLE 2

YSD $EC_{50}$ Binding Value for Yeast Clones Towards Recombinant TNFR2-His

| scFv (YSD clone ID) | $EC_{50}$ Binding value (nM) |
|---|---|
| CID_327 | 4.5 |
| CID_329 | 8.6 |
| CID_330 | 17.7 |
| CID_326 | 6 |
| CID_325 | 2.9 |
| CID_324 | 5.6 |
| CID_323 | 5.2 |
| CID_328 | 5.7 |
| CID_436 | 3.4 |

TABLE 2-continued

| YSD $EC_{50}$ Binding Value for Yeast Clones Towards Recombinant TNFR2-His | |
|---|---|
| scFv (YSD clone ID) | $EC_{50}$ Binding value (nM) |
| CID_437 | 1.2 |
| CID_251 | 1 |

Analysis of Clones that Bind TNFR2 in IgG Format

SEC Analysis

To further characterize the clones that demonstrated binding to TNFR2, clones listed in Table 1 and Table 2 that showed the most promising binding in scFv and Fab were reformatted to human IgG1, transiently expressed in expiCHO cells according to the manufacturer's instructions and purified as described herein. Additionally, DNA for clones 30.032, 30.046, 30.033 was synthesized and IgG was produced in HEK cells by Genscript antibody services (Genscript, USA).

Clones 30.113, 30.114, 30.116, 30.117, 30.118, 30.119 were reformatted to IgG1 with a heavy chain L234A/L235A mutation (LALA mutation) designed to reduce binding of the IgG's Fc to Fc-gamma receptor. Further, additional IgG1 clones comprising the heavy chain L234A/:235A mutation (LALA mutation) were produced. The list of IgG1 anti-TNFR2 antibody clones comprising a heavy chain L234A/L235A mutation includes: BDG30.113, BDG30.114, BDG30.115, BDG30.116, BDG30.117, BDG30.118, BDG30.119, BDG30.122, BDG30.123, BDG30.200, BDG30.201, BDG30.202, BDG30.203, and BDG30.204.

A summary of the scFv and Fabs that were reformatted to an IgG form is listed in Table 3; where noted, the heavy chain includes the LALA mutation.

TABLE 3

Sequences of TNFR2 Binders in Human IgG Format

| Clone_ID | IgG_ID | Human IgG | Sequences | SEQ ID NO: |
|---|---|---|---|---|
| CID_251 | BDG30.046 | Human IgG1 | VH | 233 |
| | | | VL | 234 |
| | | | H chain | 235 |
| | | | L chain | 236 |
| CID_272 | BDG30.090 | Human IgG1 | VH | 237 |
| | | | VL | 238 |
| | | | H chain | 239 |
| | | | L chain | 240 |
| CID_276 | BDG30.092 | Human IgG1 | VH | 241 |
| | | | VL | 242 |
| | | | H chain | 243 |
| | | | L chain | 244 |
| CID_277 | BDG30.093 | Human IgG1 | VH | 245 |
| | | | VL | 246 |
| | | | H chain | 247 |
| | | | L chain | 248 |
| CID_280 | BDG30.094 | Human IgG1 | VH | 249 |
| | | | VL | 250 |
| | | | H chain | 251 |
| | | | L chain | 252 |
| CID_284 | BDG30.095 | Human IgG1 | VH | 253 |
| | | | VL | 254 |
| | | | H chain | 255 |
| | | | L chain | 256 |
| CID_436 | BDG30.032 | Human IgG1 | VH | 257 |
| | | | VL | 258 |
| | | | H chain | 259 |
| | | | L chain | 260 |
| CID_437 | BDG30.033 | Human IgG1 | VH | 261 |
| | | | VL | 262 |
| | | | H chain | 263 |
| | | | L chain | 264 |
| CID_229 | BDG30.080 | Human IgG1 | VH | 265 |
| | | | VL | 266 |
| | | | H chain | 267 |
| | | | L chain | 268 |
| CID_231 | BDG30.081 | Human IgG1 | VH | 269 |
| | | | VL | 270 |
| | | | H chain | 271 |
| | | | L chain | 272 |
| CID_232 | BDG30.082 | Human IgG1 | VH | 273 |
| | | | VL | 274 |
| | | | H chain | 275 |
| | | | L chain | 276 |
| CID_234 | BDG30.084 | Human IgG1 | VH | 277 |
| | | | VL | 278 |
| | | | H chain | 279 |
| | | | L chain | 280 |
| CID_261 | BDG30.085 | Human IgG1 | VH | 281 |
| | | | VL | 282 |
| | | | H chain | 283 |
| | | | L chain | 284 |

TABLE 3-continued

Sequences of TNFR2 Binders in Human IgG Format

| Clone_ID | IgG_ID | Human IgG | Sequences | SEQ ID NO: |
|---|---|---|---|---|
| CID_262 | BDG30.086 | Human IgG1 | VH | 285 |
| | | | VL | 286 |
| | | | H chain | 287 |
| | | | L chain | 288 |
| CID_264 | BDG30.087 | Human IgG1 | VH | 289 |
| | | | VL | 290 |
| | | | H chain | 291 |
| | | | L chain | 292 |
| CID_266 | BDG30.088 | Human IgG1 | VH | 293 |
| | | | VL | 294 |
| | | | H chain | 295 |
| | | | L chain | 296 |
| CID_267 | BDG30.089 | Human IgG1 | VH | 297 |
| | | | VL | 298 |
| | | | H chain | 299 |
| | | | L chain | 300 |
| CID_332 | BDG30.109 | Human IgG1 | VH | 301 |
| | | | VL | 302 |
| | | | H chain | 303 |
| | | | L chain | 304 |
| CID_350 | BDG30.111 | Human IgG1 | VH | 305 |
| | | | VL | 306 |
| | | | H chain | 307 |
| | | | L chain | 308 |
| CID_327 | BDG30.113 | Human IgG1(L234A/L235A) | VH | 309 |
| | | | VL | 310 |
| | | | H chain | 311 |
| | | | L chain | 312 |
| CID_328 | BDG30.114 | Human IgG1(L234A/L235A) | VH | 313 |
| | | | VL | 314 |
| | | | H chain | 315 |
| | | | L chain | 316 |
| CID_262 | BDG30.116 | Human IgG1(L234A/L235A) | VH | 317 |
| | | | VL | 318 |
| | | | H chain | 319 |
| | | | L chain | 320 |
| CID_436 | BGD30.115 | Human IgG1(L234A/L235A) | VH | 257 |
| | | | VL | 258 |
| | | | H chain | 432 |
| | | | L chain | 260 |
| CID_277 | BDG30.117 | Human IgG1(L234A/L235A) | VH | 321 |
| | | | VL | 322 |
| | | | H chain | 323 |
| | | | L chain | 324 |
| CID_280 | BDG30.118 | Human IgG1(L234A/L235A) | VH | 325 |
| | | | VL | 326 |
| | | | H chain | 327 |
| | | | L chain | 328 |
| CID_284 | BDG30.119 | Human IgG1(L234A/L235A) | VH | 329 |
| | | | VL | 330 |
| | | | H chain | 331 |
| | | | L chain | 332 |
| CID_332 | BDG30.122 | Human IgG1(L234A/L235A) | VH | 301 |
| | | | VL | 302 |
| | | | H chain | 433 |
| | | | L chain | 304 |
| CID_350 | BDG30.123 | Human IgG1(L234A/L235A) | VH | 305 |
| | | | VL | 306 |
| | | | H chain | 434 |
| | | | L chain | 308 |
| CID_251 | BDG30.200 | Human IgG1(L234A/L235A) | VH | 233 |
| | | | VL | 234 |
| | | | H chain | 435 |
| | | | L chain | 236 |
| CID_276 | BDG30.201 | Human IgG1(L234A/L235A) | VH | 241 |
| | | | VL | 242 |
| | | | H chain | 436 |
| | | | L chain | 244 |
| CID_261 | BDG30.202 | Human IgG1(L234A/L235A) | VH | 281 |
| | | | VL | 282 |
| | | | H chain | 437 |
| | | | L chain | 284 |
| CID_264 | BDG30.203 | Human IgG1(L234A/L235A) | VH | 289 |
| | | | VL | 290 |
| | | | H chain | 438 |
| | | | L chain | 292 |

TABLE 3-continued

| Sequences of TNFR2 Binders in Human IgG Format | | | | |
|---|---|---|---|---|
| Clone_ID | IgG_ID | Human IgG | Sequences | SEQ ID NO: |
| CID_266 | BDG30.204 | Human IgG1(L234A/L235A) | VH | 293 |
| | | | VL | 294 |
| | | | H chain | 439 |
| | | | L chain | 296 |

Examples of amino acid sequences for the complementarity determining regions (CDRs) are shown in Tables 7-9. Table 7 shows examples of sets of three CDRs on a heavy chain (HCDR1, HCDR2, and HCDR3), and Table 8 shows sets of three CDRs on the corresponding light chain (LCDR1, LCDR2, and LCDR3). Table 9 shows yet other examples of sets of HCDR1, HCDR2, HCDR3 and sets of LCDR1, LCDR2, and LCDR3 for the anti-TNFR2 antibodies disclosed herein.

Figure 1A:
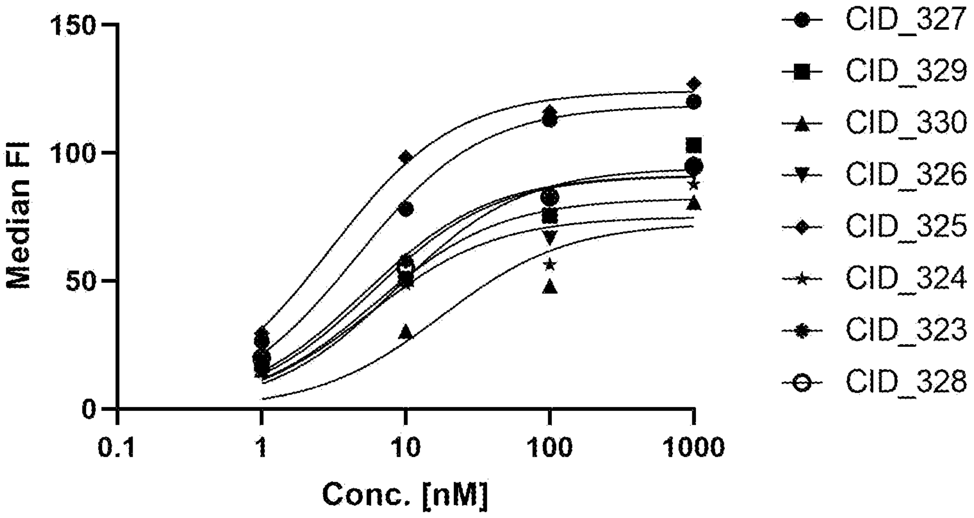
FIGS. 1A-1D show yeast surface display (YSD) $EC_{50}$ (binding) of selected clones toward TNFR2-His. Key for FIG. 1A: CID_327 (circle), CID_329 (square), CID_330 (upward triangle), CID_326 (downward triangle), CID_325 (diamond), CID_324 (star), CID_323 (asterisk), CID_328 (ring).
Figure 1B:
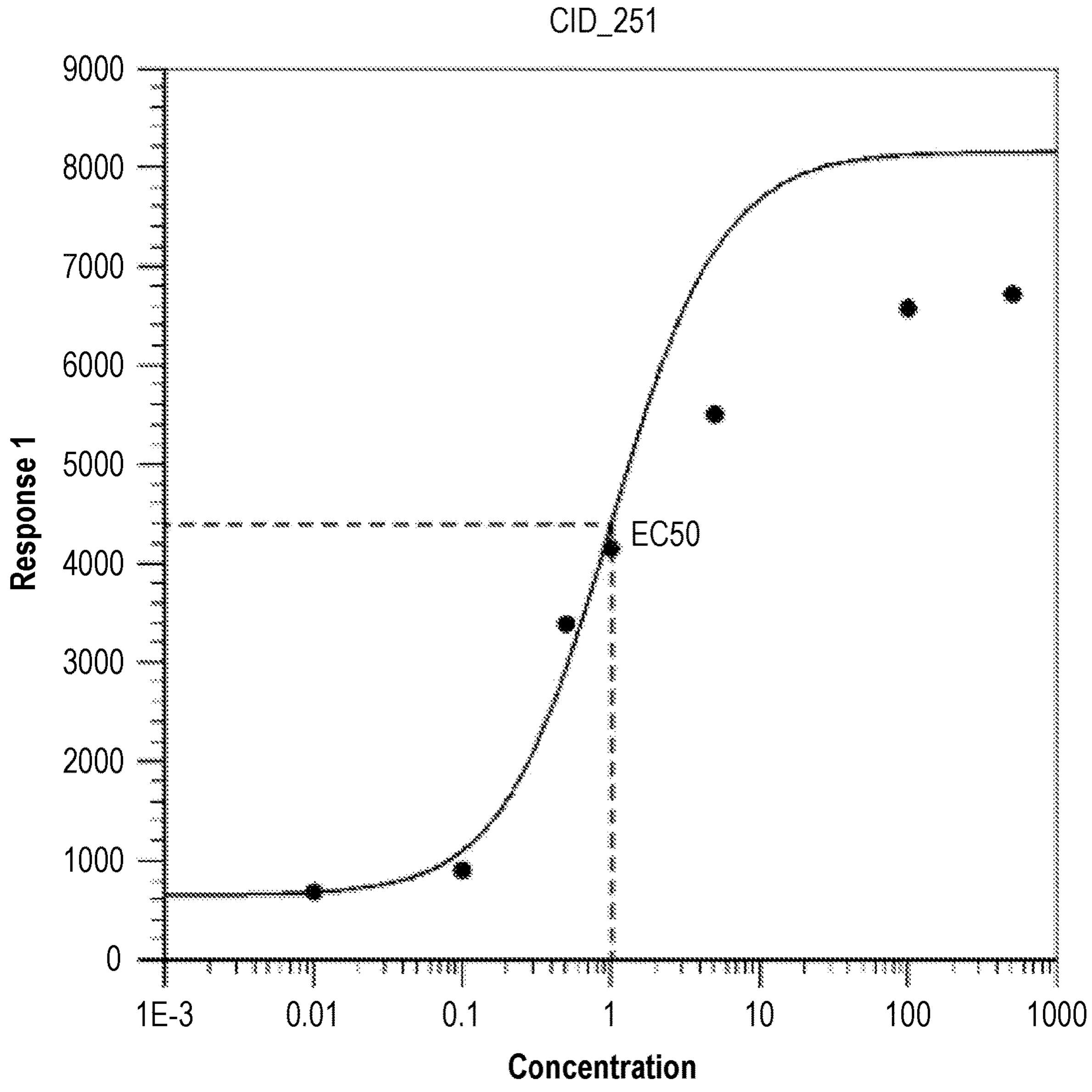
Figure 1C:
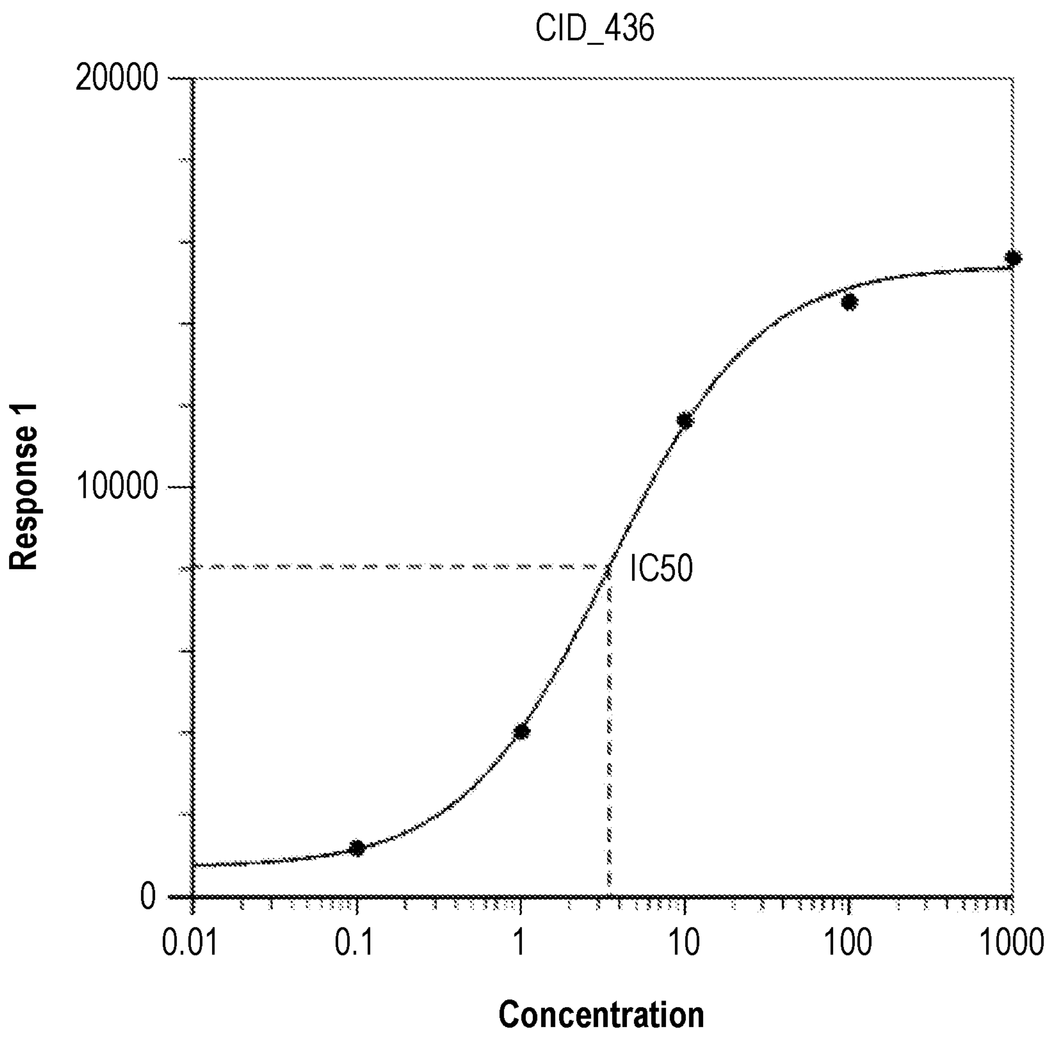
Figure 1D:
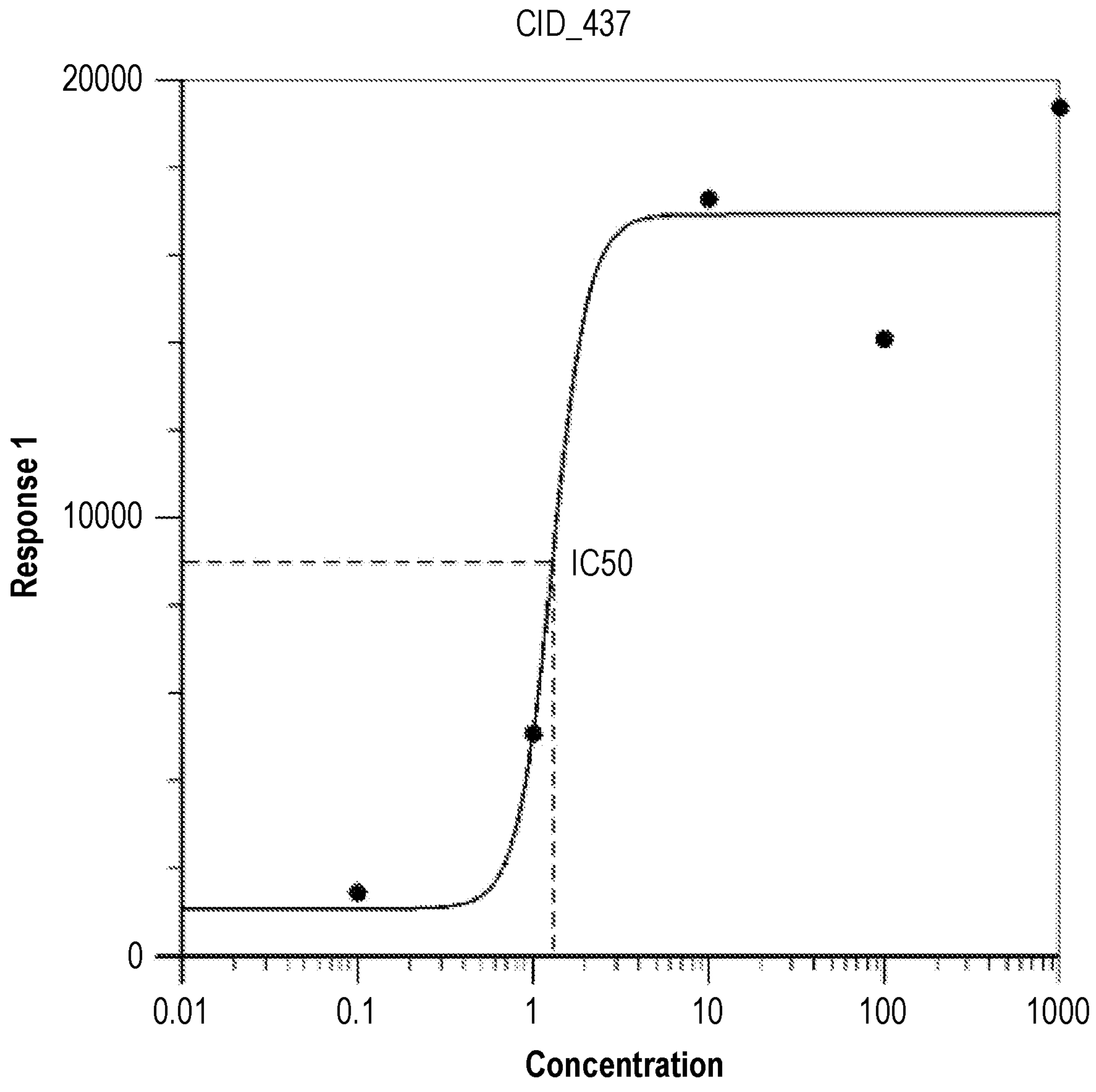
Figure 2A:
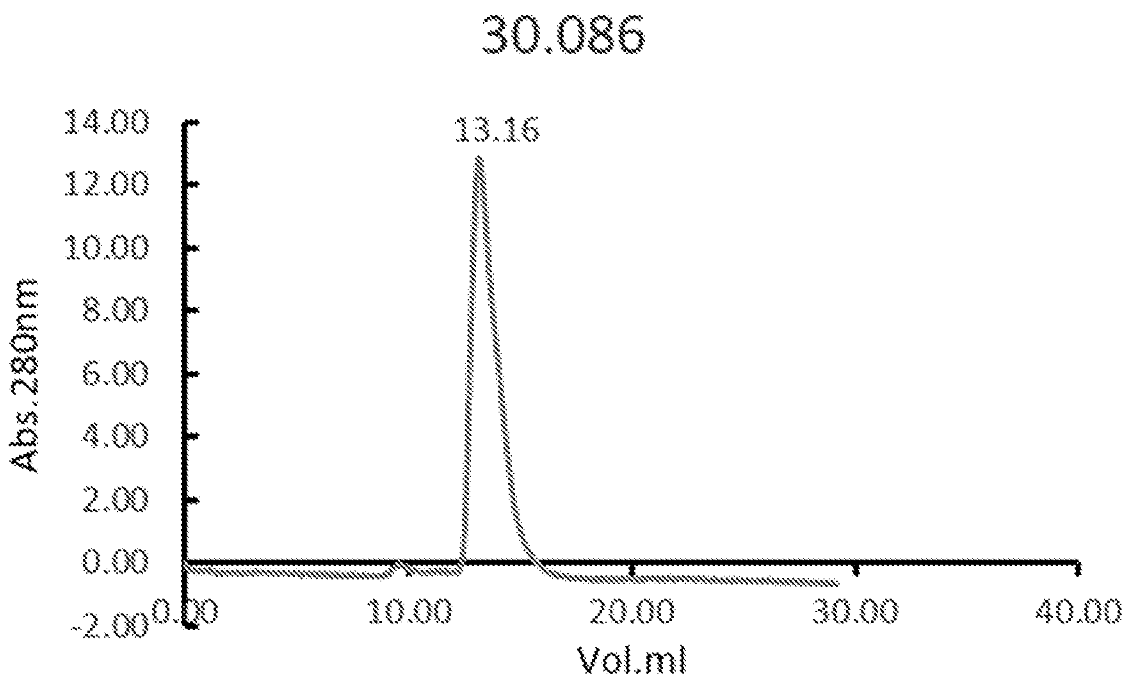
FIGS. 2A-2R show size exclusion chromatography (SEC) analyses of IgG clones 30.086 (FIG. 2A), 30.095 (FIG. 2B), 30.116 (FIG. 2C), 30.111 (FIG. 2D), 30.119 (FIG. 2E), 30.123 (FIG. 2F), 30.204 (FIG. 2G), 30.116 (FIG. 2H), 30.202 (FIG. 2I), 30.202 (FIG. 2J), 30.203 (FIG. 2K), 30.115 (FIG. 2L), 30.200 (FIG. 2M), 30.201 (FIG. 2N), 30.114 (FIG. 2O), 30.117 (FIG. 2P), 30.122 (FIG. 2Q), and 30.118 (FIG. 2R). The retention time of the indicated IgG was monitored at a wavelength of 280 nm. Samples were run under the following conditions: a 100 mg IgG sample was eluted at a rate of 0.8 ml/min on a Superdex® 200 10/300 pg column (FIGS. 2A-2F) or a 12 mg IgG sample was eluted at a rate of 0.5 ml/min on BioResolve SEC mAb column (FIGS. 2G-2R) with PBS as the mobile phase. Axes for FIGS. 2A-2F are Abs. 280 nm vs. vol. (ml) and for FIGS. 2G-2R are absorbance units (AU) vs. minutes.
Figure 2B:
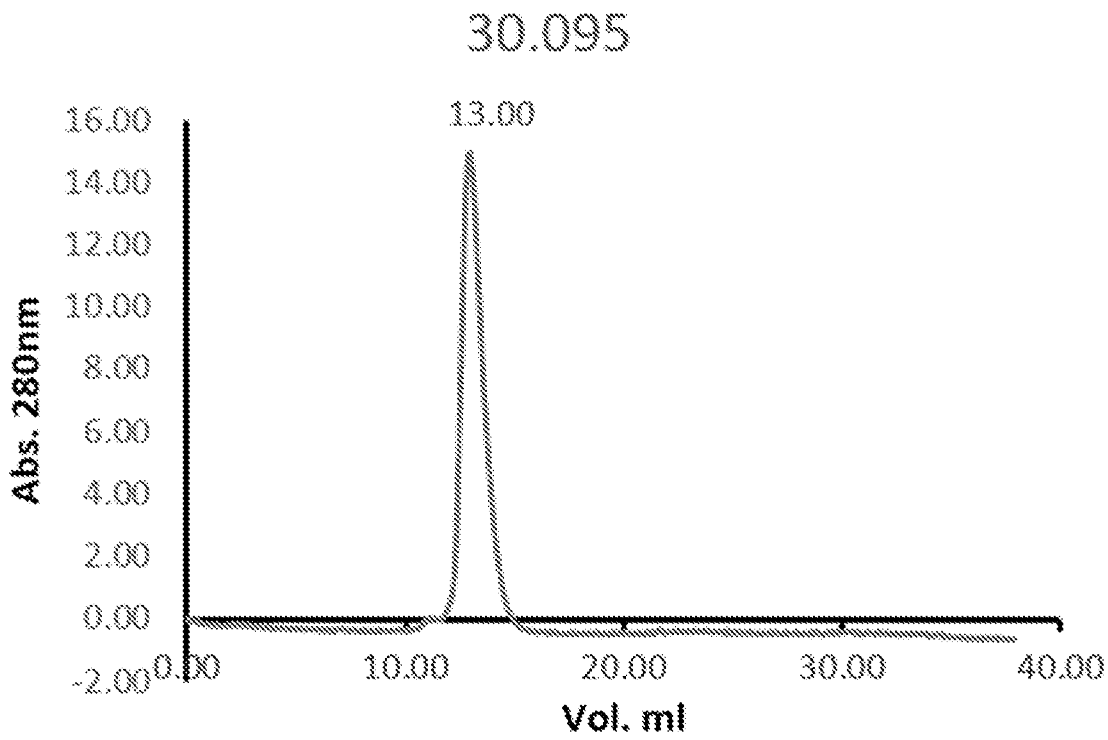
Figure 2C:
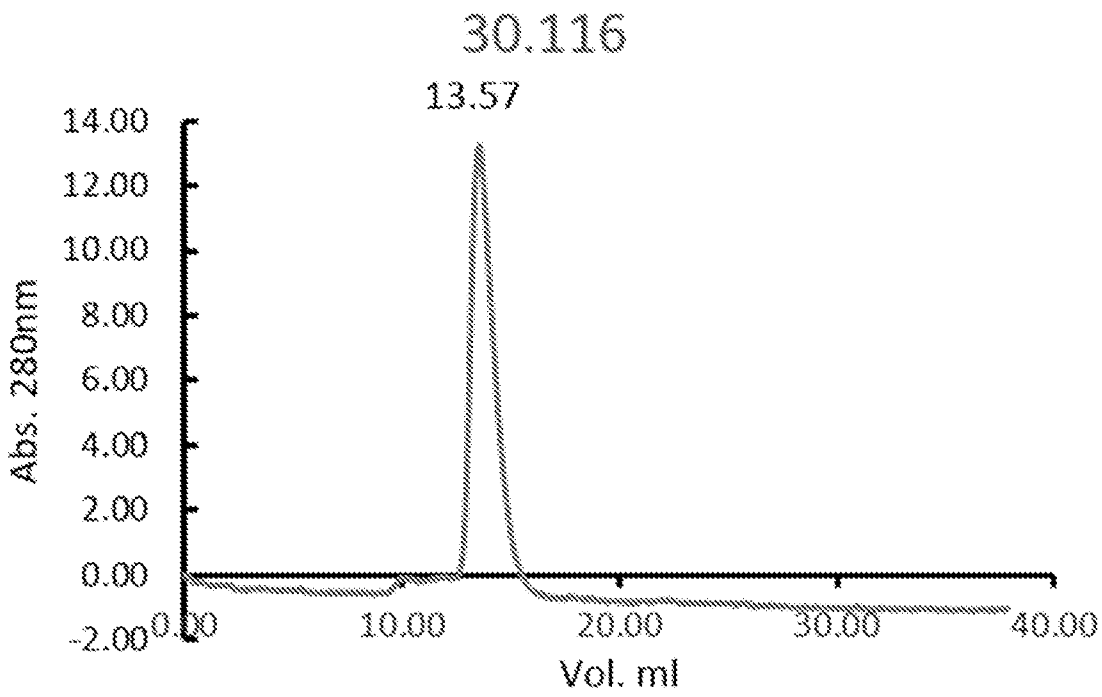
Figure 2D:
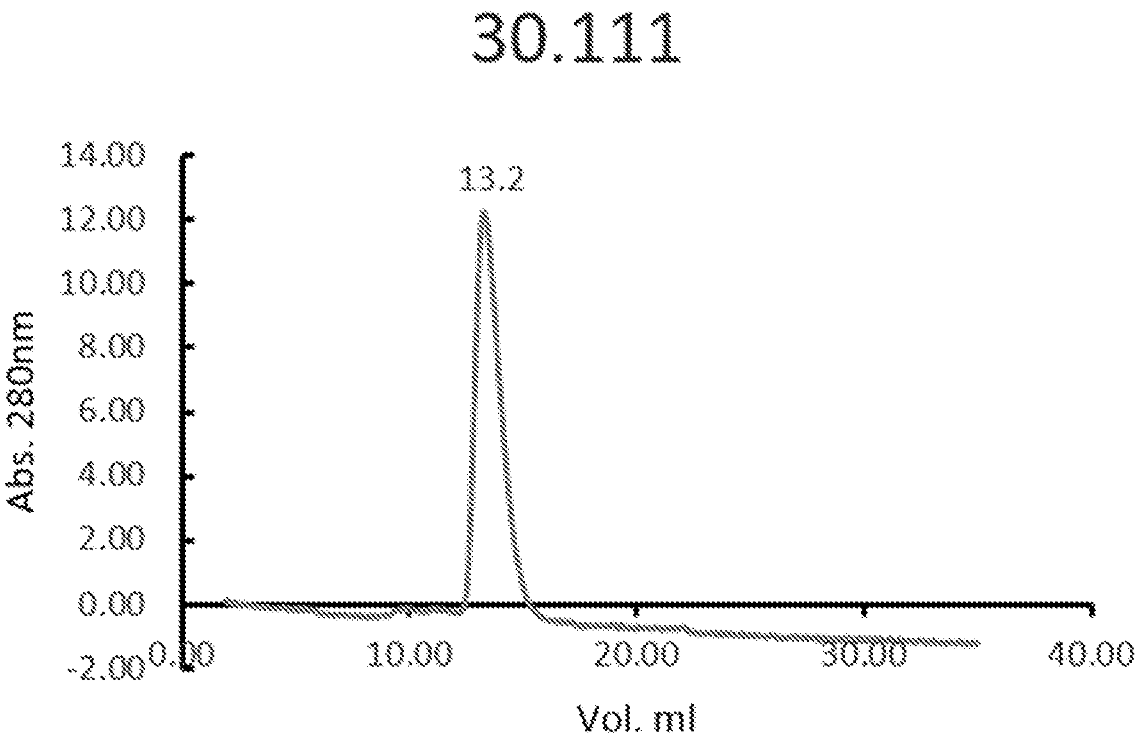
Figure 2E:
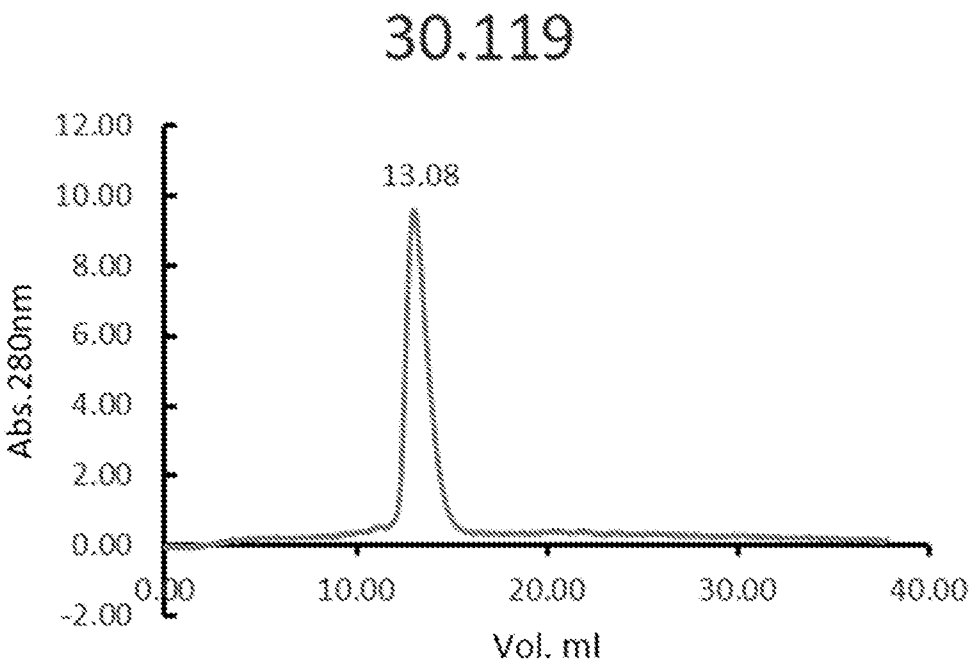
Figure 2F:
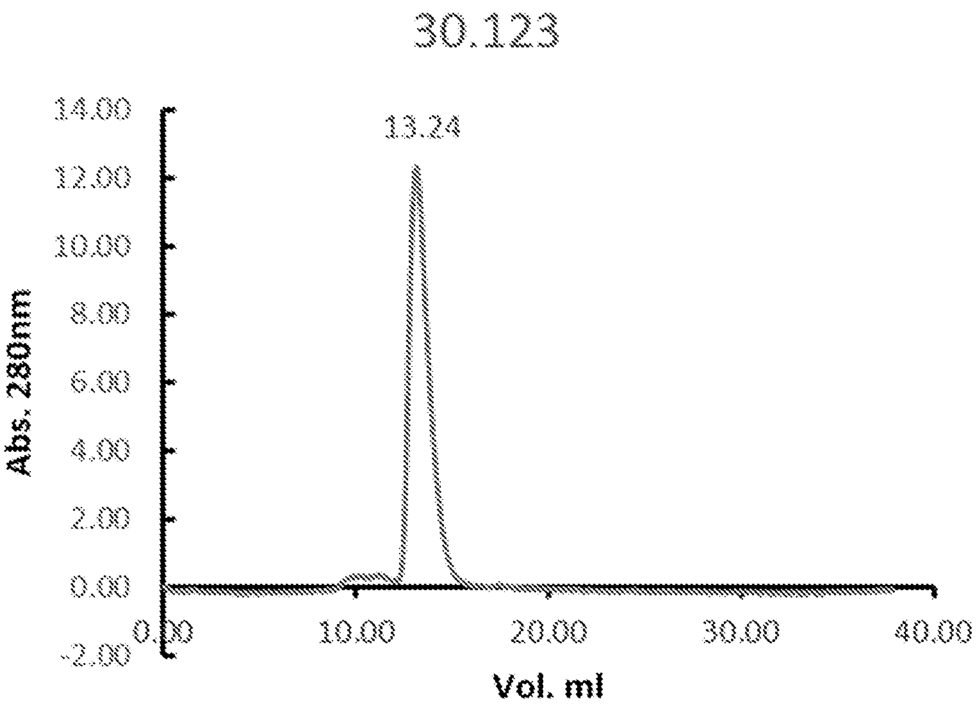
Figure 2G:
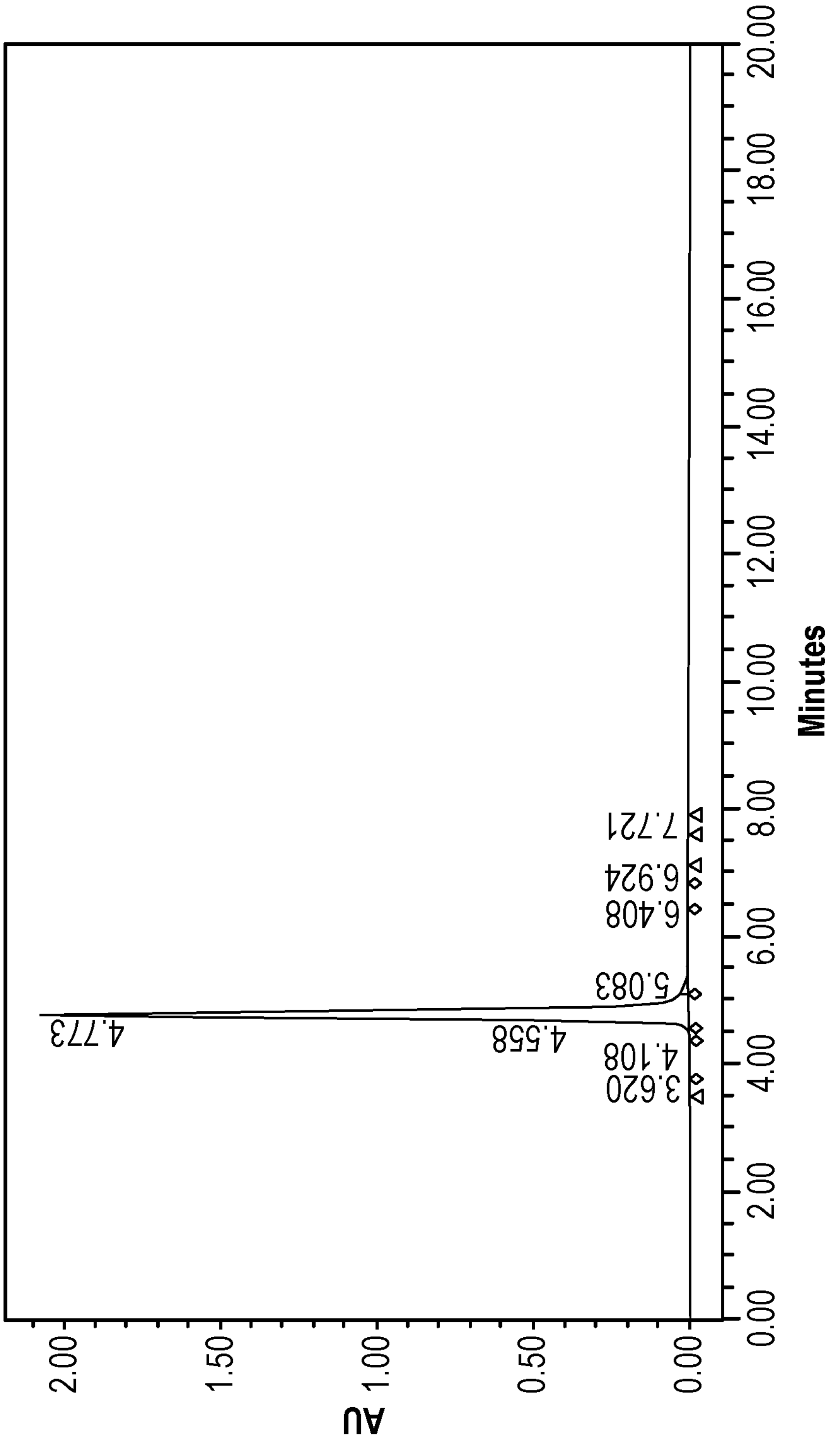
Figure 2H:
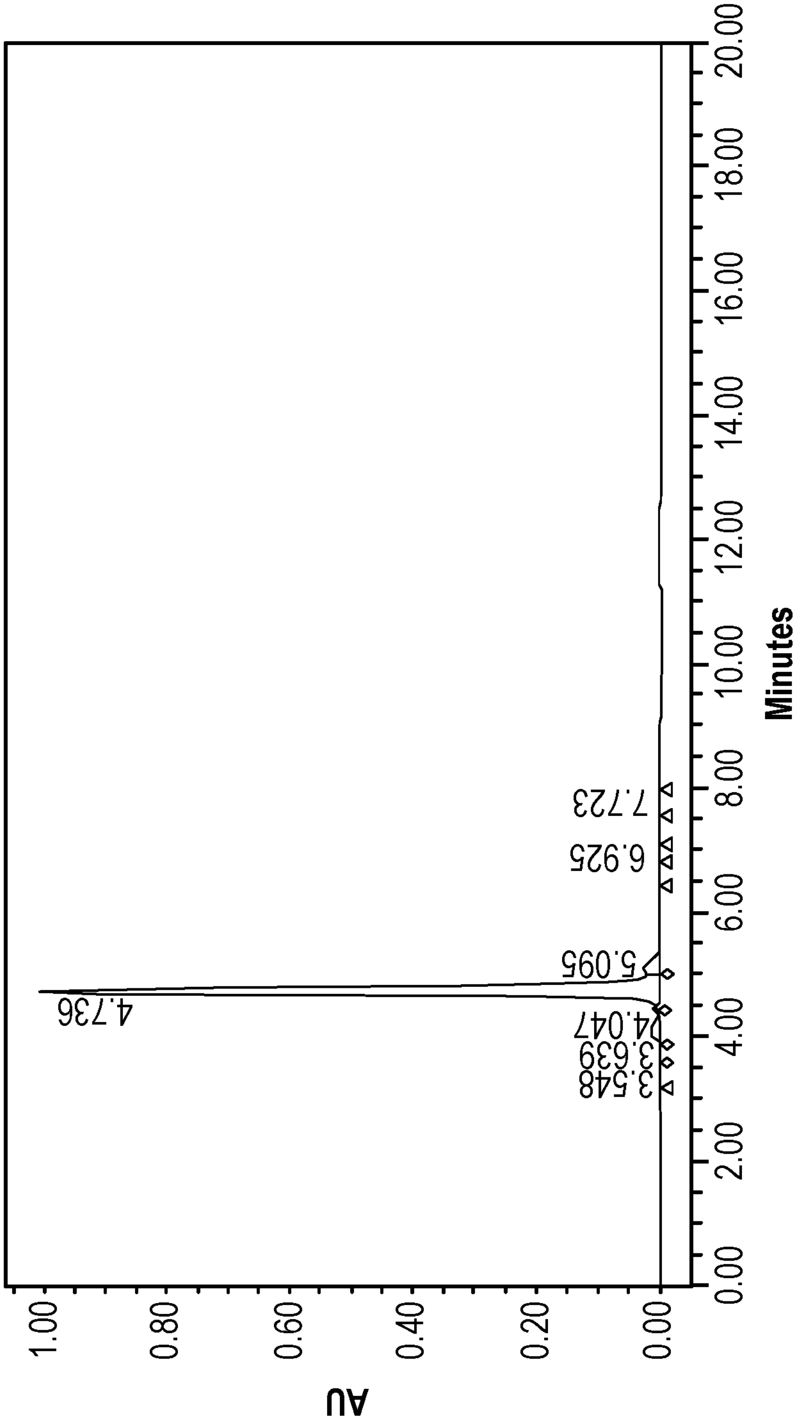
Figure 2I:
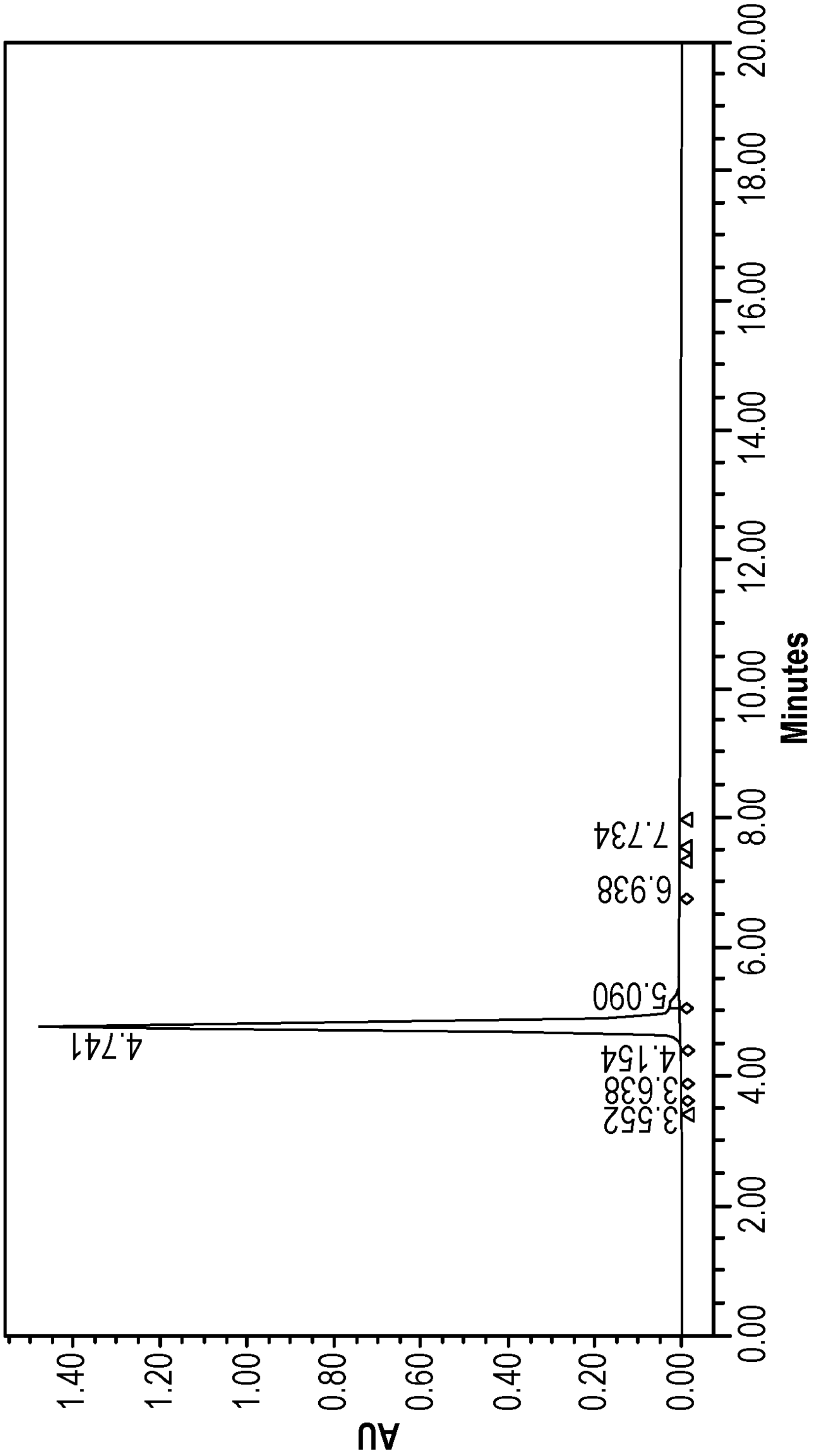
Figure 2J:
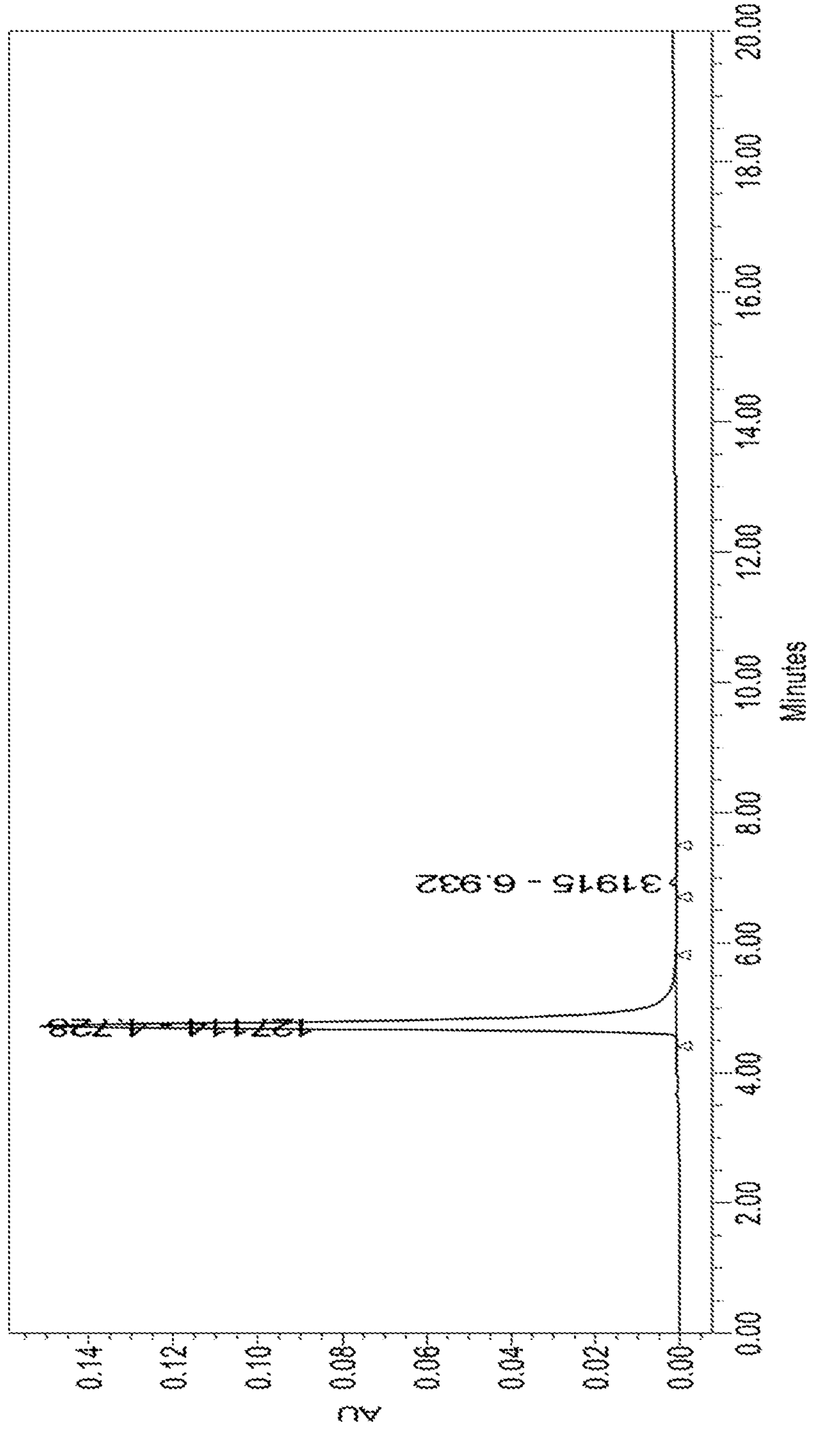
Figure 2K:
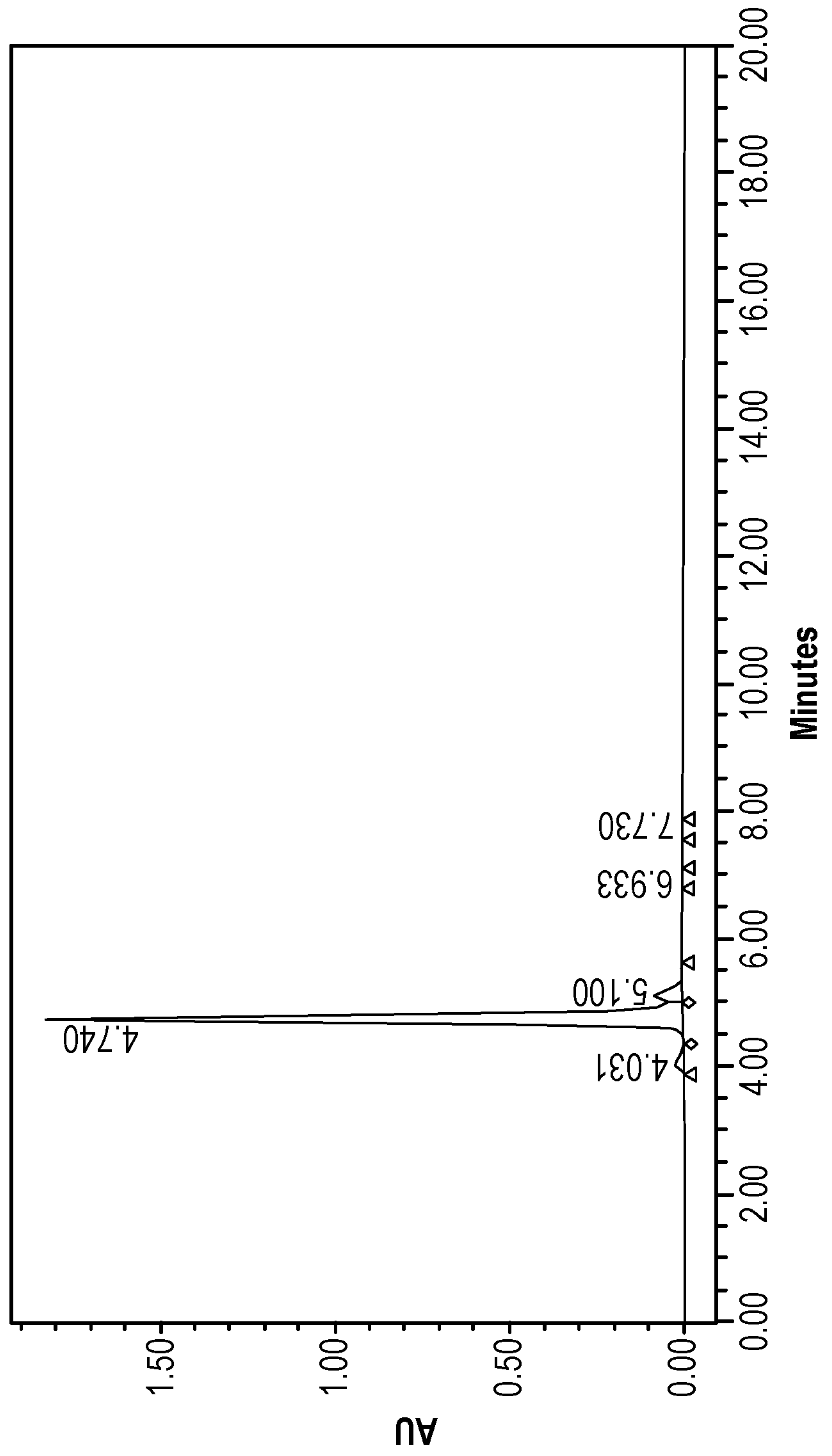
Figure 2L:
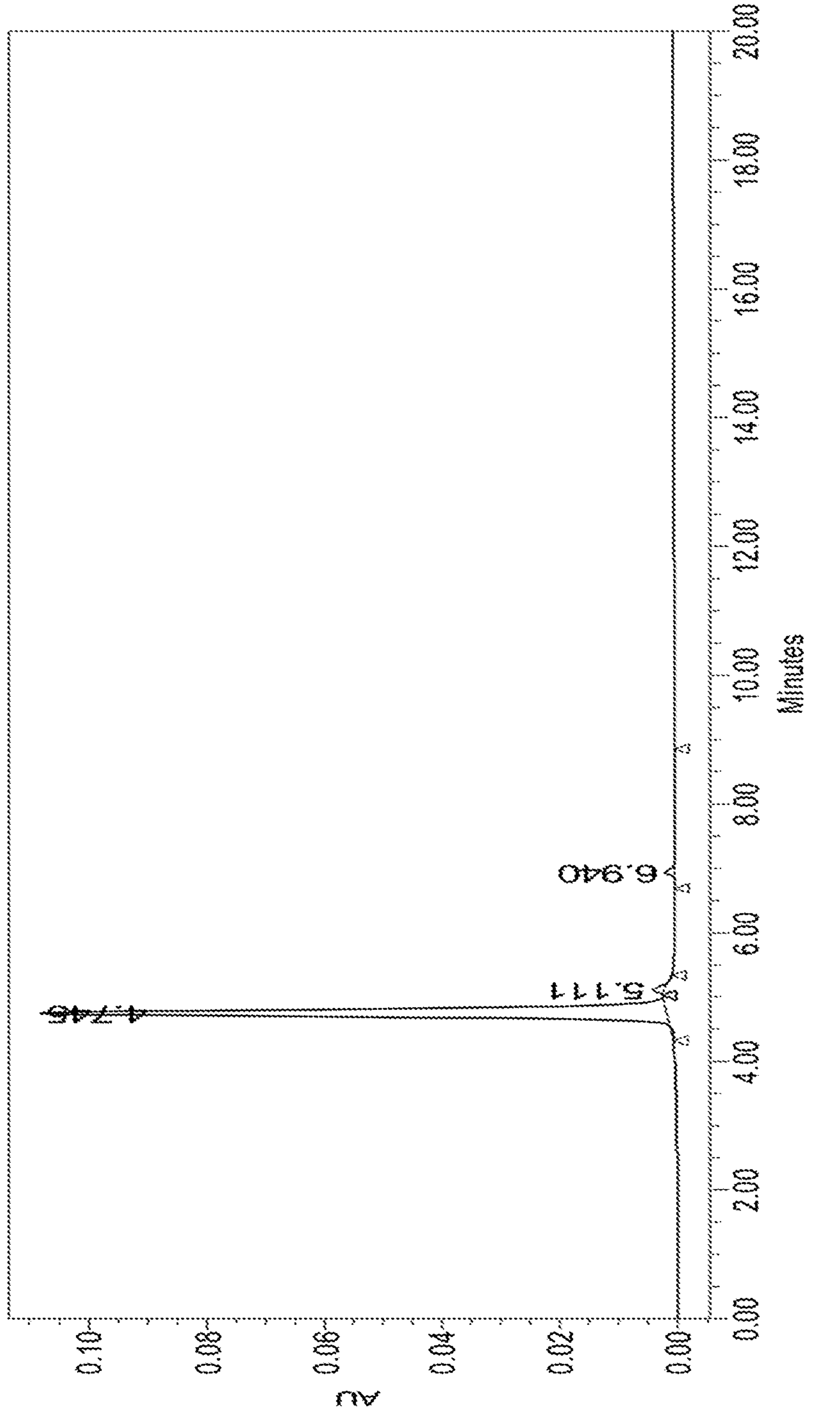
Figure 2M:
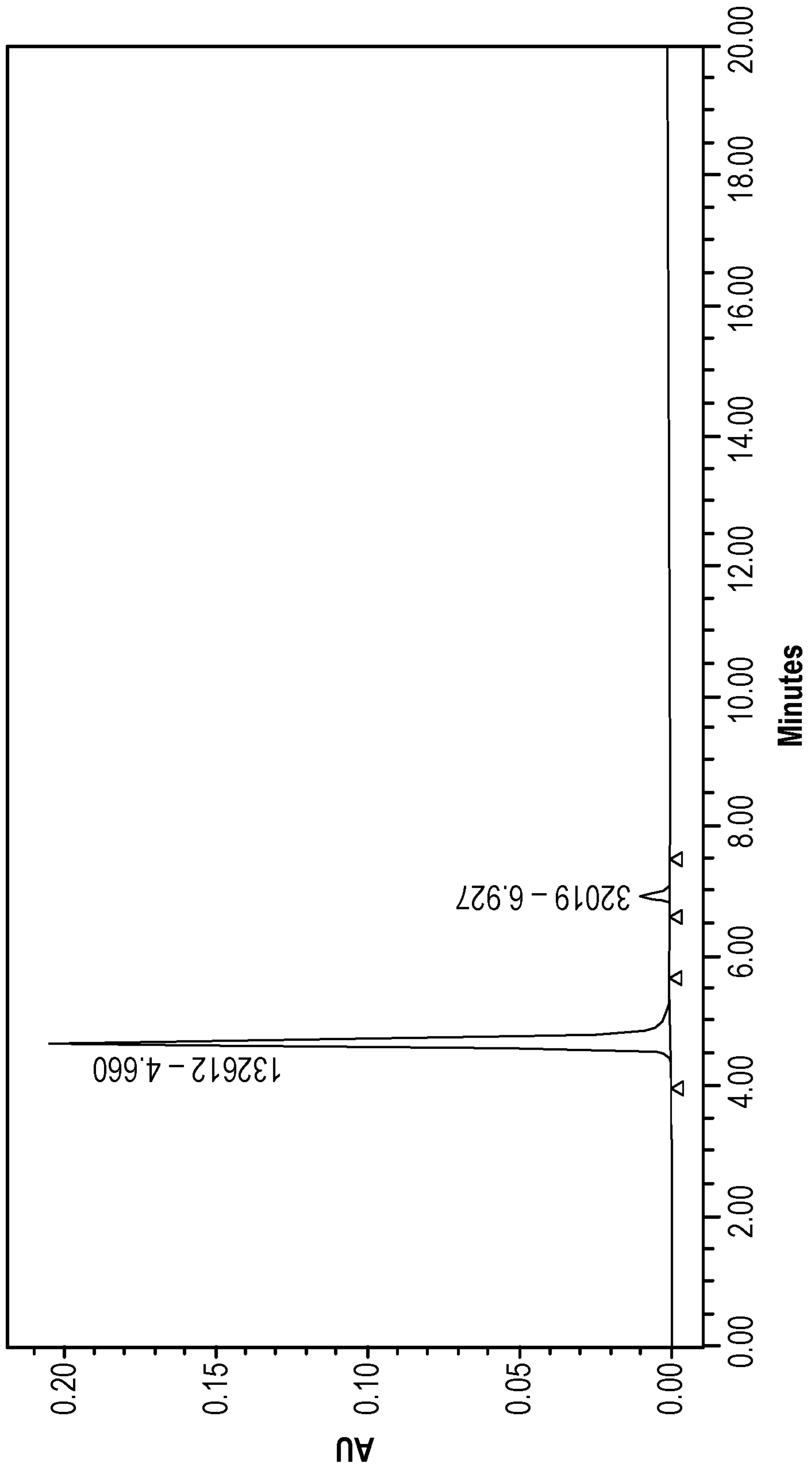
Figure 2N:
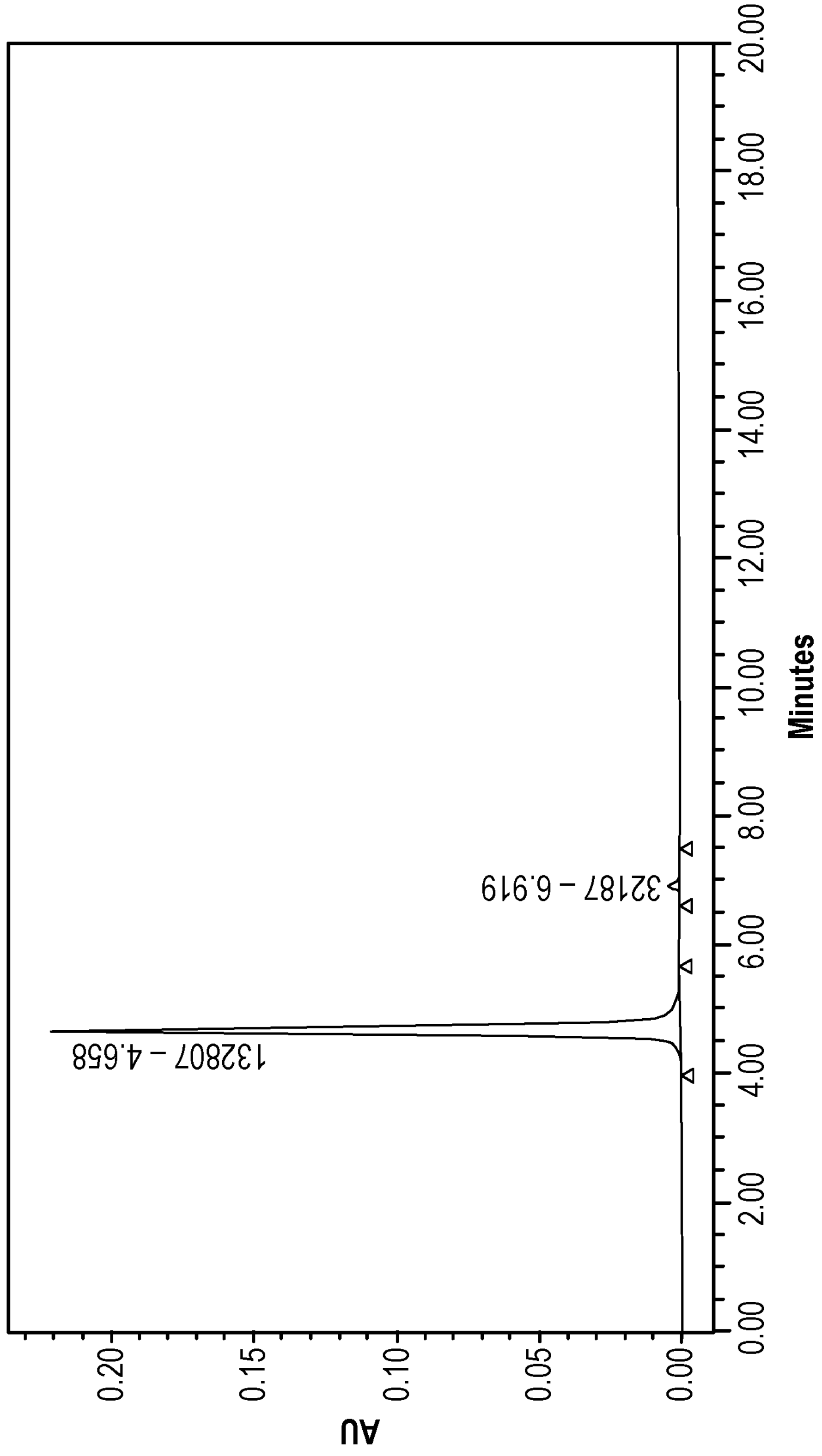
Figure 2O:
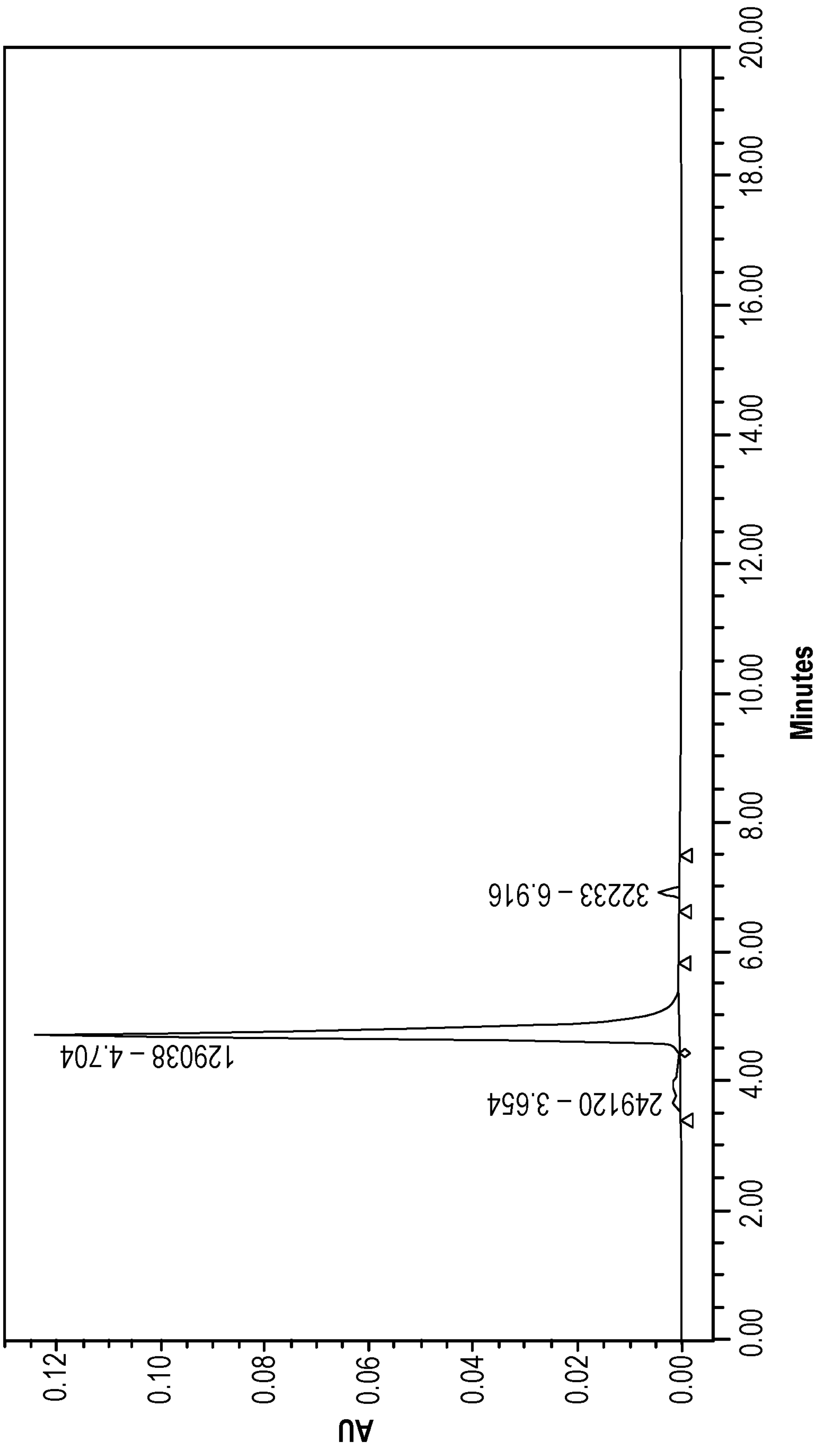
Figure 2P:
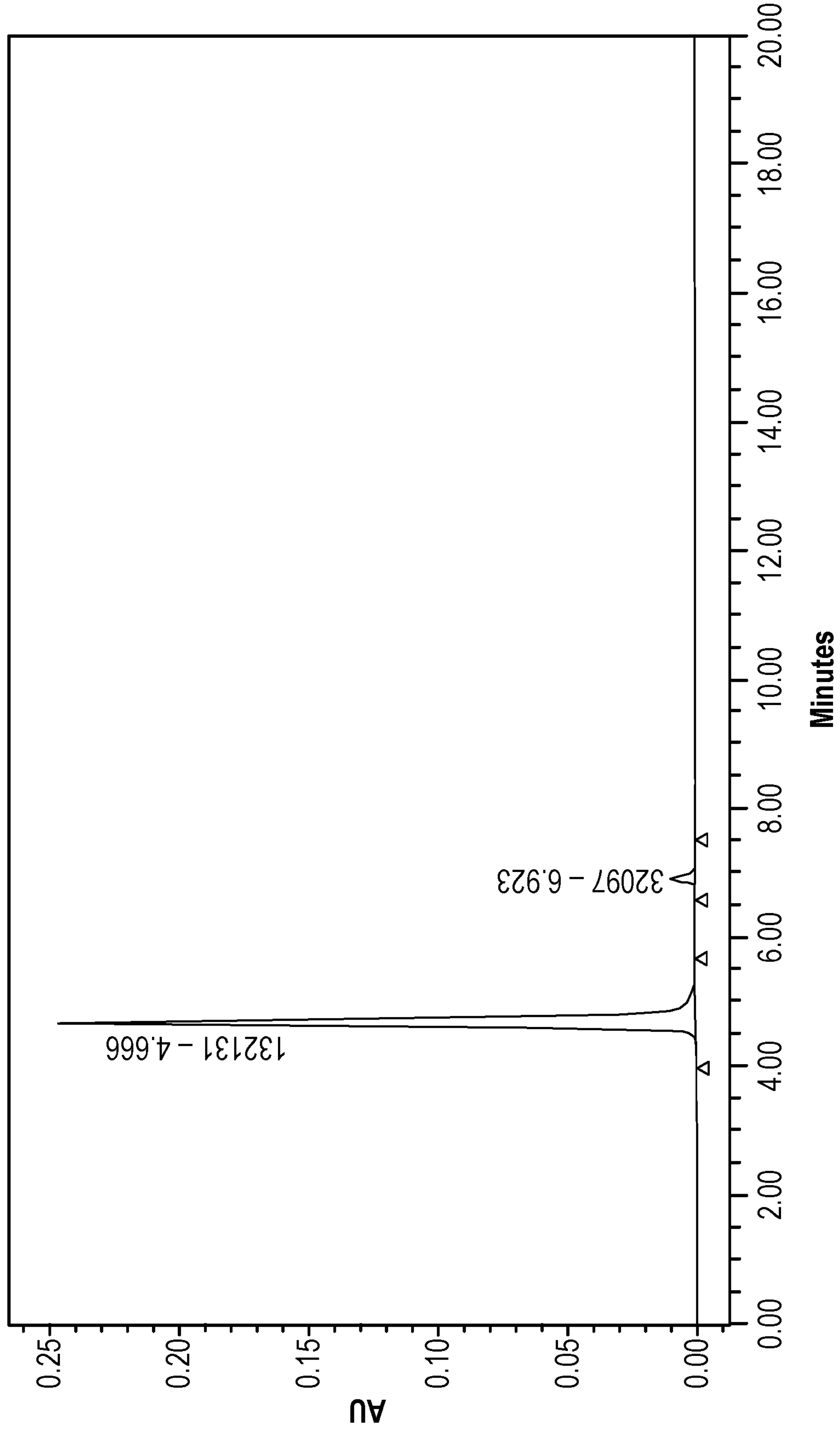
Figure 2Q:
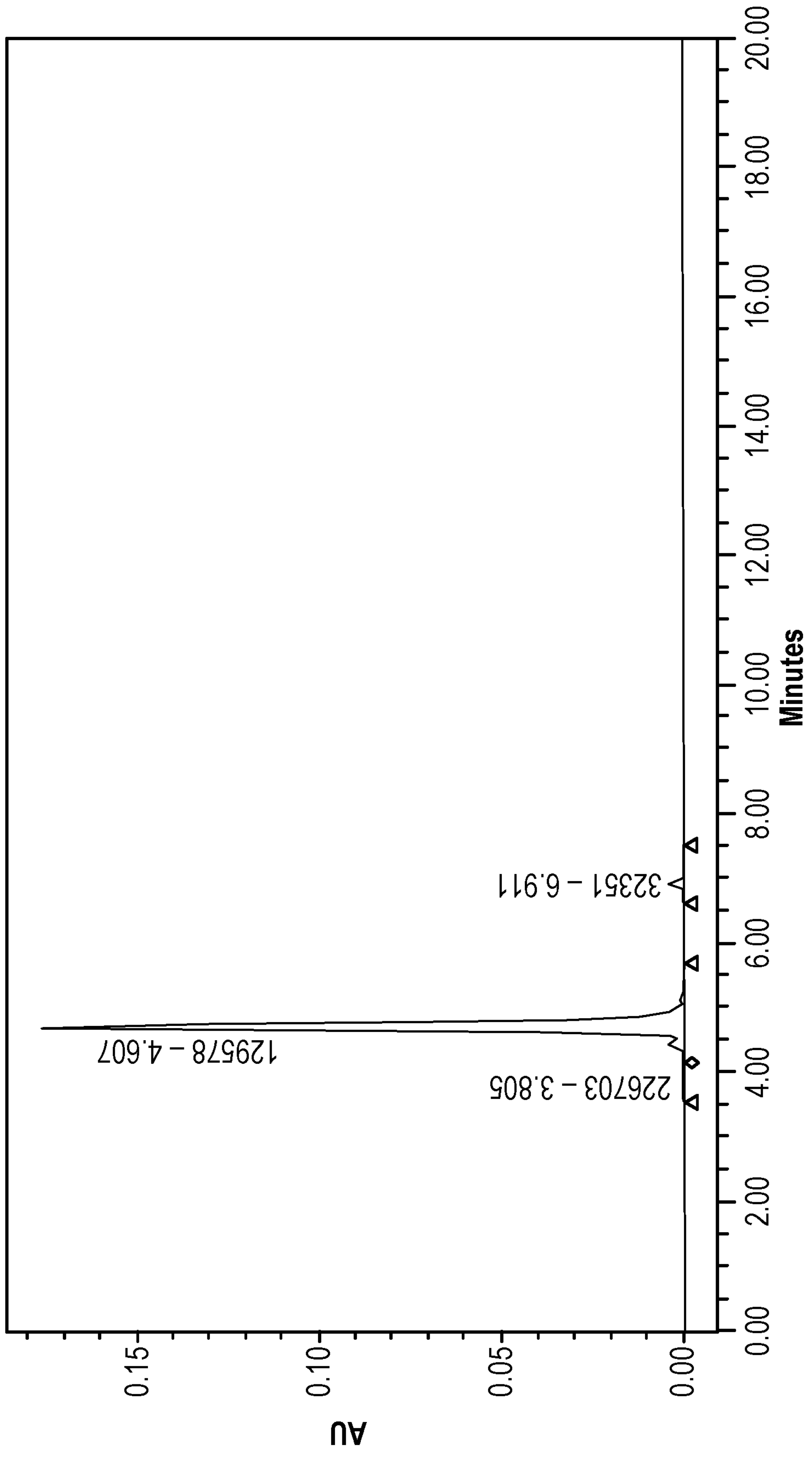
Figure 2R:
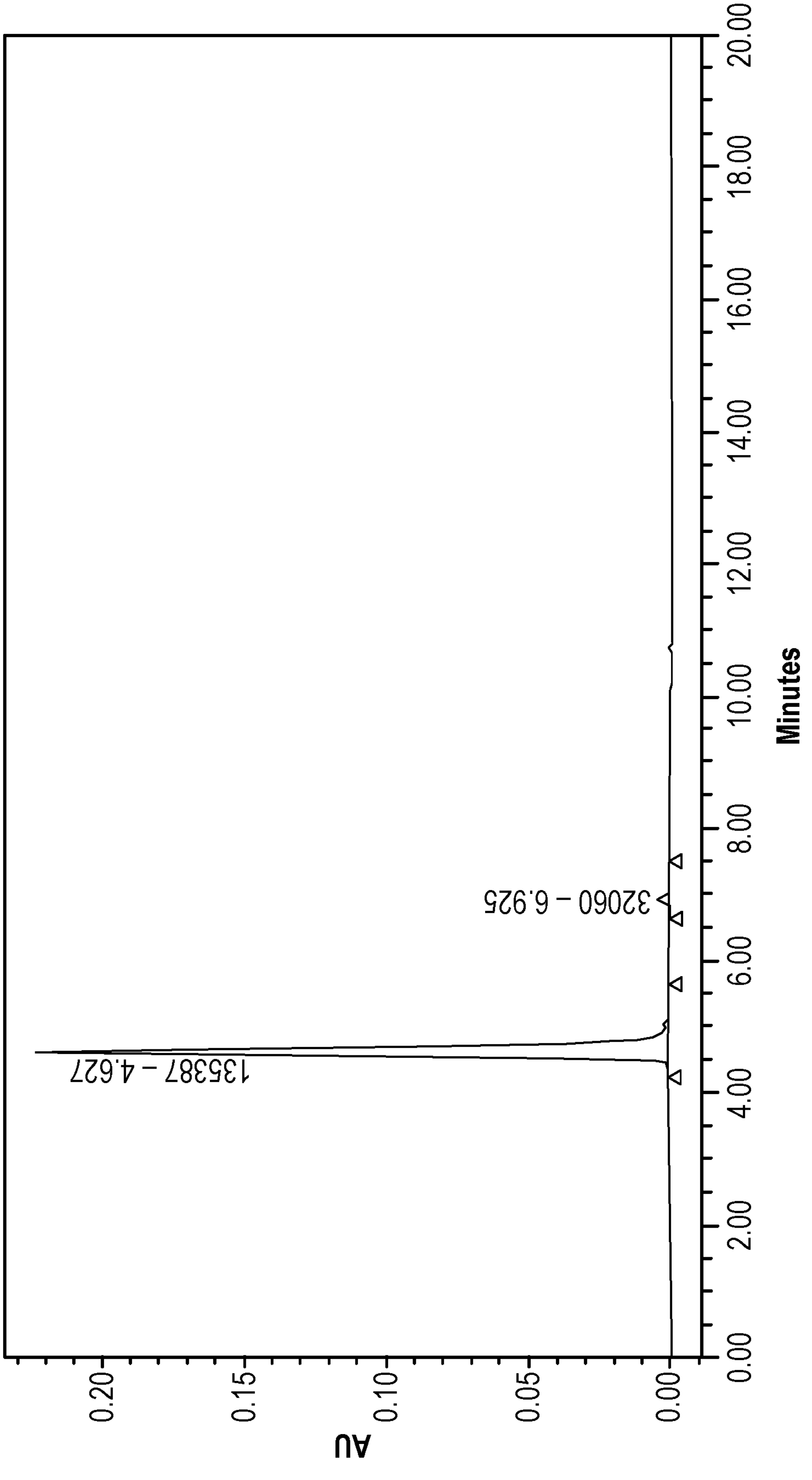

To test these antibodies' tendency to aggregate, the IgGs went through size exclusion chromatography (SEC) on an Akta, Superdex 10/300 increase column or on Waters ACQUITY arc HPLC, BioResolve SEC mAb column with PBS as mobile phase as described above. Examples of SEC analyses of selected antibodies are shown in FIGS. 2A-2R and a summary of the complete SEC analysis of the clones is presented in Table 4. These results indicate that IgGs 30.086-30.113, 30.115, 30.117-119, 30.122-30.123, 30.202 and 30.204 were eluted from protein A mostly as non-aggregated species, and migrated on the SEC columns as a typically folded IgG1.

TABLE 4

| SEC Profile of produced IgGs | | |
|---|---|---|
| IgG I.D. | Superdex 10/300 retention Volume (ml) | % Aggregation |
| 30.086 | 13.16 | 1.1 |
| 30.095 | 13.00 | 0.2 |
| 30.116 | 13.57 | 2.3 |
| 30.111 | 13.2 | 1.02 |
| 30.119 | 13.08 | 0 |
| 30.123 | 13.24 | 0.7 |
| IgG I.D. | BioResolve SEC retention Volume (time) | % Aggregation |
| 30.113 | 4.72 | 0.6 |
| 30.114 | 4.70 | 5.8 |
| 30.115 | 4.74 | 2.8 |
| IgG I.D. | Superdex 10/300 retention Volume (ml) | % Aggregation |
| 30.116 | 4.73 | 8.4 |
| 30.117 | 4.66 | 2.5 |
| 30.118 | 4.62 | 1.5 |
| 30.122 | 4.69 | 2.6 |
| 30.200 | 4.66 | 3.4 |
| 30.201 | 4.65 | 1.4 |
| 30.202 | 4.74 | 4.6 |
| 30.203 | 4.74 | 7.7 |
| 30.204 | 4.77 | 4.4 |

Specificity ELISA

Figure 3A:
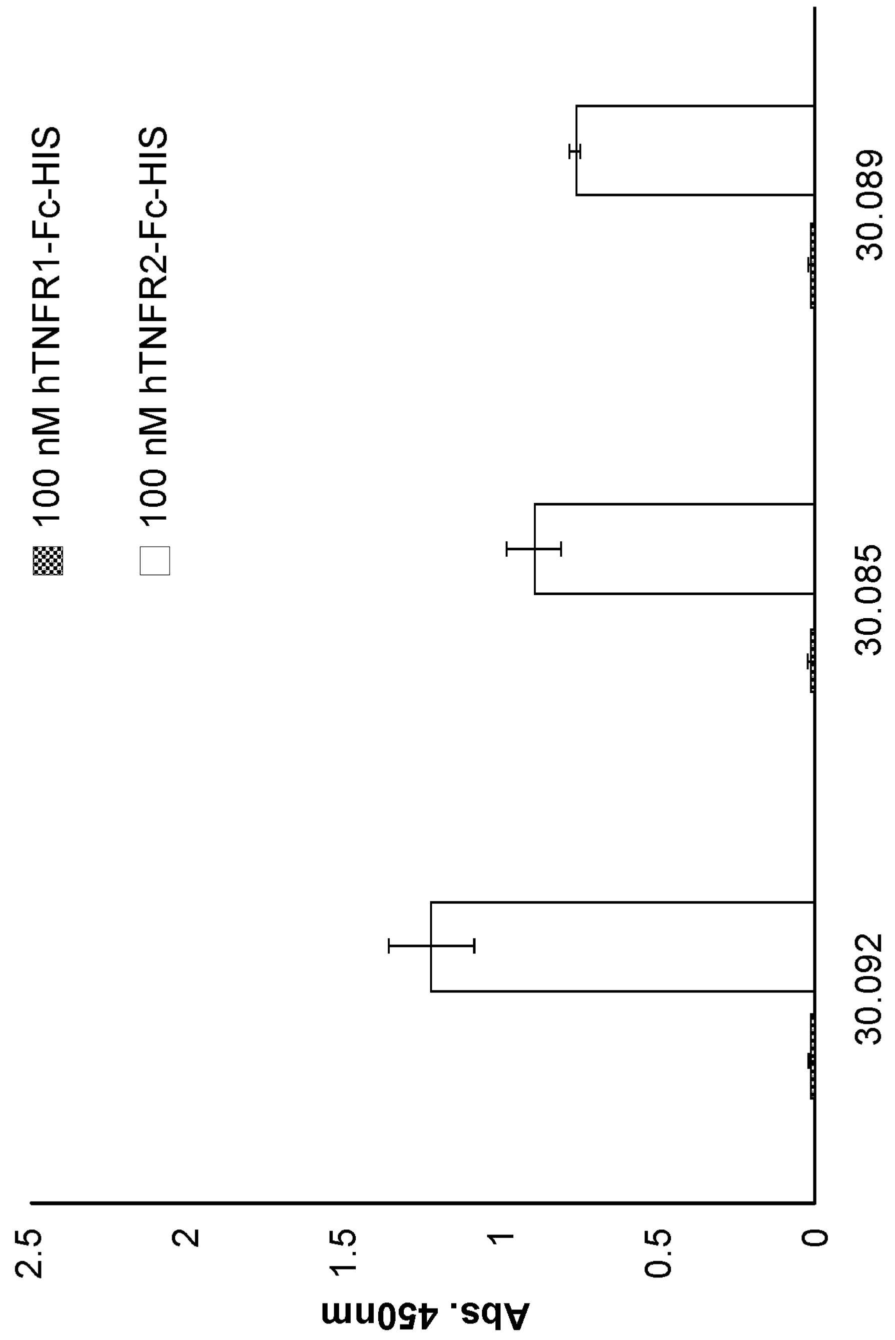
FIGS. 3A and 3B show IgG binding specificity of selected clones to TNFR2
Figure 3B:
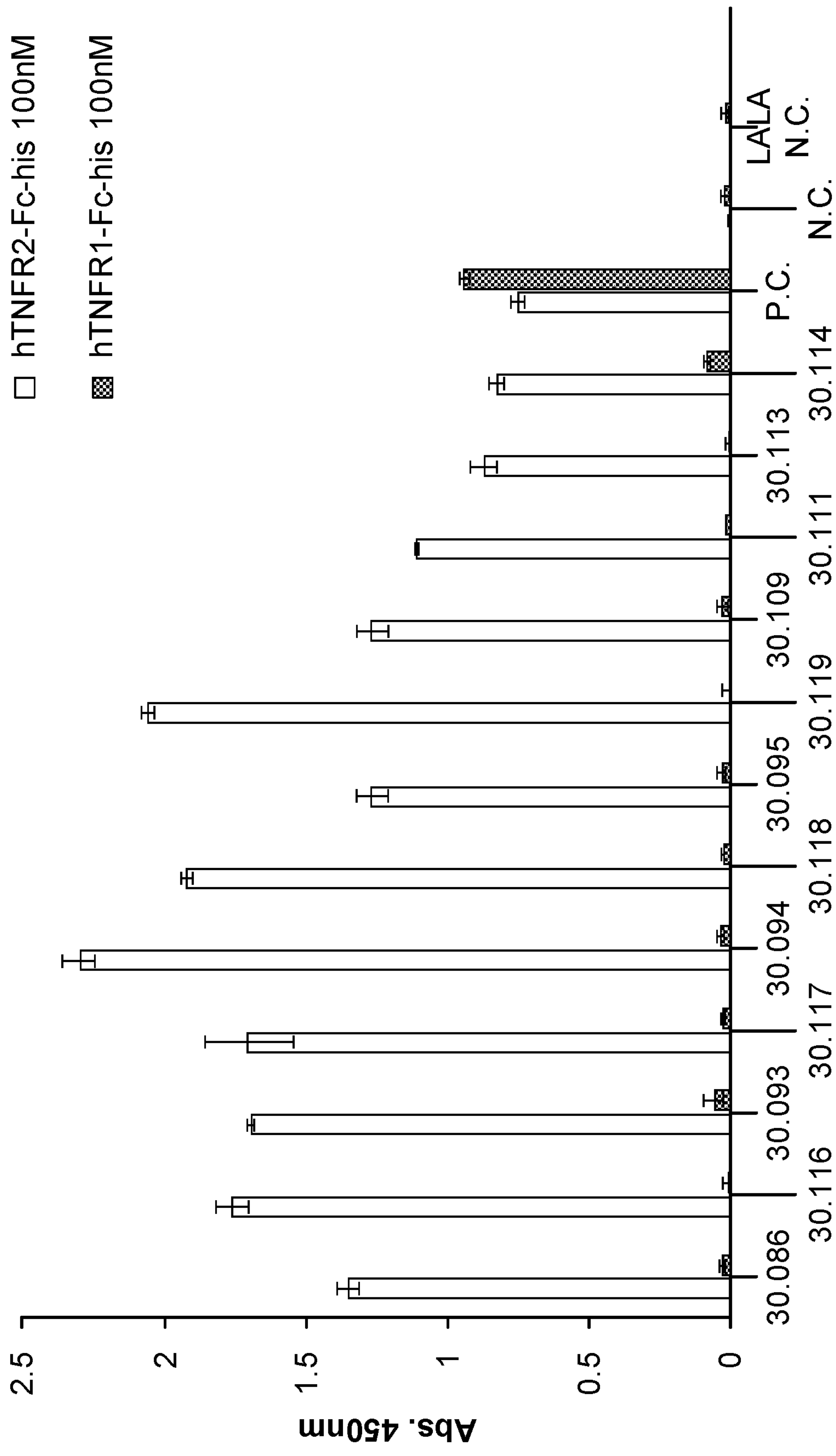

The extracellular domains of TNFR2 and TNFR1 share 27% homology. To test specificity to TNFR2, the antibodies were analyzed by an ELISA assay against TNFR1 and TNFR2 as described herein. Briefly, antibodies were coated directly on the ELISA plate wells, the wells were blocked, and 100 nM of TNFR1-His-Fc or TNFR2-His-Fc were added to the wells, washed and detected using anti His-HRP. As can be seen in FIGS. 3A-3B, the IgG 30.092, 30.093, 30.094, 30.095, 30.085, 30.089, 30.086, 30.116, 30.118, 30.119, 30.111, 30.113 and 30.114 showed specific binding to TNFR2 and did not bind TNFR1.

Binding Affinity of IgGs Towards TNFR2

IgG ELISA $EC_{50}$

To test binding affinity of clones reformatted as IgG1 and IgG1LALA to TNFR2, an ELISA $EC_{50}$ binding experiment was conducted for each antibody. As can be seen in FIGS. 4A-4F, the antibodies bind soluble TNFR2-His at an $EC_{50}$ range of 1.8 nM to 66 nM, indicating that these antibodies are tight binders. Table 5 lists the TNFR2 $EC_{50}$ value for the indicated antibodies, the values are an average of at least two biological repeats.

TABLE 5

| TNFR2 $EC_{50}$ Value for Indicated Antibodies | |
|---|---|
| Abs | $EC_{50}$ - Binding (nM) |
| 30.032 | 21.9 |
| 30.080 | 66.3 |
| 30.081 | 50.7 |
| 30.084 | 58.9 |
| 30.085 | 4.3 |
| 30.086 | 8.1 |
| 30.087 | 18.4 |
| 30.088 | 13.1 |
| 30.089 | 50.4 |
| 30.046 | 13.4 |
| 30.092 | 15.4 |
| 30.093 | 6.8 |
| 30.094 | 3.7 |
| 30.095 | 4.6 |
| 30.109 | 5.6 |
| 30.111 | 3.55 |
| 30.113 | 2.5 |
| 30.114 | 2.2 |
| 30.116 | 5.1 |
| 30.117 | 2.9 |
| 30.118 | 1.7 |
| 30.119 | 1.8 |

Establishment of TNFR2 Dependent NFκB Cell Based Assay

To characterize whether the antibodies affect the TNFR2 cellular signaling functionally, and whether they have an agonistic, antagonistic or no effect on the TNFR2, a reporter cell line was created.

HEK-Blue™ Null cells were purchased from InvivoGen (Toulouse France). These cells contain TNFR1 null mutation and a plasmid encoding soluble embryonic alkaline phosphatase (SEAP) under the control IFN-β minimal promoter fused to five NF-κB and AP-1 binding sites. A pCDNA3.1 plasmid encoding human TNFR2 (residues 1-461) under the CMV promoter was transfected into HEK-Blue™ Null cells. The cells were kept for 14 days under the selection of 50 ug/ml hygromycin B. After the selection period, TNFR2 expression was validated by Western blot analysis (FIG. 5).

Subsequently, the cells were diluted to a limiting dilution of 0.5 cells per well in 96 well plate and propagated in a growth medium containing DMEM supplemented with 10% FBS, L-Glutamin, pen/strep and 50 ug/ml hygromycin B. To identify TNFa reactive clones, a replica plate was made of the single clones and tested for TNFa dependent activation of NFκB using Quanti-Blue (QB, InvivoGen) substrate as instructed by the manufacturer (FIGS. 6A-6C).

FIGS. 7A-7B show the results of TNFα-dependent NFκB response of a specific clone, with dynamic range of 20 pM to 1000 pM. The activation was inhibited in a dose dependent manner by soluble TNFR2 (FIG. 7B), but was not affected by isotype control antibody (FIG. 7A). Clone G6 was selected for evaluating the target antibodies for agonizing or antagonizing the TNFR2 receptor.

Functional Testing of the IgGs in HEK-TNFR2 Reporter Cell Line

To test the effects of the anti-TNFR2 antibodies on cellular signaling of TNFR2, IgGs were incubated overnight with the HEK-TNFR2 reporter call line up to a concentration of 600 nM and tested for antibody dependent NFkB activation as detailed herein. (FIGS. 8A-8D)

The IgGs listed in Table 6 except 30.088 and 30.117 showed a dose dependent NFκB activation with an $EC_{50}$ functional agonism value ranging between 0.5 nM and 25.7 nM, demonstrating that these antibodies are high affinity functional agonists and can agonize the receptor without the addition of other molecules.

To validate that the NFκB activation is dependent on direct activation of TNFR2 receptor by an antibody, and could not be activated by a TNFR1 alternative route, antibodies 30.113, 30.114, 30.115, 30.116, 30.117, 30.118, 30.119, 30.123, 30.200, 30.201, 30.202, 30.203, and 30.204 were tested using HEK-Blue-TNFα cells (InvivoGen, Cat: hkb-tnfdmyd). HEK-Blue-TNFα cells do not express TNFR2, but natively express TNFR1 and contain a plasmid encoding soluble embryonic alkaline phosphatase (SEAP) under the control IFN-β minimal promoter fused to five NF-κB and AP-1 binding sites.

As can be seen in FIG. 9A HEK-Blue-TNFα cells do not express TNFR2, as evident by FACS analysis of these cells labeled with 200 nM 30.116 anti-TNFR2 Ab. On the other hand, NFκB is readily activated by the addition of 11 nM TNFα (FIG. 9B), suggesting that NFκB activation is by the TNFR1 route. While the indicated antibodies were shown to activate NFκB in a HEK-TNFR2 cell line, addition of 1 mM of 30.113, 30.114, 30.115, 30.116, 30.117, 10.118, 30.119, 30.123, 30.200, 30.201, 30.202, 30.203, or 30.204 antibodies did not activate NFκB in a HEK-TNFR1 cell line, suggesting that the activation is specific to TNFR2 (FIGS. 9B-9C).

The TNFR2 activation is independent of IgG-Fc clustering. This is supported by the fact that HEK293 reporter cell line does not express the Fc gamma receptors, and the IgGs in the above experiments were added to the cells in soluble form and were not plate bound. Moreover, 30.113 to 30.204 IgGs were expressed with a LALA mutation that is designed to reduce IgG binding to Fc-gamma receptor. Taken together, these data suggest that the TNFR2 activation is independent of IgG-Fc clustering. Table 6 presents a summary of $EC_{50}$ of functional agonism of TNFR2 in HEK293-NFκB reporter cell line. The values shown are an average of at least two biological repeats.

TABLE 6

$EC_{50}$ of Functional Agonism of TNFR2 in HEK293-NFkB Reporter Cell Line

| Abs | Functional Agonism $EC_{50}$ (nM) |
|---|---|
| 30.032 | 0.85 |
| 30.085 | 24.7 |
| 30.086 | 1.4 |
| 30.087 | 3.9 |
| 30.088 | 49 |
| 30.046 | 22 |
| 30.092 | 17.6 |
| 30.093 | 20.6 |
| 30.094 | 3.9 |
| 30.109 | 4.2 |
| 30.111 | 7.4 |
| 30.113 | 3.8 |
| 30.114 | 6.4 |
| 30.116 | 3 |
| 30.115 | 1 |
| 30.117 | 277 |
| 30.118 | 5.4 |
| 30.119 | 2.6 |
| 30.122 | 2.3 |
| 30.123 | 2.6 |
| 30.200 | 24.4 |
| 30.201 | 20 |
| 30.202 | 2.9 |
| 30.203 | 0.5 |
| 30.204 | 3.1 |

To examine the effects of TNFα on antibody dependent NFκB activation, the HEK-TNFR2 cells were incubated with 200 nM anti-TNFR2 antibodies and TNFα was added up to a concentration of 100 nM. As shown in FIGS. 10A-10D, TNFα had a minor effect on maximal activation induced by 30.116, 30.111, 30.086 and 30.119 antibodies, indicating that these antibodies activate the TNFR2 receptor to almost its full capacity, likely at an epitope that is not blocking the TNFα binding site.

Taking together, the results shown above demonstrate that the antibodies presented in this disclosure are tight binders to TNFR2 in the sub-nanomolar to low double digit nanomolar range, are specific to TNFR2 and agonize TNFR2 in an Fc independent manner.

While certain features of the anti-TNFR2 antibodies have been illustrated and described herein, many modifications, substitutions, changes, and equivalents will now occur to those of ordinary skill in the art. It is, therefore, to be understood that the appended claims are intended to cover all such modifications and changes as fall within the true spirit of the anti-TNFR2 antibodies

TABLE 7

Embodiments of Heavy Chain CDR Sequences

| CID | HCDR1 | SEQ ID NO | HCDR2 | SEQ ID NO | HCDR3 | SEQ ID NO |
|---|---|---|---|---|---|---|
| CID_251 | GDTFTSYS | 185 | IITILDDT | 190 | AGVYEGPNSEG SYDDYGFLKH | 347 |
| CID_252 | GDTFTSYS | 185 | IITILDDT | 190 | AGVYEGPNSEG SYDDYGFLKH | 347 |
| CID_253 | GDTFTSYS | 185 | IITDLDDT | 334 | AGVYEGPNSEG SYDDYGFLKH | 347 |
| CID_254 | GDTFTSYS | 185 | IITILDDT | 190 | AGVYEGPNSEG SYDDYGFLKH | 347 |

TABLE 7-continued

Embodiments of Heavy Chain CDR Sequences

| CID | HCDR1 | SEQ ID NO | HCDR2 | SEQ ID NO | HCDR3 | SEQ ID NO |
|---|---|---|---|---|---|---|
| CID_255 | GDTFTSYS | 185 | IITILDDT | 190 | AGVYEGPNSEG SYDDYGFLKH | 347 |
| CID_256 | GDTFTSYS | 185 | IITILDDT | 190 | AGVYEGPNSEG SYDDYGFLKH | 347 |
| CID_257 | GDTFTSYS | 185 | IITILDDT | 190 | AGVYEGPNSEG SYDDYGFLKH | 347 |
| CID_258 | GDTFTSYS | 185 | IITIPDDT | 335 | AGVYEGPNSEG SYDDYGFLKH | 347 |
| CID_259 | GDTFTSYS | 185 | IITILDDT | 190 | AGVYEGPNSEG SYDDYGFLKH | 347 |
| CID_272 | GDTFTSYS | 185 | IITIDDDT | 336 | AGVYEGPNSEG SYDDYGFYKH | 348 |
| CID_274 | GDTFTSYS | 185 | IITILDDS | 337 | AGVYEGPNSEG SYDDYGFLKH | 347 |
| CID_275 | GDTFTSYS | 185 | IITIDDDT | 338 | AGVYEGPNSEG SYDDYGFYKH | 348 |
| CID_276 | GDTFTSYS | 185 | IITIYDDT | 339 | AGVYEGPNSEG SYDDYGFFKH | 349 |
| CID_277 | GDTFTSYS | 185 | IITILDDT | 190 | AGVYEGPNSEG SYDDYGFLKY | 350 |
| CID_278 | GDTFTSYS | 185 | IITILDDT | 190 | AGVYEGPNSEG SYDDYGALKH | 351 |
| CID_279 | GDTFTSYS | 185 | IITDLDDT | 334 | AGVYEGPNSEG SYDDYGFLKH | 347 |
| CID_280 | GDTFTSYS | 185 | IITDLDDT | 334 | AGVYEGPNSEG SYDDYGQLKH | 352 |
| CID_281 | GDTFTSYS | 185 | IITILDDT | 190 | AGVYEGPNSEG SYDDYGQLKH | 352 |
| CID_282 | GDTFTSYS | 185 | IITDLDDT | 334 | AGVYEGPNSEG SYDDYGFLKH | 347 |
| CID_283 | GDTFTSYS | 185 | IITILDDT | 190 | AGVYEGPNSEG SYDDYGFLKH | 347 |
| CID_284 | GDTFTSYS | 185 | IITIDDDT | 336 | AGVYEGPNSEG SYDDYGQLKH | 352 |
| CID_285 | GDTFTSYS | 185 | IITIDDDT | 336 | AGVYEGPNSEG SYDDYGQLKH | 352 |
| CID_323 | GYTFTDLG | 186 | INTHTGMP | 340 | ARDHPLGLDY | 353 |
| CID_324 | GYTFTDLG | 186 | INTHTGEP | 341 | TRDHPLGLDY | 354 |
| CID_325 | GYTFTDLG | 186 | INTHTGEP | 341 | TRDHPLGLDY | 354 |
| CID_326 | GYTFTDLG | 186 | INTHTGKP | 342 | TRDHPLGLDY | 354 |
| CID_327 | GYTFTDLG | 186 | INTQTGEP | 343 | TRDHPLGLDY | 354 |
| CID_328 | GYTFTDLG | 186 | INTQTGEP | 343 | ARDHPLGLDY | 355 |
| CID_329 | GYTFTDLG | 186 | INTHTGEP | 341 | TRDHPLGLDY | 354 |
| CID_330 | GYTFTDLG | 186 | INTHTGEP | 341 | ARDHPLGLDY | 355 |
| CID_331 | GYTFTDLG | 186 | INTITGEP | 344 | TRDHPLGLDY | 354 |
| CID_332 | GYTFTDLG | 186 | INTHTGEP | 341 | TRDHPLGLDY | 354 |
| CID_333 | GYTFTDLG | 186 | INTITGEP | 344 | TRDHPLGLDY | 354 |
| CID_350 | GYTFTDLG | 186 | INTHTGEP | 341 | TRDHPLGLDY | 354 |
| CID_436 | GFNIRDTY | 187 | IDPDNGDT | 345 | SRDLADGYNAF DR | 356 |
| CID_437 | GFNIRDTF | 188 | IDPDNGDT | 345 | SREGEDGYNAW DL | 357 |
| CID_438 | GFNIRATY | 189 | IDPTNGDT | 346 | TREGDDGYNAW DK | 358 |

TABLE 8

Embodiments of Light Chain CDR Sequences

| CID | LCDR1 | SEQ ID NO | LCDR2 | SEQ ID NO | LCDR3 | SEQ ID NO |
|---|---|---|---|---|---|---|
| CID_251 | ESVAND | 359 | GAS | 372 | QQYANWPPRET | 378 |
| CID_252 | ESVAND | 359 | GAS | 372 | QQYANWPPRET | 378 |
| CID_253 | ESGAND | 360 | GAS | 372 | QQYANWPPRGT | 379 |
| CID_254 | ESVAND | 359 | GAS | 372 | QQYTNWPPRET | 380 |
| CID_255 | ESVAND | 359 | GAS | 372 | QQYAIWPPRET | 381 |
| CID_256 | RSVAND | 361 | GAS | 372 | QQYAIWPPRET | 381 |
| CID_257 | ESVANN | 362 | GAS | 372 | QQYARWPPTET | 382 |
| CID_258 | ESVATD | 363 | GAS | 372 | QQYDNWPPRET | 383 |
| CID_259 | ESVRND | 364 | GAS | 372 | QQYANWPPHET | 384 |
| CID_272 | ESVGND | 365 | GAS | 372 | QQYANWPPRET | 378 |
| CID_274 | ESVAND | 359 | DAS | 373 | QQYANWPWRET | 385 |
| CID_275 | ESVAND | 359 | GAS | 372 | QQGANWPPRET | 386 |
| CID_276 | ESVAND | 359 | GAS | 372 | QQYANWPPRET | 378 |
| CID_277 | ESVAVD | 366 | GAS | 372 | QQYANKPPRET | 387 |
| CID_278 | ESVAND | 359 | GAS | 372 | QQYANWPPRET | 378 |
| CID_279 | ESGAND | 360 | GAS | 372 | QQYANWPPRGT | 388 |
| CID_280 | ESVAND | 359 | GAS | 372 | QQYANWPPRET | 378 |
| CID_281 | ESVAND | 359 | GAS | 372 | QQYANTPPRET | 389 |
| CID_282 | ESVAND | 359 | GAS | 372 | QQYANWPPRET | 378 |
| CID_283 | ESVGND | 365 | GAS | 372 | QQYANWPPRET | 378 |
| CID_284 | ESVGND | 365 | GAS | 372 | QQYANVPPRET | 390 |
| CID_285 | ESVGND | 365 | GIS | 374 | QQYANDPPRET | 391 |
| CID_323 | QSVDVNGVSY | 367 | KAS | 375 | QQSREDPYT | 392 |
| CID_324 | QSVDVNGVSY | 367 | KAS | 375 | QQSREDPYT | 392 |
| CID_325 | QSVDVNGLSY | 368 | KAS | 375 | QQSREDPYT | 392 |
| CID_326 | QSVDVNGVSY | 367 | KAS | 375 | QQSREDPYT | 392 |

TABLE 8-continued

Embodiments of Light Chain CDR Sequences

| CID | LCDR1 | SEQ ID NO | LCDR2 | SEQ ID NO | LCDR3 | SEQ ID NO |
|---|---|---|---|---|---|---|
| CID_327 | QSVDVAGVSY | 369 | KAS | 375 | QQAREDPYT | 393 |
| CID_328 | QSVDVNGVSY | 367 | KAS | 375 | QQSREDPYT | 392 |
| CID_329 | QSVDVNGVSY | 367 | KAS | 375 | QQSREDPYT | 392 |
| CID_330 | QSVDVNGVSY | 367 | KAV | 376 | QQSREDPYT | 392 |
| CID_331 | QSLDVNGVSY | 370 | KAS | 375 | QQSREDPYT | 392 |
| CID_332 | QSVDVNGVSY | 367 | KAS | 375 | QQNREDPYT | 394 |
| CID_333 | QSVDVNGVSY | 367 | KAS | 375 | QQSREDPYT | 392 |
| CID_350 | QSVDVNGVSY | 367 | KAS | 375 | QQAREDPYT | 393 |
| CID_436 | QDVSTA | 371 | SAS | 377 | QQPTYTPPT | 395 |
| CID_437 | QDVSTA | 371 | SAS | 377 | QQPPYTPPT | 396 |
| CID_438 | QDVSTA | 371 | SAS | 377 | QQPSYTPPT | 397 |

TABLE 9

Embodiments of Heavy And Light Chain CDR Sequences

| CID | HCDR1 | SEQ ID NO | HCDR2 | SEQ ID NO | HCDR3 | SEQ ID NO | LCDR1 | SEQ ID NO | LCDR2 | SEQ ID NO | LCDR3 | SEQ ID NO |
|---|---|---|---|---|---|---|---|---|---|---|---|---|
| CID_264 | GFNIKAYY | 402 | IDPDNGDT | 345 | SREGQDGYNAWDQ | 413 | QDVSTA | 371 | PAS | 418 | QQPTLTPPT | 427 |
| CID_229 | GFNIRAMY | 398 | IDPTNGDT | 346 | TREGQDGYNAFDK | 407 | QDVSTA | 371 | SAS | 377 | QQHRYTPPT | 419 |
| CID_230 | GFNIRDTY | 187 | IDPTNGDT | 346 | SREMADGYNAFDL | 408 | QDVSTA | 371 | SAS | 377 | QQPNYTPPT | 420 |
| CID_231 | GFNIRATY | 189 | ISPDNGDT | 406 | SRDLADGYNAFDL | 409 | QDVSTA | 371 | SAS | 377 | QQHGYTPPT | 421 |
| CID_232 | GFNIRDTY | 187 | IDPDNGDT | 345 | TREGADGYNAFDL | 410 | QDVSTA | 371 | PAS | 418 | QQPDYTPPT | 422 |
| CID_234 | GFNIRAFY | 399 | IDPTNGDT | 346 | TREGEDGYNAFDQ | 411 | QDVSTA | 371 | PAS | 418 | QQPRYTPPT | 423 |
| CID_261 | GFNIKDFF | 400 | IDPTNGDT | 346 | SREGQDGYNAWDL | 412 | QDISTA | 417 | SAS | 377 | QQPSLTPPT | 424 |
| CID_262 | GFNIKDYF | 401 | IDPTNGDT | 346 | SREGQDGYNAWDQ | 413 | QDISTA | 417 | PAS | 418 | QQHPYTPPT | 425 |
| CID_263 | GFNIKDYF | 401 | IDPTNGDT | 346 | SREGQDGYNAWDM | 414 | QDISTA | 417 | PAS | 418 | QQHGYTPPT | 426 |
| CID_265 | GFNIRAMY | 398 | IDPTNGDT | 346 | TREGQDGYNAFDM | 415 | QDISTA | 417 | SAS | 377 | QQPNLTPPT | 428 |
| CID_266 | GFNIRAYY | 403 | IDPTNGDT | 346 | SREGQDGYNAWDL | 412 | QDVSTA | 371 | PAS | 418 | QQPGYTPPT | 429 |
| CID_267 | GFNIRDYY | 404 | IDPTNGDT | 346 | SREGQDGYNAWDL | 412 | QDVSTA | 371 | PAS | 418 | QQHPYTPPT | 425 |

TABLE 9-continued

Embodiments of Heavy And Light Chain CDR Sequences

| CID | HCDR1 | SEQ ID NO | HCDR2 | SEQ ID NO | HCDR3 | SEQ ID NO | LCDR1 | SEQ ID NO | LCDR2 | SEQ ID NO | LCDR3 | SEQ ID NO |
|---|---|---|---|---|---|---|---|---|---|---|---|---|
| CID_268 | GFNI KDYF | 401 | IDPT NGDT | 346 | SREGQ DGYNA WDM | 414 | QDIS TA | 417 | PAS | 418 | QQPLY TPPT | 430 |
| CID_271 | GFNI RDMF | 405 | ISPD NGDT | 406 | TREGE DGYNA FDM | 416 | QDVS TA | 371 | SAS | 377 | QQHAY TPPT | 431 |

What is claimed is:

1. An isolated anti-TNFR2 (tumor necrosis factor receptor 2) antibody comprising a set of three complementarity determining regions (CDRs) on a heavy chain (HCDR1, HCDR2, and HCDR3) and a set of three CDRs on a light chain (LCDR1, LCDR2, and LCDR3), wherein said CDRs have the amino acid sequences of SEQ ID NO: 187, SEQ ID NO:345, and SEQ ID NO: 356 (HCDR1, HCDR2, and HCDR3, respectively), and SEQ ID NO: 371, SEQ ID NO: 377, and SEQ ID NO: 395 (LCDR1, LCDR2, and LCDR3, respectively).

2. The anti-TNFR2 antibody of claim 1, comprising a heavy chain variable region (VH) having at least 90% sequence identity to SEQ ID NO:87 and a light chain variable region (VL) having at least 90% sequence identity to SEQ ID NO:88.

3. The anti-TNFR2 antibody of claim 1, wherein said heavy chain and said light chain comprise the amino acid sequences selected from:

a heavy chain having at least 90% sequence identity to SEQ ID NO: 432 and a light chain sequence having at least 90% sequence identity to SEQ ID NO:260, and a heavy chain having at least 90% sequence identity to SEQ ID NO: 259 and a light chain sequence having at least 90% sequence identity to SEQ ID NO:260.

4. The anti-TNFR2 antibody of claim 1, wherein the antibody is an IgG, a Fv, a scFv, a Fab, a F (ab') 2, a minibody, a diabody, a triabody, or a bispecific antibody.

5. The anti-TNFR2 antibody of claim 4, wherein said IgG is IgG1, IgG2, IgG3, or IgG4.

6. The anti-TNFR2 antibody of claim 1, wherein the antibody agonizes TNFR2.

7. The anti-TNFR2 antibody of claim 6, wherein the antibody agonizes TNFR2 in an Fc independent manner.

8. The anti-TNFR2 antibody of claim 1, wherein the antibody has an $EC_{50}$ binding measurement of about 0.05-100 nM.

9. The anti-TNFR2 antibody of claim 1, wherein the antibody has an $EC_{50}$ functional agonism measurement of about 0.05-100 nM.

10. The anti-TNFR2 antibody of claim 1, wherein the antibody activates signaling through TNFR2 at a level of at least 80% as compared to signaling activated by TNF.

11. The anti-TNFR2 antibody of claim 1, wherein the antibody activates signaling through TNFR2 at a level of at least 95% as compared to signaling activated by TNF.

12. A composition comprising the anti-TNFR2 antibody of claim 1 and a pharmaceutically acceptable carrier.

13. A method of modulating activities or functions of regulatory T cells (Tregs) in a subject, comprising the step of administering to the subject a composition comprising an effective amount of the anti-TNFR2 antibody of claim 1 wherein said activities or functions are selected from promoting immunosuppression, stimulating proliferation of Tregs, and activating Tregs.

14. The method of claim 13, wherein the regulatory T cells are $CD4^{+}CD25^{+}Foxp3^{+}$.

15. The method of claim 13, wherein the method stimulates proliferation of the regulatory T cells.

16. The method of claim 13, wherein the method activates said regulatory T cells.

* * * * *